US006440701B1

(12) United States Patent
Myers et al.

(10) Patent No.: US 6,440,701 B1
(45) Date of Patent: *Aug. 27, 2002

(54) TRANSFERRIN RECEPTOR GENES OF MORAXELLA

(75) Inventors: Lisa E. Myers, Guelph; Anthony B. Schryvers, Calgary; Robin E. Harkness, Willowdale; Sheena M. Loosmore, Aurora; Run-Pan Du, Thornhill; Yan-Ping Yang; Michel H. Klein, both of Willowdale, all of (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/059,584

(22) Filed: Apr. 14, 1998

Related U.S. Application Data

(63) Continuation-in-part of application No. PCT/CA97/00163, filed on Mar. 7, 1997, which is a continuation-in-part of application No. 08/778,570, filed on Jan. 3, 1997, which is a continuation-in-part of application No. 08/613,009, filed on Mar. 8, 1996.

(51) Int. Cl.[7] .......................... C12N 15/31; C12N 15/63

(52) U.S. Cl. .................... 435/69.3; 435/69.1; 435/69.3; 435/69.7; 435/71.1; 435/71.2; 435/252.1; 435/252.3; 435/325; 536/23.1; 536/23.4; 536/23.7

(58) Field of Search .............................. 536/23.7, 23.1, 536/23.4; 435/69.1, 320.1, 325, 69.3, 69.7, 243, 252.1, 252.3, 71.1, 71.2

(56) References Cited

U.S. PATENT DOCUMENTS 5,708,149 A 1/1998 Schryvers et al. .......... 530/418

FOREIGN PATENT DOCUMENTS

| | | |
|---|---|---|
| WO | WO 90/12591 | 11/1990 |
| WO | WO 93/08283 | 4/1993 |
| WO | WO 95/33049 | 12/1995 |
| WO | WO 97/13785 | 4/1997 |
| WO | WO 97/32980 | 9/1997 |

OTHER PUBLICATIONS

Myers L. E. et al, 1998, The transferrin binding protein B of Moraxella catarrhalis elicts bactericidal antibodies and is potential vaccine antigen. Infect. And immunity vol. 66, No. 8, pp. 4183–4192.

Timothy F. Murphy et al., Microbiol. Path. 1989, 6: 159–174.

Brorson, J–E., A. Axelsson, and S.E. Holm. 1976. Studies on *Branhamella catarrhalis* (*Neisseria catarrhalis*) with special reference to maxillary sinusitis. Scan J. Infect. Dis. 8:151–155.

Catlin, B.W., 1990. *Branhamella catarrhalis*: an organism gaining respect as a pathogen. Clin. Microbiol. Rev. 3: 293–320.

Hager, H., A. Verghese, S. Alvarez, and S.L. Berk. 1987. *Branhamella catarrhalis* respiratory infections, Rev. Infect. Dis. 9:1140–1149.

McLeod, D.T., F. Ahmad, M.J. Croughan, and M.A. Calder. 1986. Bronchopulmonary infection due to *M. catarrhalis*. Clinical features and therapeutic response. Drugs 31(Suppl.3):109–112.

Nicotra, B., M. Rivera, J.I. Luman, and R.J. Wallace. 1986. *Branhamella catarrhalis* as a lower respiratory tract pathogen in patients with chronic lung disease. Arch.Intern.Med. 146:890–893.

Ninane, G., J. Joly, and M. Kraytman. 1978. Bronchopulmonary infection due to *Branhamella catarrhallis* 11 cases assessed by transtracheal puncture. Br.Med.Jr. 1:276–278.

Srinivasan, G., M.J. Raff, W.C. Templeton, S.J. Givens, R.C. Graves, and J.C. Mel. 1981. *Branhamella catarrhalis* pneumonia. Report of two cases and review of the literature. Am.Rev. Respir. Dis. 123:553–555.

West, M., S.L. Berk, and J.K. Smith. 1982. *Branhamella catarrhalis* pneumonia. South.Med. J. 75:1021–1023.

Christensen, J.J., and B. Bruun. 1985. Bacteremia caused by a beta–lactamase producing strain of *Branhamella catarrhalis*. Acta.Pathol. Microbiol. Immunol. Scand. Sec.B 93:273–275.

Craig, D.B., and P.A. Wehrie. 1983. *Branhamella catarrhalis* septic arthritis. J. Rheumatol. 10:985–986.

Guthrie, R., K. Bakenhaster, R.Nelson, and R. Woskobnick. 1988. *Branhamella catarrhalis* sepsis: a case report and review of the literature. J.Infect.Dis. 158:907–908.

Hiroshi, S., E.J. Anaissie, N.Khardori, and G.P. Bodey. 1988. *Branhamella catarrhalis* septicemia in patients Cancer 61:2315–2317.

O'Neill, J.H., and P.W. Mathieson. 1987. Meningitis due to *Branhamella catarrhalis*. Aust. N.Z. J. Med. 17:241–242.

Murphy, T.F. 1989. The surface of *Branhamella catarrhalis*: a systematic approach to the surface antigens of an emerging pathogen. Pediatr. Infect. Dis. J. 8:S75–S77.

Van Hare, G.F., P.A. Shurin, C.D. Marchant, N.A. Cartelli, C.E.Johnson, D. Fulton, S. Carlin, and C.H. Kim. Acute otitis media caused by *Branhamella catarrhalis*: biology and therapy. Rev. Infect. Dis. 9:16–27.

(List continued on next page.)

*Primary Examiner*—Michael Pak
(74) *Attorney, Agent, or Firm*—Sim & McBurney

(57) ABSTRACT

Purified and isolated nucleic acid molecules are provided which encode transferrin receptor proteins of Moraxella, such as *M. catarrhalis* or a fragment or an analog of the transferrin receptor protein. The nucleic acid sequence may be used to produce recombinant transferrin receptor proteins Tbp1 and Tbp2 of the strain of Moraxella free of other proteins of the Moraxella strain for purposes of diagnostics and medical treatment. Furthermore, the nucleic acid molecule may be used in the diagnosis of infection.

13 Claims, 172 Drawing Sheets

OTHER PUBLICATIONS

Jorgensen, J.H., Doern, G.V., Maher, L.A., Howell, A.W., and Redding, J.S., 1990 Antimicrobial resistance among respiratory isolates of *Haemophilus influenza*, Moraxella catarrhalis, and *Streptococcus pneumoniae* in the United States. Antibicrob. Agents Chemother. 34: 2075–2080.

Schryvers, A.B. and Morris, L.J. 1988 Identification and Characterization of the transferrin receptor from *Neisseria meningitidis*. Mol. Microbiol. 2:281–288.

Lee, B.C., Schryvers, A.B. Specificity of the lactoferrin and transferrin receptors in *Neisseria gonorrhoeae*. Mol Microbiol. 1988; 2–827–9.

Schryvers, A.B. Characterization of the human transferrin and lactoferrin receptors in *Haemophilus influenzae*. Mol. Microbiol. 1988; 2: 467–72.

Schryvers, A.B. and Lee, B.C. (1988) Comparative analysis of the transferrin and lactoferrin binding proteins in the family Neisseriaceae. Can. J. Microbiol. 35, 409–415.

Yu, R. and Schryvers, A.B., 1993. The interaction between human transferrin and transferrin binding protein 2 from *Moraxella* (*Branhamella*) *catarrhalis* differs from that of other human pathogens. Microbiol. Pathogenesis, 15:433–445.

O'Hagan, 1992, Clin Pharmokinet. 22:1.

Ulmer et al., 1993. Curr. Opinion Invest. Drugs 2: 983–989.

Lockhoff, O., 1991. Glycolipds as immunomoclutators: Synthesis and properits. Che. Int. Ed. Engl. 30: 1611–1620.

Nixon–George, 1990. J. Immunol. 14: 4798–4802.

Wallace, R.J. Jr., Nash, D.R., and Steingrube, V.A. 1990. Antibiotic susceptibilities and drug resistance in *Moraxella* (*Branhaemella*) *catarrhalis*. Am. J. Med. 88 (5A): 465–50S.

F.M. Ausubel et al., Short protocols in Molecular Biology, Greene Publishing Associates and John Wiley and Sons.

Schryvers, A.B., Lee, B.C. 1989. Comparative analysis of the transferrin and lactoferrin binding proteins in the family Neisseriaceae. Can. J. Microbiol. 35: 409–415.

Legrain, M., V. Mazarin, S.W. Irwin, B. Bouchon, M–J. Quentin–Millet, E. Jacobs, and A.B. Schryvers 1993, Cloning and characterization of *Neisseria meningitidis* genes encoding the transferrin–binding proteins Tbp1 and Tbp2. Gene 130: 73–80.

Ogunnariwo, J.W., Woo, T.K.W., Lo, R.Y.C., Gonzalez, G.C., and Schryvers, A.B. Characterization of the Pasteurella haemolytica transferrin receptor genes and the recombinant receptor proteins. Microb. Pathog. 23:273–284 (1997).

Yang, Y.P., Myers, L.E., McGuinness, U., Chong, P., Kwok, Y., Klein, M.H. and Harkness R.E. The major outer membrane protein, C.D, extracted from *Moraxella* (Branhamella) *catarrhalis* is a potential vaccine antigen that induces bactericidal antibodies. FEMS Immun. Med. Microbiol. 17:187–199 (1997).

Needleman, S.B., and Wunsch, C.D. 1970, J. Mol Biol. 48:443–453.

Sellers, P.J. 1974 On the theory and computation of evolutionary distances, J. Appl. Math (Siam) 26:787–793.

Waterman, M.S., Smith, T.F., and Beyer, W.A. 1976. Advan. Math. 20:367–387.

Gerlach et al (1992) Infection and Immunity 60:3253–3261.

Anderson et al (1994) J. Bacteriology 176: 3162–3170.

Gray–Owen et al (1995) Infection and Immunity 63: 1201–1210.

Bowie et al (1990) Science 247: 1306–1310.

Regenmortel (1986) TIBS 11: 36–39.

George et al (1988) Macromolecular Sequencing and Synthesis (Ed. By D. H. Schlesinger) Alan R. Liss, Inc., New York, pp. 127–129.

Smith, T.F., and Waterman, M.S. 1981 Identification of common molecular subsequences. J. Mol. Biol. 147:195–197.

Jimenez–Montano, M. and Zamora–Cortina, L. 1981 Evolutionary model for the generation of amino acid sequences and its application to the study of mammal alpha–hemoglobin chains. Proc. VII Int. Biophysics Congress, Mexico City.

Sobel, E. and Martinez, H.M. 1985 A Multiple Sequence Alignment Program. Nucleic Acid Res. 14:363–374.

Rong–Hua Yu et al; Microbial Pathogenesis, vol. 15, 1993, pp.433–445 XP000612196.

AMINO ACID SEQUENCES OF A CONSERVED PORTION OF Tbp1 PROTEIN FOR CONSTRUCTION OF DEGENERATE PRIMERS USED IN PCR AMPLIFICATION OF A PORTION OF THE *M. cattarhalis* 4223 *tbp*A GENE.

| | |
|---|---|
| N E V T G L G | SEQ ID NO: 17 |
| G A I N E I E | SEQ ID NO: 18 |

Sequence of *M. catarrhalis* 4223 *tbpA* gene

```
TATTTTGACAAGCTATACACTAAAATCAAAAATTAATCACTTTGGTTGGGTGGTTTTAGCAAGCAAATGGT

TATTTTGGTAAACAATTAAGTTCTTAAAAACGATACACGCTCATAAACAGATGGTTTTTGGCATCTGCAAT

TTGATGCCTGCCTTGTGATTGGTTGGGGTGTATCGGTGTATCAAAGTGCAAAAGCCAACAGGTGGTCATTG

                                27                                      54
ATG AAT CAA TCA AAA CAA AAC AAC AAA TCC AAA AAA TCC AAA CAA GTA TTA AAA
MET Asn Gln Ser Lys Gln Asn Asn Lys Ser Lys Lys Ser Lys Gln Val Leu Lys

                                81                                     108
CTT AGT GCC TTG TCT TTG GGT CTG CTT AAC ATC ACG CAG GTG GCA CTG GCA AAC
Leu Ser Ala Leu Ser Leu Gly Leu Leu Asn Ile Thr Gln Val Ala Leu Ala Asn

                               135                                     162
ACA ACG GCC GAT AAG GCG GAG GCA ACA GAT AAG ACA AAC CTT GTT GTT GTC TTG
Thr Thr Ala Asp Lys Ala Glu Ala Thr Asp Lys Thr Asn Leu Val Val Val Leu

                               189                                     216
GAT GAA ACT GTT GTA ACA GCG AAG AAA AAC GCC CGT AAA GCC AAC GAA GTT ACA
Asp Glu Thr Val Val Thr Ala Lys Lys Asn Ala Arg Lys Ala Asn Glu Val Thr
```

FIG.5B 243 270
GGG CTT GGT AAG GTG GTC AAA ACT GCC GAG ACC ATC AAT AAA GAA CAA GTG CTA
Gly Leu Gly Lys Val Val Lys Thr Ala Glu Thr Ile Asn Lys Glu Gln Val Leu 297 324
AAC ATT CGA GAC TTA ACA CGC TAT GAC CCT GGC ATT GCT GTG GTT GAG CAA GGT
Asn Ile Arg Asp Leu Thr Arg Tyr Asp Pro Gly Ile Ala Val Val Glu Gln Gly 351 378
CGT GGG GCA AGC TCA GGC TAT TCT ATT CGT GGT ATG GAT AAA AAT CGT GTG GCG
Arg Gly Ala Ser Ser Gly Tyr Ser Ile Arg Gly MET Asp Lys Asn Arg Val Ala 405 432
GTA TTG GTT GAT GGC ATC AAT CAA GCC CAG CAC TAT GCC CTA CAA GGC CCT GTG
Val Leu Val Asp Gly Ile Asn Gln Ala Gln His Tyr Ala Leu Gln Gly Pro Val 459 486
GCA GGC AAA AAT TAT GCC GCA GGT GGG GCA ATC AAC GAA ATA GAA TAC GAA AAT
Ala Gly Lys Asn Tyr Ala Ala Gly Gly Ala Ile Asn Glu Ile Glu Tyr Glu Asn 513 540
GTC CGC TCC GTT GAG ATT AGT AAA GGT GCA AAT TCA AGT GAA TAC GGC TCT GGG
Val Arg Ser Val Glu Ile Ser Lys Gly Ala Asn Ser Ser Glu Tyr Gly Ser Gly

FIG.5C

```
                                567                                     594
GCA TTA TCT GGC TCT GTG GCA TTT GTT ACC AAA ACC GCC GAT GAC ATC ATC AAA
Ala Leu Ser Gly Ser Val Ala Phe Val Thr Lys Thr Ala Asp Asp Ile Ile Lys

                                621                                     648
GAT GGT AAA GAT TGG GGC GTG CAG ACC AAA ACC GCC TAT GCC AGT AAA AAT AAC
Asp Gly Lys Asp Trp Gly Val Gln Thr Lys Thr Ala Tyr Ala Ser Lys Asn Asn

                                675                                     702
GCA TGG GTT AAT TCT GTG GCA GCA GCA GGC AAG GCA GGT TCT TTT AGC GGT CTT
Ala Trp Val Asn Ser Val Ala Ala Ala Gly Lys Ala Gly Ser Phe Ser Gly Leu

                                729                                     756
ATC ATC TAC ACC GAC CGC CGT GGT CAA GAA TAC AAG GCA CAT GAT GAT GCC TAT
Ile Ile Tyr Thr Asp Arg Arg Gly Gln Glu Tyr Lys Ala His Asp Asp Ala Tyr

                                783                                     810
CAG GGT AGC CAA AGT TTT GAT AGA GCG GTG GCA ACC ACT GAC CCA AAT AAC CGA
Gln Gly Ser Gln Ser Phe Asp Arg Ala Val Ala Thr Thr Asp Pro Asn Asn Arg

                                837                                     864
ACA TTT TTA ATA GCA AAT GAA TGT GCC AAT GGT AAT TAT GAG GCG TGT GCT GCT
Thr Phe Leu Ile Ala Asn Glu Cys Ala Asn Gly Asn Tyr Glu Ala Cys Ala Ala

                                891                                     918
GGC GGT CAA ACC AAA CTT CAA GCC AAG CCA ACC AAT GTG CGT GAT AAG GTC AAT
Gly Gly Gln Thr Lys Leu Gln Ala Lys Pro Thr Asn Val Arg Asp Lys Val Asn
```

FIG.5D

```
                                                945                                                972
GTC AAA GAT TAT ACA GGT CCT AAC CGC CTT ATC CCA AAC CCA CTC ACC CAA GAC
Val Lys Asp Tyr Thr Gly Pro Asn Arg Leu Ile Pro Asn Pro Leu Thr Gln Asp

                                                999                                               1026
AGC AAA TCC TTA CTG CTT CGC CCA GGT TAT CAG CTA AAC GAT AAG CAC TAT GTC
Ser Lys Ser Leu Leu Leu Arg Pro Gly Tyr Gln Leu Asn Asp Lys His Tyr Val

                                               1053                                               1080
GGT GGT GTG TAT GAA ATC ACC AAA CAA AAC TAC GCC ATG CAA GAT AAA ACC GTG
Gly Gly Val Tyr Glu Ile Thr Lys Gln Asn Tyr Ala MET Gln Asp Lys Thr Val

                                               1107                                               1134
CCT GCT TAT CTG ACG GTT CAT GAC ATT GAA AAA TCA AGG CTC AGC AAC CAT GCC
Pro Ala Tyr Leu Thr Val His Asp Ile Glu Lys Ser Arg Leu Ser Asn His Ala

                                               1161                                               1188
CAA GCC AAT GGC TAT TAT CAA GGC AAT AAT CTT GGT GAA CGC ATT CGT GAT ACC
Gln Ala Asn Gly Tyr Tyr Gln Gly Asn Asn Leu Gly Glu Arg Ile Arg Asp Thr

                                               1215                                               1242
ATT GGG CCA GAT TCA GGT TAT GGC ATC AAC TAT GCT CAT GGC GTA TTT TAT GAT
Ile Gly Pro Asp Ser Gly Tyr Gly Ile Asn Tyr Ala His Gly Val Phe Tyr Asp
```

FIG.5E

```
                                             1269                                     1296
GAA AAA CAC CAA AAA GAC CGC CTA GGG CTT GAA TAT GTT TAT GAC AGC AAA GGT
Glu Lys His Gln Lys Asp Arg Leu Gly Leu Glu Tyr Val Tyr Asp Ser Lys Gly

                                             1323                                     1350
GAA AAT AAA TGG TTT GAT GAT GTG CGT GTG TCT TAT GAT AAG CAA GAC ATT ACG
Glu Asn Lys Trp Phe Asp Asp Val Arg Val Ser Tyr Asp Lys Gln Asp Ile Thr

                                             1377                                     1404
CTA CGC AGC CAG CTG ACC AAC ACG CAC TGT TCA ACC TAT CCG CAC ATT GAC AAA
Leu Arg Ser Gln Leu Thr Asn Thr His Cys Ser Thr Tyr Pro His Ile Asp Lys

                                             1431                                     1458
AAT TGT ACG CCT GAT GTC AAT AAA CCT TTT TCG GTA AAA GAG GTG GAT AAC AAT
Asn Cys Thr Pro Asp Val Asn Lys Pro Phe Ser Val Lys Glu Val Asp Asn Asn

                                             1485                                     1512
GCC TAC AAA GAA CAG CAC AAT TTA ATC AAA GCC GTC TTT AAC AAA AAA ATG GCG
Ala Tyr Lys Glu Gln His Asn Leu Ile Lys Ala Val Phe Asn Lys Lys MET Ala

                                             1539                                     1566
TTG GGC AGT ACG CAT CAT CAC ATC AAC CTG CAA GTT GGC TAT GAT AAA TTC AAT
Leu Gly Ser Thr His His His Ile Asn Leu Gln Val Gly Tyr Asp Lys Phe Asn

                                             1593                                     1620
TCA AGC CTG AGC CGT GAA GAT TAT CGT TTG GCA ACC CAT CAG TCT TAT CAA AAA
Ser Ser Leu Ser Arg Glu Asp Tyr Arg Leu Ala Thr His Gln Ser Tyr Gln Lys
```

FIG.5F

```
                                                1647                                            1674
CTT GAT TAC ACC CCA CCA AGT AAC CCT TTG CCA GAT AAG TTT AAG CCC ATT TTA
Leu Asp Tyr Thr Pro Pro Ser Asn Pro Leu Pro Asp Lys Phe Lys Pro Ile Leu

                                                1701                                            1728
GGT TCA AAC AAC AAA CCC ATT TGC CTT GAT GCT TAT GGT TAT GGT CAT GAC CAT
Gly Ser Asn Asn Lys Pro Ile Cys Leu Asp Ala Tyr Gly Tyr Gly His Asp His

                                                1755                                            1782
CCA CAG GCT TGT AAC GCC AAA AAC AGC ACT TAT CAA AAT TTT GCC ATC AAA AAA
Pro Gln Ala Cys Asn Ala Lys Asn Ser Thr Tyr Gln Asn Phe Ala Ile Lys Lys

                                                1809                                            1836
GGC ATA GAG CAA TAC AAC CAA AAA ACC AAT ACC GAT AAG ATT GAT TAT CAA GCC
Gly Ile Glu Gln Tyr Asn Gln Lys Thr Asn Thr Asp Lys Ile Asp Tyr Gln Ala

                                                1863                                            1890
ATC ATT GAC CAA TAT GAT AAA CAA AAC CCC AAC AGC ACC CTA AAA CCC TTT GAG
Ile Ile Asp Gln Tyr Asp Lys Gln Asn Pro Asn Ser Thr Leu Lys Pro Phe Glu

                                                1917                                            1944
AAA ATC AAA CAA AGT TTG GGG CAA GAA AAA TAC AAC AAG ATA GAC GAA CTT GGC
Lys Ile Lys Gln Ser Leu Gly Gln Glu Lys Tyr Asn Lys Ile Asp Glu Leu Gly
```

FIG.5G

```
                                       1971                                       1998
TTT AAA GCT TAT AAA GAT TTA CGC AAC GAA TGG GCG GGT TGG ACT AAT GAC AAC
Phe Lys Ala Tyr Lys Asp Leu Arg Asn Glu Trp Ala Gly Trp Thr Asn Asp Asn

                                       2025                                       2052
AGC CAA CAA AAT GCC AAT AAA GGC ACG GAT AAT ATC TAT CAG CCA AAT CAA GCA
Ser Gln Gln Asn Ala Asn Lys Gly Thr Asp Asn Ile Tyr Gln Pro Asn Gln Ala

                                       2079                                       2106
ACT GTG GTC AAA GAT GAC AAA TGT AAA TAT AGC GAG ACC AAC AGC TAT GCT GAT
Thr Val Val Lys Asp Asp Lys Cys Lys Tyr Ser Glu Thr Asn Ser Tyr Ala Asp

                                       2133                                       2160
TGC TCA ACC ACT CGC CAC ATC AGT GGT GAT AAT TAT TTC ATC GCT TTA AAA GAC
Cys Ser Thr Thr Arg His Ile Ser Gly Asp Asn Tyr Phe Ile Ala Leu Lys Asp

                                       2187                                       2214
AAC ATG ACC ATC AAT AAA TAT GTT GAT TTG GGG CTG GGT GCT CGC TAT GAC AGA
Asn MET Thr Ile Asn Lys Tyr Val Asp Leu Gly Leu Gly Ala Arg Tyr Asp Arg

                                       2241                                       2268
ATC AAA CAC AAA TCT GAT GTG CCT TTG GTA GAC AAC AGT GCC AGC AAC CAG CTG
Ile Lys His Lys Ser Asp Val Pro Leu Val Asp Asn Ser Ala Ser Asn Gln Leu
```

FIG.5H 2295 2322
TCT TGG AAT TTT GGC GTG GTC GTC AAG CCC ACC AAT TGG CTG GAC ATC GCT TAT
Ser Trp Asn Phe Gly Val Val Val Lys Pro Thr Asn Trp Leu Asp Ile Ala Tyr 2349 2376
AGA AGC TCG CAA GGC TTT CGC ATG CCA AGT TTT TCT GAA ATG TAT GGC GAA CGC
Arg Ser Ser Gln Gly Phe Arg MET Pro Ser Phe Ser Glu MET Tyr Gly Glu Arg 2403 2430
TTT GGC GTA ACC ATC GGT AAA GGC ACG CAA CAT GGC TGT AAG GGT CTT TAT TAC
Phe Gly Val Thr Ile Gly Lys Gly Thr Gln His Gly Cys Lys Gly Leu Tyr Tyr 2457 2484
ATT TGT CAG CAG ACT GTC CAT CAA ACC AAG CTA AAA CCT GAA AAA TCC TTT AAC
Ile Cys Gln Gln Thr Val His Gln Thr Lys Leu Lys Pro Glu Lys Ser Phe Asn 2511 2538
CAA GAA ATC GGA GCG ACT TTA CAT AAC CAC TTA GGC AGT CTT GAG GTT AGT TAT
Gln Glu Ile Gly Ala Thr Leu His Asn His Leu Gly Ser Leu Glu Val Ser Tyr 2565 2592
TTT AAA AAT CGC TAT ACC GAT TTG ATT GTT GGT AAA AGT GAA GAG ATT AGA ACC
Phe Lys Asn Arg Tyr Thr Asp Leu Ile Val Gly Lys Ser Glu Glu Ile Arg Thr 2619 2646
CTA ACC CAA GGT GAT AAT GCA GGC AAA CAG CGT GGT AAA GGT GAT TTG GGC TTT
Leu Thr Gln Gly Asp Asn Ala Gly Lys Gln Arg Gly Lys Gly Asp Leu Gly Phe

FIG.5I

```
                                    2673                                        2700
CAT AAT GGA CAA GAT GCT GAT TTG ACA GGC ATT AAC ATT CTT GGC AGA CTT GAC
His Asn Gly Gln Asp Ala Asp Leu Thr Gly Ile Asn Ile Leu Gly Arg Leu Asp

                                    2727                                        2754
CTA AAC GCT GTC AAT AGT CGC CTT CCC TAT GGA TTA TAC TCA ACA CTG GCT TAT
Leu Asn Ala Val Asn Ser Arg Leu Pro Tyr Gly Leu Tyr Ser Thr Leu Ala Tyr

                                    2781                                        2808
AAC AAA GTT GAT GTT AAA GGA AAA ACC TTA AAC CCA ACT TTG GCA GGA ACA AAC
Asn Lys Val Asp Val Lys Gly Lys Thr Leu Asn Pro Thr Leu Ala Gly Thr Asn

                                    2835                                        2862
ATA CTG TTT GAT GCC ATC CAG CCA TCT CGT TAT GTG GTG GGG CTT GGC TAT GAT
Ile Leu Phe Asp Ala Ile Gln Pro Ser Arg Tyr Val Val Gly Leu Gly Tyr Asp

                                    2889                                        2916
GCC CCA AGC CAA AAA TGG GGA GCA AAC GCC ATA TTT ACC CAT TCT GAT GCC AAA
Ala Pro Ser Gln Lys Trp Gly Ala Asn Ala Ile Phe Thr His Ser Asp Ala Lys

                                    2943                                        2970
AAT CCA AGC GAG CTT TTG GCA GAT AAG AAC TTA GGT AAT GGC AAC ATT CAA ACA
Asn Pro Ser Glu Leu Leu Ala Asp Lys Asn Leu Gly Asn Gly Asn Ile Gln Thr
```

FIG.5J

```
                                        2997                                      3024
AAA CAA GCC ACC AAA GCA AAA TCC ACG CCG TGG CAA ACA CTT GAT TTG TCA GGT
Lys Gln Ala Thr Lys Ala Lys Ser Thr Pro Trp Gln Thr Leu Asp Leu Ser Gly

                                        3051                                      3078
TAT GTA AAC ATA AAA GAT AAT TTT ACC TTG CGT GCT GGC GTG TAC AAT GTA TTT
Tyr Val Asn Ile Lys Asp Asn Phe Thr Leu Arg Ala Gly Val Tyr Asn Val Phe

                                        3105                                      3132
AAT ACC TAT TAC ACC ACT TGG GAG GCT TTA CGC CAA ACA GCA GAA GGG GCG GTC
Asn Thr Tyr Tyr Thr Thr Trp Glu Ala Leu Arg Gln Thr Ala Glu Gly Ala Val

                                        3159                                      3186
AAT CAG CAT ACA GGA CTG AGC CAA GAT AAG CAT TAT GGT CGC TAT GCC GCT CCT
Asn Gln His Thr Gly Leu Ser Gln Asp Lys His Tyr Gly Arg Tyr Ala Ala Pro

                                        3213
GGA CGC AAT TAC CAA TTG GCA CTT GAA ATG AAG TTT TAA
Gly Arg Asn Tyr Gln Leu Ala Leu Glu MET Lys Phe  .
```

FIG.6A

Sequence of *M. catarrhalis* 4223 *tbpB* gene

```
GTAAATTTGCCGTATTTTGTCTATCATAAATGCATTTATCAAATGCTCAAATAAATACGCCAAATGCACAT

TGTCAGCATGCCAAAATAGGCATCAACAGACTTTTTAGATAATACCATCAACCCATCAGAGGATTATTTT

                                27                                  54
ATG AAA CAC ATT CCT TTA ACC ACA CTG TGT GTG GCA ATC TCT GCC GTC TTA TTA
MET Lys His Ile Pro Leu Thr Thr Leu Cys Val Ala Ile Ser Ala Val Leu Leu

                                81                                 108
ACC GCT TGT GGT GGC AGT GGT GGT TCA AAT CCA CCT GCT CCT ACG CCC ATT CCA
Thr Ala Cys Gly Gly Ser Gly Gly Ser Asn Pro Pro Ala Pro Thr Pro Ile Pro

                               135                                 162
AAT GCT AGC GGT TCA GGT AAT ACT GGC AAC ACT GGT AAT GCT GGC GGT ACT GAT
Asn Ala Ser Gly Ser Gly Asn Thr Gly Asn Thr Gly Asn Ala Gly Gly Thr Asp

                               189                                 216
AAT ACA GCC AAT GCA GGT AAT ACA GGC GGT ACA AAC TCT GGT ACA GGC AGT GCC
Asn Thr Ala Asn Ala Gly Asn Thr Gly Gly Thr Asn Ser Gly Thr Gly Ser Ala

                               243                                 270
AAC ACA CCA GAG CCA AAA TAT CAA GAT GTA CCA ACT GAG AAA AAT GAA AAA GAT
Asn Thr Pro Glu Pro Lys Tyr Gln Asp Val Pro Thr Glu Lys Asn Glu Lys Asp
```

FIG.6B

```
                                        297                                          324
AAA GTT TCA TCC ATT CAA GAA CCT GCC ATG GGT TAT GGC ATG GCT TTG AGT AAA
Lys Val Ser Ser Ile Gln Glu Pro Ala MET Gly Tyr Gly MET Ala Leu Ser Lys

                                        351                                          378
ATT AAT CTA CAC AAC CGA CAA GAC ACG CCA TTA GAT GAA AAA AAT ATC ATT ACC
Ile Asn Leu His Asn Arg Gln Asp Thr Pro Leu Asp Glu Lys Asn Ile Ile Thr

                                        405                                          432
TTA GAC GGT AAA AAA CAA GTT GCA GAA GGT AAA AAA TCG CCA TTG CCA TTT TCG
Leu Asp Gly Lys Lys Gln Val Ala Glu Gly Lys Lys Ser Pro Leu Pro Phe Ser

                                        459                                          486
TTA GAT GTA GAA AAT AAA TTG CTT GAT GGC TAT ATA GCA AAA ATG AAT GTA GCG
Leu Asp Val Glu Asn Lys Leu Leu Asp Gly Tyr Ile Ala Lys MET Asn Val Ala

                                        513                                          540
GAT AAA AAT GCC ATT GGT GAC AGA ATT AAG AAA GGT AAT AAA GAA ATC TCC GAT
Asp Lys Asn Ala Ile Gly Asp Arg Ile Lys Lys Gly Asn Lys Glu Ile Ser Asp

                                        567                                          594
GAA GAA CTT GCC AAA CAA ATC AAA GAA GCT GTG CGT AAA AGC CAT GAG TTT CAG
Glu Glu Leu Ala Lys Gln Ile Lys Glu Ala Val Arg Lys Ser His Glu Phe Gln
```

FIG.6C

```
                                621                                          648
CAA GTA TTA TCA TCA CTG GAA AAC AAA ATT TTT CAT TCA AAT GAC GGA ACA ACC
Gln Val Leu Ser Ser Leu Glu Asn Lys Ile Phe His Ser Asn Asp Gly Thr Thr

                                675                                          702
AAA GCA ACC ACA CGA GAT TTA AAA TAT GTT GAT TAT GGT TAC TAC TTG GCG AAT
Lys Ala Thr Thr Arg Asp Leu Lys Tyr Val Asp Tyr Gly Tyr Tyr Leu Ala Asn

                                729                                          756
GAT GGC AAT TAT CTA ACC GTC AAA ACA GAC AAA CTT TGG AAT TTA GGC CCT GTG
Asp Gly Asn Tyr Leu Thr Val Lys Thr Asp Lys Leu Trp Asn Leu Gly Pro Val

                                783                                          810
GGT GGT GTG TTT TAT AAT GGC ACA ACG ACC GCC AAA GAG TTG CCC ACA CAA GAT
Gly Gly Val Phe Tyr Asn Gly Thr Thr Thr Ala Lys Glu Leu Pro Thr Gln Asp

                                837                                          864
GCG GTC AAA TAT AAA GGA CAT TGG GAC TTT ATG ACC GAT GTT GCC AAC AGA AGA
Ala Val Lys Tyr Lys Gly His Trp Asp Phe MET Thr Asp Val Ala Asn Arg Arg

                                891                                          918
AAC CGA TTT AGC GAA GTG AAA GAA AAC TCT CAA GCA GGC TGG TAT TAT GGA GCA
Asn Arg Phe Ser Glu Val Lys Glu Asn Ser Gln Ala Gly Trp Tyr Tyr Gly Ala
```

FIG.6D

```
                                945                                  972
TCT TCA AAA GAT GAA TAC AAC CGC TTA TTA ACT AAA GAA GAC TCT GCC CCT GAT
Ser Ser Lys Asp Glu Tyr Asn Arg Leu Leu Thr Lys Glu Asp Ser Ala Pro Asp

                                999                                 1026
GGT CAT AGC GGT GAA TAT GGC CAT AGC AGT GAG TTT ACT GTT AAT TTT AAG GAA
Gly His Ser Gly Glu Tyr Gly His Ser Ser Glu Phe Thr Val Asn Phe Lys Glu

                               1053                                 1080
AAA AAA TTA ACA GGT AAG CTG TTT AGT AAC CTA CAA GAC CGC CAT AAG GGC AAT
Lys Lys Leu Thr Gly Lys Leu Phe Ser Asn Leu Gln Asp Arg His Lys Gly Asn

                               1107                                 1134
GTT ACA AAA ACC GAA CGC TAT GAC ATC GAT GCC AAT ATC CAC GGC AAC CGC TTC
Val Thr Lys Thr Glu Arg Tyr Asp Ile Asp Ala Asn Ile His Gly Asn Arg Phe

                               1161                                 1188
CGT GGC AGT GCC ACC GCA AGC AAT AAA AAT GAC ACA AGC AAA CAC CCC TTT ACC
Arg Gly Ser Ala Thr Ala Ser Asn Lys Asn Asp Thr Ser Lys His Pro Phe Thr

                               1215                                 1242
AGT GAT GCC AAC AAT AGG CTA GAA GGT GGT TTT TAT GGG CCA AAA GGC GAG GAG
Ser Asp Ala Asn Asn Arg Leu Glu Gly Gly Phe Tyr Gly Pro Lys Gly Glu Glu
```

FIG.6E

```
                                          1269                                   1296
CTG GCA GGT AAA TTC TTA ACC AAT GAC AAC AAA CTC TTT GGC GTC TTT GGT GCT
Leu Ala Gly Lys Phe Leu Thr Asn Asp Asn Lys Leu Phe Gly Val Phe Gly Ala

                                          1323                                   1350
AAA CGA GAG AGT AAA GCT GAG GAA AAA ACC GAA GCC ATC TTA GAT GCC TAT GCA
Lys Arg Glu Ser Lys Ala Glu Glu Lys Thr Glu Ala Ile Leu Asp Ala Tyr Ala

                                          1377                                   1404
CTT GGG ACA TTT AAT ACA AGT AAC GCA ACC ACA TTC ACC CCA TTT ACC GAA AAA
Leu Gly Thr Phe Asn Thr Ser Asn Ala Thr Thr Phe Thr Pro Phe Thr Glu Lys

                                          1431                                   1458
CAA CTG GAT AAC TTT GGC AAT GCC AAA AAA TTG GTC TTA GGT TCT ACC GTC ATT
Gln Leu Asp Asn Phe Gly Asn Ala Lys Lys Leu Val Leu Gly Ser Thr Val Ile

                                          1485                                   1512
GAT TTG GTG CCT ACT GAT GCC ACC AAA AAT GAA TTC ACC AAA GAC AAG CCA GAG
Asp Leu Val Pro Thr Asp Ala Thr Lys Asn Glu Phe Thr Lys Asp Lys Pro Glu

                                          1539                                   1566
TCT GCC ACA AAC GAA GCG GGC GAG ACT TTG ATG GTG AAT GAT GAA GTT AGC GTC
Ser Ala Thr Asn Glu Ala Gly Glu Thr Leu MET Val Asn Asp Glu Val Ser Val
```

FIG.6F

```
                                        1593                                            1620
AAA ACC TAT GGC AAA AAC TTT GAA TAC CTA AAA TTT GGT GAG CTT AGT ATC GGT
Lys Thr Tyr Gly Lys Asn Phe Glu Tyr Leu Lys Phe Gly Glu Leu Ser Ile Gly

                                        1647                                            1674
GGT AGC CAT AGC GTC TTT TTA CAA GGC GAA CGC ACC GCT ACC ACA GGC GAG AAA
Gly Ser His Ser Val Phe Leu Gln Gly Glu Arg Thr Ala Thr Thr Gly Glu Lys

                                        1701                                            1728
GCC GTA CCA ACC ACA GGC ACA GCC AAA TAT TTG GGG AAC TGG GTA GGA TAC ATC
Ala Val Pro Thr Thr Gly Thr Ala Lys Tyr Leu Gly Asn Trp Val Gly Tyr Ile

                                        1755                                            1782
ACA GGA AAG GAC ACA GGA ACG GGC ACA GGA AAA AGC TTT ACC GAT GCC CAA GAT
Thr Gly Lys Asp Thr Gly Thr Gly Thr Gly Lys Ser Phe Thr Asp Ala Gln Asp

                                        1809                                            1836
GTT GCT GAT TTT GAC ATT GAT TTT GGA AAT AAA TCA GTC AGC GGT AAA CTT ATC
Val Ala Asp Phe Asp Ile Asp Phe Gly Asn Lys Ser Val Ser Gly Lys Leu Ile

                                        1863                                            1890
ACC AAA GGC CGC CAA GAC CCT GTA TTT AGC ATC ACA GGT CAA ATC GCA GGC AAT
Thr Lys Gly Arg Gln Asp Pro Val Phe Ser Ile Thr Gly Gln Ile Ala Gly Asn
```

FIG.6G

```
                                    1917                                        1944
GGC TGG ACA GGG ACA GCC AGC ACC ACC AAA GCG GAC GCA GGA GGC TAC AAG ATA
Gly Trp Thr Gly Thr Ala Ser Thr Thr Lys Ala Asp Ala Gly Gly Tyr Lys Ile

                                    1971                                        1998
GAT TCT AGC AGT ACA GGC AAA TCC ATC GCC ATC AAA GAT GCC AAT GTT ACA GGG
Asp Ser Ser Ser Thr Gly Lys Ser Ile Ala Ile Lys Asp Ala Asn Val Thr Gly

                                    2025                                        2052
GGC TTT TAT GGT CCA AAT GCA AAC GAG ATG GGC GGG TCA TTT ACA CAC AAC GCC
Gly Phe Tyr Gly Pro Asn Ala Asn Glu MET Gly Gly Ser Phe Thr His Asn Ala

                                    2079                                        2106
GAT GAC AGC AAA GCC TCT GTG GTC TTT GGC ACA AAA AGA CAA CAA GAA GTT AAG
Asp Asp Ser Lys Ala Ser Val Val Phe Gly Thr Lys Arg Gln Gln Glu Val Lys
```

FIG.10A

Q8 tbpA gene sequence

```
AATTGATACAAAATGGTTTGTATTATCACT
         10        20        30
TGTATTTGTATTATAATTTTACTTATTTTT
         40        50        60
ACAAACTATACACTAAAATCAAAAATTAAT
         70        80        90
CACTTTGGTTGGGTGGTTTTAGCAAGCAAA
        100       110       120
TGGTTATTTTGGTAAACAATTAAGTTCTTA
        130       140       150
AAAACGATACACGCTCATAAACAGATGGTT
        160       170       180
TTTGGCATCTTCAATTTGATGCCTGCCTTG
        190       200       210
TGATTGGTTGGGGGTGTATTGATGTATCCA
        220       230       240
                           MET
AGTACAAAAGCCAACAGGTGGTCATTGATG
        250       260       270
```

FIG.10B

```
ASN GLN SER LYS LYS SER LYS LYS SER LYS
A A T C A A T C C A A A A A A T C C A A A A A A T C C A A A
                280                     290                     300

GLN VAL LEU LYS LEU SER ALA LEU SER LEU
C A A G T A T T A A A A C T T A G T G C C T T G T C T T T G
                310                     320                     330

GLY LEU LEU ASN ILE THR GLN VAL ALA LEU
G G T C T G C T T A A C A T C A C G C A G G T G G C A C T G
                340                     350                     360

ALA ASN THR THR ALA ASP LYS ALA GLU ALA
G C A A A C A C A A C G G C C G A T A A G G C G G A G G C A
                370                     380                     390

THR ASP LYS THR ASN LEU VAL VAL VAL LEU
A C A G A T A A G A C A A A C C T T G T T G T T G T C T T G
                400                     410                     420

ASP GLU THR VAL VAL THR ALA LYS LYS ASN
G A T G A A A C T G T T G T A A C A G C G A A G A A A A A C
                430                     440                     450

ALA ARG LYS ALA ASN GLU VAL THR GLY LEU
G C C C G T A A A G C C A A C G A A G T T A C A G G G C T T
                460                     470                     480
```

FIG.10C

```
GLY  LYS  VAL  VAL  LYS  THR  ALA  GLU  THR  ILE
G G T A A G G T G G T C A A A A C T G C C G A G A C C A T C
                490                     500                     510
                                                        ASN  LYS  GLU  GLN  VAL  LEU  ASN  ILE  ARG  ASP
                                                        A A T A A A G A A C A A G T G C T A A A C A T T C G A G A C
                                                                        520                     530                     540

LEU  THR  ARG  TYR  ASP  PRO  GLY  ILE  ALA  VAL
T T A A C A C G C T A T G A C C C T G G C A T T G C T G T G
                550                     560                     570
                                                        VAL  GLU  GLN  GLY  ARG  GLY  ALA  SER  SER  GLY
                                                        G T T G A G C A A G G T C G T G G G G C A A G C T C A G G C
                                                                        580                     590                     600

TYR  SER  ILE  ARG  GLY  MET  ASP  LYS  ASN  ARG
T A T T C T A T T C G T G G T A T G G A T A A A A A T C G T
                610                     620                     630
                                                        VAL  ALA  VAL  LEU  VAL  ASP  GLY  ILE  ASN  GLN
                                                        G T G G C G G T A T T G G T T G A T G G C A T C A A T C A A
                                                                        640                     650                     660

ALA  GLN  HIS  TYR  ALA  LEU  GLN  GLY  PRO  VAL
G C C C A G C A C T A T G C C C T A C A A G G C C C T G T G
                670                     680                     690
```

FIG.10D

```
                                                  ALA GLY LYS ASN TYR ALA ALA GLY GLY ALA
                                                  G C A G G C A A A A A T T A T G C C G C A G G T G G G G C A
                                                                      700                 710                 720

ILE ASN GLU ILE GLU TYR GLU ASN VAL ARG
A T C A A C G A A A T A G A A T A C G A A A A T G T C C G C
                730                 740                 750
                                                  SER VAL GLU ILE SER LYS GLY ALA ASN SER
                                                  T C C G T T G A G A T T A G T A A A G G T G C A A A T T C A
                                                                      760                 770                 780

SER GLU TYR GLY SER GLY ALA LEU SER GLY
A G T G A A T A C G G C T C T G G G G C A T T A T C T G G C
                790                 800                 810
                                                  SER VAL ALA PHE VAL THR LYS THR ALA ASP
                                                  T C T G T G G C A T T T G T T A C C A A A A C C G C C G A T
                                                                      820                 830                 840

ASP ILE ILE LYS ASP GLY LYS ASP TRP GLY
G A C A T C A T C A A A G A T G G T A A A G A T T G G G G C
                850                 860                 870
                                                  VAL GLN THR LYS THR ALA TYR ALA SER LYS
                                                  G T G C A G A C C A A A A C C G C C T A T G C C A G T A A A
                                                                      880                 890                 900
```

FIG.10E

```
ASN ASN ALA TRP VAL ASN SER VAL ALA ALA
A A T A A C G C A T G G G T T A A T T C T G T G G C A G C A
                910                     920                     930
ALA GLY LYS ALA GLY SER PHE SER GLY LEU
G C A G G C A A G G C A G G T T C T T T T A G C G G T C T T
                940                     950                     960

ILE ILE TYR THR ASP ARG ARG GLY GLN GLU
A T C A T C T A C A C C G A C C G C C G T G G T C A A G A A
                970                     980                     990
TYR LYS ALA HIS ASP ASP ALA TYR GLN GLY
T A C A A G G C A C A T G A T G A T G C C T A T C A G G G T
                1000                    1010                    1020

SER GLN SER PHE ASP ARG ALA VAL ALA THR
A G C C A A A G T T T T G A T A G A G C G G T G G C A A C C
                1030                    1040                    1050
THR ASP PRO ASN ASN PRO LYS PHE LEU ILE
A C T G A C C C A A A T A A C C C A A A A T T T T T A A T A
                1060                    1070                    1080

ALA ASN GLU CYS ALA ASN GLY ASN TYR GLU
G C A A A T G A A T G T G C C A A T G G T A A T T A T G A G
                1090                    1100                    1110
```

FIG.10F

```
                                          ALA  CYS  ALA  ALA  GLY  GLY  GLN  THR  LYS  LEU
                                          G C G T G T G C T G C T G G C G G T C A A A C C A A A C T C
                                                        1120                1130                1140
GLN  ALA  LYS  PRO  THR  ASN  VAL  ARG  ASP  LYS
C A A G C T A A G C C A A C C A A T G T G C G T G A T A A G
              1150                1160                1170
                                          VAL  ASN  VAL  LYS  ASP  TYR  THR  GLY  PRO  ASN
                                          G T C A A T G T C A A A G A T T A T A C A G G T C C T A A C
                                                        1180                1190                1200
ARG  LEU  ILE  PRO  ASN  PRO  LEU  THR  GLN  ASP
C G C C T T A T C C C A A A C C C A C T C A C C C A A G A C
              1210                1220                1230
                                          SER  LYS  SER  LEU  LEU  LEU  ARG  PRO  GLY  TYR
                                          A G C A A A T C C T T A C T G C T T C G C C C A G G T T A T
                                                        1240                1250                1260
GLN  LEU  ASN  ASP  LYS  HIS  TYR  VAL  GLY  GLY
C A G C T A A A C G A T A A G C A C T A T G T C G G T G G T
              1270                1280                1290
                                          VAL  TYR  GLU  ILE  THR  LYS  GLN  ASN  TYR  ALA
                                          G T G T A T G A A A T C A C C A A A C A A A A C T A C G C C
                                                        1300                1310                1320
```

FIG.10G

```
MET GLN ASP LYS THR VAL PRO ALA TYR LEU
A T G C A A G A T A A A A C C G T G C C T G C T T A T C T G
              1330                1340                1350
THR VAL HIS ASP ILE GLU LYS SER ARG LEU
A C G G T T C A T G A C A T T G A A A A A T C A A G G C T C
              1360                1370                1380

SER ASN HIS GLY GLN ALA ASN GLY TYR TYR
A G C A A C C A T G G C C A A G C C A A T G G C T A T T A T
              1390                1400                1410
GLN GLY ASN ASN LEU GLY GLU ARG ILE ARG
C A A G G C A A T A A C C T T G G T G A A C G C A T T C G T
              1420                1430                1440

ASP ALA ILE GLY ALA ASN SER GLY TYR GLY
G A T G C C A T T G G G G C A A A T T C A G G T T A T G G C
              1450                1460                1470
ILE ASN TYR ALA HIS GLY VAL PHE TYR ASP
A T C A A C T A T G C T C A T G G C G T A T T T T A T G A C
              1480                1490                1500

GLU LYS HIS GLN LYS ASP ARG LEU GLY LEU
G A A A A A C A C C A A A A A G A C C G C C T A G G G C T T
              1510                1520                1530
```

FIG.10H

```
                                                   GLU   TYR   VAL   TYR   ASP   SER   LYS   GLY   GLU   ASN
                                                   G A A T A T G T T T A T G A C A G C A A A G G T G A A A A T
                                                                 1540                1550                1560

LYS   TRP   PHE   ASP   ASP   VAL   ARG   VAL   SER   TYR
A A A T G G T T T G A T G A T G T G C G T G T G T C T T A T
              1570                1580                1590
                                                   ASP   LYS   GLN   ASP   ILE   THR   LEU   ARG   SER   GLN
                                                   G A C A A G C A A G A C A T T A C G C T A C G T A G C C A G
                                                                 1600                1610                1620

LEU   THR   ASN   THR   HIS   CYS   SER   THR   TYR   PRO
C T G A C C A A C A C G C A C T G T T C A A C C T A T C C G
              1630                1640                1650
                                                    HIS   ILE   ASP  LYS   ASN   CYS   THR   PRO   ASP   VAL
                                                   C A C A T T G A C A A A A A T T G T A C G C C T G A T G T C
                                                                 1660                1670                1680

ASN   LYS   PRO   PHE   SER   VAL   LYS   GLU   VAL   ASP
A A T A A A C C T T T T T C G G T A A A A G A G G T G G A T
              1690                1700                1710
                                                    ASN   ASN   ALA  TYR   LYS   GLU   GLN   HIS   ASN   LEU
                                                   A A C A A T G C C T A C A A A G A A C A G C A C A A T T T A
                                                                 1720                1730                1740
```

FIG.10I

```
ILE   LYS   ALA   VAL   PHE   ASN   LYS   LYS   MET   ALA
A T C A A A G C C G T C T T T A A C A A A A A A A T G G C A
              1750                1760                1770
                                          LEU   GLY   ASN   THR   HIS   HIS   HIS   ILE   ASN   LEU
                                          T T G G G C A A T A C G C A T C A T C A C A T C A A T C T G
                                                        1780                1790                1800

GLN   VAL   GLY   TYR   ASP   LYS   PHE   ASN   SER   SER
C A A G T T G G C T A T G A T A A A T T C A A T T C A A G C
              1810                1820                1830
                                          LEU   SER   ARG   GLU   ASP   TYR   ARG   LEU   ALA   THR
                                          C T T A G C C G T G A A G A T T A T C G T T T G G C A A C C
                                                        1840                1850                1860

HIS   GLN   SER   TYR   GLN   LYS   LEU   ASP   TYR   THR
C A T C A A T C T T A T C A A A A A C T T G A T T A C A C C
              1870                1880                1890
                                          PRO   PRO   SER   ASN   PRO   LEU   PRO   ASP   LYS   PHE
                                          C C A C C A A G T A A C C C T T T G C C A G A T A A G T T T
                                                        1900                1910                1920

LYS   PRO   ILE   LEU   GLY   SER   ASN   ASN   ARG   PRO
A A G C C C A T T T T A G G T T C A A A C A A C A G A C C C
              1930                1940                1950
```

FIG.10J

```
                                        ILE CYS LEU ASP ALA TYR GLY TYR GLY HIS
                                        A T T T G C C T T G A T G C T T A T G G T T A T G G T C A T
                                                    1960                1970                1980
ASP HIS PRO GLN ALA CYS ASN ALA LYS ASN
G A C C A T C C A C A G G C T T G T A A C G C C A A A A A C
            1990                2000                2010
                                        SER THR TYR GLN ASN PHE ALA ILE LYS LYS
                                        A G C A C T T A T C A A A A C T T T G C C A T C A A A A A A
                                                    2020                2030                2040
GLY ILE GLU GLN TYR ASN GLN THR ASN THR
G G C A T A G A G C A A T A C A A C C A A A C C A A T A C C
            2050                2060                2070
                                        ASP LYS ILE ASP TYR GLN ALA VAL ILE ASP
                                        G A T A A G A T T G A T T A T C A A G C C G T C A T T G A C
                                                    2080                2090                2100
GLN TYR ASP LYS GLN ASN PRO ASN SER THR
C A A T A T G A T A A A C A A A A C C C C A A C A G C A C C
            2110                2120                2130
                                        LEU LYS PRO PHE GLU LYS ILE LYS GLN SER
                                        C T A A A A C C C T T T G A G A A A A T C A A A C A A A G T
                                                    2140                2150                2160
```

FIG.10K

```
LEU   GLY   GLN   GLU   LYS   TYR   ASP   GLU   ILE   ASP
T T G G G G C A A G A A A A A T A C G A C G A G A T A G A C
              2170                2180                2190
                                          ARG   LEU   GLY   PHE   ASN   ALA   TYR   LYS   ASP   LEU
                                          A G A C T G G G C T T T A A T G C T T A T A A A G A T T T A
                                                        2200                2210                2220

ARG   ASN   GLU   TRP   ALA   GLY   TRP   THR   ASN   ASP
C G C A A C G A A T G G G C G G G T T G G A C T A A T G A C
              2230                2240                2250
                                          ASN   SER   GLN   GLN   ASN   ALA   ASN   LYS   GLY   THR
                                          A A C A G C C A A C A A A A C G C C A A T A A A G G C A C G
                                                        2260                2270                2280

ASP   ASN   ILE   TYR   GLN   PRO   ASN   GLN   ALA   THR
G A T A A T A T C T A T C A G C C A A A T C A A G C A A C T
              2290                2300                2310
                                          VAL   VAL   LYS   ASP   ASP   LYS   CYS   LYS   TYR   SER
                                          G T G G T C A A A G A T G A C A A A T G T A A A T A T A G C
                                                        2320                2330                2340

GLU   THR   ASN   SER   TYR   ALA   ASP   CYS   SER   THR
G A G A C C A A C A G C T A T G C T G A T T G C T C A A C C
              2350                2360                2370
```

FIG.10L

```
THR ARG HIS ILE SER GLY ASP ASN TYR PHE
A C T C G C C A C A T C A G C G G T G A T A A T T A T T T C
                2380                2390                2400
ILE ALA LEU LYS ASP ASN MET THR ILE ASN
A T C G C T T T A A A A G A C A A C A T G A C C A T C A A T
                2410                2420                2430
LYS TYR VAL ASP LEU GLY LEU GLY ALA ARG
A A A T A T G T T G A T T T G G G G C T G G G T G C T C G C
                2440                2450                2460
TYR ASP ARG ILE LYS HIS LYS SER ASP VAL
T A T G A C A G A A T C A A A C A C A A A T C T G A T G T G
                2470                2480                2490
PRO LEU VAL ASP ASN SER ALA SER ASN GLN
C C T T T G G T A G A C A A C A G T G C C A G C A A C C A G
                2500                2510                2520
LEU SER TRP ASN PHE GLY VAL VAL VAL LYS
C T G T C T T G G A A T T T T G G C G T G G T C G T C A A G
                2530                2540                2550
PRO THR ASN TRP LEU ASP ILE ALA TYR ARG
C C C A C C A A T T G G C T G G A C A T C G C T T A T A G A
                2560                2570                2580
```

FIG.10M

```
SER   SER   GLN   GLY   PHE   ARG   MET   PRO   SER   PHE
A G C T C G C A A G G C T T T C G C A T G C C A A G T T T T
              2590                2600                2610
                              SER   GLU   MET   TYR   GLY   GLU   ARG   PHE   GLY   VAL
                              T C T G A A A T G T A T G G C G A A C G C T T T G G C G T A
                                            2620                2630                2640

THR   ILE   GLY   LYS   GLY   THR   GLN   HIS   GLY   CYS
A C C A T C G G T A A A G G C A C G C A A C A T G G C T G T
              2650                2660                2670
                              LYS   GLY   LEU   TYR   TYR   ILE   CYS   GLN   GLN   THR
                              A A G G G T C T T T A T T A C A T T T G T C A G C A G A C T
                                            2680                2690                2700

VAL   HIS   GLN   THR   LYS   LEU   LYS   PRO   GLU   LYS
G T C C A T C A A A C C A A G C T A A A A C C T G A A A A A
              2710                2720                2730
                              SER   PHE   ASN   GLN   GLU   ILE   GLY   ALA   THR   LEU
                              T C C T T T A A C C A A G A A A T C G G A G C G A C T T T A
                                            2740                2750                2760

HIS   ASN   HIS   LEU   GLY   SER   LEU   GLU   VAL   SER
C A T A A C C A C T T A G G C A G T C T T G A G G T T A G T
              2770                2780                2790
```

FIG.10N

```
                                        TYR   PHE   LYS   ASN   ARG   TYR   THR   ASP   LEU   ILE
                                        T A T T T T A A A A A T C G C T A T A C C G A T T T G A T T
                                                       2800                2810                2820

VAL   GLY   LYS   SER   GLU   GLU   ILE   ARG   THR   LEU
G T T G G T A A A A G T G A A G A G A T T A G A A C C C T A
           2830                2840                2850
                                        THR   GLN   GLY   ASP   ASN   ALA   GLY   LYS   GLN   ARG
                                        A C C C A A G G T G A T A A T G C A G G C A A A C A G C G T
                                                       2860                2870                2880

GLY   LYS   GLY   ASP   LEU   GLY   PHE   HIS   ASN   GLY
G G T A A A G G T G A T T T G G G C T T T C A T A A T G G G
           2890                2900                2910
                                        GLN   ASP   ALA   ASP   LEU   THR   GLY   ILE   ASN   ILE
                                        C A A G A T G C T G A T T T G A C A G G C A T T A A C A T T
                                                       2920                2930                2940

LEU   GLY   ARG   LEU   ASP   LEU   ASN   ALA   VAL   ASN
C T T G G C A G A C T T G A C C T A A A C G C T G T C A A T
           2950                2960                2970
                                        SER   ARG   LEU   PRO   TYR   GLY   LEU   TYR   SER   THR
                                        A G T C G C C T T C C C T A T G G A T T A T A C T C A A C A
                                                       2980                2990                3000
```

FIG.10O

```
LEU   ALA   TYR   ASN   LYS   VAL   ASP   VAL   LYS   GLY
C T G G C T T A T A A C A A A G T T G A T G T T A A A G G A
            3010                3020                3030
                                          LYS   THR   LEU   ASN   PRO   THR   LEU   ALA   GLY   THR
                                          A A A A C C T T A A A C C C A A C T T T G G C A G G A A C A
                                                      3040                3050                3060

ASN   ILE   LEU   PHE   ASP   ALA   ILE   GLN   PRO   SER
A A C A T A C T G T T T G A T G C C A T T C A G C C A T C T
            3070                3080                3090
                                          ARG   TYR   VAL   VAL   GLY   LEU   GLY   TYR   ASP   ALA
                                          C G T T A T G T G G T G G G G C T T G G C T A T G A T G C C
                                                      3100                3110                3120

PRO   SER   GLN   LYS   TRP   GLY   ALA   ASN   ALA   ILE
C C A A G C C A A A A A T G G G G A G C A A A C G C C A T A
            3130                3140                3150
                                          PHE   THR   HIS   SER   ASP   ALA   LYS   ASN   PRO   SER
                                          T T T A C C C A T T C T G A T G C C A A A A A T C C A A G C
                                                      3160                3170                3180

GLU   LEU   LEU   ALA   ASP   LYS   ASN   LEU   GLY   ASN
G A G C T T T T G G C A G A T A A G A A C T T A G G T A A T
            3190                3200                3210
```

FIG.10P

```
                                        GLY  ASN  ILE  GLN  THR  LYS  GLN  ALA  THR  LYS
                                        G G C A A C A T T C A A A C A A A A C A A G C C A C C A A A
                                                       3220                3230                3240
ALA  LYS  SER  THR  PRO  TRP  GLN  THR  LEU  ASP
G C A A A A T C C A C G C C G T G G C A A A C A C T T G A T
           3250                3260                3270
                                        LEU  SER  GLY  TYR  VAL  ASN  ILE  LYS  ASP  ASN
                                        T T G T C A G G T T A T G T A A A C A T A A A A G A T A A T
                                                       3280                3290                3300
PHE  THR  LEU  ARG  ALA  GLY  VAL  TYR  ASN  VAL
T T T A C C T T G C G T G C T G G C G T G T A C A A T G T A
           3310                3320                3330
                                        PHE  ASN  THR  TYR  TYR  THR  THR  TRP  GLU  ALA
                                        T T T A A T A C C T A T T A C A C C A C T T G G G A G G C T
                                                       3340                3350                3360
LEU  ARG  GLN  THR  ALA  GLU  GLY  ALA  VAL  ASN
T T A C G C C A A A C A G C A G A A G G G G C G G T C A A T
           3370                3380                3390
                                        GLN  HIS  THR  GLY  LEU  SER  GLN  ASP  LYS  HIS
                                        C A G C A T A C A G G A C T G A G C C A A G A T A A G C A T
                                                       3400                3410                3420
```

FIG.10Q

```
TYR GLY ARG TYR ALA ALA PRO GLY ARG ASN
T A T G G T C G C T A T G C C G C T C C T G G A C G C A A T
3430 3440 3450
TYR GLN LEU ALA LEU GLU MET LYS PHE ***
T A C C A A T T G G C A C T T G A A A T G A A G T T T T A A
S 3460 3470
3480

C C A G T G G C T T T G A T G T G A T C A T G C C A A A T C
3490 3500 3510
C C A A T C A A C C A A T G A A T A A A G C C C C C A T C T
3520 3530 3540

A C C A T G A G G G C T T T A T T T T A T C A T C G C T G A
3550 3560 3570
G T A T G C T C T T A G C G G T C A T C A C T C A G A T T A
3580 3590 3600

G T C A T T A A T T T A T T A G C G A T T A A T T T A T T A
3610 3620 3630
G T A A T C A C G C T G C T C T T T G A T G A T T T T A A G
3640 3650 3660
```

Q8 tbpB Sequence.

```
CCTAGGGCTGACAGTAACAACACTTTATAC
         10        20        30
                              AGCACATCATTGATTTATTACCCAAATGCC
                                       40        50        60

ACACGCTATTATCTTTTGGGGGCAGACTTT
         70        80        90
                              TATGATGAAAAAGTGCCACAAGACCCATCT
                                      100       110       120

GACAGCTATGAGCGTCGTGGCATACGCACA
        130       140       150
                              GCTTGGGGGCAAGAATGGGCGGGCGGTCTT
                                      160       170       180

TCAAGCCGTGCCCAAATCAGCATCAACAAA
        190       200       210
                              CGCCATTACCAAGGAGCAAACCTAACCAGC
                                      220       230       240

GGTGGACAAATTCGCCAGGATAAACAGATG
        250       260       270
                              CAAGCGTCTTTATCGCTTTGGCACAGAGAC
                                      280       290       300
```

```
A T T C A C A A A T G G G G C A T C A C G C C A C G G C T G
                  310                 320                 330
                                        A C C A T C A G C A C A A A C A T C A A T A A A A G C A A T
                                                          340                 350                 360

G A C A T C A A G G C A A A T T A T C A C A A A A A T C A A
                  370                 380                 390
                                        A T G T T T G T T G A G T T T A G T C G C A T T T T T T G A
                                                          400                 410                 420

T G G G A T A A G C A T G C C C T A C T T T T G T T T T T T
                  430                 440                 450
                                        G T A A A A A A A T G T A C C A T C A T A G A C A A T A T C
                                                          460                 470                 480

A A G A A A A A A T C A A G A A A A A A G A T T A C A A A T
                  490                 500                 510
                                        T T A A T G A T A A T T G T T A T T G T T T A T G T T A T T
                                                          520                 530                 540

A T T T A T C A A T G T A A A T T T G C C G T A T T T T G T
                  550                 560                 570
                                        C C A T C A T A A A C G C A T T T A T C A A A T G C T C A A
                                                          580                 590                 600
```

```
A T A A A T A C G C C A A A T G C A C A T T G T C A A C A T
                610                 620                 630
                                        G C C A A A A T A G G C A T T A A C A G A C T T T T T T A G
                                                            640                 650                 660

A T A A T A C C A T C A A C C C A T C A G A G G A T T A T T
                670                 680                 690
                                            MET   LYS   HIS   ILE   PRO   LEU   THR   THR   LEU   C
                                        T T A T G A A A C A C A T T C C T T T A A C C A C A C T G T
                                                            700                 710                 720

YS    VAL   ALA   ILE   SER   ALA   VAL   LEU   LEU   THR
G T G T G G C A A T C T C T G C C G T C T T A T T A A C C G
                730                 740                 750
                                        ALA   CYS   GLY   GLY   SER   SER   GLY   GLY   PHE   ASN   P
                                         C T T G T G G T G G T A G C A G T G G T G G T T T C A A T C
                                                            760                 770                 780

RO    PRO   ALA   SER   THR   PRO   ILE   PRO   ASN   ALA
C A C C T G C C T C T A C G C C C A T C C C A A A T G C A G
                790                 800                 810
                                        GLY   ASN   SER   GLY   ASN   ALA   GLY   ASN   ALA   GLY   A
                                         G T A A T T C A G G T A A T G C T G G C A A T G C T G G C A
                                                            820                 830                 840
```

FIG.11D

```
SN   ALA  GLY  GLY  THR  GLY  GLY  ALA  ASN  SER
A T G C T G G C G G T A C T G G C G G T G C A A A C T C T G
                850                 860                 870
                                         GLY  ALA  GLY  ASN  ALA  GLY  GLY  THR  GLY  GLY  A
                                          G T G C A G G T A A T G C T G G C G G T A C T G G C G G T G
                                                          880                 890                 900

LA   ASN  SER  GLY  ALA  GLY  SER  ALA  SER  THR
C A A A C T C T G G T G C A G G C A G T G C C A G C A C A C
                910                 920                 930
                                         PRO  GLU  PRO  LYS  TYR  LYS  ASP  VAL  PRO  THR  A
                                          C A G A A C C A A A A T A T A A A G A T G T G C C A A C C G
                                                          940                 950                 960

SP   GLU  ASN  LYS  LYS  ALA  GLU  VAL  SER  GLY
A T G A A A A T A A A A A A G C T G A A G T T T C A G G C A
                970                 980                 990
                                         ILE  GLN  GLU  PRO  ALA  MET  GLY  TYR  GLY  VAL  G
                                          T T C A A G A A C C T G C C A T G G G T T A T G G C G T G G
                                                         1000                1010                1020

LU   LEU  LYS  LEU  ARG  ASN  TRP  ILE  PRO  GLN
A A T T A A A G C T T C G T A A C T G G A T A C C A C A A G
               1030                1040                1050
```

FIG.11E

```
                                                 GLU  GLN  GLU  GLU  HIS  ALA  LYS  ILE  ASN  THR  A
                                                  A A C A G G A A G A A C A T G C C A A A A T C A A T A C A A
                                                                 1060                1070                1080

SN   ASP   VAL   VAL   LYS   LEU   GLU   GLY   ASP   LEU
A T G A T G T T G T A A A A C T T G A A G G T G A C T T G A
              1090                1100                1110
                                                 LYS  HIS  ASN  PRO  PHE  ASP  ASN  SER  ILE  TRP  G
                                                  A G C A T A A T C C A T T T G A C A A C T C T A T T T G G C
                                                                 1120                1130                1140

LN   ASN   ILE   LYS   ASN   SER   LYS   GLU   VAL   GLN
A A A A C A T C A A A A A T A G C A A A G A A G T A C A A A
              1150                1160                1170
                                                 THR  VAL  TYR  ASN  GLN  GLU  LYS  GLN  ASN  ILE  G
                                                  C T G T T T A C A A C C A A G A G A A G C A A A A C A T T G
                                                                 1180                1190                1200

LU   ASP   GLN   ILE   LYS   ARG   GLU   ASN   LYS   GLN
A A G A T C A A A T C A A A A G A G A A A A T A A A C A A C
              1210                1220                1230
                                                 ARG  PRO  ASP  LYS  LYS  LEU  ASP  ASP  VAL  ALA  L
                                                  G C C C T G A C A A A A A A C T T G A T G A C G T G G C A C
                                                                 1240                1250                1260
```

FIG.11F

```
EU  GLN  ALA  TYR  ILE  GLU  LYS  VAL  LEU  ASP
T A C A A G C T T A T A T T G A A A A A G T T C T T G A T G
              1270                1280                1290
                                        ASP  ARG  LEU  THR  GLU  LEU  ALA  LYS  PRO  ILE  T
                                         A C C G T C T A A C A G A A C T T G C T A A A C C C A T T T
                                                      1300                1310                1320

YR  GLU  LYS  ASN  ILE  ASN  TYR  SER  HIS  ASP
A T G A A A A A A A T A T T A A T T A T T C A C A T G A T A
              1330                1340                1350
                                        LYS  GLN  ASN  LYS  ALA  ARG  THR  ARG  ASP  LEU  L
                                         A G C A G A A T A A A G C A C G C A C T C G T G A T T T G A
                                                      1360                1370                1380

YS  TYR  VAL  ARG  SER  GLY  TYR  ILE  TYR  ARG
A G T A T G T G C G T T C T G G T T A T A T T T A T C G C T
              1390                1400                1410
                                        SER  GLY  TYR  SER  ASN  ILE  ILE  PRO  LYS  LYS  I
                                         C A G G T T A T T C T A A T A T C A T T C C A A A G A A A A
                                                      1420                1430                1440

LE  ALA  LYS  THR  GLY  PHE  ASP  GLY  ALA  LEU
T A G C T A A A A C T G G T T T T G A T G G T G C T T T A T
              1450                1460                1470
```

FIG.11G

```
                                   PHE TYR GLN GLY THR GLN THR ALA LYS GLN L
                                   T T T A T C A A G G T A C A C A A A C T G C T A A A C A A T
                                                 1480                1490                1500
EU PRO VAL SER GLN VAL LYS TYR LYS GLY
T G C C T G T A T C T C A A G T T A A G T A T A A A G G C A
              1510                1520                1530
                                   THR TRP ASP PHE MET THR ASP ALA LYS LYS G
                                   C T T G G G A T T T T A T G A C C G A T G C C A A A A A A G
                                                 1540                1550                1560
LY GLN SER PHE SER SER PHE GLY THR SER
G A C A A T C A T T T A G C A G T T T T G G T A C A T C G C
              1570                1580                1590
                                   GLN ARG LEU ALA GLY ASP ARG TYR SER ALA M
                                   A A C G T C T T G C T G G T G A T C G T T A T A G T G C A A
                                                 1600                1610                1620
ET SER TYR HIS GLU TYR PRO SER LEU LEU
T G T C T T A C C A T G A A T A C C C A T C T T T A T T A A
              1630                1640                1650
                                   THR ASP GLU LYS ASN LYS PRO ASP ASN TYR A
                                   C T G A T G A G A A A A A C A A A C C A G A T A A T T A T A
                                                 1660                1670                1680
```

FIG.11H

```
SN   GLY  GLU  TYR  GLY  HIS  SER  SER  GLU  PHE
A C G G T G A A T A T G G T C A T A G C A G T G A G T T T A
               1690                1700                1710
                                   THR  VAL  ASP  PHE  SER  LYS  LYS  SER  LEU  LYS  G
                                    C G G T A G A T T T T A G T A A A A A G A G C C T A A A A G
                                                  1720                1730                1740

LY   GLU  LEU  SER  SER  ASN  ILE  GLN  ASP  GLY
G T G A G C T G T C T A G T A A C A T A C A A G A C G G C C
               1750                1760                1770
                                   HIS  LYS  GLY  SER  VAL  ASN  LYS  THR  LYS  ARG  T
                                    A T A A G G G C A G T G T T A A T A A A A C C A A A C G C T
                                                  1780                1790                1800

YR   ASP  ILE  ASP  ALA  ASN  ILE  TYR  GLY  ASN
A T G A C A T C G A T G C C A A T A T C T A C G G C A A C C
               1810                1820                1830
                                   ARG  PHE  ARG  GLY  SER  ALA  THR  ALA  SER  ASP  T
                                    G C T T C C G T G G C A G T G C C A C C G C A A G C G A T A
                                                  1840                1850                1860

HR   THR  GLU  ALA  SER  LYS  SER  LYS  HIS  PRO
C A A C A G A A G C A A G C A A A A G C A A A C A C C C C T
               1870                1880                1890
```

FIG.11.I

```
                                          PHE  THR  SER  ASP  ALA  LYS  ASN  SER  LEU  GLU  G
                                           T T A C C A G C G A T G C C A A A A A T A G C C T A G A A G
                                                           1900                1910                1920

LY  GLY  PHE  TYR  GLY  PRO  ASN  ALA  GLU  GLU
G C G G T T T T T A T G G A C C A A A C G C C G A G G A G C
              1930                1940                1950
                                          LEU  ALA  GLY  LYS  PHE  LEU  THR  ASN  ASP  ASN  L
                                           T G G C A G G T A A A T T C C T A A C C A A T G A C A A C A
                                                           1960                1970                1980

YS  LEU  PHE  GLY  VAL  PHE  GLY  ALA  LYS  ARG
A A C T C T T T G G C G T C T T T G G T G C T A A A C G A G
              1990                2000                2010
                                          GLU  SER  GLU  ALA  LYS  GLU  LYS  THR  GLU  ALA  I
                                           A G A G T G A A G C T A A G G A A A A A A C C G A A G C C A
                                                           2020                2030                2040

LE  LEU  ASP  ALA  TYR  ALA  LEU  GLY  THR  PHE
T C T T A G A T G C C T A T G C A C T T G G G A C A T T T A
              2050                2060                2070
                                          ASN  LYS  PRO  GLY  THR  THR  ASN  PRO  ALA  PHE  T
                                           A T A A A C C T G G T A C G A C C A A T C C C G C C T T T A
                                                           2080                2090                2100
```

FIG.11J

```
HR  ALA  ASN  SER  LYS  LYS  GLU  LEU  ASP  ASN
C C G C T A A C A G C A A A A A A G A A C T G G A T A A C T
              2110                2120                2130
                                    PHE  GLY  ASN  ALA  LYS  LYS  LEU  VAL  LEU  GLY  S
                                     T T G G C A A T G C C A A A A A G T T G G T C T T G G G T T
                                                 2140                2150                2160

ER  THR  VAL  ILE  ASP  LEU  VAL  PRO  THR  GLY
C T A C C G T C A T T G A T T T G G T G C C T A C C G G T G
              2170                2180                2190
                                    ALA  THR  LYS  ASP  VAL  ASN  GLU  PHE  LYS  GLU  L
                                     C C A C C A A A G A T G T C A A T G A A T T C A A A G A A A
                                                 2200                2210                2220

YS  PRO  LYS  SER  ALA  THR  ASN  LYS  ALA  GLY
A G C C A A A G T C T G C C A C A A A C A A A G C G G G C G
              2230                2240                2250
                                    GLU  THR  LEU  MET  VAL  ASN  ASP  GLU  VAL  ILE  V
                                     A G A C T T T G A T G G T G A A T G A T G A A G T T A T C G
                                                 2260                2270                2280

AL  LYS  THR  TYR  GLY  TYR  GLY  ARG  ASN  PHE
T C A A A A C C T A T G G C T A T G G C A G A A A C T T T G
              2290                2300                2310
```

FIG.11K

```
                                       GLU  TYR  LEU  LYS  PHE  GLY  GLU  LEU  SER  ILE  G
                                        A A T A C C T A A A A T T T G G T G A G C T T A G T A T C G
                                                      2320                2330                2340

LY   GLY  SER  HIS  SER  VAL  PHE  LEU  GLN  GLY
G T G G T A G C C A T A G C G T C T T T T T A C A A G G C G
              2350                2360                2370
                                       GLU  ARG  THR  ALA  GLU  LYS  ALA  VAL  PRO  THR  G
                                        A A C G C A C C G C T G A G A A A G C C G T A C C A A C C G
                                                      2380                2390                2400

LU   GLY  THR  ALA  LYS  TYR  LEU  GLY  ASN  TRP
A A G G C A C A G C C A A A T A T C T G G G G A A C T G G G
              2410                2420                2430
                                       VAL  GLY  TYR  ILE  THR  GLY  LYS  ASP  THR  GLY  T
                                        T A G G A T A C A T C A C A G G A A A G G A C A C A G G A A
                                                      2440                2450                2460

HR   SER  THR  GLY  LYS  SER  PHE  ASN  GLU  ALA
C G A G C A C A G G A A A A A G C T T T A A T G A G G C C C
              2470                2480                2490
                                       GLN  ASP  ILE  ALA  ASP  PHE  ASP  ILE  ASP  PHE  G
                                        A A G A T A T T G C T G A T T T T G A C A T T G A C T T T G
                                                      2500                2510                2520
```

FIG.11L

```
LU  ARG  LYS  SER  VAL  LYS  GLY  LYS  LEU  THR
A G A G A A A A T C A G T T A A A G G C A A A C T G A C C A
              2530                2540                2550
THR  GLN  GLY  ARG  GLN  ASP  PRO  VAL  PHE  ASN  I
C C C A A G G C C G C C A A G A C C C T G T A T T T A A C A
              2560                2570                2580
LE  THR  GLY  GLN  ILE  ALA  GLY  ASN  GLY  TRP
T C A C A G G T C A A A T C G C A G G T A A T G G C T G G A
              2590                2600                2610
THR  GLY  THR  ALA  SER  THR  ALA  LYS  ALA  ASN  V
C A G G C A C A G C C A G C A C C G C C A A A G C G A A C G
              2620                2630                2640
AL  GLY  GLY  TYR  LYS  ILE  ASP  SER  SER  SER
T A G G G G C T A C A A G A T A G A T T C T A G C A G T A
              2650                2660                2670
THR  GLY  LYS  SER  ILE  VAL  ILE  GLU  ASN  ALA  L
C A G G C A A A T C C A T C G T C A T C G A A A A T G C C A
              2680                2690                2700
YS  VAL  THR  GLY  GLY  PHE  TYR  GLY  PRO  ASN
A G G T T A C A G G T G G C T T T T A T G G T C C A A A T G
              2710                2720                2730
```

FIG.11M

```
                                          ALA  ASN  GLU  MET  GLY  GLY  SER  PHE  THR  HIS  A
                                           C A A A C G A G A T G G G C G G G T C A T T T A C A C A C G
                                                         2740                2750                2760

SP   THR  ASP  ASP  SER  LYS  ALA  SER  VAL  VAL
A T A C C G A T G A C A G T A A A G C C T C T G T G G T C T
              2770                2780                2790
                                          PHE  GLY  THR  LYS  ARG  GLN  GLU  GLU  VAL  LYS  *
                                           T T G G C A C A A A A A G A C A A G A A G A A G T T A A G T
                                                         2800                2810                2820

**
A G T A A T T T A A A C A C A A T G C T T G G T T C G G C T
              2830                2840                2850
                                           G A T G G G A T T G A C G C T T A A T C A A A C A T G A A T
                                                         2860                2870                2880

G A T T A A G A T G A T A A A C C C A A G C C A T G C C A A
              2890                2900                2910
                                           T G A T T G A T A G C A A C G A T G G C A G A T G A T G A G
                                                         2920                2930                2940

T T T T C A T T A T C T G C C A T T A T T A T T G C T T A A
              2950                2960                2970
                                           T T A T T G C T T G T C A T T T G G T G G T G T T A T C A C
                                                         2980                2990                3000
```

```
A T T A A T C A T T A A A A T T A A C A T A A T A A A T G A
                 3010                3020                3030
                                          T T A A A T G A T A T T T A A T G A A A G T C A G G G T T A
                                                           3040                3050                3060

T T T T G G T C A T G G T T T T T C A T G A T T A T T T A A
                 3070                3080                3090
                                          C T T A T A A T G C G T T A T G G T T A G C A A A A A G C T
                                                           3100                3110                3120

A A G T C T G T C A A T G A A G C T A T G G T G A G T G A T
                 3130                3140                3150
                                          T G T G C A A A A G A T G G T C A A A A A A A T C G G T A T
                                                           3160                3170                3180

G G T G C T G T C A G G C G T G G T G A T G G T T C T G T T
                 3190                3200                3210
                                          A A T G A T A A T A A C A A C G C C A A G C C A T G C T A C
                                                           3220                3230                3240

T G C C A A G T T G T T G C C G A C C T C T C A A G A A A A
                 3250                3260                3270
                                          T C C A A C C A A A A C T A T G G T A G A T A G C T T T G G
                                                           3280                3290                3300
```

```
T C G T G A A A C G C C A C G A G G G G C A G T T C A G G G
                  3310                3320                3330
G C T A T T G C G T G C A A T T G C A G C A G A A G A C T A
                  3340                3350                3360
T G A G C T G G C T G C C A A C T A T T T G G A C G G C C G
                  3370                3380                3390
T T A T T T G G C A A A A A C C C A A A C G C C C A A T C G
                  3400                3410                3420
T G A G A T T G T T G A G C A
                  3430
```

Tbp1 alignment

```
         10         20           30         40          50         60
MNQSKQNNKSKKSKQVLKLSALSLGLLNI--TQVALANTTADKAEA-TDKTNLVVVLDETVVT
.....---....................--..............-................
.Q.QHLFR--------.NILC...--------MT..PVY----..NVQAEQAQEKQ..TIQ.K
.Q.QHLFR--------.NILC...--------MT..PAY----..NVQAGQAQEKQ..TIQ.K
.Q.QHLFR--------.NILC...--------MT..PAY----..NVQAGQAQEKQ..TIQ.K
.TKKPYFR-------LSIISC.LI.CYVKAE..SIKDTKE.ISS.VD.QS.E-DSE.ETIS..
                                                   70        80        90        100
                                               AKKNA-RKANEVTGLGKVVKTAETINKEQVLNIRDLTRYDP    4223
                                               .....-...................................    Q8
                                               ...QKT.RD........L..SSD.LS...............    B16B6
                                               ...QKT.RD........L....D.LS.....D.........    M982
                                               ...QKT.RD........L....D.LS.....D.........    FA19
                                               .E.IRD..D.......II..S.S.SR...............    Eagan

        110        120        130        140        150         160
GIAVVEQGRGASSGYSIRGMDKNRVAVLVDGINQAQHYALQGPVAGKNYA-AGGAINEIEYEN
.................................................-...........
........................SLT...VS.I.S.TA.AALG.TRT.GSS..........
........................SLT...LA.I.S.TA.AALG.TRT.GSS..........
........................SLT...LA.I.S.TA.AALG.TRT.GSS..........
..S.................R....L....LP.T.S.VV.S.LVATSGYSGT..........
```

FIG.12B

```
                170       180       190       200
               VRSVEISKGANSSEYGSGALSGSVAFVTKTADDIIKDG     4223
               ......................................     Q8
               .KA......S......N..A.....Q....A...GE.      B16B6
               .KA......S..V.Q.....A.....Q......V.GE.     M982
               .KA......S..V.Q.....A.....Q......V.GE.     FA19
               .KA......GS.....N..A...T.QS.S.A..LEGD      Eagan

      210       220       230       240       250       260
KDWGVQTKTAYASKNNAWVNSVAAAGKAGSFSGLIIYTDRRGQEYKAHDDAYQGSQSFDRAVA
...............................................................
.Q..I.S....SG.DH.LTQ.L.L..RS.GAEA.L...K...R.IH..K..GK.V...N.L.L
RQ..I.S....SG..RGLTQ.I.L..RI.GAEA.L.H.G..AG.IR..E..GR.V...N.L.P
RQ..I.S....SG..RGLTQ.I.L..RI.GAEA.L.H.G.HAG.IR..EA.GR.V...N.LAP
.S..I...N..S...KGFTH.L.V...Q.G.E..A...Q.NSI.TQV.K..LK.V..Y..LI.

                      270       280       290       300
               TTD-----PNNRTFLIANECANFNYEACAAGGQTKLQAKPTN     4223
               ...-----...PK.............................     Q8
               DE.KKEGGSQY.Y.IVEE..H..-.A..KNKL--.ED.SVKD     B16B6
               VE.----SSEYAY.IVED..EGK...T.KSKP--.KDVVGKD     M982
               VE.----GSKYAY.IVEE..K..GH.K.K.NP--.KDVVGED     FA19
               ...-----KSSGY.V.QG..P..DDK-...----.PP.TLST     Eagan
```

FIG.12C

```
      310       320       330        340       350       360
VRDKVNVKDYTGPNRLIPNPLTQDSKSLLLRPGYQLNDK-HYVGGVYEITKQNYAMQDKTVPA
.......................................-.......................
E.KT.STQ....S...LA...EYG.Q.W.F...WH.DNR-....A.L.R.Q.TFDTR.M....
E.QT.STR.......FLAD..SYE.R.W.F...FRFENKR..I..IL.H.Q.TFDTR.M....
K.QT.STR.......FLAD..SYE.R.W.F...FRFENKR..I..IL.R.Q.TFDTR.M....
QSET.S.S....A..IK...MKYE.Q.WF..G..HFSEQ-..I..IF.F.Q.KFDIR.M.F..
                                              370       380        390       400
                                          YLTVHDIEKSRLSNHAQA--NGYYQGNNLGERIRDTIGPD      4223
                                          ..............G..--...............A..AN      Q8
                                          .F.SE.YVPGS.KGL------.K.S.D.KA..LFVQGEGS      B16B6
                                          F..KAVFDANSKQAGSLPG-..K.A..HKYGGLFTNGENG      M982
                                          F..KAVFDANQKQAGSLPG-..K.A..HKYGGLFTSGENN      FA19
                                          ..SPTERRDDSSRSFYPMQDH.A..HIE------------      Eagan

         410       420       430       440       450       460
----SGYGINYAHGVFYDEKHQKDELGLEYVYDSKGENKWFDDVRVSYDKQDITLRSQLTNTHC
----............................................................
TLQGI...----T......R.T.N.Y.V....HNADKDT.A.YA.L...R.G.D.DNR.QQ...
----ALV.AE.GT......T.T.S.Y......TNADKDT.A.YA.L...R.G.G.DNHFQQ...
----APV.AE.GT......T.T.S.Y......TNADKDT.A.YA.L...R.G.G.DNHFQQ...
----D.R.VK..S.LYF..H.R.Q.V.I..I.EN.NKAGII.KAVL.ANQ.N.I.D.YMRH...
```

FIG.12D

```
           470       480       490       500
STYPHIDKNCTPDVNKPFSVKEVDNNAYKEQHNLIKAVFN        4223
........................................        Q8
.HDGS-....R..G...Y.FYKS.RMI.E.SR..FQ...K        B16B6
.ADGS-..Y.R.SAD....YYKS.RVI.G.S.R.LQ.A.K        M982
.ADGS-..Y.R.SAD....YYKS.RVI.G.S.K.LQ.A.K        FA19
.L..NPS...R.TLD..Y.YYRS.R.V...K..MLQLNLE        Eagan

      510       520       530       540       550        560
KKMALGSTHHHINLQVGYDKFNSSLSREDYRLATHQSYQKLDYTPPSNPLPDKF-KPILGSNN
......N.............................................-........
.AFDTAKIR.NLSINL...R.K.Q..HS..Y.QNAVQAYD.I-...KP.F.NGS-.------D
.SFDTAJUR.NKSVNK.F.R.S.B.RHQ..YYQHANRAYSSK-...KTAN.NGD-.------S
.SFDTAKIR.NLSVNL...T.G.N.RHQ..YYQSANRAYS.K-...Q.NGKKTS---PN.REK
..IQQNWLT.Q.VFNL.F.D.T.A.QHK..-.TRRVIATA-.SI.RK---.GETG..RN.LQS

          570       580       590       600
KPICLDAYGYGHDHPQACNAKNSTYQNFAIKKGIEQYN          4223
R.....................................          Q8
N.YRVSIGK-----------------------------          B16B6
..YWVSIG.-----------------------------          M982
N.YWVSIGR-----------------------------          FA19
Q.YLYPKPEP----------------------------          Eagan
```

FIG.12E

```
        610       620       630       640       650       660
QKTNTDKIDYQAIIDQYDKQNPNSTLKPFEKIKQSLGQEKYNKIDELGFKAYKDLRNEWAGWT
.-.........V.........................DE..R...N.............
---------------------------------------------------------------
---------------------------------------------------------------
---------------------------------------------------------------
---------------------------------------------------------------
                                                670       680       690       700
                                                NDNSQQNANKGRDNIYQPNQA-TVVKDDKCKYSETNS-Y   4223
                                                .....................-...............-.  Q8
                                                ---------------------T..NTSPI.RFGN-.T-.   B16B6
                                                ---------------------GN..TGQI.LFGN-.T-.   M982
                                                ---------------------GN..TRQI.LFGN-.T-.   FA19
                                                ---------------------YFAGQDH-.N.QGSS.N.   Eagan

         710       720       730       740       750       760
ADCSTTRHISGDNYFIALKDNMTINKYVDLGLGARYDRIKHKSDVPLVDNSASNQLSWNFGVV
...............................................................
T..-.P.N.G.NG.YA.VQ..VRLGRWA.V.A.I...YRSTH.EDKS.STGTHRN....A...
T..-.P.S.N.KS.YA.VR..VRLGRWA.V.A.L...YRSTH..DGS.STGTHRT....A.I.
T..-.P.S.N.KS.YA.VR..VRLGRWA.V.A.L...YRSTH..DGS.STGTHRT....A.I.
R..-KV.L.K.K..YF.ARN..ALG........I...VSRT.ANESTISVGKFKNF...T.I.
```

FIG.12F

```
                                           770       780       790       800
                                       VKPTNWLDIAYRSSQGFRMPSFSEMYGERFGVTIGKG        4223
                                       .....................................        Q8
                                       L..FT.M.LT..A.T...L...A....W.A.ESLKTL        B16B6
                                       L..AD...LT..T.T...L...A....W.S..OSKAV        M982
                                       L..AD...LT..T.T...L...A....W.S.DK.KAV        FA19
                                       I...E...LS..L.T...N........W.Y.GKNDEV        Eagan

       810       820       830       840       850       860
TQHGCKGLYYICQQTVHQTKLKPEKSFNQEIGATLHNHLGSLEVSYFKNRYTDLIVGKSEEIR
...............................................................
-------------------D........R.A.IVFKGDF.N..A...N.A.R...AFGY-.T.
--------------------.ID......K.A.IVFKGDF.N..A.W.N.A.R....RGY.AQI
--------------------.ID......K.A.IVFKGDF.N..A.W.N.A.R....RGY.AQI
----------------YVG.F...T.R...F.LA.KGDF.NI.I.H.S.A.RN..AFA-..LS
                                           870       880       890       900
                                       TLTQGDNAGKQRGKGDLGFHNGQDADLTGINILGRLD        4223
                                       ......................N..........K..        Q8
                                       .-----QN.QTSAS..P.YR.A.N.RIA......KI.        B16B6
                                       K------N..EEA...PAYL.A.S.RI.......KI.        M982
                                       K------D..EQV..NPAYL.A.S.RI.......KI.        FA19
                                       K--------NGT...NY.Y..A.N.K.V.V..TAQ..        Eagan
```

FIG.12G

```
        910         920         930         940         950         960
LNAVNSRLPYGLYSTLAYNKVDVKGKTLNPTLAG-TNILFDAIQPSRYVVGLGYDAPSQKWGA
...............................-..........................
WHG.WGG..D.........RIK..DADIRADRTFV.SY....V......L.....H.DGI..I
WNG.WDK..E.W...F...R.H.RDIKKRADRTDIQSH.................Q.EG...V
WNG.WDK..E.W...F...R.H.RDIKKRADRTDIQSH.............S...Q.EG...V
F.GLWK.I...W.A.F...Q.K..DQKI.AG..SVSSY..........II.....H..NT..I
                                                  970         980         990        1000
                                         NAIFTHSDAKNPSELLADKNLGNGNIQ-TKQATKAKSTP       4223
                                         ...........................-...........       Q8
                                         .TM..Y.K..SVD...GSQA.L...ANAK.A-ASRRTR.       B16B6
                                         .GML.Y.K..EIT...GSRA.L...SRN..A-.ARRTR.       M982
                                         .GML.Y.K..EIT...GSRA.L...SRN..A-.ARRTR.       FA19
                                         .TM..Q.K..SQN...GKRA...-.SRDV.S-.RKLTRA       Eagan

      1010        1020        1030        1040        1050        1060        1070
WQTLDLSGYVNIKDNFTLRAGVYNVFNTYYTTWEALRQTAEGAVNQHTGLSQDKHYGRYAAPGRNYQLALEMKF*   4223
..........................................................................*   Q8
.YVT.V...Y...KHL........LL.YR.V...NV....G......---KNVGV.N.........TFS.....*   B16B6
.YIV.V...YT..KH.........LL.YR.V...NV....G......---KNVGV.N.........TFS.....*   M982
.YIV.V...YTV.KH.........LL.HR.V...NV....A......---KNVGV.N.........TFS.....*   FA19
.HI..V...YMANK.IM..L.I..L..YR.V....V....Q......---QNVGS.T....S....T.T.....*   Eagan
```

FIG.13A

Tbp2 comparison

```
        10         20         30         40         50         60
MKHIPLTTLCVAISAV-LLTACGGS-GGSNPPAPTPIPNASGSGNTGNTGNAGGTDNT-ANAG
...............-........S..F....S......GN...A..A......GGANSG..
.NN-..VNQAAMVLP.F..S..L.G-...----------------------------------
.NN-..VNQAAMVLP.F..S..L.G-...----------------------------------
.NN-..VNQAAMVLP.F..S..L.G-...----------------------------------
..SV..ISGGLS----F..S..S.--...----------------------------------
                                                      70        80        90       100
                                              NTGGT---NSGTGSANTPEPKYQDVPTEKNEKDK-VSSIQEPAM     4223
                                              .A...GGA...A...S......K....DE.K.AE-..G......     Q8
                                              -FDLDSVE---.VQDMHSK...EDEKS-QP.SQQD..ENSGA.-     B16B6
                                              -FDLDSVD---.EAPRPA-......SS..PQAQ.D-------QG     M982
                                              -FDLDSVD---.EAPRPA-......PSK.P.AR.D-------QG     FA19
                                              -FDVDNV--.N.P.---SK.R...DTSNQRK.S-NLKKLFI.SL     Eagan

       110        120        130        140        150
GYGMALSKINLHNRQDTPLD-EKNIITL--DGKKQVAEG-KKSPLPFS-LDV-ENKLLDGYIA
...VE.-.LRNWIP.EQEEH-A.IN-.N--.VV.LEGDL-.HN.FDN.IWQNIK.SKEVQTVY
-..F.V-.LPRR.AHFN.KYK..HKP.GSM.W--------..-LQRGEPNSFS.RDE.E----
...F.M-RLKRR.WYP--GAE.SEVK.NES.WEATGLPTKP.E-..KRQKS.I.KVET..D-S
...F.M-RFKRR.WHPSANPK.DEVK.KND.WEATGLPTEP.K-..LKQQS.ISEVETN.N-S
.G..K.VAQ..RGNKEPSFLN.DDY.-----------------SY..S.STI.KDVK.NNK-
```

FIG.13B

```
160        170        180        190        200
KMNVADKNAIGDRIKKGNKEISDEELAKQIKEAVRKSHEFQQV-     4223
NQEKQNIEDQIK.EN.QRPDKKLDDV.L.AYIEKVLDDRLTELA     Q8
-------------K.R.SS.LI-.SKWEDGQSR.VGYTN.T---     B16B6
DIYSSPYLTPSNHQNG-----.AGNGVN.P.NQATGHEN..---     M982
..YTSPYLSQDADS-------.HANG.N.P.NE.TDYKK.----     FA19
--.G..--L..S-.--------..PSTTNPP.K----.HG.---     Eagan

     210        220        230        240        250        260
LSSLENKIFHSNDGTTKATTRDLKYVDYGY-YLANDGNYLTVKTDKLWNLGPVGGVFYNGTTT
KPIY.KN.NY.H.KQN..R.......RS..I.RSGYS.---IIPK.IAKT.FD.AL..Q..Q.
------------------------..RS..V..-.KN.IDIKNNIV.F--..D.YLY.K.KEP
------------------------..YS.WF.KH.ASEKDFSN.KI.S---.DD.YI..H.EK
-----------------------...YS.WF.KH.KSEVKNENGLVSAKR-..D.YI..H.DK
-----------------------...YS.LY.TPSWSLNDS-.N-.FY-..YY.YA..Y.NK.

     270        280        290        300
AKELPTQDAVKYKGHWDFMTDVANRRNRFSEVKENS--QA     4223
..Q..VSQ-.....T......-.KKGQS..SFGT-.QRL.     Q8
S....-SEKIT...T..YV..AME-KQ..-.GLG-.A..G     B16B6
PSRQ..ASGK.I...V.H.V..TKKGQD.R.IIQP.KK.G     M982
PSRQ..ASE..T...V.H.V..TKQGQK.NDIL.T.KG.G     FA19
.TN..VNGVA....T...I.ATK.-GK.YPLLSNG.H.--     Eagan
```

FIG.13C

```
     310        320       330       340       350         360
GWYYGASSKD-EYNRLLTKEDSAPDGHSGEYGHSSEFTVNFKEKKLTGKLFSN---LQDRHKGN
.DR.S.M.YH-..PS...D.KNK..NYN...........D.SK.S.K.E.S..---I..G...S
DK-S..L.AL-.EGV.RNQAE-ASS..TD-F.MT...E.D.SD.TIK.T.YR.NRIT.NNSENK
DR.S.F.GDGS.EYSNKN-.STLK.D.E.-..FT.NLE.D.GN.......IR.NAS.NNNTNND
DK.S.F.GDEG.TTSNR.-DSNLN.K.E.-..FT.N.K.D.NN.......IR.NKVINTAASDG
--..RR-.AIP.DID.EN-DSKNG.-I.----LI...SADGGT.....Q.-.YTKRKTNNQPYE
     370       380        390       400
                                         VTKTERYDIDANIHGNRFRGSATASNK--NDTSK-HPFTSDAN   4223
                                         .N..K........Y..........DTTEASK..-.......K    Q8
                                         QI..T..T.Q.TL.....K.K.L.AD.--GA.NGS...I..SD   B16B6
                                         KHT.QY.SL..Q.T....N.T...TD.K-ENET.L...V..SS   M982
                                         Y.-..Y.SL..TLR....S.K.I.TD.PNTGGT.L...VF.SS   FA19
                                         KK.L--.....D.YS.....TVKPTE.---.SEE-.....EGT   Eagan

     410       420       430            440
NRLEGGFYGPKGEELAGKFLTNDNKLFGVFGAKRESK------AEEKTE--------------
.S........NA.......................E------.K....--------------
S-..................S....VAA.....QKD.KDGENA.GPA..--------------
S-.S...F..Q....GFR..SD.Q.VAV.GS..TKD.LENGAA.SGS.G-AAASGGAAGTSSE
S-.S...F..Q....GFR..SD.G.VAV.GS..TKDST-----.NGNAP-AASSGPGAATMPS
--........NA...G....AT..RV....S..ETEETKKEALSK.TLIDGKLITFSTKKTDA
```

FIG.13D

```
                  450       460          470       480
-----AILDAYALGTFNTSNAT--TFTPFTEKQLDNFGNAKKLV     4223
-----............KPGT.NPA..ANSK.E...........     Q8
-----TVI...RIT-----------GEEFKKE.I.S..DV...L     B16B6
NSKLTTV...VE.T-----------LNDKKI.N....S..AQ..     M982
ETRLTTV...VE.T-----------PDGKEI.N....S..TR..     FA19
KTNATTSTA.NTTTDTTANTI.D--EKN.KTEDISS..E.DY.L     Eagan

   490                    510                    520
LGSTVIDLVP------------TDATK--NEFTKDK---PESATNEAGETLMVNDEVSV----
..........------------.G...DV...-.E.---.K....K..........I.----
VDGVELS.L.--SE-GNKAA--------------FQHEI.----------------------
VDGIM.P.L.KDSESGNTQADKGKNGG--T...RKFEHT...DKKD.QAGTQTNGAQTASNTA
VDGIM.P.L.--TESGNGQADKGKNGG--TD..YETTYT...DKKDTKAQTGAGGMQTASGTA
IDKYP.P.L.----------DKNTN-----------------------------.FI.SK---
    530                    540

---------KTYGKN------FEYLKFGELSIGGSH     4223
---------....YGRN----...............     Q8
--QNGVKAT-------VCCSNLD.MS..K..KENKD     B16B6
GDTNGK--T...EVE-VCCSNLN...Y.M.TRKN.K     M982
GVNGGQVGT...KVQ-VCCSNLN...Y.L..RENNN     FA19
--HHTVGN-.R.KVEAVCCSNSDVKS.MYYEDPLKE     Eagan
```

FIG.13E

```
                                           550        560        570
------------------------------------SVFLQGERTATTGEKAVPTTGTAKYLG
------------------------------------..........---......E.......
------------------------------------DM....V..PVSDVA.-R.EAN...R.
SAMQAGG---------------NSSQADAKTEQVEQ.M.......---D..EI..DQNVV.R.
SVMQAVK---------------NSSQADAKTKQIEQ.M.......---D.NKI.QEQGIV...
KETETETETEKDKEKEKEKDKDKEKQTAATTNTYYQ--..L.H..---PKDDI.K..S...H.
                                                      580        590        600        610
                                                      NWVGYIT-GKDTGTGTGKSFTDAQDVADFTIDFGNKSVSGK         4223
                                                      .......-......S.....NE...I...D...ER...K..         Q8
                                                      T.Y...AN.-TSWS.EA-.NQEGGNR.E.DV..ST.KI..T         B16B6
                                                      S.Y.H.AN.-TSWS.NA-.DKEGGNR.E..VN.AD.KIT..         M982
                                                      F.Y.R.AN.-TSWS.KA-.NATDGNR.K..VN.DR.EIT.T         FA19
                                                      S.Y....D..TSYSPS.DKKR.KNA..E.NV..AE.KLT.E         Eagan

        620          630        640        650          660        670
LITKGRQDPVFSITGQIAG--NGWTGTASTTKADAGGYKIDSSSTGKSIA--IKDANVTGGFYG
.T.Q.......N.......--.........A..NV.............V--.EN.K.......
.TA.D.TS.A.T..AM.KD--..FS.V.K.---GEN.FAL.PQN..N.HYTH.-E.T.S.....
.TAEN..AQT.T.E.M.Q.--..FE...K.---AES.FDL.QKN.TRTPKAY.T..K.K.....
.TAEN.SEAT.T.DAM.E.--..FK...K.---GND.FAP.QNNSTVTHKVH.AN.E.Q.....
.KRHDTGN.....EANFNNSS.AF....TA.-----NFV..GKNSQNKNTPINITTK.N.A...
```

FIG.13F

```
       680                                690
PNANEMGGSFT--------------------NADDSKASV        4223
...........-------------------HDT.......        Q8
K..I......SFPGNAPEGKQE--------------....        B16B6
.K.E.L..W.AYPGDKQTEKATATSSDG---.SAS.-.T.        M982
...E.L..W.AYPGNEQTKNATVESGNG---.SAS.-.T.        FA19
.K.S.L..Y..YNGNSTATNSESSSTVSSSS.SKNAP.A.        Eagan

      700
VFGTKRQQEV-K*                                   4223
.......E..-.*                                   Q8
...A....L.Q-*                                   B16B6
...A....P.Q-*                                   M982
...A...KL.-.*                                   FA19
...ARQ.V.TT.*                                   Eagan
```

Construction of TBP1 Expression Plasmid

Expression of rTbp1 in *E. coli*

1. Prestained molecular weight markers
2. pLEM29B-1 lysate, non-induced
3. pLEM29B-1 lysate, 1 hr post-induction
4. pLEM29B-1 lysate, 3 hr post-induction Purification of Tbp1 from *E.Cole*

Purification of rTbp1 from *E. coli*

1. *E. coli* Whole cells
2. Soluble proteins after 50 mM Tris/ NaCl extraction
3. Soluble proteins after Tris/ Triton X-100/ EDTA extraction
4. Soluble proteins after Tris/ urea/ DTT extraction
5. Left-over pellet (rTbp1 inclusion bodies)

6.7. Purified rTbp1

CONSTRUCTION OF TBP2 EXPRESSION PLASMID

Expression of rTbp2 in *E. coli*

1. Prestained molecular weight markers
2. pLEM37B-2 lysate, non-induced
3. pLEM37B-2 lysate, induced

Fig 21. Expression of Q8 rTbp2 protein in *E. coli*
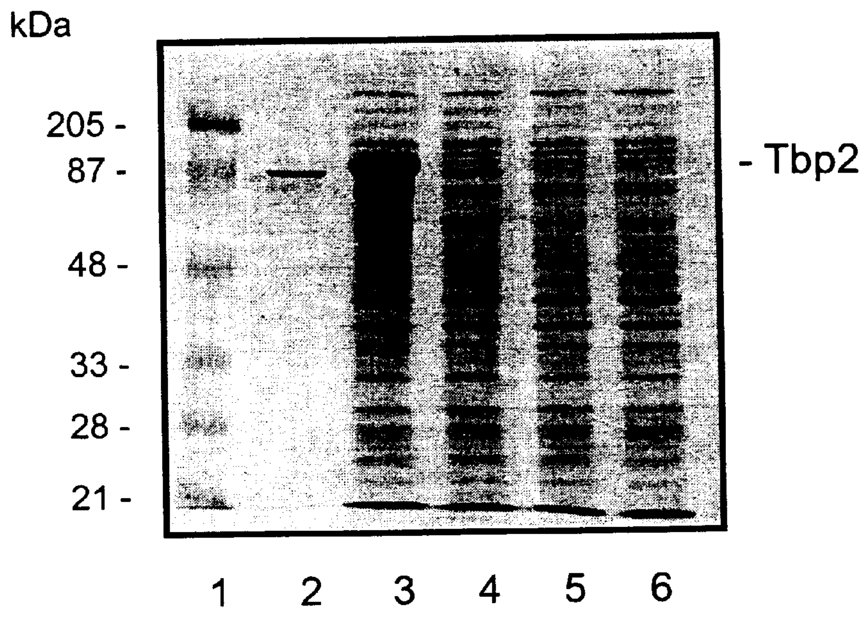
1. Prestained molecular weight markers
2. 4223 rTbp2 protein
3. SLRD35A lysate, 3 hr post-induction
4. SLRD35B lysate, 3 hr post-induction
5. SLRD35A lysate, non-induced
6. SLRD35B lysate, non-induced Purification of Tbp2 from *E.Coli*

Purification of rTbp2 from *E. coli*

1. *E. coli* Whole cells
2. Soluble proteins after 50 mM Tris extraction
3. Soluble proteins after Tris/ Triton X-100/ EDTA extraction
4. Left-over pellet (rTbp2 inclusion bodies)
5. Purified rTbp2

Binding of Tbp2 to Human Transferrin 1. rTbp2 (strain 4223)
2. rTbp2 (strain Q8)

1. Strain 5191
2. Strain 56
3. Strain 135
4. Strain 4223
5. Strain ATCC25240
6. Strain 585
7. Strain 3
8. Strain 8185

Fig. 26 Restriction map of *M. catarrhalis* strain M35 *tbpB* gene
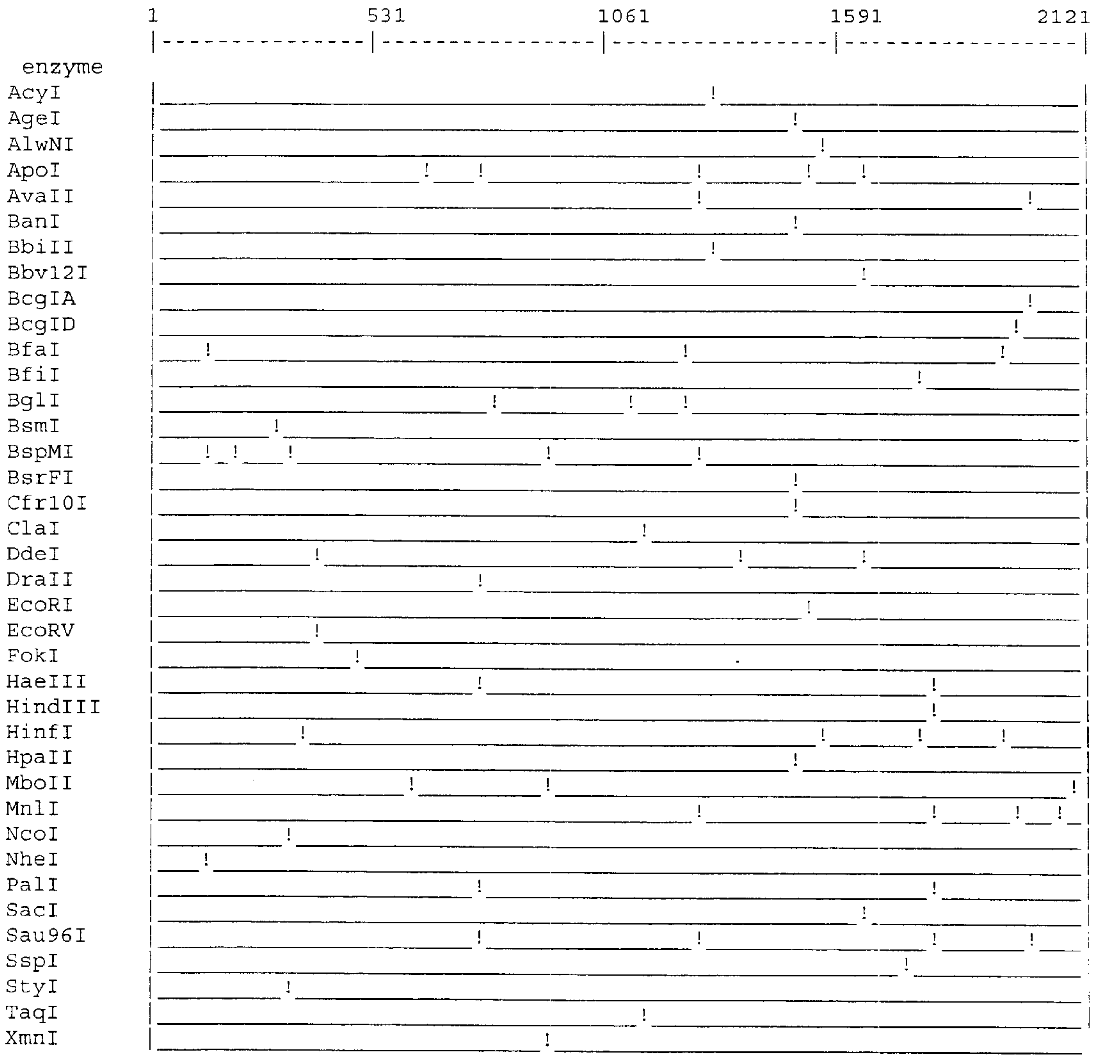

FIG.27A

*M. catarrhalis* strain M35 *tbpB* sequence

```
MET   LYS   HIS   ILE   PRO   LEU   THR   THR   LEU   ...
A T G A A A C A C A T T C C T T T A A C C A C A C T G T...
                  10                    20            ...
                  ...CYS   VAL   ALA   ILE   SER   ALA   VAL   LEU   LEU   THR   ALA
                  ... G T G T G G C A A T C T C T G C C G T C T T A T T A A C C G C T
                  ...  30                   40                   50                   60

CYS   GLY   GLY   SER   GLY   GLY   SER   ASN   PRO   ...
T G T G G T G G C A G T G G T G G T T C A A A T C C A C...
                  70                    80            ...
                  ...PRO   ALA   PRO   THR   PRO   ILE   PRO   ASN   ALA   SER   GLY
                  ... C T G C T C C T A C G C C C A T T C C A A A T G C T A G C G G T
                  ...  90                   100                  110                  120

SER   GLY   ASN   THR   GLY   ASN   THR   GLY   ASN   ...
T C A G G T A A T A C T G G C A A C A C T G G T A A T G...
                  130                   140           ...
                  ...ALA   GLY   GLY   THR   ASP   ASN   THR   ALA   ASN   ALA   GLY
                  ... C T G G C G G T A C T G A T A A T A C A G C C A A T G C A G G T
                  ... 150                  160                  170                  180
```

FIG.27B

```
ASN THR GLY GLY THR ASN SER GLY THR ...
A A T A C A G G C G G T A C A A A C T C T G G T A C A G...
               190                     200            ...

            ...GLY SER ALA ASN THR PRO GLU PRO LYS TYR LYS
            ... G C A G T G C C A A C A C A C C A G A A C C A A A A T A T A A A
            ... 210                   220                   230                   240

ASP VAL PRO THR ASP GLU ASN LYS LYS ...
G A T G T G C C A A C C G A T G A A A A T A A A A A A G...
               250                     260            ...
            ...ASP GLU VAL SER GLY ILE GLN GLU PRO ALA MET
            ... A T G A A G T G T C A G G C A T T C A A G A A C C T G C C A T G
            ... 270                   280                   290                   300

GLY TYR GLY MET ALA LEU SER LYS MET ...
G G T T A T G G C A T G G C T T T G A G T A A A A T G A...
               310                     320            ...
            ...ASN LEU HIS LYS GLN GLN ASP THR PRO LEU ASP
            ... A T C T A C A C A A A C A A C A A G A C A C G C C A T T A G A T
            ... 330                   340                   350                   360

GLU LYS ASP ILE ILE THR LEU ASP GLY ...
G A A A A A G A T A T C A T T A C C T T A G A C G G T A...
               370                     380            ...
```

FIG.27C

```
                                  ...LYS  LYS  GLN  VAL  ALA  LYS  GLY  GLU  LYS  SER  PRO
                                  ... A A A A A C A A G T T G C A A A A G G T G A A A A A T C G C C A
                                  ... 390                400                410                420

LEU  PRO  PHE  SER  LEU  ASP  VAL  GLU  ASN  ...
T T G C C A T T T T C G T T G G A T G T A G A A A A T A...
                430                440                ...

                                  ...LYS  LEU  LEU  ASP  GLY  TYR  ILE  ALA  LYS  MET  ASN
                                  ... A A T T G C T T G A T G G C T A T A T A G C A A A A A T G A A T
                                  ... 450                460                470                480

GLU  ALA  ASP  LYS  ASN  ALA  ILE  GLY  ASP  ...
G A A G C G G A T A A A A A T G C C A T T G G T G A C A...
                490                500                ...
                                  ...ARG  ILE  LYS  LYS  ASP  ASN  LYS  ASP  LYS  SER  LEU
                                  ... G A A T T A A G A A A G A T A A T A A A G A C A A G T C A T T A
                                  ... 510                520                530                540

SER  LYS  ALA  GLU  LEU  ALA  LYS  GLN  ILE  ...
T C T A A A G C A G A G C T T G C C A A A C A A A T C A...
                550                560                ...
                                  ...LYS  GLU  ASP  VAL  ARG  LYS  SER  HIS  GLU  PHE  GLN
                                  ... A A G A A G A T G T G C G T A A A A G C C A T G A G T T T C A G
                                  ... 570                580                590                600
```

FIG.27D

```
GLN   VAL   LEU   SER   SER   LEU   LYS   ASN   LYS   ...
C A A G T A T T A T C A T C A C T G A A A A A C A A A A...
                  610               620             ...
           ...ILE   PHE   HIS   SER   ASN   ASP   GLY   THR   THR   LYS   ALA
           ... T T T T T C A T T C A A A T G A T G G A A C A A C C A A A G C A
           ... 630               640               650               660

THR   THR   ARG   ASP   LEU   GLN   TYR   VAL   ASP   ...
A C C A C A C G A G A T T T A C A A T A T G T T G A T T...
                  670               680             ...

           ...TYR   GLY   TYR   TYR   LEU   VAL   ASN   ASP   GLY   ASN   TYR
           ... A T G G T T A C T A C T T G G T G A A T G A T G G C A A T T A T
           ... 690               700               710               720

LEU   THR   VAL   LYS   THR   ASP   GLU   LEU   TRP   ...
C T A A C C G T C A A A A C A G A C G A A C T T T G G A...
                  730               740             ...
           ...ASN   LEU   GLY   PRO   VAL   GLY   GLY   VAL   PHE   TYR   ASN
           ... A T T T A G G C C C T G T G G G C G G T G T G T T T T A T A A T
           ... 750               760               770               780

GLY   THR   THR   THR   ALA   LYS   GLU   LEU   PRO   ...
G G C A C A A C G A C C G C C A A A G A G C T A C C C A...
                  790               800             ...
```

FIG.27E

```
                            ...THR  GLN  ASP  ALA  VAL  LYS  TYR  LYS  GLY  HIS  TRP
                            ... C A C A A G A T G C G G T C A A A T A T A A A G G A C A T T G G
                            ... 810                 820                 830                 840

ASP  PHE  MET  THR  ASP  VAL  ALA  LYS  GLN  ...
G A C T T T A T G A C C G A T G T T G C C A A A C A A A...
              850                 860                    ...
                            ...ARG  ASN  ARG  PHE  SER  GLU  VAL  LYS  GLU  ASN  LEU
                            ... G A A A C C G A T T T A G C G A A G T G A A A G A A A A C C T T
                            ... 870                 880                 890                 900

GLN  ALA  GLY  ARG  TYR  TYR  GLY  ALA  SER  ...
C A A G C A G G T C G G T A T T A T G G A G C A T C T T...
              910                 920                    ...

                            ...SER  LYS  ASP  GLU  TYR  ASN  ARG  LEU  LEU  THR  ASP
                            ... C A A A A G A T G A A T A C A A C C G C T T A T T A A C T G A T
                            ... 930                 940                 950                 960

GLU  LYS  ASN  LYS  PRO  GLU  ARG  TYR  ASN  ...
G A G A A A A A C A A A C C A G A G C G T T A T A A C G...
              970                 980                    ...
                            ...GLY  GLU  TYR  GLY  HIS  SER  SER  GLU  PHE  THR  VAL
                            ... G T G A A T A T G G T C A T A G C A G T G A G T T T A C T G T T
                            ... 990                 1000                1010                1020
```

FIG.27F

```
ASN   PHE   LYS   ASP   LYS   LYS   LEU   THR   GLY   ...
A A T T T T A A G G A C A A A A A A T T A A C A G G T G...
          1030                  1040                  ...
          ...GLU   LEU   PHE   SER   ASN   LEU   GLN   ASP   SER   ARG   LYS
          ... A G C T G T T T A G T A A C C T A C A A G A C A G C C G T A A G
          ...1050              1060                1070                1080

GLY   ASN   VAL   THR   LYS   THR   LYS   ARG   TYR   ...
G G C A A T G T T A C G A A A A C C A A A C G C T A T G...
          1090                  1100                  ...
          ...ASP   ILE   ASP   ALA   ASN   ILE   TYR   GLY   ASN   ARG   PHE
          ... A C A T C G A T G C C A A T A T C T A C G G C A A C C G C T T C
          ...1110              1120                1130                1140

ARG   GLY   SER   ALA   THR   ALA   SER   ASP   LYS   ...
C G T G G C A G T G C C A C C G C A A G C G A T A A A G...
          1150                  1160                  ...
          ...ALA   GLU   ALA   SER   LYS   THR   LYS   HIS   PRO   PHE   THR
          ... C A G A A G C A A G C A A A A C C A A A C A C C C C T T T A C C
          ...1170              1180                1190                1200

SER   ASP   ALA   LYS   ASN   SER   LEU   GLU   GLY   ...
A G C G A T G C C A A A A A T A G C C T A G A A G G C G...
          1210                  1220                  ...
```

FIG.27G

```
...GLY PHE TYR GLY PRO ASN ALA GLU GLU LEU ALA
... G T T T T T A T G G A C C A A A C G C C G A G G A G C T G G C A
...1230 1240 1250 1260

GLY LYS PHE LEU THR ASN ASP ASN LYS ...
G G T A A A T T C C T A A C C A A T G A C A A C A A A C...
1270 1280 ...
...LEU PHE GLY VAL PHE GLY ALA LYS ARG GLU SER
... T C T T T G G C G T C T T T G G T G C T A A A C G A G A G A G T
...1290 1300 1310 1320

LYS ALA GLY GLU LYS THR GLU ALA ILE ...
A A A G C T G G G G A A A A A A C C G A A G C C A T C T...
1330 1340 ...
...LEU ASP ALA TYR ALA LEU GLY THR PHE ASN LYS
... T A G A T G C C T A T G C A C T T G G G A C A T T T A A C A A A
...1350 1360 1370 1380

ASN ASN ALA THR THR PHE THR PRO PHE ...
A A T A A C G C A A C C A C A T T C A C C C C A T T T A...
1390 1400 ...

...THR LYS LYS GLN LEU ASP ASN PHE GLY ASN ALA
... C C A A A A A A C A A C T G G A T A A C T T T G G C A A T G C C
...1410 1420 1430 1440
```

FIG.27H

```
LYS   LYS   LEU   VAL   LEU   GLY   SER   THR   VAL   ...
A A A A A G T T G G T C T T G G G T T C T A C C G T C A...
            1450                    1460                ...
          ...ILE   ASP   LEU   VAL   PRO   THR   GLY   VAL   THR   LYS   ASP
          ... T T G A T T T G G T G C C T A C C G G T G T C A C C A A A G A T
          ...1470                1480                  1490                  1500

VAL   ASN   GLU   PHE   THR   LYS   ASN   LYS   PRO   ...
G T C A A T G A A T T C A C C A A A A A C A A G C C A G...
            1510                    1520                ...
          ...ASP   SER   ALA   THR   ASN   LYS   ALA   GLY   GLU   THR   LEU
          ... A T T C T G C C A C A A A C A A A G C G G G C G A G A C T T T G
          ...1530                1540                  1550                  1560

MET   VAL   ASN   ASP   LYS   VAL   SER   VAL   LYS   ...
A T G G T G A A T G A T A A A G T T A G C G T C A A A A...
            1570                    1580                ...
          ...THR   TYR   GLY   TYR   GLY   ARG   ASN   PHE   GLU   TYR   LEU
          ... C C T A T G G C T A T G G C A G A A A C T T T G A A T A C C T A
          ...1590                1600                  1610                  1620

LYS   PHE   GLY   GLU   LEU   SER   VAL   GLY   THR   ...
A A A T T T G G T G A G C T C A G T G T C G G C A C A A...
            1630                    1640                ...
```

FIG.27I

```
                ...SER  ASN  SER  VAL  PHE  LEU  GLN  GLY  GLU  ARG  THR
                ... G C A A C A G C G T C T T T T T A C A A G G C G A A C G C A C C
                ...1650          1660          1670          1680

ALA  THR  THR  GLY  GLU  LYS  ALA  VAL  PRO  ...
G C T A C C A C A G G C G A G A A A G C C G T A C C A A...
        1690          1700          ...
                ...THR  LYS  GLY  THR  ALA  LYS  TYR  LEU  GLY  ASN  TRP
                ... C C A A A G G C A C A G C C A A A T A T T T G G G G A A C T G G
                ...1710          1720          1730          1740

VAL  GLY  TYR  ILE  THR  GLY  LYS  ASP  SER  ...
G T A G G A T A C A T C A C A G G A A A G G A C T C A T...
        1750          1760          ...
                ...SER  LYS  SER  PHE  ASN  GLU  ALA  GLN  ASP  VAL  ALA
                ... C A A A A A G C T T T A A T G A G G C C C A A G A T G T T G C T
                ...1770          1780          1790          1800

ASP  PHE  ASP  ILE  ASP  PHE  GLU  LYS  LYS  ...
G A T T T T G A C A T T G A C T T T G A G A A A A A A T...
        1810          1820          ...
                ...SER  VAL  LYS  GLY  LYS  LEU  THR  THR  LYS  ASP  ARG
                ... C A G T T A A A G G C A A A C T G A C C A C C A A A G A C C G C
                ...1830          1840          1850          1860
```

FIG.27J

```
GLN  ASP  PRO  VAL  PHE  ASN  ILE  THR  GLY  ...
C A A G A C C C T G T A T T T A A C A T C A C A G G T G...
          1870                     1880                   ...

            ...ASP  ILE  ALA  GLY  ASN  GLY  TRP  THR  GLY  LYS  ALA
            ... A C A T C G C A G G C A A T G G C T G G A C A G G C A A A G C C
            ...1890            1900                1910               1920

SER  THR  THR  LYS  ALA  ASP  ALA  GLY  GLY  ...
A G C A C C A C C A A A G C G G A C G C A G G G G G C T...
          1930                     1940                   ...
            ...TYR  LYS  ILE  ASP  SER  SER  SER  THR  GLY  LYS  SER
            ... A C A A G A T A G A T T C T A G C A G T A C A G G C A A A T C C
            ...1950            1960                1970               1980

ILE  VAL  ILE  LYS  ASP  ALA  GLU  VAL  THR  ...
A T C G T C A T C A A A G A T G C C G A G G T T A C A G...
          1990                     2000                   ...
            ...GLY  GLY  PHE  TYR  GLY  PRO  ASN  ALA  ASN  GLU  MET
            ... G G G G C T T T T A T G G T C C A A A T G C A A A C G A G A T G
            ...2010            2020                2030               2040

GLY  GLY  SER  PHE  THR  HIS  ASN  THR  ASP  ...
G G C G G G T C A T T T A C A C A C A A C A C C G A T G...
          2050                     2060                   ...
```

FIG.27K

```
...ASP   SER   LYS   ALA   SER   VAL   VAL   PHE   GLY   THR   LYS
... A C A G T A A A G C C T C T G T G G T C T T T G G C A C A A A A
...2070            2080            2090            2100

ARG   GLN   GLU   GLU   VAL   LYS   ***
A G A C A A G A A G A A G T T A A G T A G
            2110            2120
```

Fig. 28 Restriction map of *M. catarrhalis* strain R1 *tbpB*
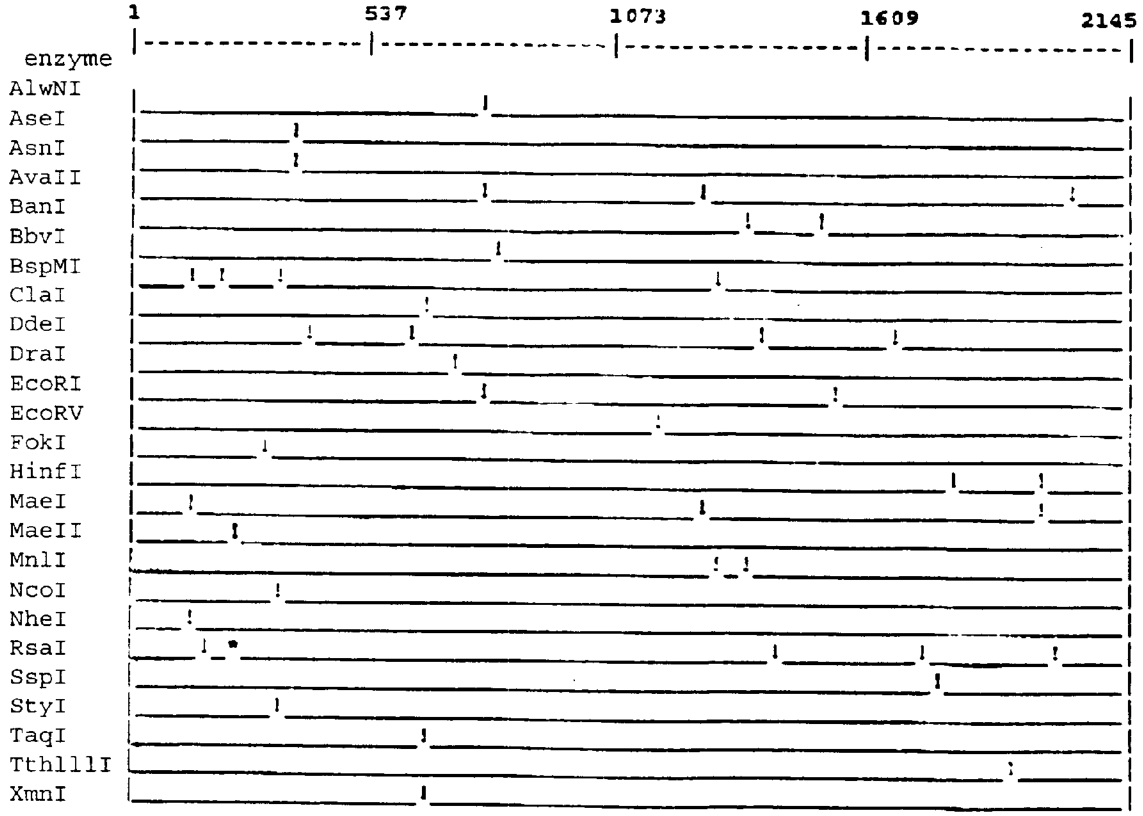

Fig. 29 Restriction map of *M. catarrhalis* strain 3 *tbpB* gene
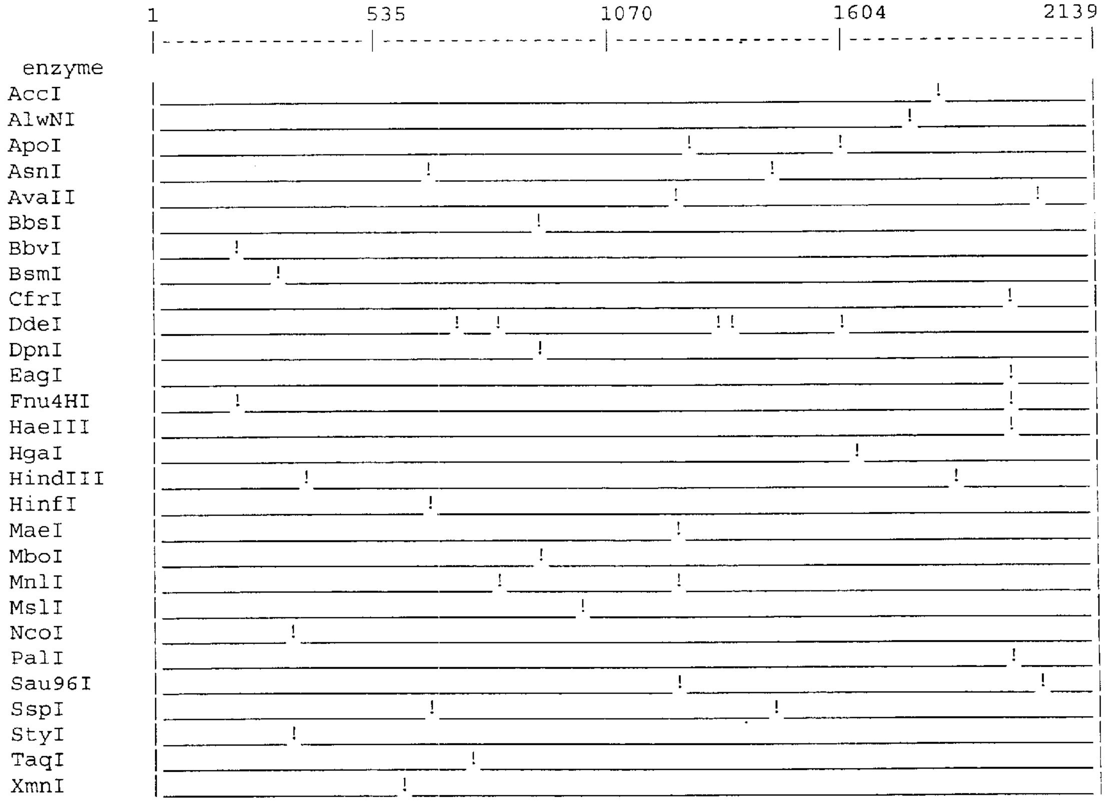
```
              1           535          1070         1604         2139
              |------------|------------|------------|------------|
   enzyme
   AccI       |_____!_____|
   AlwNI      |_____!___|
   ApoI       |_____!_____!_____|
   AsnI       |_____!_____!_____|
   AvaII      |_____!_____!__|
   BbsI       |_____!_____|
   BbvI       |____!_____|
   BsmI       |_____!_____|
   CfrI       |_____!___|
   DdeI       |_____!_!_____!!_____!_____|
   DpnI       |_____!_____|
   EagI       |_____!___|
   Fnu4HI     |____!_____!___|
   HaeIII     |_____!___|
   HgaI       |_____!_____|
   HindIII    |_____!_____!_____|
   HinfI      |_____!_____|
   MaeI       |_____!_____|
   MboI       |_____!_____|
   MnlI       |_____!_____!_____|
   MslI       |_____!_____|
   NcoI       |_____!_____|
   PalI       |_____!___|
   Sau96I     |_____!_____!__|
   SspI       |_____!_____!_____|
   StyI       |_____!_____|
   TaqI       |_____!_____|
   XmnI       |_____!_____|
```

Fig. 30 Restriction map of *M. catarrhalis* strain LES1 *tbpB* gene
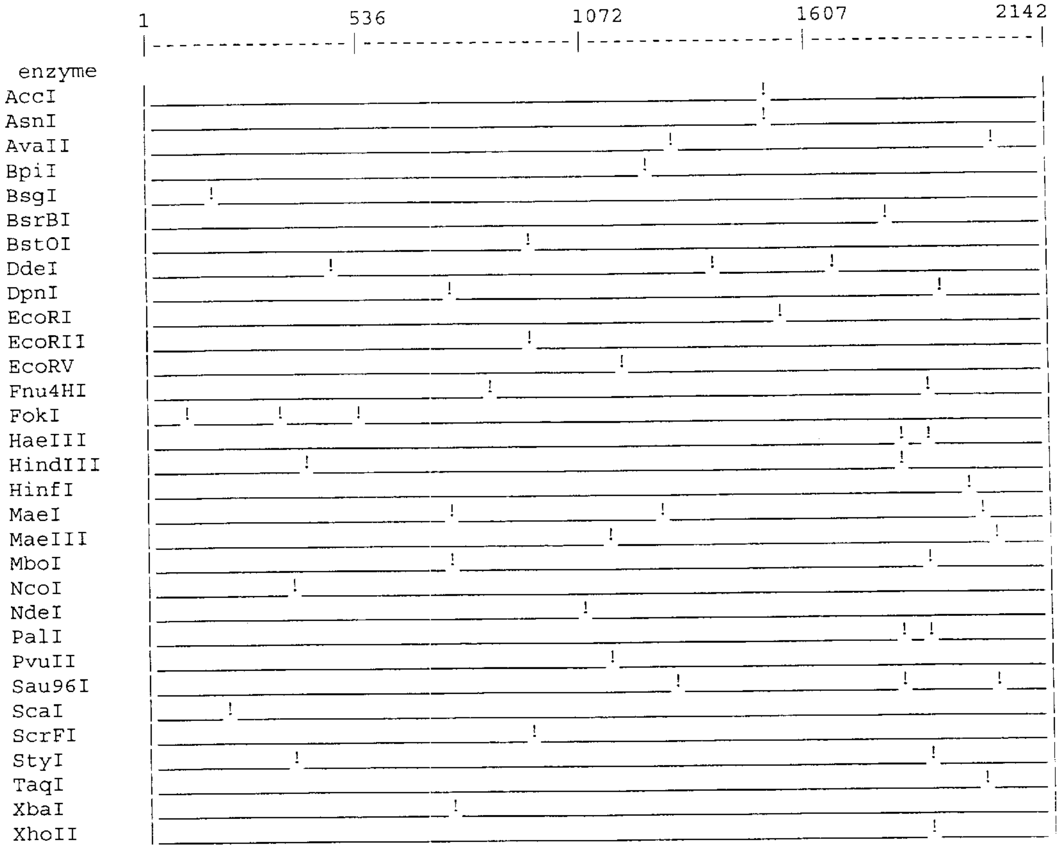

FIG.31A

Nucleotide and deduced amino acid sequence of M. catarrhalis R1 tbpB

AAATTTGCCGTATTTTGTCTATCATAAATGCATTTATCATCAATGCCCAAACAAATACGCCAAATGCACAT

TGTCAGCATGCCAAAATAGGCATTAACAGACTTTTTTAGATAATACCATCAACCCATCAGAGGATTATTTT 27 54
ATG AAA CAC ATT CCT TTA ACC ACA CTG TGT GTG GCA ATC TCT GCC GTC TTA TTA
MET Lys His Ile Pro Leu Thr Thr Leu Cys Val Ala Ile Ser Ala Val Leu Leu 81 108
ACC GCT TGT GGT GGC AGT GGT GGT TCA AAT CCA CCT GCT CCT ACG CCC ATT CCA
Thr Ala Cys Gly Gly Ser Gly Gly Ser Asn Pro Pro Ala Pro Thr Pro Ile Pro 135 162
AAT GCT AGC GGT TCA GGT AAT ACT GGC AAC ACT GGT AAT GCT GGC GGT ACT GAT
Asn Ala Ser Gly Ser Gly Asn Thr Gly Asn Thr Gly Asn Ala Gly Gly Thr Asp 189 216
AAT ACA GCC AAT GCA GGT AAT ACA GGC GGT ACA AGC TCT GGT ACA GGC AGT GCC
Asn Thr Ala Asn Ala Gly Asn Thr Gly Gly Thr Ser Ser Gly Thr Gly Ser Ala

FIG.31B

```
                              243                                       270
AGC ACG TCA GAA CCA AAA TAT CAA GAT GTG CCA ACA ACG CCC AAT AAC AAA GAA
Ser Thr Ser Glu Pro Lys Tyr Gln Asp Val Pro Thr Thr Pro Asn Asn Lys Glu

                                297                                     324
CAA GTT TCA TCC ATT CAA GAA CCT GCC ATG GGT TAT GGC ATG GCT TTG AGT AAA
Gln Val Ser Ser Ile Gln Glu Pro Ala MET Gly Tyr Gly MET Ala Leu Ser Lys

                                351                                     378
ATT AAT CTA TAC GAC CAA CAA GAC ACG CCA TTA GAT GCA AAA AAT ATC ATT ACC
Ile Asn Leu Tyr Asp Gln Gln Asp Thr Pro Leu Asp Ala Lys Asn Ile Ile Thr

                                405                                     432
TTA GAC GGT AAA AAA CAA GTT GCT GAC AAT CAA AAA TCA CCA TTG CCA TTT TCG
Leu Asp Gly Lys Lys Gln Val Ala Asp Asn Gln Lys Ser Pro Leu Pro Phe Ser

                                459                                     486
TTA GAT GTA GAA AAT AAA TTG CTT GAT GGC TAT ATA GCA AAA ATG AAT GAA GCG
Leu Asp Val Glu Asn Lys Leu Leu Asp Gly Tyr Ile Ala Lys MET Asn Glu Ala

                                513                                     540
GAT AAA AAT GCC ATT GGT GAA AGA ATT AAG AGA GAA AAT GAA CAA AAT AAA AAA
Asp Lys Asn Ala Ile Gly Glu Arg Ile Lys Arg Glu Asn Glu Gln Asn Lys Lys
```

FIG.31C

```
                                          567                                   594
ATA TCC GAT GAA GAA CTT GCC AAA AAA ATC AAA GAA AAT GTG CGT AAA AGC CCT
Ile Ser Asp Glu Glu Leu Ala Lys Lys Ile Lys Glu Asn Val Arg Lys Ser Pro

                                          621                                   648
GAG TTT CAG CAA GTA TTA TCA TCG ATA AAA GCG AAA ACT TTC CAT TCA AAT GAC
Glu Phe Gln Gln Val Leu Ser Ser Ile Lys Ala Lys Thr Phe His Ser Asn Asp

                                          675                                   702
AAA ACA ACC AAA GCA ACC ACA CGA GAT TTA AAA TAT GTT GAT TAT GGT TAC TAC
Lys Thr Thr Lys Ala Thr Thr Arg Asp Leu Lys Tyr Val Asp Tyr Gly Tyr Tyr

                                          729                                   756
TTG GTG AAT GAT GCC AAT TAT CTA ACC GTC AAA ACA GAC AAC CCA AAA CTT TGG
Leu Val Asn Asp Ala Asn Tyr Leu Thr Val Lys Thr Asp Asn Pro Lys Leu Trp

                                          783                                   810
AAT TCA GGT CCT GTG GGC GGT GTG TTT TAT AAT GGC TCA ACG ACC GCC AAA GAG
Asn Ser Gly Pro Val Gly Gly Val Phe Tyr Asn Gly Ser Thr Thr Ala Lys Glu

                                          837                                   864
CTG CCC ACA CAA GAT GCG GTC AAA TAT AAA GGA CAT TGG GAC TTT ATG ACC GAT
Leu Pro Thr Gln Asp Ala Val Lys Tyr Lys Gly His Trp Asp Phe MET Thr Asp
```

FIG.31D

```
                                                891                                         918
GTT GCC AAA AAA AGA AAC CGA TTT AGC GAA GTA AAA GAA ACC TAT CAA GCA GGC
Val Ala Lys Lys Arg Asn Arg Phe Ser Glu Val Lys Glu Thr Tyr Gln Ala Gly

                                                945                                         972
TGG TGG TAT GGG GCA TCT TCA AAA GAT GAA TAC AAC CGC TTA TTA ACC AAA GCA
Trp Trp Tyr Gly Ala Ser Ser Lys Asp Glu Tyr Asn Arg Leu Leu Thr Lys Ala

                                                999                                        1026
GAT GCC GCA CCT GAT AAT TAT AGC GGT GAA TAT GGT CAT AGC AGT GAA TTT ACT
Asp Ala Ala Pro Asp Asn Tyr Ser Gly Glu Tyr Gly His Ser Ser Glu Phe Thr

                                               1053                                        1080
GTT AAT TTT AAG GAA AAA AAA TTA ACA GGT GAG CTG TTT AGT AAC CTA CAA GAC
Val Asn Phe Lys Glu Lys Lys Leu Thr Gly Glu Leu Phe Ser Asn Leu Gln Asp

                                               1107                                        1134
AGC CAT AAA CAA AAA GTA ACC AAA ACA AAA CGC TAT GAT ATT AAG GCT GAT ATC
Ser His Lys Gln Lys Val Thr Lys Thr Lys Arg Tyr Asp Ile Lys Ala Asp Ile

                                               1161                                        1188
CAC GGC AAC CGC TTC CGT GGC AGT GCC ACC GCA AGC GAT AAG GCA GAA GAC AGC
His Gly Asn Arg Phe Arg Gly Ser Ala Thr Ala Ser Asp Lys Ala Glu Asp Ser
```

FIG.31E

```
                                                1215                                    1242
AAA AGC AAA CAC CCC TTT ACC AGC GAT GCC AAA GAT AAG CTA GAA GGT GGT TTT
Lys Ser Lys His Pro Phe Thr Ser Asp Ala Lys Asp Lys Leu Glu Gly Gly Phe

                                                1269                                    1296
TAT GGA CCA AAA GGC GAG GAG CTG GCA GGT AAA TTC TTA ACC GAT GAT AAC AAA
Tyr Gly Pro Lys Gly Glu Glu Leu Ala Gly Lys Phe Leu Thr Asp Asp Asn Lys

                                                1323                                    1350
CTC TTT GGT GTC TTT GGT GCC AAA CAA GAG GGT AAT GTA GAA AAA ACC GAA GCC
Leu Phe Gly Val Phe Gly Ala Lys Gln Glu Gly Asn Val Glu Lys Thr Glu Ala

                                                1377                                    1404
ATC TTA GAT GCT TAT GCA CTT GGG ACA TTT AAT AAA CCT GGT ACG ACC AAT CCC
Ile Leu Asp Ala Tyr Ala Leu Gly Thr Phe Asn Lys Pro Gly Thr Thr Asn Pro

                                                1431                                    1458
GCC TTT ACC GCT AAC AGC AAA AAA GAA CTG GAT AAC TTT GGC AAT GCC AAA AAG
Ala Phe Thr Ala Asn Ser Lys Lys Glu Leu Asp Asn Phe Gly Asn Ala Lys Lys

                                                1485                                    1512
TTG GTC TTG GGT TCT ACC GTC ATT GAT TTG GTG CCT ACT GAT GCC ACC AAA GAT
Leu Val Leu Gly Ser Thr Val Ile Asp Leu Val Pro Thr Asp Ala Thr Lys Asp
```

FIG.31F

```
                                       1539                              1566
GTC AAT GAA TTC AAA GAA AAG CCA AAG TCT GCC ACA AAC AAA GCG GGC GAA ACT
Val Asn Glu Phe Lys Glu Lys Pro Lys Ser Ala Thr Asn Lys Ala Gly Glu Thr

                                       1593                              1620
TTG ATG GTG AAT GAT GAA GTT AGC GTC AAA ACC TAT GGC AAA AAC TTT GAA TAC
Leu MET Val Asn Asp Glu Val Ser Val Lys Thr Tyr Gly Lys Asn Phe Glu Tyr

                                       1647                              1674
CTA AAA TTT GGT GAG CTT AGT GTC GGT GGT AGC CAT AGC GTC TTT TTA CAA GGC
Leu Lys Phe Gly Glu Leu Ser Val Gly Gly Ser His Ser Val Phe Leu Gln Gly

                                       1701                              1728
GAA CGC ACC GCT ACC ACA GGC GAG AAA GCC GTA CCA ACC ACA GGC AAA GCC AAA
Glu Arg Thr Ala Thr Thr Gly Glu Lys Ala Val Pro Thr Thr Gly Lys Ala Lys

                                       1755                              1782
TAT TTG GGG AAC TGG GTA GGA TAT ATC ACA GGA GCG GAC TCA TCA AAA GGC TCT
Tyr Leu Gly Asn Trp Val Gly Tyr Ile Thr Gly Ala Asp Ser Ser Lys Gly Ser

                                       1809                              1836
ACC GAT GGC AAA GGC TTT ACC GAT GCC AAA GAT ATT GCT GAT TTT GAC ATT GAC
Thr Asp Gly Lys Gly Phe Thr Asp Ala Lys Asp Ile Ala Asp Phe Asp Ile Asp
```

FIG.31G

```
                                    1863                                1890
TTT GAG AAA AAA TCA GTT AAT GGC AAA CTG ACC ACC AAA GAC CGC CAA GAC CCT
Phe Glu Lys Lys Ser Val Asn Gly Lys Leu Thr Thr Lys Asp Arg Gln Asp Pro

                                    1917                                1944
GTC TTT AAC ATC ACA GGT GAA ATC GCA GGC AAT GGC TGG ACA GGT AAA GCC AGC
Val Phe Asn Ile Thr Gly Glu Ile Ala Gly Asn Gly Trp Thr Gly Lys Ala Ser

                                    1971                                1998
ACC GCC GAA GCG AAC GCA GGG GGC TAT AAG ATA GAT TCT AGC AGT ACA GGC AAA
Thr Ala Glu Ala Asn Ala Gly Gly Tyr Lys Ile Asp Ser Ser Ser Thr Gly Lys

                                    2025                                2052
TCC ATC GTC ATC AAA GAT GCC GTG GTT ACA GGT GGC TTT TAT GGT CCA AAT GCA
Ser Ile Val Ile Lys Asp Ala Val Val Thr Gly Gly Phe Tyr Gly Pro Asn Ala

                                    2079                                2106
ACC GAG ATG GGT GGG TCA TTT ACA CAC AAC AGC GGT AAT GAT GGT AAA GTC TCT
Thr Glu MET Gly Gly Ser Phe Thr His Asn Ser Gly Asn Asp Gly Lys Val Ser

                                    2133
GTG GTC TTT GGC ACA AAA AAA CAA GAA GTT AAG AAG TGA
Val Val Phe Gly Thr Lys Lys Gln Glu Val Lys Lys  *
```

FIG.32A

*M. catarrhalis* strain 3 *tbpB* sequence

```
MET   LYS   HIS   ILE   PRO   LEU   THR   THR   LEU   CYS ...
A T G A A A C A C A T T C C T T T A A C C A C A C T G T G T...
                  10                   20                  30...
                 ... VAL   ALA   ILE   SER   ALA   VAL   LEU   LEU   THR   ALA
                 ... G T G G C A A T C T C T G C C G T C T T A T T A A C C G C T
                 ...                40                   50                   60

CYS   GLY   GLY   SER   GLY   GLY   SER   ASN   PRO   PRO ...
T G T G G T G G C A G T G G T G G T T C A A A T C C A C C T...
                  70                   80                  90...
                 ... ALA   PRO   THR   PRO   ILE   PRO   ASN   ALA   GLY   GLY
                 ... G C T C C T A C G C C C A T T C C A A A T G C A G G C G G T
                 ...                100                  110                  120

ALA   GLY   ASN   ALA   GLY   SER   GLY   THR   GLY   GLY ...
G C A G G T A A T G C T G G T A G C G G T A C T G G C G G T...
                 130                  140                  150...
                 ... ALA   GLY   SER   THR   ASP   ASN   ALA   ALA   ASN   ALA
                 ... G C A G G T A G C A C T G A T A A T G C A G C C A A T G C A
                 ...                160                  170                  180
```

FIG.32B

```
GLY  SER  THR  GLY  GLY  ALA  SER  SER  GLY  THR ...
G G C A G T A C A G G C G G T G C A A G C T C T G G T A C A...
              190            200            210...
                  ... GLY  SER  ALA  SER  THR  GLN  LYS  PRO  LYS  TYR
                  ... G G C A G T G C C A G C A C A C A A A A A C C A A A A T A T
                  ...            220            230            240

GLN  ASP  VAL  PRO  THR  ASP  LYS  ASN  LYS  LYS ...
C A A G A T G T G C C A A C C G A T A A A A A T A A A A A A...
              250            260            270...
                  ... ASP  GLU  VAL  SER  GLY  ILE  GLN  GLU  PRO  ALA
                  ... G A T G A A G T G T C A G G C A T T C A A G A A C C T G C C
                  ...            280            290            300

MET  GLY  TYR  GLY  VAL  GLU  LEU  LYS  LEU  ARG ...
A T G G G T T A T G G C G T G G A A T T A A A G C T T C G T...
              310            320            330...
                  ... ASN  TRP  ILE  PRO  GLN  GLU  GLN  GLU  GLU  HIS
                  ... A A C T G G A T A C C A C A A G A A C A G G A A G A A C A T
                  ...            340            350            360

ALA  LYS  ILE  ASN  THR  ASN  ASP  VAL  VAL  LYS ...
G C C A A A A T C A A T A C A A A T G A T G T T G T A A A A...
              370            380            390...
```

FIG.32C

```
                          ... LEU GLU GLY ASP LEU LYS HIS ASN PRO PHE
                          ... C T T G A A G G T G A C T T G A A G C A T A A T C C A T T T
                          ...                 400                 410                 420

ASP ASN SER ILE TRP GLN ASN ILE LYS ASN ...
G A C A A C T C T A T T T G G C A A A A C A T C A A A A A T...
            430                 440                 450...
                          ... SER LYS GLU VAL GLN THR VAL TYR ASN GLN
                          ... A G C A A A G A A G T A C A A A C T G T T T A C A A C C A A
                          ...                 460                 470                 480

GLU LYS GLN ASN ILE GLU ASN GLN ILE LYS ...
G A G A A G C A A A A C A T T G A A A A T C A A A T C A A A...
            490                 500                 510...
                          ... LYS GLU ASN LYS GLU LEU ASP LYS THR ALA
                          ... A A A G A A A A T A A A G A A C T T G A T A A A A C G G C A
                          ...                 520                 530                 540

LEU LYS ALA LEU ILE GLU LYS VAL LEU ASP ...
C T A A A A G C T C T T A T T G A A A A A G T T C T T G A T...
            550                 560                 570...
                          ... ASP TYR LEU THR SER LEU ALA LYS PRO ILE
                          ... G A C T A T C T A A C A A G T C T T G C T A A A C C C A T T
                          ...                 580                 590                 600
```

FIG.32D

```
TYR  GLU  LYS  ASN  ILE  ASN  ASP  SER  HIS  ASP ...
T A T G A A A A A A A T A T T A A T G A T T C A C A T G A T...
              610                620                630...
       ... LYS  GLN  ASN  LYS  ALA  ARG  THR  ARG  ASP  LEU
       ... A A G C A G A A T A A A G C A C G C A C T C G T G A T T T G
       ...                 640                650                660

LYS  TYR  VAL  ARG  SER  GLY  TYR  ILE  TYR  ARG ...
A A G T A T G T G C G T T C T G G T T A T A T T T A T C G C...
              670                680                690...
       ... SER  GLY  TYR  SER  ASN  ILE  ASP  ILE  GLN  LYS
       ... T C A G G T T A T T C T A A T A T C G A C A T T C A A A A G
       ...                 700                710                720

LYS  ILE  ALA  LYS  THR  GLY  PHE  ASP  GLY  ALA ...
A A A A T A G C T A A A A C T G G T T T T G A T G G T G C T...
              730                740                750...
       ... LEU  PHE  TYR  LYS  GLY  THR  GLN  THR  ALA  LYS
       ... T T A T T T T A T A A A G G T A C A C A A A C T G C T A A A
       ...                 760                770                780

GLN  LEU  PRO  VAL  SER  GLU  VAL  LYS  TYR  LYS ...
C A A T T G C C T G T A T C T G A G G T T A A G T A T A A A...
              790                800                810...
```

FIG.32E

... GLY THR TRP ASP PHE MET THR ASP ALA LYS
... G G C A C T T G G G A T T T T A T G A C C G A T G C C A A A
... 820 830 840

LYS GLY GLN SER PHE SER SER PHE GLU ARG ...
A A A G G A C A A T C A T T T A G C A G T T T T G A A A G A...
850 860 870...

... ARG ALA GLY ASP ARG TYR SER ALA MET SER
... C G A G C T G G T G A T C G C T A T A G T G C A A T G T C T
... 880 890 900

SER HIS GLU TYR PRO SER LEU LEU THR ASP ...
T C C C A T G A G T A C C C A T C T T T A T T A A C T G A T...
910 920 930...

... ASP LYS ASN LYS PRO ASP ASN TYR ASN ASP
... G A T A A A A A C A A A C C A G A T A A T T A T A A C G A T
... 940 950 960

GLU TYR GLY HIS SER SER GLU PHE THR VAL ...
G A A T A T G G T C A T A G C A G T G A G T T T A C G G T A...
970 980 990...

... ASP PHE SER LYS LYS SER LEU THR GLY GLY
... G A T T T T A G T A A A A A G A G C C T A A C A G G T G G G
... 1000 1010 1020

FIG.32F

```
LEU   PHE   SER   ASN   LEU   GLN   ASP   HIS   HIS   LYS ...
C T G T T T A G T A A C C T A C A A G A C C A C C A T A A G...
            1030                  1040                  1050...
                        ... GLY   LYS   VAL   THR   LYS   THR   LYS   ARG   TYR   ASP
                        ... G G C A A G G T T A C G A A A A C C A A A C G C T A T G A C
                        ...             1060                  1070                  1080

ILE   ASN   ALA   ARG   ILE   HIS   GLY   ASN   ARG   PHE ...
A T C A A T G C C C G T A T C C A C G G T A A C C G C T T C...
            1090                  1100                  1110...
                        ... ARG   GLY   SER   ALA   THR   ALA   ILE   ASN   LYS   ASP
                        ... C G T G G C A G T G C C A C C G C A A T C A A T A A A G A T
                        ...             1120                  1130                  1140

ASN   GLU   SER   LYS   ALA   LYS   HIS   PRO   PHE   THR ...
A A T G A A A G C A A A G C C A A A C A C C C C T T T A C C...
            1150                  1160                  1170...
                        ... SER   ASP   ALA   ASP   ASN   ARG   LEU   GLU   GLY   GLY
                        ... A G C G A T G C C G A C A A T A G G C T A G A A G G C G G T
                        ...             1180                  1190                  1200

PHE   TYR   GLY   PRO   ASN   ALA   GLU   GLU   LEU   ALA ...
T T T T A T G G A C C A A A C G C C G A G G A G C T G G C A...
            1210                  1220                  1230...
```

FIG.32G

... GLY LYS PHE LEU THR ASP ASP ASN LYS LEU
... G G T A A A T T C C T A A C C G A T G A C A A C A A A C T C
... 1240 1250 1260

PHE GLY VAL PHE GLY ALA LYS GLN GLU SER ...
T T T G G T G T C T T T G G T G C T A A A C A A G A G A G T...
1270 1280 1290...

... GLU ALA LYS GLU THR GLU ALA ILE LEU ASP
... G A A G C T A A G G A A A C C G A A G C C A T C T T A G A T
... 1300 1310 1320

ALA TYR ALA LEU GLY THR PHE ASN LYS SER ...
G C T T A T G C A C T T G G G A C A T T T A A T A A A T C T...
1330 1340 1350...

... GLY THR THR ASN PRO ALA PHE THR ALA ASN
... G G T A C G A C C A A T C C T G C C T T T A C C G C C A A T
... 1360 1370 1380

SER LYS LYS GLU LEU ASP ASN PHE GLY ASN ...
A G T A A A A A A G A A C T G G A T A A C T T T G G C A A T...
1390 1400 1410...

... ILE ASN LYS LEU VAL LEU GLY SER THR VAL
... A T T A A T A A A T T G G T C T T G G G T T C T A C T G T G
... 1420 1430 1440

FIG.32H

```
ILE   ASP   LEU   THR   GLN   GLY   ASN   ASP   PHE   VAL ...
A T A G A C C T T A C T C A A G G T A A T G A T T T T G T A...
              1450                1460                1470...
                ...  LYS   THR   ILE   ASP   LYS   GLU   LYS   PRO   ALA   THR
                ... A A A A C C A T T G A T A A A G A A A A G C C A G C C A C C
                ...              1480                1490                1500

THR   THR   ASN   GLN   ALA   GLY   GLU   PRO   LEU   THR ...
A C T A C C A A T C A A G C A G G C G A G C C T T T G A C G...
              1510                1520                1530...
                ...  VAL   ASN   ASP   LYS   VAL   ARG   VAL   GLN   VAL   CYS
                ... G T G A A T G A T A A G G T T C G G G T A C A A G T T T G T
                ...              1540                1550                1560

CYS   SER   ASN   LEU   GLU   HIS   LEU   LYS   PHE   GLY ...
T G T A G C A A T C T T G A G C A T C T A A A A T T T G G C...
              1570                1580                1590...
                ...  SER   LEU   SER   ILE   GLY   ASP   SER   ASN   SER   VAL
                ... T C A C T G A G T A T C G G T G A T A G T A A T A G C G T C
                ...              1600                1610                1620

PHE   LEU   GLN   GLY   GLU   ARG   THR   ALA   THR   LYS ...
T T T T T A C A A G G T G A A C G C A C C G C T A C C A A A...
              1630                1640                1650...
```

FIG.32I

```
                          ... GLY ASP LYS ASP LYS ALA MET PRO VAL ALA
                          ... G G T G A T A A A G A T A A A G C C A T G C C A G T T G C A
                          ...             1660              1670              1680

GLY ASN ALA LYS TYR ARG GLY THR TRP ALA ...
G G A A A T G C T A A A T A C C G T G G T A C A T G G G C A...
            1690              1700              1710...
                          ... GLY TYR VAL ALA GLY SER GLY ASN THR SER
                          ... G G C T A T G T T G C A G G C T C T G G C A A T A C C A G C
                          ...             1720              1730              1740

LYS ALA TYR GLU ALA GLN GLN PHE ALA ASP ...
A A A G C C T A T G A A G C C C A A C A A T T T G C T G A C...
            1750              1760              1770...
                          ... ASN ALA ASN ARG ALA GLU PHE ASP VAL ASP
                          ... A A T G C C A A C C G T G C C G A G T T T G A T G T A G A C
                          ...             1780              1790              1800

PHE ALA ASN LYS SER LEU THR GLY LYS LEU ...
T T T G C T A A C A A A A G C C T A A C T G G T A A G C T T...
            1810              1820              1830...
                          ... ILE PRO ASN THR SER SER ASP GLY LYS SER
                          ... A T T C C A A A T A C G A G C A G T G A T G G T A A A T C T
                          ...             1840              1850              1860
```

FIG.32J

```
ALA  PHE  ASP  ILE  THR  ALA  THR  ILE  ASP  GLY ...
G C T T T T G A T A T T A C T G C T A C A A T T G A T G G C...
            1870                     1880                     1890...
              ... ASN  GLY  PHE  SER  GLY  LYS  ALA  ASN  THR  PRO
              ... A A T G G T T T T A G T G G T A A A G C C A A T A C A C C A
              ...                   1900                     1910                     1920

ASP  ILE  GLU  THR  GLY  GLY  LEU  LYS  ILE  ASP ...
G A T A T T G A A A C A G G T G G G T T A A A G A T T G A C...
            1930                     1940                     1950...
              ... SER  LYS  ASN  SER  GLU  SER  GLY  ARG  VAL  ILE
              ... A G T A A G A A C A G T G A A A G C G G C C G A G T A A T T
              ...                   1960                     1970                     1980

VAL  LYS  ASP  ALA  ILE  VAL  ILE  GLY  GLY  PHE ...
G T G A A A G A T G C T A T A G T T A T A G G T G G C T T T...
            1990                     2000                     2010...
              ... TYR  GLY  PRO  GLN  ALA  ASN  GLU  LEU  GLY  GLY
              ... T A T G G T C C A C A A G C T A A T G A A C T G G G T G G C
              ...                   2020                     2030                     2040

SER  PHE  THR  TYR  LYS  SER  ASN  ASP  ALA  GLY ...
T C A T T T A C C T A C A A G A G C A A T G A T G C T G G A...
            2050                     2060                     2070...
```

FIG.32K

```
... ASN GLN ASP LYS ASP SER SER ALA SER VAL
... A A T C A A G A C A A A G A C A G T A G T G C A T C T G T G
                  2080                2090                2100
...

VAL PHE GLY ALA ARG LYS GLN GLN GLU VAL ...
G T C T T T G G T G C A A G A A A A C A A C A A G A A G T C...
            2110                2120                2130

... LYS PRO ***
... A A A C C A T G A
```

FIG.33A

*M. catarrhalis* strain LES1 *tbpB* sequence

```
MET LYS HIS ILE PRO LEU THR THR LEU CYS
A T G A A A C A C A T T C C T T T A A C C A C A C T G T G T
                  10                  20                  30
... VAL ALA ILE SER ALA VAL LEU LEU THR ALA
... G T G G C A A T C T C T G C C G T C T T A T T A A C C G C T
...                  40                  50                  60

CYS GLY GLY SER GLY GLY SER ASN PRO PRO ...
T G T G G T G G C A G T G G T G G T T C A A A T C C A C C T...
                  70                  80                  90...
... ALA PRO THR PRO ILE PRO ASN ALA GLY SER
... G C T C C T A C G C C C A T C C C A A A T G C A G G C A G T
...                 100                 110                 120

ALA GLY ASN ALA GLY GLY THR GLY ASN THR ...
G C A G G T A A T G C T G G C G G T A C A G G A A A T A C A...
                 130                 140                 150...
... GLY GLY THR GLY SER THR ASP ASN VAL GLY
... G G C G G T A C T G G C A G T A C T G A T A A T G T A G G C
...                 160                 170                 180
```

FIG.33B

```
ASN   ALA   GLY   GLY   ALA   ASN   SER   GLY   THR   GLY ...
A A T G C T G G C G G T G C A A A C T C T G G T A C A G G C...
                190                     200                     210...
                          ...  ASN   ALA   GLY   ASN   SER   GLY   ASN   ALA   ASN   SER
                          ... A A T G C A G G T A A T T C A G G T A A T G C A A A C T C T
                          ...                     220                     230                     240

GLY   THR   GLY   SER   ALA   ASN   THR   PRO   GLU   PRO ...
G G T A C A G G C A G T G C C A A C A C A C C A G A A C C A...
                250                     260                     270...
                          ...  LYS   TYR   GLN   ASP   VAL   PRO   THR   ASP   LYS   ASN
                          ... A A A T A T C A A G A T G T G C C A A C C G A T A A A A A T
                          ...                     280                     290                     300

GLU   LYS   GLU   GLN   VAL   SER   SER   ILE   GLN   GLU ...
G A A A A A G A A C A A G T T T C A T C C A T T C A A G A A...
                310                     320                     330
                          ...  PRO   ALA   MET   GLY   TYR   ALA   MET   GLU   LEU   LYS
                          ... C C T G C C A T G G G T T A T G C A A T G G A A T T A A A G
                          ...                     340                     350                     360

LEU   ARG   ASN   ALA   HIS   PRO   LEU   ASN   PRO   ASN ...
C T T C G T A A T G C T C A C C C T C T T A A C C C A A A T...
                370                     380                     390...
```

FIG.33C

```
... LYS ASN LYS GLU ALA GLU LYS ARG ILE ALA
... A A A A A T A A A G A G G C T G A A A A A C G C A T T G C C
...                   400                 410                 420

LEU ASP GLN LYS ASP LEU VAL ALA VAL GLU ...
T T A G A C C A A A A A G A T T T G G T G G C A G T A G A G...
                430                 440                 450...
... GLY ASP LEU THR ASN ILE PRO PHE ASP LYS
... G G C G A C C T A A C C A A C A T T C C T T T T G A T A A A
...                   460                 470                 480

ASN LEU ILE GLU TYR LEU LYS LYS SER SER ...
A A T C T T A T T G A A T A C C T T A A A A A A T C A T C C...
                490                 500                 510...
... GLU VAL VAL SER LYS PHE GLU ALA GLN LYS
... G A G G T T G T A A G T A A A T T T G A A G C A C A A A A A
...                   520                 530                 540

GLY GLY ILE GLU ASN ASN THR ARG LEU THR ...
G G C G G T A T T G A A A A T A A C A C A A G A C T G A C A...
                550                 560                 570...
... HIS LYS ASP LEU SER SER GLU GLN LYS GLU
... C A C A A A G A T T T A T C A T C A G A G C A A A A A G A A
...                   580                 590                 600
```

FIG.33D

```
ALA  LYS  VAL  LYS  GLU  ALA  LEU  ASP  ASN  ALA ...
G C A A A A G T C A A A G A A G C G T T G G A C A A T G C T...
              610                 620                 630...
                 ... LEU  THR  GLN  PHE  ALA  GLN  GLU  LYS  TYR  LYS
                 ... T T A A C T C A A T T T G C C C A A G A A A A A T A C A A G
                 ...                640                 650                 660

GLU  LEU  ILE  GLU  ASN  ALA  HIS  ASP  LYS  LYS ...
G A G C T A A T T G A G A A C G C C C A T G A T A A A A A A...
              670                 680                 690...
                 ... SER  ASP  ALA  ARG  ASN  ARG  ASP  LEU  GLU  TYR
                 ... T C T G A C G C A C G C A A C C G T G A T C T A G A A T A T
                 ...                700                 710                 720

VAL  LYS  SER  GLY  PHE  ASN  TYR  LEU  SER  GLY ...
G T C A A G T C T G G T T T T A A C T A T C T T T C T G G A...
              730                 740                 750...
                 ... TYR  THR  ALA  THR  ASP  HIS  ASP  LYS  LYS  THR
                 ... T A T A C C G C C A C C G A C C A C G A C A A A A A A A C C
                 ...                760                 770                 780

ASN  TYR  ARG  GLY  TYR  TYR  GLY  ALA  LEU  TYR ...
A A T T A T C G T G G C T A T T A T G G T G C G T T G T A T...
              790                 800                 810...
```

FIG.33E

```
                    ... TYR LYS GLY SER GLU THR ALA LYS GLU LEU
                    ... T A T A A A G G C A G C G A A A C C G C C A A A G A G C T A
                    ...                    820                 830                 840

PRO GLN THR SER ALA LYS TYR LYS GLY TYR ...
C C A C A A A C A A G T G C A A A A T A T A A A G G T T A T...
                850                 860                 870...
                    ... TRP ASP PHE MET THR ASP ALA THR LEU ASP
                    ... T G G G A C T T T A T G A C A G A T G C C A C A C T T G A T
                    ...                    880                 890                 900

ASN LYS TYR THR ASP LEU PRO GLY ILE ALA ...
A A C A A A T A C A C G G A T T T G C C A G G T A T C G C C...
                910                 920                 930...
                    ... ARG GLN THR GLN TRP ARG SER LEU VAL SER
                    ... A G A C A A A C C C A G T G G C G T A G T C T T G T T T C T
                    ...                    940                 950                 960

THR ASP GLU TYR ALA THR LEU LEU THR ASP ...
A C T G A T G A G T A T G C A A C G C T C T T G A C A G A C...
                970                 980                 990...
                    ... LYS ASN ASN LYS PRO SER ASP TYR ASN GLY
                    ... A A A A A T A A C A A G C C C A G T G A T T A C A A T G G T
                    ...                   1000                1010                1020
```

FIG.33F

```
ALA TYR GLY HIS SER SER GLU PHE ASP VAL ...
GCATATGGTCATAGCAGTGAATTTGATGTT...
1030 1040 1050...
... ASN PHE ALA ASP LYS LYS ILE LYS GLY LYS
...AATTTTGCTGATAAAAAAATTAAAGGCAAA
... 1060 1070 1080

LEU ILE SER ASN GLN LEU SER GLY THR ALA ...
CTTATCAGTAATCAGTTATCAGGCACAGCT...
1090 1100 1110...
... VAL THR ALA LYS GLU ARG TYR LYS ILE GLU
...GTAACCGCCAAAGAGCGTTATAAAATAGAA
... 1120 1130 1140

ALA ASP ILE HIS GLY ASN ARG PHE ARG GLY ...
GCTGATATCCACGGCAACCGCTTCCGTGGC...
1150 1160 1170...
... SER ALA THR ALA SER ASP LYS ALA GLU ASP
...AGTGCCACCGCAAGCGATAAAGCAGAAGAC
... 1180 1190 1200

SER LYS THR GLN HIS PRO PHE THR SER ASP ...
AGCAAAACCCAACACCCCTTTACCAGCGAT...
1210 1220 1230...
```

FIG.33G

```
                   ... ALA THR ASN LYS LEU GLU GLY GLY PHE TYR
                   ... G C T A C A A A C A A G C T A G A A G G T G G T T T T T A T
                   ...                 1240                1250                1260

GLY PRO LYS GLY GLU GLU LEU ALA GLY LYS ...
G G A C C A A A A G G C G A G G A G C T G G C A G G T A A A...
              1270                1280                1290...
                   ... PHE LEU THR ASP ASP ASN LYS LEU PHE GLY
                   ... T T C T T A A C C G A T G A C A A C A A A C T C T T T G G G
                   ...                 1300                1310                1320

VAL PHE GLY ALA LYS ARG ASP LYS VAL GLU ...
G T C T T T G G T G C T A A A C G A G A T A A A G T A G A A...
              1330                1340                1350...
                   ... LYS THR GLU ALA ILE LEU ASP ALA TYR ALA
                   ... A A A A C C G A A G C C A T C T T A G A T G C C T A T G C A
                   ...                 1360                1370                1380

LEU GLY THR PHE ASN ASN THR ASN LYS ALA ...
C T T G G G A C A T T T A A T A A T A C A A A T A A A G C A...
              1390                1400                1410...
                   ... THR THR PHE THR PRO PHE THR LYS LYS GLN
                   ... A C C A C A T T C A C C C C A T T T A C C A A A A A A C A A
                   ...                 1420                1430                1440
```

FIG.33H

```
LEU  ASP  ASN  PHE  GLY  ASN  ALA  LYS  LYS  LEU ...
C T G G A T A A C T T T G G C A A T G C C A A A A A G T T G...
          1450                1460                1470...
                    ... VAL  LEU  GLY  SER  THR  VAL  ILE  ASN  LEU  VAL
                    ... G T C T T G G G T T C T A C C G T C A T T A A T T T G G T G
                    ...             1480                1490                1500

SER  THR  ASP  ALA  THR  LYS  ASN  GLU  PHE  THR ...
T C T A C C G A T G C C A C C A A A A A T G A A T T C A C C...
          1510                1520                1530...
                    ... LYS  LYS  PHE  THR  LYS  ASP  LYS  PRO  THR  SER
                    ... A A A A A A T T C A C C A A A G A C A A G C C A A C T T C T
                    ...             1540                1550                1560

ALA  THR  ASN  LYS  ALA  GLY  GLU  THR  LEU  MET ...
G C C A C A A A C A A A G C G G G C G A G A C T T T G A T G...
          1570                1580                1590...
                    ... VAL  ASN  ASP  GLU  VAL  ILE  VAL  LYS  THR  TYR
                    ... G T G A A T G A T G A A G T T A T C G T C A A A A C C T A T
                    ...             1600                1610                1620

GLY  LYS  ASN  PHE  GLU  TYR  LEU  LYS  PHE  GLY ...
G G C A A A A A C T T T G A A T A C C T A A A A T T T G G T...
          1630                1640                1650...
```

FIG.33I

```
                    ... GLU LEU SER VAL GLY ASP SER HIS SER VAL
                    ... G A G C T T A G T G T C G G T G A T A G C C A T A G C G T C
                    ...            1660           1670           1680

PHE LEU GLN GLY GLU ARG THR ALA THR THR ...
T T T T T A C A A G G C G A A C G C A C C G C T A C C A C A...
        1690           1700           1710...
                    ... GLY GLU LYS ALA VAL PRO THR THR GLY LYS
                    ... G G C G A G A A A G C C G T A C C A A C C A C A G G C A A A
                    ...            1720           1730           1740

ALA LYS TYR LEU GLY ASN TRP VAL GLY TYR ...
G C C A A A T A T C T G G G G A A C T G G G T A G G A T A C...
        1750           1760           1770...
                    ... ILE THR GLY ALA GLY THR GLY LYS SER PHE
                    ... A T C A C A G G A G C G G G C A C A G G A A A A A G C T T T
                    ...            1780           1790           1800

ASN GLU ALA GLN ASP ILE ALA ASP PHE ASP ...
A A T G A G G C C C A A G A T A T T G C T G A T T T T G A C...
        1810           1820           1830...
                    ... ILE ASP PHE GLU ARG LYS SER VAL LYS GLY
                    ... A T T G A C T T T G A G A G A A A A T C A G T T A A A G G C
                    ...            1840           1850           1860
```

FIG.33J

```
LYS   LEU   THR   THR   GLN   GLY   ARG   THR   ASP   PRO ...
A A A C T G A C C A C C C A A G G C C G C A C A G A T C C T...
              1870                1880                1890...
                      ... VAL   PHE   ASN   ILE   LYS   GLY   GLU   ILE   ALA   GLY
                      ... G T C T T T A A C A T C A A A G G T G A A A T T G C A G G C
                      ...             1900                1910                1920

ASN   GLY   TRP   THR   GLY   LYS   ALA   SER   THR   THR ...
A A T G G C T G G A C A G G C A A A G C C A G C A C C A C C...
              1930                1940                1950...
                      ... LYS   ALA   ASP   ALA   GLY   GLY   TYR   LYS   ILE   ASP
                      ... A A A G C G G A C G C A G G A G G C T A C A A G A T A G A T
                      ...             1960                1970                1980

SER   SER   SER   THR   GLY   LYS   SER   ILE   VAL   ILE ...
T C T A G C A G T A C A G G C A A A T C C A T C G T C A T C...
              1990                2000                2010...
                      ... GLU   ASN   ALA   GLU   VAL   THR   GLY   GLY   PHE   TYR
                      ... G A A A A T G C C G A A G T T A C T G G G G G C T T T T A T
                      ...             2020                2030                2040

GLY   PRO   ASN   ALA   ASN   GLU   MET   GLY   GLY   SER ...
G G T C C A A A T G C A A A C G A G A T G G G C G G G T C A...
              2050                2060                2070...
```

FIG.33K

```
... PHE   THR   HIS   ASP   THR   ASP   ASP   SER   LYS   ALA
... T T T A C A C A C G A T A C C G A T G A C A G T A A A G C C
...               2080                2090                2100

SER   VAL   VAL   PHE   GLY   THR   LYS   ARG   GLN   GLN ...
T C T G T G G T C T T T G G C A C A A A A A G A C A A C A A...
              2110                2120                2130...
... GLU   VAL   LYS   ***
... G A A G T T A A G T A G
...               2140
```

FIG.34A

Alignment of *M. catarrhalis* TbpB protein sequences

```
10        20         30        40        50         60  ...
MKHIPLTTLCVAISAVLLTACGGSGGS-NPPAPTPIPNASGSGNTGN-TGNAGGTD...
..........................-...................-...........
..........................-...................-...........
..........................-...........GSA..A.G-...T...G...
.......................S.GF....S......GN...A..-A......G...
..........................-...........G.A..A.SG..G..S.....
                      ...                      70        80        90        100
                      ...NTAN-AGNTGGT-------------NSGTGSANTPEPKYQDVPTEKNEKDKVSSIQEPAM  4223
                      .......-.......-------------S......S.S.........TP.N.EQ.........  R1
                      .......-.......-------------..............K....DE.K..E..G......  M35
                      ...S.D.-V..A..ANSGTGNAGNSGNA...................D....EQ.........  LES1
                      ...GANSG...A...----------GGA...A...S......K....DE.K.AE..G......  Q8
                      ....A..-..S...A-------------S......S.QK........D..K..E..G......  3

      110        120        130        140        150  ...
GYGMALSKINLHNRQDTPLDEKNI-ITLDGKKQVA-EGKKSPLPFSLDVENKLLDG...
...........YDQ......A...-...........-DNQ....................
........M...KQ........D.-...........-K.E....................
..A.E.KLR.A.PLNPNKNK.AEKR.A..Q.DL..V..DLTNI..DKNLIEY.KKS...
...VE.KLR.WIPQ-------.QEEHAKINTNDV.KL..DLKHN..DNSIWQNIKNS...
...VE.KLR.WIPQ-------.QEEHAKINTNDV.KLEGDLKHN..DNSIWQNIKNS...
```

FIG.34B

```
...    160         170          180         190       200
...YIAKMNV-ADKNAIGDRIKKG---NKEISDE--ELAKQIKEAVRKSHEFQQV--   4223
.........E-.......E...RENEQ..K....--....K...N....P.....--   R1
.........E-...........D---..DK.LSKA........D.........--   M35
...SEVVSKFE.Q.GG.ENNIRLT---H.DL.S.QKE-..-V...---LDNALT.FA   LES1
...KEVQIVYNQE.QN.EDQ..RE---..QRP.KK.DDVALQAYIEKVLDDRLTELA   Q8
...KEVQIVYNQE.QN.ENQ...E---...------LDKTALKALIEKVLDDYLTSLA   3

   210         220         230         240          250    ...
LSSLENKIFHSNDGTTKATTRDLKYVDYGYYLANDGNYLTVKTD--KLWNLGPVGG...
...IKA.T.....K.................V..A........NP....S........
....K.................Q.......V...........-E............
QEKYKEL.ENAH.KKSD.RN...E..KS.FNYLSGYTATDHDK---.TNYR.YY.A...
KPIY.KN.NY.H.KQN..R.......RS..IYRSGYSNIIP.----.IAKT.FD.A...
KPIY.KN.ND.H.KQN..R.......RS..IYRSGYSNIDIQK---.IAKT.FD.A...

...    260         270         280         290         300
...VFYNGTTTAKELPTQDAVKYKGHWDFMIDVANRRNRFSEVKENSQA   4223
........S......................KK.........TY..   R1
...............................KQ..........L..   M35
...LY.K.SE......QTS.-....Y......ATLDNKYTDLPGIAR.T   LES1
...L..Q..Q...Q..VSQ-.....T......AKKGQSFS.FGTSQRL.   Q8
...L..K..Q...Q..VSE-.....T......AKKGQSFS.FERRAGDR   3
```

FIG.34C

```
        310        320        330        340        350       ...
GWYYGASSKDEYNRLLTKEDSAPDGHSGEYGHSSEFTVNFKEKKLTGKLFSNLQDR...
..W...............A.A...NY....................E.......S...
.R...............D.KNK.ERYN.............D.....E.......S...
Q.-RSLV.T...AT...DKNNK.SDYN.A.......D...AD..IK...I..QLSG...
.DR.S.M.YH..PS...D.KNK..NYN...........D.SK.S.K.E.S..I..G...
--.SAM..H-..PS...DDKNK..NYND..........D.SK.S...G.......H...
                      ... 360       370       380       390        400
                      ...HKGNVTKTERYDIDANIHGNRFRGSATASNKNDTSK--HPFTSDAN   4223
                      .....QK....K....K.D.............D.AED..SK.......K   R1
                      ...R.......K.........Y..........D.AEA..TK.......K   M35
                      ...--TA..AK...K.E.D.............D.AED..TQ.......T   LES1
                      ......S.N..K........Y...........DTTEA..SK.......K   Q8
                      ......K....K....N.R............I..DNE..AK.......D   3

        410        420        430        440        450       ...
NRLEGGFYGPKGEELAGKFLTNDNKLFGVFGAKRESKAEEKTEAILDAYALGTFNT...
DK.................D..........Q.GNV-................K...
.S........NA..........................G.............K...
.K.................D...........D-.V-................N...
.S........NA.........................E.K............K...
..........NA.........D..........Q..E.K.-............K...
                      ...  460       470       480       490       500
                      ...SN-ATT--FTPFTEKQLDNFGNAKKLVLGSTVIDLVPTDATK--NEFTK----   4223
                      ...PG-T.NPA..ANSK.E.........................DV...-.----   R1
                      ...NN-...--.....K.......................GV..DV.....----   M35
                      ...T.K...--.....K..................N..S.....--.....KFTK   LES1
                      ...PG-T.NPA..ANSK.E.....................G...DV...-.----   Q8
                      ...SG-T.NPA..ANSK.E......IN...........TQG------.D.V.TIDK   3
```

FIG.34D

```
        510       520          530       540       550      ...
DKPESATNEAGETLMVNDEVSVKTYG--KNFEYLKFGELSIGGSHSVFLQGERTAT...
E..K....K...............—...........V................
N..D....K.........K......YGR..........V.T.N.............
...T....K...........I.....—...........V.D...............
E..K....K...........I.....YGR.........................-...
E..ATT..Q...P.T...K.R.QVCC—S.L.H....S....D.N.............
                     ...   560       570       580         590       600
                     ...TGE—KAVPTTGTAKYLGNWVGYTTGKDTGTGT—GKSFTDAQDVADFDI    4223
                     ......—.......K.............A.SSK.STD..G....K.I.....   R1
                     ......—.....K.................S———S...NE.........     M35
                     ......—.......K.............——A..—....NE...I.....      LES1
                     ...—.—.....E..................S.—....NE...I.....       Q8
                     ...K.D.D..M.VA.N...R.T.A..VA.SGNTSKAYEAQQ.A.NANR.E..V  3

        610       620          630       640       650      ...
DFGNKSVSGKLITKGRQDPV—FSITGQIAGNGWTGTASTTKADAGGYKIDSSSTG...
..EK...N...T..D.....—.N...E........K...AE.N..............
..EK...K...T..D.....—.N...D........K.....................
..ER...K...T.Q..T...—.N.K.E........K.....................
..ER...K...T.Q......—.N................A..NV.............
..A...LT....PNTSS.GKSA.D..AT.D...FS.K.N.PDIET..L....KNSE...
     660       670       680         690       700
                     ...KS-IVIKDANVTGGFYGPNANEMGGSFTHNA———DDSKASVVFGTKRQQEVK-*   4223
                     .....-......V.........T.........S———GN.G.V.......K.-...K*   R1
                     .....-......E...................T———..............E...-*   M35
                     .....-...EN.E..................DT———..................*    LES1
                     .....-...EN.K..................DT———..............E...-*   Q8
                     ...SGRVIV...I.I......Q...L.....YKSNDAGNQDK..S......ARK.....P*  3
```

FIG.35A

*M. catarrhalis* strain 4223 *tbpA* - *orf3* - *tbpB* locus gene sequences

```
G A T G C C T G C C T T G T G A T T G G T T G G G T G T A...
                10                  20                  30...
                   ... T C G G T G T A T C A A A G T G C A A A A G C C A A C A G G
                   ...                    40                  50                  60

                tbpA
                MET   ASN   GLN   SER   LYS   GLN   ASN ...
T G G T C A T T G A T G A A T C A A T C A A A A C A A A A C...
                70                  80                  90...
                   ...  ASN   LYS   SER   LYS   LYS   SER   LYS   GLN   VAL   LEU
                   ... A A C A A A T C C A A A A A A T C C A A A C A A G T A T T A
                   ...                   100                 110                 120

LYS   LEU   SER   ALA   LEU   SER   LEU   GLY   LEU   LEU ...
A A A C T T A G T G C C T T G T C T T T G G G T C T G C T T...
               130                 140                 150...
                   ...  ASN   ILE   THR   GLN   VAL   ALA   LEU   ALA   ASN   THR
                   ... A A C A T C A C G C A G G T G G C A C T G G C A A A C A C A
                   ...                   160                 170                 180

THR   ALA   ASP   LYS   ALA   GLU   ALA   THR   ASP   LYS ...
A C G G C C G A T A A G G C G G A G G C A A C A G A T A A G...
               190                 200                 210...
```

FIG.35B

```
                ... THR ASN LEU VAL VAL VAL LEU ASP GLU THR
                ... A C A A A C C T T G T T G T T G T C T T G G A T G A A A C T
                ...               220                230               240

VAL VAL THR ALA LYS LYS ASN ALA ARG LYS ...
G T T G T A A C A G C G A A G A A A A A C G C C C G T A A A...
             250               260             270...
                ... ALA ASN GLU VAL THR GLY LEU GLY LYS VAL
                ... G C C A A C G A A G T T A C A G G G C T T G G T A A G G T G
                ...               280                290               300

VAL LYS THR ALA GLU THR ILE ASN LYS GLU ...
G T C A A A A C T G C C G A G A C C A T C A A T A A A G A A...
             310               320             330...
                ... GLN VAL LEU ASN ILE ARG ASP LEU THR ARG
                ... C A A G T G C T A A A C A T T C G A G A C T T A A C A C G C
                ...               340                350               360

TYR ASP PRO GLY ILE ALA VAL VAL GLU GLN ...
T A T G A C C C T G G C A T T G C T G T G G T T G A G C A A...
             370               380             390...
                ... GLY ARG GLY ALA SER SER GLY TYR SER ILE
                ... G G T C G T G G G G C A A G C T C A G G C T A T T C T A T T
                ...               400                410               420
```

FIG.35C

```
ARG GLY MET ASP LYS ASN ARG VAL ALA VAL ...
C G T G G T A T G G A T A A A A A T C G T G T G G C G G T A...
              430                 440                 450...
                   ... LEU VAL ASP GLY ILE ASN GLN ALA GLN HIS
                   ... T T G G T T G A T G G C A T C A A T C A A G C C C A G C A C
                   ...                460                 470                 480

TYR ALA LEU GLN GLY PRO VAL ALA GLY LYS ...
T A T G C C C T A C A A G G C C C T G T G G C A G G C A A A...
              490                 500                 510...
                   ... ASN TYR ALA ALA GLY GLY ALA ILE ASN GLU
                   ... A A T T A T G C C G C A G G T G G G G C A A T C A A C G A A
                   ...                520                 530                 540

ILE GLU TYR GLU ASN VAL ARG SER VAL GLU ...
A T A G A A T A C G A A A A T G T C C G C T C C G T T G A G...
              550                 560                 570...
                   ... ILE SER LYS GLY ALA ASN SER SER GLU TYR
                   ... A T T A G T A A A G G T G C A A A T T C A A G T G A A T A C
                   ...                580                 590                 600

GLY SER GLY ALA LEU SER GLY SER VAL ALA ...
G G C T C T G G G G C A T T A T C T G G C T C T G T G G C A...
              610                 620                 630...
```

FIG.35D

```
... PHE VAL THR LYS THR ALA ASP ASP ILE ILE
... T T T G T T A C C A A A A C C G C C G A T G A C A T C A T C
...                 640            650            660

LYS ASP GLY LYS ASP TRP GLY VAL GLN THR ...
A A A G A T G G T A A A G A T T G G G G C G T G C A G A C C...
          670            680            690...

... LYS THR ALA TYR ALA SER LYS ASN ASN ALA
... A A A A C C G C C T A T G C C A G T A A A A A T A A C G C A
...                 700            710            720

TRP VAL ASN SER VAL ALA ALA ALA GLY LYS ...
T G G G T T A A T T C T G T G G C A G C A G C A G G C A A G...
          730            740            750...

... ALA GLY SER PHE SER GLY LEU ILE ILE TYR
... G C A G G T T C T T T T A G C G G T C T T A T C A T C T A C
...                 760            770            780

THR ASP ARG ARG GLY GLN GLU TYR LYS ALA ...
A C C G A C C G C C G T G G T C A A G A A T A C A A G G C A...
          790            800            810...

... HIS ASP ASP ALA TYR GLN GLY SER GLN SER
... C A T G A T G A T G C C T A T C A G G G T A G C C A A A G T
...                 820            830            840
```

FIG.35E

```
PHE  ASP  ARG  ALA  VAL  ALA  THR  THR  ASP  PRO ...
T T T G A T A G A G C G G T G G C A A C C A C T G A C C C A...
                850                 860                 870...
                  ... ASN  ASN  ARG  THR  PHE  LEU  ILE  ALA  ASN  GLU
                  ... A A T A A C C G A A C A T T T T T A A T A G C A A A T G A A
                  ...                 880                 890                 900

CYS  ALA  ASN  GLY  ASN  TYR  GLU  ALA  CYS  ALA ...
T G T G C C A A T G G T A A T T A T G A G G C G T G T G C T...
                910                 920                 930...
                  ... ALA  GLY  GLY  GLN  THR  LYS  LEU  GLN  ALA  LYS
                  ... G C T G G C G G T C A A A C C A A A C T T C A A G C C A A G
                  ...                 940                 950                 960

PRO  THR  ASN  VAL  ARG  ASP  LYS  VAL  ASN  VAL ...
C C A A C C A A T G T G C G T G A T A A G G T C A A T G T C...
                970                 980                 990...
                  ... LYS  ASP  TYR  THR  GLY  PRO  ASN  ARG  LEU  ILE
                  ... A A A G A T T A T A C A G G T C C T A A C C G C C T T A T C
                  ...                1000                1010                1020

PRO  ASN  PRO  LEU  THR  GLN  ASP  SER  LYS  SER ...
C C A A A C C C A C T C A C C C A A G A C A G C A A A T C C...
               1030                1040                1050...
```

FIG.35F

```
                        ... LEU LEU LEU ARG PRO GLY TYR GLN LEU ASN
                        ... T T A C T G C T T C G C C C A G G T T A T C A G C T A A A C
                        ...              1060                1070                1080

ASP LYS HIS TYR VAL GLY GLY VAL TYR GLU ...
G A T A A G C A C T A T G T C G G T G G T G T G T A T G A A...
            1090                1100                1110...
                        ... ILE THR LYS GLN ASN TYR ALA MET GLN ASP
                        ... A T C A C C A A A C A A A A C T A C G C C A T G C A A G A T
                        ...              1120                1130                1140

LYS THR VAL PRO ALA TYR LEU ALA VAL HIS ...
A A A A C C G T G C C T G C T T A T C T G G C G G T T C A T...
            1150                1160                1170...
                        ... ASP ILE GLU LYS SER ARG LEU SER ASN HIS
                        ... G A C A T T G A A A A A T C A A G G C T C A G C A A C C A T
                        ...              1180                1190                1200

ALA GLN ALA ASN GLY TYR TYR GLN GLY ASN ...
G C C C A A G C C A A T G G C T A T T A T C A A G G C A A T...
            1210                1220                1230...
                        ... ASN LEU GLY GLU ARG ILE ARG ASP THR ILE
                        ... A A T C T T G G T G A A C G C A T T C G T G A T A C C A T T
                        ...              1240                1250                1260
```

FIG.35G

```
GLY   PRO   ASP   SER   GLY   TYR   GLY   ILE   ASN   TYR ...
G G G C C A G A T T C A G G T T A T G G C A T C A A C T A T...
                1270                1280                1290...
      ... ALA   HIS   GLY   VAL   PHE   TYR   ASP   GLU   LYS   HIS
      ... G C T C A T G G C G T A T T T T A T G A T G A A A A A C A C
      ...                1300                1310                1320

GLN   LYS   ASP   ARG   LEU   GLY   LEU   GLU   TYR   VAL ...
C A A A A A G A C C G C C T A G G G C T T G A A T A T G T T...
                1330                1340                1350...
      ... TYR   ASP   SER   LYS   GLY   GLU   ASN   LYS   TRP   PHE
      ... T A T G A C A G C A A A G G T G A A A A T A A A T G G T T T
      ...                1360                1370                1380

ASP   ASP   VAL   ARG   VAL   SER   TYR   ASP   LYS   GLN ...
G A T G A T G T G C G T G T G T C T T A T G A T A A G C A A...
                1390                1400                1410...
      ... ASP   ILE   THR   LEU   ARG   SER   GLN   LEU   THR   ASN
      ... G A C A T T A C G C T A C G C A G C C A G C T G A C C A A C
      ...                1420                1430                1440

THR   HIS   CYS   SER   THR   TYR   PRO   HIS   ILE   ASP ...
A C G C A C T G T T C A A C C T A T C C G C A C A T T G A C...
                1450                1460                1470...
```

FIG.35H

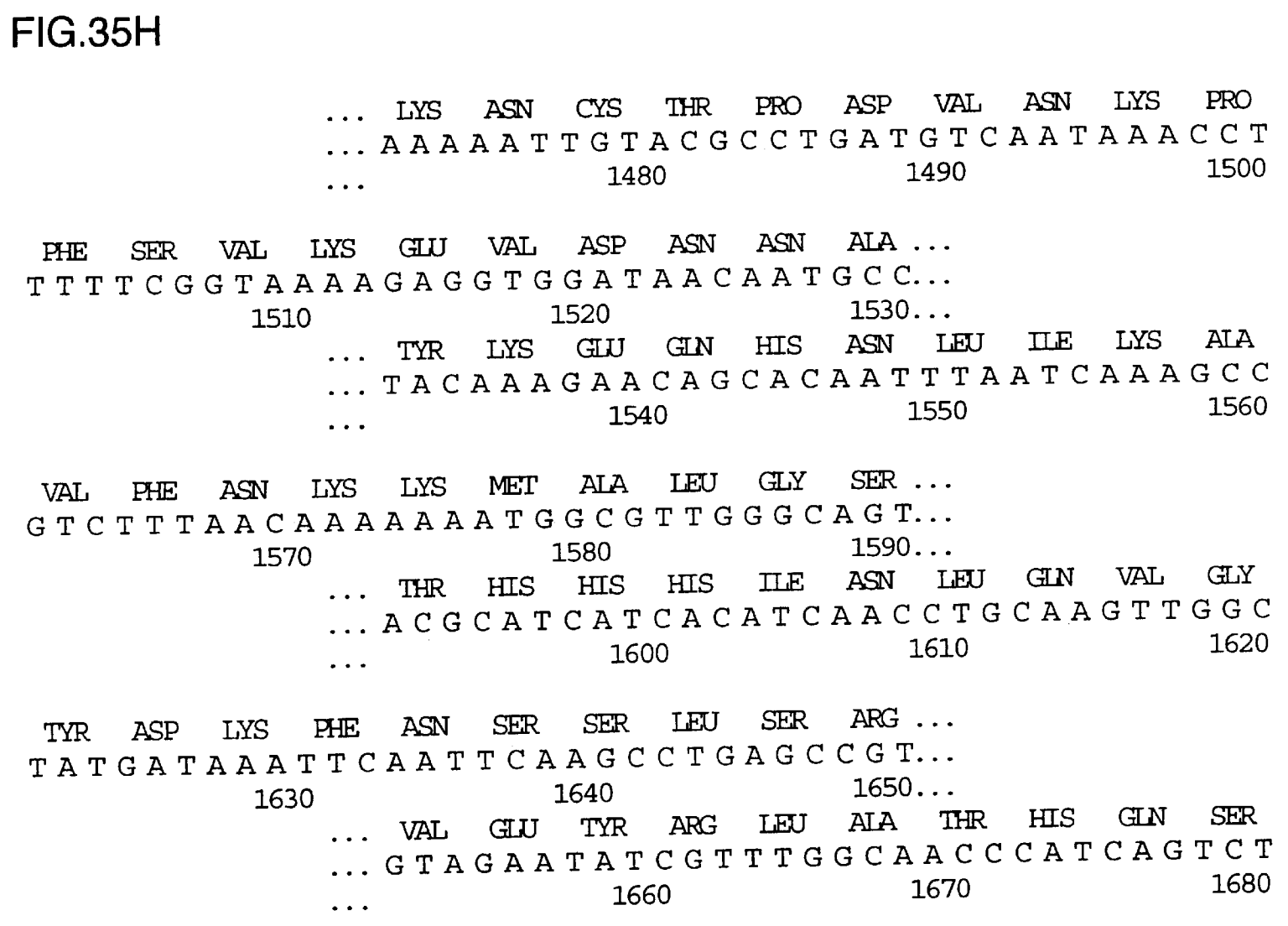

```
... LYS ASN CYS THR PRO ASP VAL ASN LYS PRO
... A A A A A T T G T A C G C C T G A T G T C A A T A A A C C T
...                   1480                1490               1500

PHE SER VAL LYS GLU VAL ASP ASN ASN ALA ...
T T T T C G G T A A A A G A G G T G G A T A A C A A T G C C...
          1510                1520                1530...
... TYR LYS GLU GLN HIS ASN LEU ILE LYS ALA
... T A C A A A G A A C A G C A C A A T T T A A T C A A A G C C
...                   1540                1550               1560

VAL PHE ASN LYS LYS MET ALA LEU GLY SER ...
G T C T T T A A C A A A A A A A T G G C G T T G G G C A G T...
          1570                1580                1590...
... THR HIS HIS HIS ILE ASN LEU GLN VAL GLY
... A C G C A T C A T C A C A T C A A C C T G C A A G T T G G C
...                   1600                1610               1620

TYR ASP LYS PHE ASN SER SER LEU SER ARG ...
T A T G A T A A A T T C A A T T C A A G C C T G A G C C G T...
          1630                1640                1650...
... VAL GLU TYR ARG LEU ALA THR HIS GLN SER
... G T A G A A T A T C G T T T G G C A A C C C A T C A G T C T
...                   1660                1670               1680
```

FIG.35I

```
TYR   GLN   LYS   LEU   ASP   TYR   THR   PRO   PRO   SER ...
T A T C A A A A A C T T G A T T A C A C C C C A C C A A G T...
                1690                 1700                1710...
                    ... ASN   PRO   LEU   PRO   ASP   LYS   PHE   LYS   PRO   ILE
                    ... A A C C C T T T G C C A G A T A A G T T T A A G C C C A T T
                    ...               1720                1730                1740

LEU   GLY   SER   ASN   ASN   LYS   PRO   ILE   CYS   LEU ...
T T A G G T T C A A A C A A C A A A C C C A T T T G C C T T...
                1750                 1760                1770...
                    ...ASP   ALA   TYR   GLY   TYR   GLY   HIS   ASP   HIS   PRO
                    ... G A T G C T T A T G G T T A T G G T C A T G A C C A T C C A
                    ...               1780                1790                1800

GLN   ALA   CYS   ASN   ALA   LYS   ASN   SER   THR   TYR ...
C A G G C T T G T A A C G C C A A A A A C A G C A C T T A T...
                1810                 1820                1830...
                    ... GLN   ASN   PHE   ALA   ILE   LYS   LYS   GLY   ILE   GLU
                    ... C A A A A T T T T G C C A T C A A A A A A G G C A T A G A G
                    ...               1840                1850                1860

GLN   TYR   ASN   GLN   LYS   THR   ASN   THR   ASP   LYS ...
C A A T A C A A C C A A A A A A C C A A T A C C G A T A A G...
                1870                 1880                1890...
```

FIG.35J

```
... ILE  ASP  TYR  GLN  ALA  ILE  ILE  ASP  GLN  TYR
...ATTGATTATCAAGCCATCATTGACCAATAT
...          1900          1910          1920
ASP  LYS  GLN  ASN  PRO  ASN  SER  THR  LEU  LYS ...
GATAAACAAAACCCCAACAGCACCCTAAAA...
        1930          1940          1950...
... PRO  PHE  GLU  LYS  ILE  LYS  GLN  SER  LEU  GLY
...CCCTTTGAGAAAATCAAACAAAGTTTGGGG
...          1960          1970          1980
GLN  GLU  LYS  TYR  ASN  LYS  ILE  ASP  GLU  LEU ...
CAAGAAAAATACAACAAGATAGACGAACTT...
        1990          2000          2010...
... GLY  PHE  LYS  ALA  TYR  LYS  ASP  LEU  ARG  ASN
...GGCTTTAAAGCTTATAAAGATTTACGCAAC
...          2020          2030          2040
GLU  TRP  ALA  GLY  TRP  THR  ASN  ASP  ASN  SER ...
GAATGGGCGGGTTGGACTAATGACAACAGC...
        2050          2060          2070...
... GLN  GLN  ASN  ALA  ASN  LYS  GLY  THR  ASP  ASN
...CAACAAAATGCCAATAAAGGCACGGATAAT
...          2080          2090          2100
```

FIG.35K

```
ILE   TYR   GLN   PRO   ASN   GLN   ALA   THR   VAL   VAL ...
A T C T A T C A G C C A A A T C A A G C A A C T G T G G T C...
            2110                    2120                2130...
                  ... LYS   ASP   ASP   LYS   CYS   LYS   TYR   SER   GLU   THR
                  ... A A A G A T G A C A A A T G T A A A T A T A G C G A G A C C
                  ...                     2140                2150                2160

ASN   SER   TYR   ALA   ASP   CYS   SER   THR   THR   ARG ...
A A C A G C T A T G C T G A T T G C T C A A C C A C T C G C...
            2170                    2180                2190...
                  ... HIS   ILE   SER   GLY   ASP   ASN   TYR   PHE   ILE   ALA
                  ... C A C A T C A G T G G T G A T A A T T A T T T C A T C G C T
                  ...                     2200                2210                2220

LEU   LYS   ASP   ASN   MET   THR   ILE   ASN   LYS   TYR ...
T T A A A A G A C A A C A T G A C C A T C A A T A A A T A T...
            2230                    2240                2250...
                  ... VAL   ASP   LEU   GLY   LEU   GLY   ALA   ARG   TYR   ASP
                  ... G T T G A T T T G G G G C T G G G T G C T C G C T A T G A C
                  ...                     2260                2270                2280

ARG   ILE   LYS   HIS   LYS   SER   ASP   VAL   PRO   LEU ...
A G A A T C A A A C A C A A A T C T G A T G T G C C T T T G...
            2290                    2300                2310...
```

FIG.35L

```
                              ...  VAL  ASP  ASN  SER  ALA  SER  ASN  GLN  LEU  SER
                              ... G T A G A C A A C A G T G C C A G C A A C C A G C T G T C T
                              ...                 2320                 2330                 2340

TRP  ASN  PHE  GLY  VAL  VAL  VAL  LYS  PRO  THR ...
T G G A A T T T T G G C G T G G T C G T C A A G C C C A C C...
            2350                 2360                 2370...
                              ...  ASN  TRP  LEU  ASP  ILE  ALA  TYR  ARG  SER  SER
                              ... A A T T G G C T G G A C A T C G C T T A T A G A A G C T C G
                              ...                 2380                 2390                 2400

GLN  GLY  PHE  ARG  MET  PRO  SER  PHE  SER  GLU ...
C A A G G C T T T C G C A T G C C A A G T T T T T C T G A A...
            2410                 2420                 2430...
                              ...  MET  TYR  GLY  GLU  ARG  PHE  GLY  VAL  THR  ILE
                              ... A T G T A T G G C G A A C G C T T T G G C G T A A C C A T C
                              ...                 2440                 2450                 2460

GLY  LYS  GLY  THR  GLN  HIS  GLY  CYS  LYS  GLY ...
G G T A A A G G C A C G C A A C A T G G C T G T A A G G G T...
            2470                 2480                 2490...
                              ...  LEU  TYR  TYR  ILE  CYS  GLN  GLN  THR  VAL  HIS
                              ... C T T T A T T A C A T T T G T C A G C A G A C T G T C C A T
                              ...                 2500                 2510                 2520
```

FIG.35M

```
GLN THR LYS LEU LYS PRO GLU LYS SER PHE ...
CAAACCAAGCTAAAACCTGAAAAATCCTTT...
        2530      2540      2550...
    ... ASN GLN GLU ILE GLY ALA THR LEU HIS ASN
    ...AACCAAGAAATCGGAGCGACTTTACATAAC
    ...       2560      2570      2580

HIS LEU GLY SER LEU GLU VAL SER TYR PHE ...
CACTTAGGCAGTCTTGAGGTTAGTTATTTT...
        2590      2600      2610...
    ... LYS ASN ARG TYR THR ASP LEU ILE VAL GLY
    ...AAAAATCGCTATACCGATTTGATTGTTGGT
    ...       2620      2630      2640

LYS SER GLU GLU ILE ARG THR LEU THR GLN ...
AAAAGTGAAGAGATTAGAACCCTAACCCAA...
        2650      2660      2670...
    ... GLY ASP ASN ALA GLY LYS GLN ARG GLY LYS
    ...GGTGATAATGCAGGCAAACAGCGTGGTAAA
    ...       2680      2690      2700

GLY ASP LEU GLY PHE HIS ASN GLY GLN ASP ...
GGTGATTTGGGCTTTCATAATGGACAAGAT...
        2710      2720      2730...
```

FIG.35N

```
                    ... ALA ASP LEU THR GLY ILE ASN ILE LEU GLY
                    ... G C T G A T T T G A C A G G A A T T A A C A T T C T T G G C
                    ...                2740                2750                2760

ARG LEU ASP LEU ASN ALA ALA ASN SER ARG ...
A G A C T T G A C C T A A A C G C T G C C A A T A G T C G C...
          2770                2780                2790...
                    ... LEU PRO TYR GLY LEU TYR SER THR LEU ALA
                    ... C T T C C C T A T G G A T T A T A C T C A A C A C T G G C T
                    ...                2800                2810                2820

TYR ASN LYS VAL ASP VAL LYS GLY LYS THR ...
T A T A A C A A A G T T G A T G T T A A A G G A A A A A C C...
          2830                2840                2850...
                    ... LEU ASN PRO THR LEU ALA GLY THR ASN ILE
                    ... T T A A A C C C A A C T T T G G C A G G A A C A A A C A T A
                    ...                2860                2870                2880

LEU PHE ASP ALA ILE GLN PRO SER ARG TYR ...
C T G T T T G A T G C C A T C C A G C C A T C T C G T T A T...
          2890                2900                2910...
                    ... VAL VAL GLY LEU GLY TYR ASP ALA PRO SER
                    ... G T G G T G G G G C T T G G C T A T G A T G C C C C A A G C
                    ...                2920                2930                2940
```

FIG.35O

GLN LYS TRP GLY ALA ASN ALA ILE PHE THR ...
C A A A A A T G G G G A G C A A A C G C C A T A T T T A C C...
2950 2960 2970...
... HIS SER ASP ALA LYS ASN PRO SER GLU LEU
... C A T T C T G A T G C C A A A A A T C C A A G C G A G C T T
... 2980 2990 3000

LEU ALA ASP LYS ASN LEU GLY ASN GLY ASN ...
T T G G C A G A T A A G A A C T T A G G T A A T G G C A A C...
3010 3020 3030...
... ILE GLN THR LYS GLN ALA THR LYS ALA LYS
... A T T C A A A C A A A A C A A G C C A C C A A A G C A A A A
... 3040 3050 3060

SER THR PRO TRP GLN THR LEU ASP LEU SER ...
T C C A C G C C G T G G C A A A C A C T T G A T T T G T C A...
3070 3080 3090...
... GLY TYR VAL ASN ILE LYS ASP ASN PHE THR
... G G T T A T G T A A A C A T A A A A G A T A A T T T T A C C
... 3100 3110 3120

LEU ARG ALA GLY VAL TYR ASN VAL PHE ASN ...
T T G C G T G C T G G C G T G T A C A A T G T A T T T A A T...
3130 3140 3150...

FIG.35P

```
                        ... THR TYR TYR THR THR TRP GLU ALA LEU ARG
                        ... A C C T A T T A C A C C A C T T G G G A G G C T T T A C G C
                        ...             3160           3170           3180

GLN THR ALA LYS GLY ALA VAL ASN GLN HIS ...
C A A A C A G C A A A A G G G G C G G T C A A T C A G C A T...
            3190           3200           3210...
                        ... THR GLY LEU SER GLN ASP LYS HIS TYR GLY
                        ... A C A G G A C T G A G C C A A G A T A A G C A T T A T G G T
                        ...             3220           3230           3240

ARG TYR ALA ALA PRO GLY ARG ASN TYR GLN ...
C G C T A T G C C G C T C C T G G A C G C A A T T A C C A A...
            3250           3260           3270...
                        ... LEU ALA LEU GLU MET LYS PHE ***
                        ... T T G G C A C T T G A A A T G A A G T T T T A A C C A G T G
                        ...             3280           3290           3300

G C T T T G A T G T G A T T T T G G C A T G C C A A A T C C...
            3310           3320           3330...
                        ... C A A T C A A C C A A T G A A T A A A G C C C C C A T T A C
                        ...             3340           3350           3360
```

```
CATGAGGGCTTTATTTTATCATCGCTGAGT...
                    3370                3380                3390...
                       ...ATGCTCTTAGCGGTCATCACTCAGATTAGT
                       ...          3400               3410               3420

CATTAATTTATTAGCGATTAATTTATTAGT...
                    3430                3440                3450...
                       ...AATCACGCTGCTCTTTGATGATTTTAAGTG
                       ...          3460               3470               3480

ATGGGTATTCAAGAACGATGTCATACTCAG...
                    3490                3500                3510...
                       ...CACCGTTTTTATAGGCTTCTACTTCAAAGA
                       ...          3520               3530               3540

CAGGCTTGCCTAAAAAGTCATCAACTTCTA...
                    3550                3560                3570...
                       ...TATCGCCGACTTGATAGCCACGAGCAGCAA
                       ...          3580               3590               3600

GCATTTGAATGGCTTTTTGACGATTTTGGG...
                    3610                3620                3630...
```

```
                  ... C A A A G T T G C T G T C G C C A T A A G C T T G T G C T T
                                   3640                3650                3660
                  ...
T A A T A C G G T C G T T A G C A A C T G C G G T G G T A G...
              3670                3680                3690...
                  ... A G A T A C C A A C G G C A G G C A A C A A A A C A G C A G
                                   3700                3710                3720
                  ...
C A C T T A G T A C G C C A G C C A A C A G T T T A T T G G...
              3730                3740                3750...
                  ... T T A A A T T T T T C A T A G T A G T T T C C T A A T T A T
                                   3760                3770                3780
                  ...
T A T C A T T G T A A T T C A T G T T T A T C G T T A T A A...
              3790                3800                3810...
                  ... A C A A T C G T T A T A A A T A A C T G T G T C G T G A T A
                                   3820                3830                3840
                  ...
A C C A T T A A T C A C A A G T G G G T T A A A T G C C T T...
              3850                3860                3870...
                  ... T T G C C C A A T G G C A A A T A G G C A C A A T G C T C T
                                   3880                3890                3900
                  ...
```

```
GCTTGTTCTATGATGGTCTATTATGATCAT...
          3910      3920      3930...
   ...CATTTTATTGACCTATTTTTTTAATCGTAA
              3940      3950      3960
   ...

TGTTTGTTTGATGTTAGTATAAATTTTATC...
          3970      3980      3990...
   ...AATCAAACAATCACAAATTATATCAATCAT
              4000      4010      4020
   ...

AGACGGTAAACAGGCTTCATATTTTACGCA...
          4030      4040      4050...
   ...TATTTCCCCAGATGTCTGTAGTGTTTCATA
              4060      4070      4080
   ...

GATGATTTGTAAAACAATTGTCGGTCATTA...
          4090      4100      4110...
   ...TTATCAATTGTAAACTGATGGCTAATTTGT
              4120      4130      4140
   ...

AACCTTATGGCTAATGATAATATGAATAAA...
          4150      4160      4170...
```

```
                    ... G C G T T A T A C T G T A T C A A A G A A T G A G T A A A A
                                          4180                4190                4200
                    ...

A C C A T C A A T G G T A T C T T A T T T A T C A T C A G G...
              4210                4220                4230...
                    ... T T G T G T T A A T A A G A T G C C A A T T A A G C G A C T
                                          4240                4250                4260
                    ...

A A T T T T G T A A A T T A A T T A A T A A T C A T T C A T...
              4270                4280                4290...
                    ... A T T T G T A T T T T T A A A T A C C A T A A A A A A T G G
                                          4300                4310                4320
                    ...

            orf3
            MET   LEU   ALA   PHE   LEU   ILE   GLY   ALA ...
T A A A A T A T G C T C G C T T T T T T G A T A G G A G C T...
              4330                4340                4350...
                    ... VAL   MET   THR   ILE   THR   PRO   VAL   TYR   THR   THR
                    ... G T C A T G A C A A T C A C G C C T G T T T A T A C C A C A
                                          4360                4370                4380
                    ...

PHE   THR   PRO   THR   LYS   THR   PRO   ILE   LYS   PHE ...
T T C A C C C C C A C C A A A A C A C C C A T A A A A T T T...
              4390                4400                4410...
```

FIG.35U

```
                 ... PHE MET ALA GLY LEU THR PHE LEU ILE ALA
                 ... T T T A T G G C T G G C T T G A C T T T T C T A A T C G C T
                 ...            4420           4430           4440

HIS ILE SER HIS ALA ASP ASP GLY ARG THR ...
C A T A T C A G C C A T G C C G A T G A T G G T C G C A C C...
          4450           4460           4470...
                 ... ASP ASN GLN GLU LEU ILE ASN GLN GLU ILE
                 ... G A C A A T C A A G A G C T A A T C A A T C A A G A A A T A
                 ...            4480           4490           4500

ALA THR LEU GLU PRO ILE ILE ASN HIS ALA ...
G C C A C C C T T G A A C C C A T C A T T A A C C A T G C T...
          4510           4520           4530...
                 ... GLN PRO GLU LEU LEU SER HIS ASP ALA LEU
                 ... C A G C C T G A G T T A T T G T C C C A T G A T G C A T T A
                 ...            4540           4550           4560

THR PRO LYS ILE GLU PRO ILE LEU ALA GLN ...
A C A C C A A A A A T A G A A C C A A T A C T G G C A C A A...
          4570           4580           4590...
                 ... THR PRO ASN PRO ALA GLU ASP THR LEU ILE
                 ... A C A C C A A A T C C T G C C G A A G A T A C G C T C A T C
                 ...            4600           4610           4620
```

FIG.35V

```
ALA   ASP   GLU   ALA   LEU   LEU   LEU   ASP   ASN   PRO ...
G C C G A T G A G G C G T T A C T G C T T G A T A A C C C T...
              4630                4640                4650...
                    ...  ASP   LEU   LEU   ASN   HIS   ALA   LEU   ASN   SER   ALA
                    ... G A T T T G C T C A A T C A C G C C C T A A A T T C T G C T
                    ...                4660                4670                4680

VAL   MET   THR   ASN   HIS   MET   ALA   GLY   VAL   HIS ...
G T C A T G A C C A A T C A T A T G G C A G G C G T T C A C...
              4690                4700                4710...
                    ...  ALA   LEU   LEU   PRO   ILE   TYR   GLN   LYS   LEU   PRO
                    ... G C A T T A T T G C C C A T T T A T C A A A A A C T G C C C
                    ...                4720                4730                4740

LYS   ASP   HIS   GLN   ASN   GLY   ILE   LEU   LEU   GLY ...
A A A G A C C A T C A A A A T G G C A T T T T A C T T G G G...
              4750                4760                4770...
                    ...  TYR   ALA   ASN   ALA   LEU   ALA   ALA   LEU   ASP   LYS
                    ... T A T G C C A A T G C C T T G G C T G C T T T G G A T A A G
                    ...                4780                4790                4800

GLY   ASN   ALA   LYS   LYS   ALA   ILE   ASP   GLU   LEU ...
G G C A A C G C C A A A A A A G C C A T T G A T G A G C T A...
              4810                4820                4830...
```

FIG.35W

```
                                  ... ARG  ARG  ILE  ILE  ALA  ILE  MET  PRO  GLU  TYR
                                  ... C G T C G C A T C A T C G C C A T C A T G C C T G A A T A T
                                  ...              4840              4850              4860

ASN  VAL  VAL  ARG  PHE  HIS  LEU  ALA  ARG  ALA ...
A A T G T G G T G C G T T T T C A T C T G G C A A G G G C A...
            4870              4880              4890...
                                  ... LEU  PHE  MET  ASP  LYS  GLN  ASN  GLU  ALA  ALA
                                  ... T T A T T T A T G G A C A A A C A A A A T G A A G C C G C C
                                  ...              4900              4910              4920

LEU  ASP  GLN  PHE  ASN  LYS  LEU  HIS  ALA  ASP ...
C T T G A C C A G T T T A A T A A A T T A C A T G C T G A C...
            4930              4940              4950...
                                  ... ASN  LEU  PRO  GLU  GLU  VAL  ARG  GLN  VAL  VAL
                                  ... A A C T T G C C A G A G G A G G T G C G G C A G G T T G T T
                                  ...              4960              4970              4980

GLY  GLN  TYR  ARG  GLN  ALA  LEU  LYS  GLN  ARG ...
G G G C A G T A C A G A C A A G C G C T A A A A C A A C G A...
            4990              5000              5010...
                                  ... ASP  SER  TRP  THR  TRP  GLN  VAL  GLY  MET  ASN
                                  ... G A T T C A T G G A C A T G G C A A G T A G G C A T G A A T
                                  ...              5020              5030              5040
```

FIG.35X

```
LEU ALA LYS GLU ASP ASN ILE ASN GLN THR ...
C T G G C C A A A G A A G A C A A C A T C A A T C A A A C C...
5050 5060 5070...
... PRO LYS ASN THR THR GLN GLY GLN TRP THR
... C C C A A A A A C A C C A C G C A A G G T C A A T G G A C T
5080 5090 5100
...

PHE ASP LYS PRO ILE ASP ALA ILE THR LEU ...
T T T G A C A A A C C C A T T G A C G C C A T C A C C C T A...
5110 5120 5130...
... SER TYR GLN LEU GLY ALA ASP LYS LYS TRP
... A G C T A C C A A T T G G G G G C G G A T A A A A A G T G G
5140 5150 5160
...

SER LEU PRO LYS GLY ALA TYR VAL GLY ALA ...
T C T T T G C C C A A A G G G G C A T A T G T G G G A G C G...
5170 5180 5190...
... ASN ALA GLN ILE TYR GLY LYS HIS HIS GLN
... A A C G C C C A A A T C T A T G G C A A A C A T C A T C A A
5200 5210 5220
...

ASN HIS LYS LYS TYR ASN ASP HIS TRP GLY ...
A A T C A C A A A A A A T A C A A C G A C C A T T G G G G C...
5230 5240 5250...
```

FIG.35Y

```
                 ... ARG   LEU   GLY   ALA   ASN   LEU   GLY   PHE   ALA   ASP
                 ... A G A C T G G G G G C A A A T T T G G G C T T T G C T G A T
                 ...               5260                5270                5280

ALA   LYS   LYS   ASP   LEU   SER   ILE   GLU   THR   TYR ...
G C C A A A A A A G A C C T T A G C A T T G A G A C C T A T...
            5290                5300                5310...
                 ... GLY   GLU   LYS   ARG   PHE   TYR   GLY   HIS   GLU   ARG
                 ... G G T G A A A A A A G A T T T T A T G G G C A T G A G C G T
                 ...               5320                5330                5340

TYR   THR   ASP   THR   ILE   GLY   ILE   ARG   MET   SER ...
T A T A C C G A C A C C A T T G G C A T A C G C A T G T C G...
            5350                5360                5370...
                 ... VAL   ASP   TYR   ARG   ILE   ASN   PRO   LYS   PHE   GLN
                 ... G T T G A T T A T A G A A T C A A C C C A A A A T T T C A A
                 ...               5380                5390                5400

SER   LEU   ASN   ALA   ILE   ASP   ILE   SER   ARG   LEU ...
A G C C T A A A C G C C A T A G A C A T A T C A C G C C T A...
            5410                5420                5430...
                 ... THR   ASN   HIS   ARG   THR   PRO   ARG   ALA   ASP   SER
                 ... A C C A A C C A T C G G A C G C C T A G G G C T G A C A G T
                 ...               5440                5450                5460
```

FIG.35Z

ASN ASN THR LEU TYR SER THR SER LEU ILE ...
A A T A A C A C T T T A T A C A G T A C C T C A T T G A T T...
5470 5480 5490...

... TYR TYR PRO ASN ALA THR ARG TYR TYR LEU
... T A T T A C C C A A A T G C C A C A C G C T A T T A T C T T
... 5500 5510 5520

LEU GLY ALA ASP PHE TYR ASP GLU LYS VAL ...
T T G G G G G C A G A C T T T T A T G A T G A A A A A G T G...
5530 5540 5550...

... PRO GLN ASP PRO SER ASP SER TYR GLN ARG
... C C A C A A G A C C C A T C T G A C A G T T A T C A A C G C
... 5560 5570 5580

ARG GLY ILE ARG THR ALA TRP GLY GLN GLU ...
C G T G G C A T A C G C A C A G C G T G G G G G C A A G A A...
5590 5600 5610...

... TRP ALA GLY GLY LEU SER SER ARG ALA GLN
... T G G G C G G G T G G T C T T T C A A G C C G T G C C C A A
... 5620 5630 5640

ILE SER ILE ASN LYS ARG HIS TYR GLN GLY ...
A T C A G C A T C A A C A A A C G C C A T T A C C A A G G G...
5650 5660 5670...

FIG.35A'

```
                     ... ALA  ASN  LEU  THR  SER  GLY  GLY  GLN  ILE  ARG
                     ... G C A A A C C T A A C C A G C G G T G G A C A A A T T C G C
                                   5680           5690           5700
                     ...

HIS  ASP  LYS  GLN  MET  GLN  ALA  SER  LEU  SER ...
C A T G A T A A A C A G A T G C A A G C G T C T T T A T C G...
        5710           5720           5730...
                     ... LEU  TRP  HIS  ARG  ASP  ILE  HIS  LYS  TRP  GLY
                     ... C T T T G G C A C A G A G A C A T T C A C A A A T G G G G C
                                   5740           5750           5760
                     ...

ILE  THR  PRO  ARG  LEU  THR  ILE  SER  THR  ASN ...
A T C A C G C C A C G G C T G A C C A T C A G C A C A A A C...
        5770           5780           5790...
                     ... ILE  ASN  LYS  SER  ASN  ASP  ILE  LYS  ALA  ASN
                     ... A T C A A T A A A A G C A A T G A C A T C A A G G C A A A T
                                   5800           5810           5820
                     ...

TYR  HIS  LYS  ASN  GLN  MET  PHE  VAL  GLU  PHE ...
T A T C A C A A A A A T C A A A T G T T T G T T G A G T T T...
        5830           5840           5850...
                     ... SER  ARG  ILE  PHE  ***
                     ... A G T C G C A T T T T T T G A T G G G A T A A G C A C G C C
                                   5860           5870           5880
                     ...
```

FIG.35B'

```
CTACTTTTGTTTTTGTAAAAAAATGTGCCA...
               5890                5900                5910...
                   ...TCATAGACAATATCAAGAAAAAATCAAGAA
                   ...             5920                5930                5940

AAAAAGATTACAAATTTAATGATAATTGTT...
               5950                5960                5970...
                   ...ATTGTTTATGTTATTATTTATCAATGTAAA
                   ...             5980                5990                6000

TTTGCCGTATTTTGTCTATCATAAATGCAT...
               6010                6020                6030...
                   ...TTATCAAATGCTCAAATAAATACGCCAAAT
                   ...             6040                6050                6060

GCACATTGTCAGCATGCCAAAATAGGCATC...
               6070                6080                6090...
                   ...AACAGACTTTTTTAGATAATACCATCAACC
                   ...             6100                6110                6120
```

FIG.35C'

```
                                   tbpB
                                   MET  LYS  HIS  ILE  ...
CATCAGAGGATTATTTTATGAAACACATTC...
          6130          6140          6150...
                  ...PRO  LEU  THR  THR  LEU  CYS  VAL  ALA  ILE  SER  A
                  ... CTTTAACCACACTGTGTGTGGCAATCTCTG
                  ...          6160          6170          6180

LA  VAL  LEU  LEU  THR  ALA  CYS  GLY  GLY  SER  ...
CCGTCTTATTAACCGCTTGTGGTGGCAGTG...
          6190          6200          6210...
                  ...GLY  GLY  SER  ASN  PRO  PRO  ALA  PRO  THR  PRO  I
                  ... GTGGTTCAAATCCACCTGCTCCTACGCCCA
                  ...          6220          6230          6240

LE  PRO  ASN  ALA  SER  GLY  SER  GLY  ASN  THR  ...
TTCCAAATGCTAGCGGTTCAGGTAATACTG...
          6250          6260          6270...
                  ...GLY  ASN  THR  GLY  ASN  ALA  GLY  GLY  THR  ASP  A
                  ... GCAACACTGGTAATGCTGGCGGTACTGATA
                  ...          6280          6290          6300
```

FIG.35D'

```
SN  THR ALA ASN ALA GLY ASN THR GLY GLY ...
A T A C A G C C A A T G C A G G T A A T A C A G G C G G T A...
        6310                6320                6330...
            ...THR ASN SER GLY THR GLY SER ALA ASN THR P
            ... C A A A C T C T G G T A C A G G C A G T G C C A A C A C A C
            ...          6340                6350                6360

RO  GLU PRO LYS TYR GLN ASP VAL PRO THR ...
C A G A G C C A A A A T A T C A A G A T G T A C C A A C T G...
        6370                6380                6390...
            ...GLU LYS ASN GLU LYS ASP LYS VAL SER SER I
            ... A G A A A A A T G A A A A A G A T A A A G T T T C A T C C A
            ...          6400                6410                6420

LE  GLN GLU PRO ALA MET GLY TYR GLY MET ...
T T C A A G A A C C T G C C A T G G G T T A T G G C A T G G...
        6430                6440                6450...
            ...ALA LEU SER LYS ILE ASN LEU HIS ASN ARG G
            ... C T T T G A G T A A A A T T A A T C T A C A C A A C C G A C
            ...          6460                6470                6480

LN  ASP THR PRO LEU ASP GLU LYS ASN ILE ...
A A G A C A C G C C A T T A G A T G A A A A A A A T A T C A...
        6490                6500                6510...
```

FIG.35E'

```
                    ...ILE THR LEU ASP GLY LYS LYS GLN VAL ALA G
                    ... T T A C C T T A G A C G G T A A A A A A C A A G T T G C A G
                    ...            6520            6530            6540

LU GLY LYS LYS SER PRO LEU PRO PHE SER ...
A A G G T A A A A A A T C G C C A T T G C C A T T T T C G T...
          6550            6560            6570...
                    ...LEU ASP VAL GLU ASN LYS LEU LEU ASP GLY T
                    ... T A G A T G T A G A A A A T A A A T T G C T T G A T G G C T
                    ...            6580            6590            6600

YR ILE ALA LYS MET ASN VAL ALA ASP LYS ...
A T A T A G C A A A A A T G A A T G T A G C G G A T A A A A...
          6610            6620            6630...
                    ...ASN ALA ILE GLY ASP ARG ILE LYS LYS GLY A
                    ... A T G C C A T T G G T G A C A G A A T T A A G A A A G G T A
                    ...            6640            6650            6660

SN LYS GLU ILE SER ASP GLU GLU LEU ALA ...
A T A A A G A A A T C T C C G A T G A A G A A C T T G C C A...
          6670            6680            6690...
                    ...LYS GLN ILE LYS GLU ALA VAL ARG LYS SER H
                    ... A A C A A A T C A A A G A A G C T G T G C G T A A A A G C C
                    ...            6700            6710            6720
```

FIG.35F'

```
IS  GLU PHE GLN GLN VAL LEU SER SER LEU ...
A T G A G T T T C A G C A A G T A T T A T C A T C A C T G G...
              6730                6740                6750...
          ...GLU ASN LYS ILE PHE HIS SER ASN ASP GLY T
          ... A A A A C A A A A T T T T T C A T T C A A A T G A C G G A A
          ...           6760              6770              6780

HR  THR LYS ALA THR THR ARG ASP LEU LYS ...
C A A C C A A A G C A A C C A C A C G A G A T T T A A A A T...
              6790                6800                6810...
          ...TYR VAL ASP TYR GLY TYR TYR LEU ALA ASN A
          ... A T G T T G A T T A T G G T T A C T A C T T G G C G A A T G
          ...           6820              6830              6840

SP  GLY ASN TYR LEU THR VAL LYS THR ASP ...
A T G G C A A T T A T C T A A C C G T C A A A A C A G A C A...
              6850                6860                6870...
          ...LYS LEU TRP ASN LEU GLY PRO VAL GLY GLY V
          ... A A C T T T G G A A T T T A G G C C C T G T G G G T G G T G
          ...           6880              6890              6900

AL  PHE TYR ASN GLY THR THR THR ALA LYS ...
T G T T T T A T A A T G G C A C A A C G A C C G C C A A A G...
              6910                6920                6930...
```

FIG.35G'

```
                  ...GLU  LEU  PRO  THR  GLN  ASP  ALA  VAL  LYS  TYR  L
                  ... A G T T G C C C A C A C A A G A T G C G G T C A A A T A T A
                  ...              6940              6950              6960

YS  GLY  HIS  TRP  ASP  PHE  MET  THR  ASP  VAL  ...
A A G G A C A T T G G G A C T T T A T G A C C G A T G T T G...
            6970              6980              6990...
                  ...ALA  ASN  ARG  ARG  ASN  ARG  PHE  SER  GLU  VAL  L
                  ... C C A A C A G A A G A A A C C G A T T T A G C G A A G T G A
                  ...              7000              7010              7020

YS  GLU  ASN  SER  GLN  ALA  GLY  TRP  TYR  TYR  ...
A A G A A A A C T C T C A A G C A G G C T G G T A T T A T G...
            7030              7040              7050...
                  ...GLY  ALA  SER  SER  LYS  ASP  GLU  TYR  ASN  ARG  L
                  ... G A G C A T C T T C A A A A G A T G A A T A C A A C C G C T
                  ...              7060              7070              7080

EU  LEU  THR  LYS  GLU  ASP  SER  ALA  PRO  ASP  ...
T A T T A A C T A A A G A A G A C T C T G C C C C T G A T G...
            7090              7100              7110...
                  ...GLY  HIS  SER  GLY  GLU  TYR  GLY  HIS  SER  SER  G
                  ... G T C A T A G C G G T G A A T A T G G C C A T A G C A G T G
                  ...              7120              7130              7140
```

FIG.35H'

```
LU   PHE  THR  VAL  ASN  PHE  LYS  GLU  LYS  LYS  ...
A G T T T A C T G T T A A T T T T A A G G A A A A A A A A T...
              7150                7160                7170...
                   ...LEU  THR  GLY  LYS  LEU  PHE  SER  ASN  LEU  GLN  A
                   ... T A A C A G G T A A G C T G T T T A G T A A C C T A C A A G
                   ...           7180                7190                7200

SP   ARG  HIS  LYS  GLY  ASN  VAL  THR  LYS  THR  ...
A C C G C C A T A A G G G C A A T G T T A C A A A A A C C G...
              7210                7220                7230...
                   ...GLU  ARG  TYR  ASP  ILE  ASP  ALA  ASN  ILE  HIS  G
                   ... A A C G C T A T G A C A T C G A T G C C A A T A T C C A C G
                   ...           7240                7250                7260

LY   ASN  ARG  PHE  ARG  GLY  SER  ALA  THR  ALA  ...
G C A A C C G C T T C C G T G G C A G T G C C A C C G C A A...
              7270                7280                7290...
                   ...SER  ASN  LYS  ASN  ASP  THR  SER  LYS  HIS  PRO  P
                   ... G C A A T A A A A A T G A C A C A A G C A A A C A C C C C T
                   ...           7300                7310                7320

HE   THR  SER  ASP  ALA  ASN  ASN  ARG  LEU  GLU  ...
T T A C C A G T G A T G C C A A C A A T A G G C T A G A A G...
              7330                7340                7350...
```

FIG.35I'

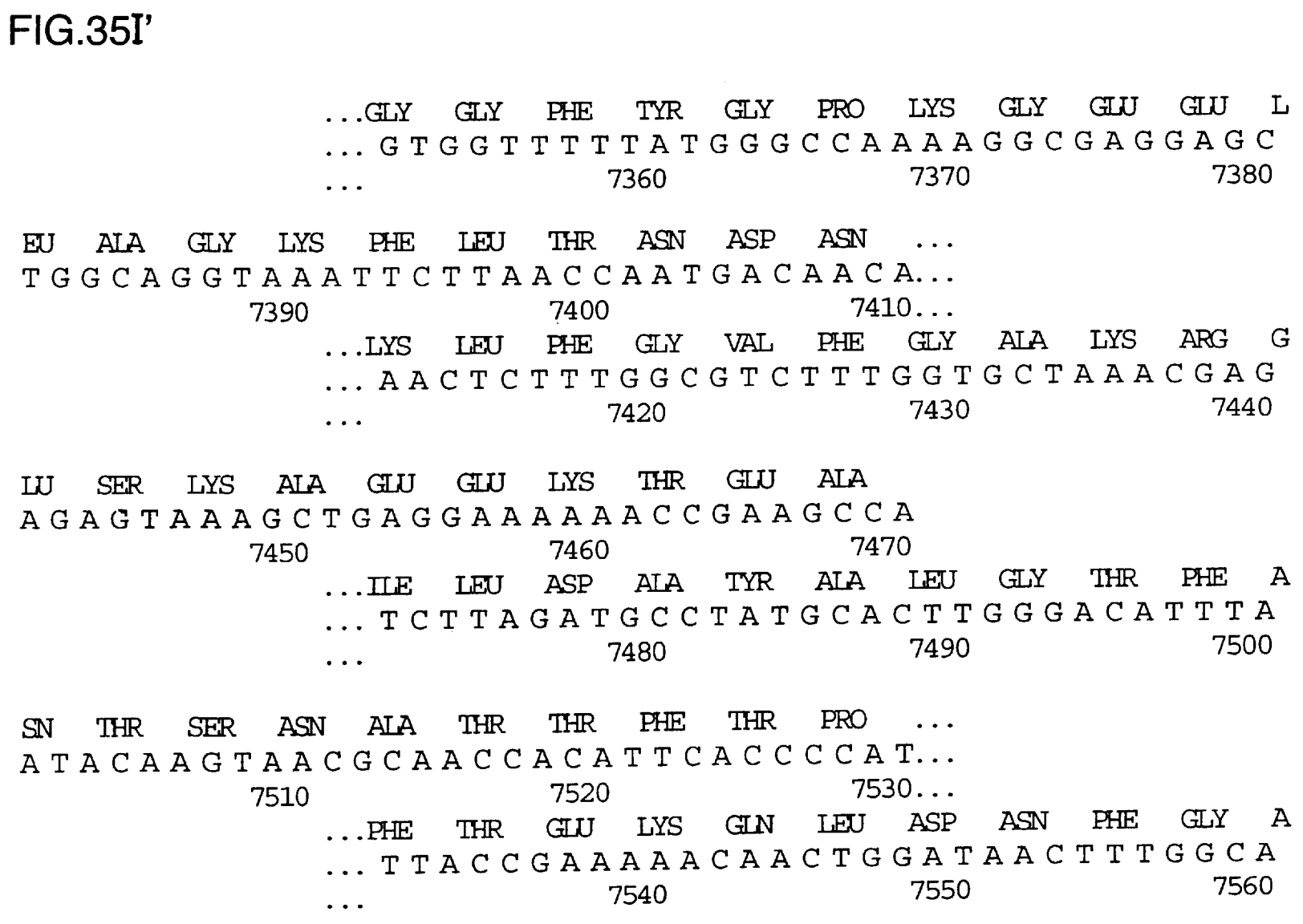

...GLY GLY PHE TYR GLY PRO LYS GLY GLU GLU L
... G T G G T T T T A T G G G C C A A A A G G C G A G G A G C
... 7360 7370 7380

EU ALA GLY LYS PHE LEU THR ASN ASP ASN ...
T G G C A G G T A A A T T C T T A A C C A A T G A C A A C A...
7390 7400 7410...

...LYS LEU PHE GLY VAL PHE GLY ALA LYS ARG G
... A A C T C T T T G G C G T C T T T G G T G C T A A A C G A G
... 7420 7430 7440

LU SER LYS ALA GLU GLU LYS THR GLU ALA
A G A G T A A A G C T G A G G A A A A A A C C G A A G C C A
7450 7460 7470

...ILE LEU ASP ALA TYR ALA LEU GLY THR PHE A
... T C T T A G A T G C C T A T G C A C T T G G G A C A T T T A
... 7480 7490 7500

SN THR SER ASN ALA THR THR PHE THR PRO ...
A T A C A A G T A A C G C A A C C A C A T T C A C C C C A T...
7510 7520 7530...

...PHE THR GLU LYS GLN LEU ASP ASN PHE GLY A
... T T A C C G A A A A A C A A C T G G A T A A C T T T G G C A
... 7540 7550 7560

FIG.35J'

```
SN   ALA  LYS  LYS  LEU  VAL  LEU  GLY  SER  THR  ...
A T G C C A A A A A A T T G G T C T T A G G T T C T A C C G...
           7570           7580           7590...
                  ...VAL  ILE  ASP  LEU  VAL  PRO  THR  ASP  ALA  THR  L
                  ... T C A T T G A T T T G G T G C C T A C T G A T G C C A C C A
                  ...           7600           7610           7620

YS   ASN  GLU  PHE  THR  LYS  ASP  LYS  PRO  GLU  ...
A A A A T G A A T T C A C C A A A G A C A A G C C A G A G T...
           7630           7640           7650...
                  ...SER  ALA  THR  ASN  GLU  ALA  GLY  GLU  THR  LEU  M
                  ... C T G C C A C A A A C G A A G C G G G C G A G A C T T T G A
                  ...           7660           7670           7680

ET   VAL  ASN  ASP  GLU  VAL  SER  VAL  LYS  THR  ...
T G G T G A A T G A T G A A G T T A G C G T C A A A A C C T...
           7690           7700           7710...
                  ...TYR  GLY  LYS  ASN  PHE  GLU  TYR  LEU  LYS  PHE  G
                  ... A T G G C A A A A A C T T T G A A T A C C T A A A A T T T G
                  ...           7720           7730           7740

LY   GLU  LEU  SER  ILE  GLY  GLY  SER  HIS  SER  ...
G T G A G C T T A G T A T C G G T G G T A G C C A T A G C G...
           7750           7760           7770...
```

FIG.35K'

```
...VAL  PHE  LEU  GLN  GLY  GLU  ARG  THR  ALA  THR  T
... T C T T T T T A C A A G G C G A A C G C A C C G C T A C C A
...                7780                 7790                 7800

HR  GLY  GLU  LYS  ALA  VAL  PRO  THR  THR  GLY  ...
C A G G C G A G A A A G C C G T A C C A A C C A C A G G C A...
                7810                 7820                 7830...
...THR  ALA  LYS  TYR  LEU  GLY  ASN  TRP  VAL  GLY  T
... C A G C C A A A T A T T T G G G G A A C T G G G T A G G A T
...                7840                 7850                 7860

YR  ILE  THR  GLY  LYS  ASP  THR  GLY  THR  GLY  ...
A C A T C A C A G G A A A G G A C A C A G G A A C G G G C A...
                7870                 7880                 7890...
...THR  GLY  LYS  SER  PHE  THR  ASP  ALA  GLN  ASP  V
... C A G G A A A A A G C T T T A C C G A T G C C C A A G A T G
...                7900                 7910                 7920

AL  ALA  ASP  PHE  ASP  ILE  ASP  PHE  GLY  ASN  ...
T T G C T G A T T T T G A C A T T G A T T T T G G A A A T A...
                7930                 7940                 7950...
...LYS  SER  VAL  SER  GLY  LYS  LEU  ILE  THR  LYS  G
... A A T C A G T C A G C G G T A A A C T T A T C A C C A A A G
...                7960                 7970                 7980
```

FIG.35L'

```
LY   ARG  GLN  ASP  PRO  VAL  PHE  SER  ILE  THR  ...
G C C G C C A A G A C C C T G T A T T T A G C A T C A C A G...
                7990             8000             8010...
                    ...GLY  GLN  ILE  ALA  GLY  ASN  GLY  TRP  THR  GLY  T
                    ... G T C A A A T C G C A G G C A A T G G C T G G A C A G G G A
                    ...             8020             8030             8040

HR   ALA  SER  THR  THR  LYS  ALA  ASP  ALA  GLY  ...
C A G C C A G C A C C A C C A A A G C G G A C G C A G G A G...
                8050             8060             8070...
                    ...GLY  TYR  LYS  ILE  ASP  SER  SER  SER  THR  GLY  L
                    ... G C T A C A A G A T A G A T T C T A G C A G T A C A G G C A
                    ...             8080             8090             8100

YS   SER  ILE  ALA  ILE  LYS  ASP  ALA  ASN  VAL  ...
A A T C C A T C G C C A T C A A A G A T G C C A A T G T T A...
                8110             8120             8130...
                    ...THR  GLY  GLY  PHE  TYR  GLY  PRO  ASN  ALA  ASN  G
                    ... C A G G G G G C T T T T A T G G T C C A A A T G C A A A C G
                    ...             8140             8150             8160

LU   MET  GLY  GLY  SER  PHE  THR  HIS  ASN  ALA  ...
A G A T G G G C G G G T C A T T T A C A C A C A A C G C C G...
                8170             8180             8190...
```

FIG.35M'

```
...ASP  ASP  SER  LYS  ALA  SER  VAL  VAL  PHE  GLY  T
... A T G A C A G C A A A G C C T C T G T G G T C T T T G G C A
...               8200                8210                8220

HR  LYS  ARG  GLN  GLN  GLU  VAL  LYS  ***
C A A A A A G A C A A C A A G A A G T T A A G T A G T A A T...
              8230                8240                8250...

... T T A A A C A C A A T G T T T G
...               8260
```

Fig. 36 Alignment of *M. catarrhalis* ORF3 proteins

```
        10        20        30        40        50        60        70        80        90       100
MLAFLIGAVMTITPVYTTFTPTKTPIKFFMAGLTFLIAHISHADDGRTDNQELINQEIATLEPIINHAQPELLSHDALTPKIEPILAQTPNPAEDTLIAD 4223
....................................................P......................G.....T.................. Q8

       110       120       130       140       150       160       170       180       190       200
EALLLDNPDLLNHALNSAVMTNHMAGVHALLPIYQKLPKDHQNGILLGYANALAALDKGNAKKAIDELRRIIAIMPEYNVVRFHLARALFMDKQNEAALD 4223
......................N..............................V........A..G.................................. Q8

       210       220       230       240       250       260       270       280       290       300
QFNKLHADNLPEEVRQVVGQYRQALKQRDSWTWQVGMNLAKEDNINQTPKNTTQGQWTFDKPIDAITLSYQLGADKKWSLPKGAYVGANAQIYGKHHQNH 4223
...............R.................................................................................... Q8

       310       320       330       340       350       360       370       380       390       400
KKYNDHWGRLGANLGFADAKKDLSIETYGEKRFYGHERYTDTIGIRMSVDYRINPKFQSLNAIDISRLTNHRTPRADSNNTLYSTSLIYYPNATRYYLLG 4223
................................................A................................................... Q8

       410       420       430       440       450       460       470       480       490       500
ADFYDEKVPQDPSDSYQRRGIRTAWGQEWAGGLSSRAQISINKRHYQGANLTSGGQIRHDKQMQASLSLWHRDIHKWGITPRLTISTNINKSNDIKANYH 4223
................E.........................................Q......................................... Q8

       510
KNQMFVEFSRIF*                                                                                        4223
............*                                                                                        Q8
```

TRANSFERRIN RECEPTOR GENES OF MORAXELLA

REFERENCE TO RELATED APPLICATION

This application is a continuation-in-part of International Patent Application No. PCT/CA97/00163 filed Mar. 7, 1997 which itself is a continuation-in-part of copending U.S. patent application Ser. No. 08/778,570 filed Jan. 3, 1997, which itself is a continuation-in-part of U.S. patent application Ser. No. 08/613,009 filed Mar. 8, 1996.

FIELD OF INVENTION

The present invention relates to the molecular cloning of genes encoding transferrin receptor (TfR) proteins and, in particular, to the cloning of transferrin receptor genes from *Moraxella* (Branhamella) *catarrhalis.*

BACKGROUND OF THE INVENTION

*Moraxella* (Branhamella) *catarrhalis* bacteria are Gram-negative diplococcal pathogens which are carried asymptomatically in the healthy human respiratory tract. In recent years, *M. catarrhalis* has been recognized as an important causative agent of otitis media. In addition, *M. catarrhalis* has been associated with sinusitis, conjunctivitis, and urogenital infections, as well as with a number of inflammatory diseases of the lower respiratory tract in children and adults, including pneumonia, chronic bronchitis, tracheitis, and emphysema (refs. 1 to 8). (Throughout this application, various references are cited in parentheses to describe more fully the state of the art to which this invention pertains. Full bibliographic information for each citation is found at the end of the specification, immediately preceding the claims. The disclosures of these references are hereby incorporated by reference into the present disclosure). Occasionally, *M. catarrhalis* invades to cause septicaemia, arthritis, endocarditis, and meningitis (refs. 9 to 13).

Otitis media is one of the most common illnesses of early childhood and approximately 80% of all children suffer at least one middle ear infection before the age of three (ref. 14). Chronic otitis media has been associated with auditory and speech impairment in children, and in some cases, has been associated with learning disabilities. Conventional treatments for otitis media include antibiotic administration and surgical procedures, including tonsillectomies, adenoidectomies, and tympanocentesis. In the United States, treatment costs for otitis media are estimated to be between one and two billion dollars per year.

In otitis media cases, *M. catarrhalis* commonly is co-isolated from middle ear fluid along with *Streptococcus pneumoniae* and non-typable *Haemophilus influenzae*, which are believed to be responsible for 50% and 30% of otitis media infections, respectively. *M. catarrhalis* is believed to be responsible for approximately 20% of otitis media infections (ref. 15). Epidemiological reports indicate that the number of cases of otitis media attributable to *M. catarrhalis* is increasing, along with the number of antibiotic-resistant isolates of *M. catarrhalis.* Thus, prior to 1970, no β-lactamase-producing *M. catarrhalis* isolates had been reported, but since the mid-seventies, an increasing number of β-lactamase-expressing isolates have been detected. Recent surveys suggest that 75% of clinical isolates produce β-lactamase (ref. 16, 26).

Iron is an essential nutrient for the growth of many bacteria. Several bacterial species, including *M. catarrhalis*, obtain iron from the host by using transferrin receptor proteins to capture transferrin. A number of bacteria including *Neisseria meningitidis* (ref. 17), *N. gonorrhoeae* (ref. 18), *Haemophilus influenzae* (ref. 19), as well as *M. catarrhalis* (ref. 20), produce outer membrane proteins which specifically bind human transferrin. The expression of these proteins is regulated by the amount of iron in the environment.

The two transferrin receptor proteins of *M. catarrhalis*, designated transferrin binding protein 1 (Tbp1) and transferrin binding protein 2 (Tbp2), have molecular weights of 115 kDa (Tbp1) and approximately 80 to 90 kDa (Tbp2). Unlike the transferrin receptor proteins of other bacteria which have an affinity for apotransferrin, the *M. catarrhalis* Tbp2 receptors have a preferred affinity for iron-saturated (i.e., ferri-) transferrin (ref. 21).

*M. catarrhalis* infection may lead to serious disease. It would be advantageous to provide a recombinant source of transferrin binding proteins as antigens in immunogenic preparations including vaccines, carriers for other antigens and immunogens and the generation of diagnostic reagents. The genes encoding transferrin binding proteins and fragments thereof are particularly desirable and useful in the specific identification and diagnosis of Moraxella and for immunization against disease caused by *M. catarrhalis* and for the generation of diagnostic reagents.

SUMMARY OF THE INVENTION

The present invention is directed towards the provision of purified and isolated nucleic acid molecules encoding a transferrin receptor of a strain of Moraxella or a fragment or an analog of the transferrin receptor protein. The nucleic acid molecules provided herein are useful for the specific detection of strains of Moraxella and for diagnosis of infection by Moraxella. The purified and isolated nucleic acid molecules provided herein, such as DNA, are also useful for expressing the tbp genes by recombinant DNA means for providing, in an economical manner, purified and isolated transferrin receptor proteins as well as subunits, fragments or analogs thereof. The transferrin receptor, subunits or fragments thereof or analogs thereof, as well as nucleic acid molecules encoding the same and vectors containing such nucleic acid molecules, are useful in immunogenic compositions for vaccinating against diseases caused by Moraxella, the diagnosis of infection by Moraxella and as tools for the generation of immunological reagents. Monoclonal antibodies or mono-specific antisera (antibodies) raised against the transferrin receptor protein, produced in accordance with aspects of the present invention, are useful for the diagnosis of infection by Moraxella, the specific detection of Moraxella (in, for example, in vitro and in vivo assays) and for the treatment of diseases caused by Moraxella.

In accordance with one aspect of the present invention, there is provided a purified and isolated nucleic acid molecule encoding a transferrin receptor protein of a strain of Moraxella, more particularly, a strain of *M. catarrhalis*, specifically *M. catarrhalis* strain 4223, Q8, R1, M35, 3 or LES1, or a fragment or an analog of the transferrin receptor protein.

In one preferred embodiment of the invention, the nucleic acid molecule may encode only the Tbp1 protein of the Moraxella strain or only the Tbp2 protein of the Moraxella strain. In another preferred embodiment of the invention, the nucleic acid may encode a fragment of the transferrin receptor protein of a strain of Moraxella having an amino acid sequence which is conserved.

In another aspect of the present invention, there is provided a purified and isolated nucleic acid molecule having a DNA sequence selected from the group consisting of (a) a DNA sequence as set out in FIG. 5, 6, 10, 11, 27, 31, 32 or 33 (SEQ ID NOS: 1, 2, 3, 4, 5, 6, 7, 8, 45, 47, 48, 50 or 52 or the complementary DNA sequence thereto; (b) a DNA sequence encoding an amino acid sequence as set out in FIG. 5, 6, 10, 11, 27, 31, 32 or 33 (SEQ ID NOS: 9, 10, 11, 12, 13, 14, 15, 16, 46, 49, 51 or 53 or the complementary DNA sequence thereto; and (c) a DNA sequence encoding a functional transferrin receptor protein of a strain of Moraxella, which may be a DNA sequence which hybridizes under stringent conditions to any one of the DNA sequences defined in (a) or (b). The DNA sequence defined in (c) may have at least about 90% sequence identity with any one of the DNA sequences defined in (a) and (b). The functional transferrin receptor protein of a strain of Moraxella encoded by the DNA sequence defined in (c) is the equivalent transferrin receptor protein from another strain of Moraxella.

In an additional aspect, the present invention includes a vector adapted for transformation of a host, comprising a nucleic acid molecule as provided herein and may have the characteristics of a nucleotide sequence contained within vectors LEM3-24, pLEM3, pLEM25, pLEM23, SLRD-A, DS-1698-1-1, DS-1754-1, pSLRD2, pSLRD3, pSLRD4 and pSLRD5.

The vector may be adapted for expression of the encoded transferrin receptor, fragments or analogs thereof, in a heterologous or homologous host, in either a lipidated or non-lipidated form. Accordingly, a further aspect of the present invention provides an expression vector adapted for transformation of a host comprising a nucleic acid molecule as provided herein and expression means operatively coupled to the nucleic acid molecule for expression by the host of the transferrin receptor protein or the fragment or analog of the transferrin receptor protein. In specific embodiments of this aspect of the invention, the nucleic acid molecule may encode substantially all the transferrin receptor protein, only the Tbp1 protein, only the Tbp2 protein of the Moraxella strain or fragments of the Tbp1 or Tbp2 proteins. The expression means may include a promoter and a nucleic acid portion encoding a leader sequence for secretion from the host of the transferrin receptor protein or the fragment or the analog of the transferrin receptor protein. The expression means also may include a nucleic acid portion encoding a lipidation signal for expression from the host of a lipidated form of the transferrin receptor protein or the fragment or the analog of the transferrin receptor protein. The host may be selected from, for example, *Escherichia coli*, Bordetella, Bacillus, Haemophilus, *Moraxella, fungi*, yeast or baculovirus and Semliki Forest virus expression systems may be used. In a particular embodiment, the plasmid adapted for expression of Tbp1 is pLEM29 and that for expression of Tbp2 is pLEM33. Further vectors include pLEM-37, SLRD35-A and SLRD-35-B.

In an additional aspect of the invention, there is provided a transformed host containing an expression vector as provided herein. The invention further includes a recombinant transferrin receptor protein or fragment or analog thereof of a strain of Moraxella producible by the transformed host.

Such recombinant transferrin receptor protein may be provided in substantially pure form according to a further aspect of the invention, which provides a method of forming a substantially pure recombinant transferrin receptor protein, which comprises growing the transformed host provided herein to express a transferrin receptor protein as inclusion bodies, purifying the inclusion bodies free from cellular material and soluble proteins, solubilizing transferrin receptor protein from the purified inclusion bodies, and purifying the transferrin receptor protein free from other solubilized materials. The substantially pure recombinant transferrin receptor protein may comprise Tbp1 alone, Tbp2 alone or a mixture thereof. The recombinant protein is generally at least about 70% pure, preferably at least about 90% pure.

Further aspects of the present invention, therefore, provide recombinantly-produced Tbp1 protein of a strain of Moraxella devoid of the Tbp2 protein of the Moraxella strain and any other protein of the Moraxella strain and recombinantly-produced Tbp2 protein of a strain of Moraxella devoid of the Tbp1 protein of the Moraxella strain and any other protein of the Moraxella strain. The Moraxella strain may be *M. catarrhalis* 4223 strain, *M. catarrhalis* Q8 strain or *M. catarrhalis* R1 strain, *M. catarrhalis* M35 strain, *M. catarrhalis* 3 strain or *M. catarrhalis* LES1 strain.

In accordance with another aspect of the invention, an immunogenic composition is provided which comprises at least one active component selected from at least one nucleic acid molecule as provided herein and at least one recombinant protein as provided herein, and a pharmaceutically acceptable carrier therefor or vector therefor. The at least one active component produces an immune response when administered to a host.

The immunogenic compositions provided herein may be formulated as vaccines for in vivo administration to a host. For such purpose, the compositions may be formulated as a microparticle, capsule, ISCOM (immunostimulatory complex) or liposome preparation. The immunogenic composition may be provided in combination with a targeting molecule for delivery to specific cells of the immune system or to mucosal surfaces. The immunogenic compositions of the invention (including vaccines) may further comprise at least one other immunogenic or immunostimulating material and the immunostimulating material may be at least one adjuvant or at least one cytokine. Suitable adjuvants for use in the present invention include (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein. Advantageous combinations of adjuvants are described in copending U.S. patent applications Ser. Nos. 08/261,194 filed Jun. 16, 1994 and Ser. No. 08/483,856, filed Jun. 7, 1995, assigned to the assignee hereof and the disclosures of which are incorporated herein by reference thereto (WO 95/34308).

In accordance with another aspect of the invention, there is provided a method for generating an immune response in a host, comprising the step of administering to a susceptible host, such as a human, an effective amount of the immunogenic composition provided herein. The immune response may be a humoral or a cell-mediated immune response and may provide protection against disease caused by Moraxella. Hosts in which protection against disease may be conferred include primates, including humans.

In a further aspect, there is provided a live vector for delivery of transferrin receptor to a host, comprising a vector containing the nucleic acid molecule as described above. The vector may be selected from Salmonella, BCG, adenovirus, poxvirus, vaccinia and poliovirus.

The nucleic acid molecules provided herein are useful in diagnostic applications. Accordingly, in a further aspect of the invention, there is provided a method of determining the presence, in a sample, of nucleic acid encoding a transferrin receptor protein of a strain of Moraxella, comprising the steps of:

(a) contacting the sample with a nucleic acid molecule as provided herein to produce duplexes comprising the nucleic acid molecule and any nucleic acid molecule encoding the transferrin receptor protein of a strain of Moraxella present in the sample and specifically hybridizable therewith; and (b) determining the production of the duplexes.

In addition, the present invention provides a diagnostic kit for determining the presence, in a sample, of nucleic acid encoding a transferrin receptor protein of a strain of Moraxella, comprising:

(a) a nucleic acid molecule as provided herein;

(b) means for contacting the nucleic acid molecule with the sample to produce duplexes comprising the nucleic acid molecule and any such nucleic acid present in the sample and hybridizable with the nucleic acid molecule; and (c) means for determining production of the duplexes.

The invention further includes the use of the nucleic acid molecules and proteins provided herein as medicines. The invention additionally includes the use of the nucleic acid molecules and proteins provided herein in the manufacture of medicaments for protection against infection by strains of Moraxella.

Advantages of the present invention include:

an isolated and purified nucleic acid molecule encoding a transferrin receptor protein of a strain of Moraxella or a fragment or an analog of the transferrin receptor protein;

recombinantly-produced transferrin receptor proteins, including Tbp1 and Tbp2, free from each other and other Moraxella proteins; and diagnostic kits and immunological reagents for specific identification of Moraxella.

BRIEF DESCRIPTION OF DRAWINGS

The present invention will be further understood from the following description with reference to the drawings, in which:

FIG. 1 shows the amino acid sequences (SEQ ID NOS: 17 and 18) of a conserved portion of Tbp1 proteins used for synthesis of degenerate primers used for PCR amplification of a portion of the *M. catarrhalis* 4223 tbpA gene;

FIGS. 5A to 5J show the nucleotide sequence of the tbpA gene (SEQ ID NO: 1—entire sequence and SEQ ID NO: 2—coding sequence) and the deduced amino acid sequence of the Tbp1 protein from *M. catarrhalis* 4223 (SEQ ID NO: 9—full length and SEQ ID NO: 10—mature protein). The leader sequence (SEQ ID NO: 19) is shown by underlining;

FIGS. 6A to 6G show the nucleotide sequence of the tbpB gene (SEQ ID NO: 3—entire sequence and SEQ ID NO: 4—coding sequence) and the deduced amino acid sequence of the Tbp2 protein from *M. catarrhalis* 4223 (SEQ ID NOS: 11—full length and SEQ ID NO: 12—mature protein). The leader sequence (SEQ ID NO: 20) is shown by underlining;

FIGS. 10A to 10Q show the nucleotide sequence of the tbpA gene (SEQ. ID NO: 5—entire sequence and SEQ ID NO: 6—coding sequence) and the deduced amino acid sequence of the Tbp1 protein from *M. catarrhalis* Q8 (SEQ ID NO: 13—full length and SEQ ID NO: 14—mature protein);

FIGS. 11A to 11O show the nucleotide sequence of the tbpB gene (SEQ. ID NO: 7—entire sequence and SEQ ID NO: 8—coding sequence) and the deduced amino acid sequence of the Tbp2 protein from *M. catarrhalis* Q8 (SEQ ID NO: 15—full length and SEQ ID NO: 16—mature protein);

FIGS. 12A to 12G show a comparison of the amino acid sequences of Tbp1 from *M. catarrhalis* strain 4223 (SEQ ID NO: 9) and Q8 (SEQ ID NO: 13), *H. influenzae* strain Eagan (SEQ ID NO: 21), *N. meningitidis* strains B16B6 (SEQ ID NO: 22) and M982 (SEQ ID NO: 23), and *N. gonorrhoeae* strain FA19 (SEQ ID NO: 24). Dots indicate identical residues and dashes have been inserted for maximum alignment;

FIGS. 13A to 13F show a comparison of the amino acid sequences of Tbp2 from *M. catarrhalis* isolate 4223 (SEQ ID NO: 11) and Q8 (SEQ ID NO: 15), *H. influenzae* strain Eagan (SEQ ID NO: 25), *N. meningitidis* strains B16B6 (SEQ ID NO: 26) and M918 (SEQ ID NO: 27), and *N. gonorrhoeae* strain FA19 (SEQ ID NO: 28). Dots indicate identical residues and dashes have been inserted for maximum alignment;

FIG. 21 shows SDS PAGE analysis of the expression of rTbp2 protein in *E. coli* cells, transformed with plasmids SLRD35A and SLRD35B;

FIG. 26 shows a partial restriction map of the *M. catarrhalis* strain M35 tbpB gene;

FIGS. 27A to 27K show the nucleotide sequence of the tbpB gene (SEQ ID NO: 45) and deduced amino acid sequence of the Tbp2 protein of *M. catarrhalis* strain M35 (SEQ ID NO: 46);

FIG. 28 shows a restriction map of the tbpB gene for *M. catarrhalis* R1;

FIG. 29 shows a partial restriction map of the tbpB gene for *M. catarrhalis* strain 3;

FIG. 30 shows a partial restriction map of the tbpB genes for *M. catarrhalis* strain LES1;

FIGS. 31A to 31G show the nucleotide sequence of the tbpB gene (SEQ ID NO: 47—entire sequence and SEQ ID NO: 48—coding sequence) and the deduced amino acid sequence of the Tbp2 protein of *M. catarrhalis* strain R1 (SEQ ID NO: 49);

FIGS. 32A to 32K show the nucleotide sequence of tbpB gene (SEQ ID NO: 50) and the deduced amino acid sequence of the Tbp2 protein of *M. catarrhalis* strain 3 (SEQ ID NO: 51);

FIGS. 33A to 33K show the nucleotide sequence of the tbpB gene (SEQ ID NO: 52) and deduced amino acid sequence of the Tbp2 *M. catarrhalis* strain LES1 (SEQ ID NO: 53);

FIGS. 34A to 34D show an alignment of the Tbp2 proteins from strains 4223 (SEQ ID NO: 11), R1 (SEQ ID NO: 49), M35 (SEQ ID NO: 46), LES1 (SEQ ID NO: 53), Q8 (SEQ ID NO: 15) and 3 (SEQ ID NO: 51). Dots indicate identical residues and spaces have been introduced to maximize the sequence alignment. Underlining indicates those sequences conserved amongst the *M. catarrhalis* Tbp2 proteins and those from *A. pleuropneumoniae, H. influenzae, N. gonorrhoeae, N. meningitidis* and *P. haemolytica;*

FIGS. 35A to 35M' show the nucleotide and deduced amino acid sequences of the *M. catarrhalis* strain 4223 tbpA-orf3-tbpB gene locus (SEQ ID NO: 54, nucleotide sequence of intergenic region, SEQ ID NO: 55, orf3 coding sequence; SEQ ID NO: 56, ORF3 amino acid sequence); and FIG. 36 shows an alignment of the ORF3 proteins from *M. catarrhalis* strain 4223 (SEQ ID NO: 56) and Q8 (SEQ ID NO: 57). Dots indicate identical residues.

GENERAL DESCRIPTION OF THE INVENTION

Any Moraxella strain may be conveniently used to provide the purified and isolated nucleic acid, which may be in the form of DNA molecules, comprising at least a portion of the nucleic acid coding for a transferrin receptor as typified by embodiments of the present invention. Such strains are generally available from clinical sources and from bacterial culture collections, such as the American Type Culture Collection. Strains 4223, LES-1 and M35 are all derived from patients with otitis media while strains 3, R1 and Q8 were from spectrum or bronchial secretion.

In this application, the terms "transferrin receptor" (TfR) and "transferrin binding proteins" (Tbp) are used to define a family of Tbp1 and/or Tbp2 proteins which includes those having variations in their amino acid sequences including those naturally occurring in various strains of, for example, Moraxella. The purified and isolated DNA molecules comprising at least a portion coding for transferrin receptor of the present invention also include those encoding functional analogs of transferrin receptor proteins Tbp1 and Tbp2 of Moraxella. In this application, a first protein is a "functional analog" of a second protein if the first protein is immunologically related to and/or has the same function as the second protein. The functional analog may be, for example, a fragment of the protein, or a substitution, addition or deletion mutant thereof.

Chromosomal DNA from *M. catarrhalis* 4223, a clinical isolate provided by Dr. T. Murphy (State University of New York, Buffalo, N.Y.), was digested with Sau3A in order to generate fragments within a 15 to 23 kb size range, and cloned into the BamHI site of the lambda vector EMBL3. The library was screened with anti-Tbp1 guinea pig antisera, and a positive clone LEM3-24, containing an insert approximately 13.2 kb in size was selected for further analysis. Lysate from *E. coli* LE392 infected with LEM3-24 was found to contain a protein approximately 115 kDa in size, which reacted on Western blots with anti-Tbp1 antisera. A second protein, approximately 80 kDa in size, reacted with the anti-Tbp2 guinea pig antisera on Western blots.

Figure 2:
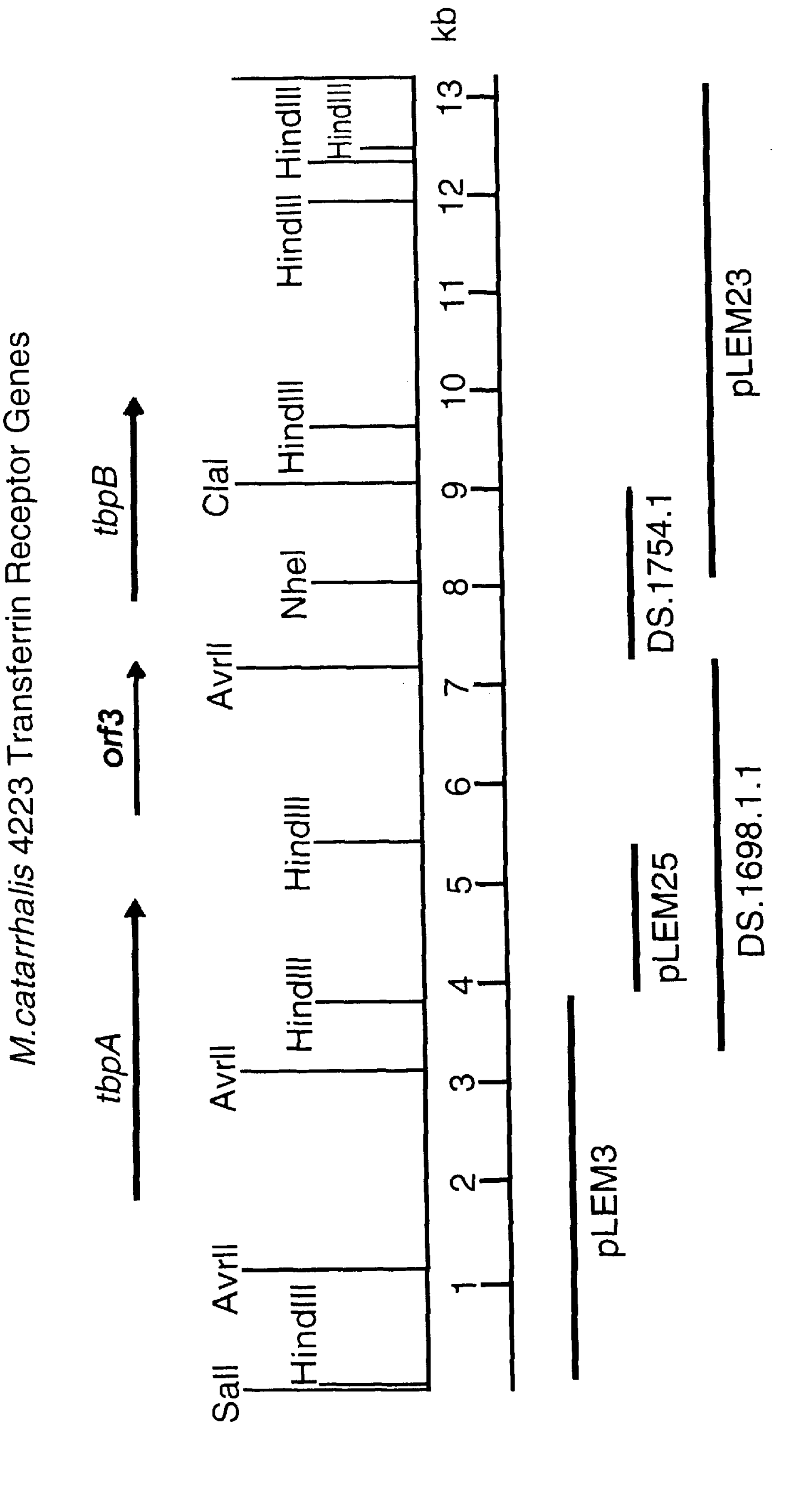
FIG. 2 shows a restriction map of clone LEM3-24 containing the tbpA and tbpB genes and orf 3 gene from *M. catarrhalis* isolate 4223.

In order to localize the tbpA gene on the 13.2 kb insert of LEM3-24, degenerate PCR primers were used to amplify a small region of the putative tbpA gene of *M. catarrhalis* 4223. The sequences of the degenerate oligonucleotide primers were based upon conserved amino acid sequences within the Tbp1 proteins of several Neisseria and Haemophilus species and are shown in FIG. 1 (SEQ ID NOS: 17 and 18). A 300 base-pair amplified product was generated and its location within the 4223 tbpA gene is indicated by bold letters in FIG. 5 (SEQ ID NO: 29). The amplified product was subcloned into the vector pCRII, labelled, and used to probe a Southern blot containing restriction-endonuclease digested clone LEM3-24 DNA. The probe hybridized to a 3.8 kb HindIII-HindIII, a 2.0 kb AvrII-AvrII, and 4.2 kb SalI-SphI fragments (FIG. 2).

The 3.8 kb HindIII-HindIII fragment was subcloned into pACYC177, and sequenced. A large open reading frame was identified, and subsequently found to contain approximately 2 kb of the putative tbpA gene. The remaining 1 kb of the tbpA gene was obtained by. subcloning an adjacent downstream HindIII-HindIII fragment into vector pACYC177. The nucleotide sequence of the tbpA gene from *M. catarrhalis* 4223 (SEQ ID NOS: 1 and 2), and the deduced amino acid sequence (SEQ ID NO: 9—full length; SEQ ID NO: 10 mature protein) are shown in FIGS. 5A–5J.

Chromosomal DNA from *M. catarrhalis* strain Q8 was digested with Sau3A I and 15–23 kb fragments were ligated with BamHI arms of EMBL3. (Strain Q8 was a gift from Dr. M. G. Bergeron, Centre Hospitalier de l'Université Laval, St. Foy, Quebec.) A high titre library was generated in *E. coli* LE392 cells and was screened using oligonucleotide probes based on the 4223 tbpA sequence. Phage DNA was prepared and restriction enzyme analysis revealed that inserts of about 13–15 kb had been cloned. Phage clone SLRD-A was used to subclone fragments for sequence analysis. A cloning vector (pSKMA) was generated to facilitate cloning of the fragments and plasmids pSLRD1, pSLRD2, pSLRD3, pSLRD4 and pSLRD5 were generated which contain all of tbpA and most of tbpB. The nucleotide (SEQ ID NOS: 5 and 6) and deduced amino acid sequence (SEQ ID NO: 13—full length, SEQ ID NO: 14—mature protein) of the tbpA gene from strain Q8 are shown in FIGS. 10A to 10Q.

The deduced amino acid sequences for the Tbp1 protein encoded by the tbpA genes were found to share some homology with the amino acid sequences encoded by genes from a number of Neisseria and Haemophilus species (FIGS. 12A to 12G; SEQ ID NOS: 21, 22, 23 and 24).

Prior to the present discovery, tbpA genes identified in species of Neisseria, Haemophilus, and Actinobacillus have been found to be preceded by a tbpB gene with several conserved regions. The two genes typically are separated by a short intergenic sequence. However, a tbpB gene was not found upstream of the tbpA gene in *M. catarrhalis* 4223. In order to localize the tbpB gene within the 13.2 kb insert of clone LEM3-24, a denerate oligonucleotide probe was synthesized based upon an amino acid sequence EGGFYGP (SEQ ID NO: 30), conserved among Tbp2 proteins of several species. The oligonucleotide was labelled and used to probe a Southern blot containing different restriction endonuclease fragments of clone LEM3-24. The probe hybridized to a 5.5 kb NheI-SalI fragment, which subsequently was subcloned into pBR328, and sequenced. The fragment contained most of the putative tbpB gene, with the exception of the promoter region. The clone LEM3-24 was sequenced to obtain the remaining upstream sequence. The tbpB gene was located approximately 3 kb downstream from the end of the tbpA gene, in contrast to the genetic organization of the tbpA and tbpB genes in Haemophilus and Neisseria. The nucleotide sequence (SEQ ID NOS: 3 and 4) of the tbpB gene from *M. catarrhalis* 4223 and the deduced amino acid sequence (SEQ ID NOS: 11, 12) are shown in FIGS. 6A to 6G.

The tbpB gene from *M. catarrhalis* Q8 was also cloned and sequenced. The nucleotide sequence (SEQ ID NOS: 7 and 8) and the deduced amino acid sequence (SEQ ID NOS: 15 and 16) are shown in FIGS. 11A to 11O.

The tbpB gene from *M. catarrhalis* R1, 3, M35 and LES1 were also cloned and sequenced. (Strain 3 is an isolate provided by Dr. T. Murphy; strain R1 was a gift from Dr. M. G. Bergeron; strain M35 was obtained from Dr. G. D. Campbell (Louisiana State University, Shreveport, La.) and strain LES1 was obtained from Dr. L. Stanfors (University of Tromso, Finland).). FIGS. 27A to 27K, 31A to 31G, 32A to 32K and 33A to 33K show the nucleotide sequence of the tbpB gene (SEQ ID NOS: 45, 47, 48, 50, 52) and deduced amino acid sequence of the Tbp2 protein (SEQ ID NOS: 46, 49, 51, 53) of the *M. catarrhalis* strains M35, R1, 3 and LES1 respectively. Regions of homology are evident between the *M. catarrhalis* Tbp2 amino acid sequences as shown in the comparative alignment of FIGS. 34A to 34D (SEQ ID NOS: 11, 15, 46, 49, 51 and 53)) and between the *M. catarrhalis* Tbp2 amino acid sequences and the Tbp2 sequences of a number of Neisseria and Haemophilus species, as shown in the comparative alignment in FIGS. 13A to 13F (SEQ ID NOS: 25, 26, 27, 28). Underlining in FIGS. 34A to 34D indicates those sequences which are conserved among the *M. catarrhalis* Tbp2 proteins and those of *A. pleuropneumoniae, H. influenzae, N. gonorrhoeae, N. meningitidis* and *P. haemolytica.*

Cloned tbpA and tbpB genes were expressed in *E. coli* to produce recombinant Tbp1 and Tbp2 proteins free of other Moraxella proteins. These recombinant proteins were purified and used for immunization.

Figure 25:
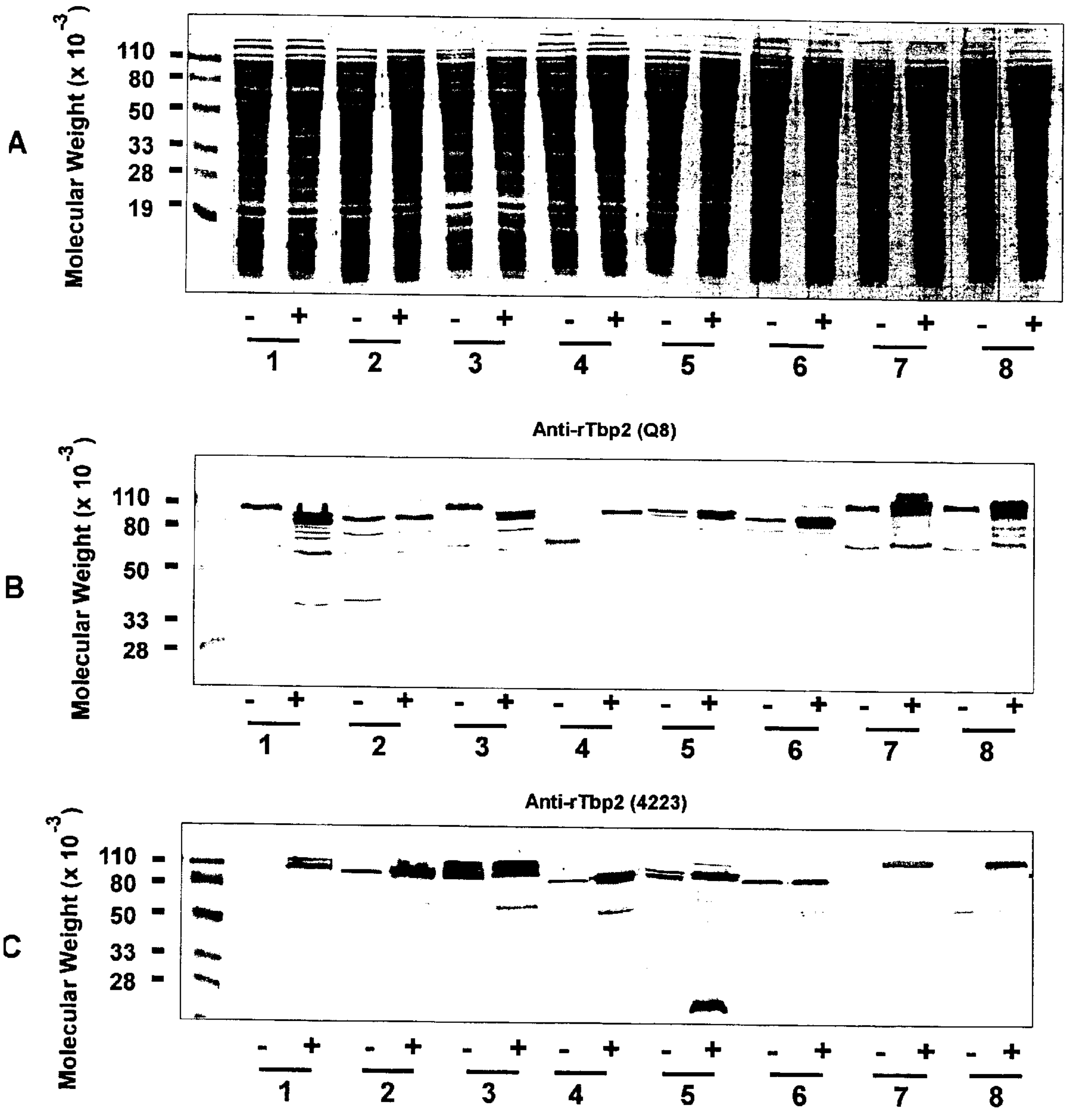
FIG. 25, which includes Panels A, B and C, shows the antigenic conservation of Tbp2 protein amongst strains of *M. catarrhalis;*

The antigenic conservation of Tbp2 protein amongst strains of *M. catarrhalis* was demonstrated by separation of the proteins in whole cell lysates of *M. catarrhalis* or strains of *E. coli* expressing recombinant Tbp2 proteins by SDS PAGE and antiserum immunoblotting with anti-4223 rTbp2 antiserum or anti-Q8 rTbp2 antiserum raised in guinea pigs. *M. catarrhalis* strains 3, 56, 135, 585, 4223, 5191, 8185 and ATCC 25240 were tested in this way and all showed specific reactivity with anti-4223 rTbp2 or anti-Q8 rTbp2 antibody (FIG. 25).

Sequence analysis indicated that at least two families could be identified for *M. catarrhalis* tbpB genes, one comprising strains 4223, R1 and M35 and other containing strains Q8 and 3, with strain LES1 being equally related to both families. Anti-rTbp2 bactericidal antibody activity (Table 4) correlated with the putative gene families identified by sequencing.

In addition, the ability of anti-rTbp2 antibodies from one strain to recognize native or recombinant protein from the homologous or heterologous strain by ELISA is shown in Table 1 below.

Amino acid sequencing of the N-termini and cyanogen bromide fragments of transferrin receptor from *M. catarrhalis* 4223 was undertaken. Both N-termini of Tbp1 and Tbp2 were blocked. The putative signal sequences of Tbp1 and Tbp2 are indicated by underlining in FIGS. 5A to 5J and 6A to 6G (SEQ ID NOS: 19 and 20) respectively. The deduced amino acid sequences for the N-terminal region of Tbp2 suggests a lipoprotein structure.

Results shown in Tables 1 and 2 below illustrate the ability of anti-Tbp1 and anti-Tbp2 guinea pig antisera, produced by the immunization with Tbp1 or Tbp2, to lyze *M. catarrhalis*. The results show that the antisera produced by immunization with Tbp1 or Tbp2 protein isolated from *M. catarrhalis* isolate 4223 were bactericidal against a homologous non-clumping *M. catarrhalis* strain RH408 (a strain previously deposited in connection with U.S. patent application Ser. No. 08/328,589, assigned to the assignee hereof, (WO 96/12733) with the American Type Culture Collection, located at 1301 Parklawn Drive, Rockville, Md. 20852, USA under the terms of the Budapest Treaty on Dec. 13, 1994 under ATCC Deposit No. 55,637) derived from isolate 4223. In addition, antisera produced by immunization with Tbp1 protein isolated from *M. catarrhalis* 4223 were bactericidal against the heterologous non-clumping strain Q8. In addition, antiserum raised against recombinant Tbp2 (rTbp2) protein was bacteriacidal against the homologous strain of *M. catarrhalis.*

The ability of isolated and purified transferrin binding proteins to generate bactericidal antibodies is in vivo evidence of utility of these proteins as vaccines to protect against disease caused by Moraxella.

Thus, in accordance with another aspect of the present invention, there is provided a vaccine against infection caused by Moraxella strains, comprising an immunogenically-effective amount of a transferrin binding protein from a strain of Moraxella and a physiologically-acceptable carrier therefor. Vaccine preparations may comprise antigenically or sequence divergent transferrin binding proteins.

The transferrin binding protein provided herein is useful as a diagnostic reagent, as an antigen for the generation of anti-transferrin protein binding antibodies, as an antigen for vaccination against the disease caused by species of Moraxella and for detecting infection by Moraxella and other such bacteria.

The transferrin binding protein provided herein may also be used as a carrier protein for haptens, polysaccharides or peptides to make conjugate vaccines against antigenic determinants unrelated to transferrin binding proteins. In additional embodiments of the present invention, therefore, the transferrin binding protein as provided herein may be used as a carrier molecule to prepare chimeric molecules and conjugate vaccines (including glycoconjugates) against pathogenic bacteria, including encapsulated bacteria. Thus, for example, glycoconjugates of the present invention may be used to confer protection against disease and infection caused by any bacteria having polysaccharide antigens including lipooligosaccharides (LOS) and PRP. Such bacterial pathogens may include, for example, *Haemophilus influenzae, Streptococcus pneumoniae, Escherichia coli, Neisseria meningitidis, Salmonella typhi, Streptococcus mutans, Cryptococcus neoformans*, Klebsiella, *Staphylococcus aureus* and *Pseudomonas aeruginosa*. Particular antigens which can be conjugated to transferrin binding protein and methods to achieve such conjugations are described in U.S. patent application Ser. No. 08/433,522 filed Nov. 23, 1993 (WO 94/12641), assigned to the assignee hereof and the disclosure of which is hereby incorporated by reference thereto.

In another embodiment, the carrier function of transferrin binding protein may be used, for example, to induce an immune response against abnormal polysaccharides of tumour cells, or to produce anti-tumour antibodies that can be conjugated to chemotherapeutic or bioactive agents.

Additional sequence analysis of the entire *M. catarrhalis* strains 4223 and Q8 tbpA-tbpB locus gene sequence (FIGS. 35A to 35M') identified an intergenic open reading frame termed "orf3" (SEQ ID NO: 54, nucleotide sequence of intergenic region, SEQ ID NO: 55, orf3 coding sequence; SEQ ID NO: 56, ORF3 amino acid sequence), (see also FIGS. 2 and 7 for location of orf3). The encoded ORF3 proteins from 4223 and Q8 are 98% identical, as seen from the sequence alignment of FIG. 36 (SEQ ID NOS: 56, 57).

The invention extends to transferrin binding proteins from *Moraxella catarrhalis* for use as an active ingredient in a vaccine against disease caused by infection with Moraxella. The invention also extends to a pharmaceutical vaccinal composition containing transferrin binding proteins from *Moraxella catarrhalis* and optionally, a pharmaceutically acceptable carrier and/or diluent.

In a further aspect the invention provides the use of transferrin binding proteins for the preparation of a pharmaceutical vaccinal composition for immunization against disease caused by infection with Moraxella.

It is clearly apparent to one skilled in the art, that the various embodiments of the present invention have many applications in the fields of vaccination, diagnosis, treatment of, for example, Moraxella infections and the generation of immunological and other diagnostic reagents. A further non-limiting discussion of such uses is further presented below.

1. Vaccine Preparation and Use

Immunogenic compositions, suitable to be used as vaccines, may be prepared from immunogenic transferrin receptor proteins, analogs and fragments thereof encoded by the nucleic acid molecules as well as the nucleic acid molecules disclosed herein. The vaccine elicits an immune response which produces antibodies, including anti-transferrin receptor antibodies and antibodies that are opsonizing or bactericidal. Should the vaccinated subject be challenged by Moraxella, the antibodies bind to the transferrin receptor and thereby prevent access of the bacteria to an iron source which is required for viability. Furthermore, opsonizing or bactericidal anti-transferrin receptor antibodies may also provide protection by alternative mechanisms.

Immunogenic compositions, including vaccines, may be prepared as injectables, as liquid solutions or emulsions. The transferrin receptor proteins, analogs and fragments thereof and encoding nucleic acid molecules may be mixed with pharmaceutically acceptable excipients which are compatible with the transferrin receptor proteins, fragments, analogs or nucleic acid molecules. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants, to enhance the effectiveness of the vaccines. Immunogenic compositions and vaccines may be administered parenterally, by injection subcutaneously, intradermally or intramuscularly. Alternatively, the immunogenic compositions provided according to the present invention, may be formulated and delivered in a manner to evoke an immune response at mucosal surfaces. Thus, the immunogenic composition may be administered to mucosal surfaces by, for example, the nasal or oral (intragastric) routes. The immunogenic composition may be provided in combination with a targeting molecule for delivery to specific cells of the immune system or to mucosal surfaces. Some such targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al). Alternatively, other modes of administration, including suppositories and oral formulations, may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions may take the form of solutions, suspensions, tablets, pills, capsules, sustained release formulations or powders and contain about 1 to 95% of the transferrin receptor proteins, fragments, analogs and/or nucleic acid molecules.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and, if needed, to produce a cell-mediated immune response. Precise amounts of active ingredient required to be administered depend on the judgment of the practitioner. However, suitable dosage ranges are readily determinable by one skilled in the art and may be of the order of micrograms of the transferrin receptor proteins, analogs and fragments thereof and/or nucleic acid molecules. Suitable regimes for initial administration and booster doses are also variable, but may include an initial administration followed by subsequent administrations. The dosage of the vaccine may also depend on the route of administration and will vary according to the size of the host.

The nucleic acid molecules encoding the transferrin receptor of Moraxella may be used directly for immunization by administration of the DNA directly, for example, by injection for genetic immunization or by constructing a live vector, such as Salmonella, BCG, adenovirus, poxvirus, vaccinia or poliovirus containing the nucleic acid molecules. A discussion of some live vectors that have been used to carry heterologous antigens to the immune system is contained in, for example, O'Hagan (ref 22). Processes for the direct injection of DNA into test subjects for genetic immunization are described in, for example, Ulmer et al. (ref. 23).

Immunogenicity can be significantly improved if the antigens are co-administered with adjuvants, commonly used as an 0.05 to 1.0 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and an HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:

(1) lack of toxicity;

(2) ability to stimulate a long-lasting immune response;

(3) simplicity of manufacture and stability in long-term storage;

(4) ability to elicit both CMI and HIR to antigens administered by various routes, if required;

(5) synergy with other adjuvants;

(6) capability of selectively interacting with populations of antigen presenting cells (APC);

(7) ability to specifically elicit appropriate $T_H1$ or $T_H2$ cell-specific immune responses; and (8) ability to selectively increase appropriate antibody isotype levels (for example, IgA) against antigens.

U.S. Pat. No. 4,855,283 granted to Lockhoff et al on Aug. 8, 1989, which is incorporated herein by reference thereto, teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. 1991 (ref. 24) reported that N-glycolipid analogs displaying structural similarities to the naturally-occurring glycolipids, such as glycophospholipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990, (ref. 25) reported that octadecyl esters of aromatic amino acids complexed with a recombinant hepatitis B surface antigen, enhanced the host immune responses against hepatitis B virus.

2. Immunoassays

The transferrin receptor proteins, analogs and/or fragments thereof of the present invention are useful as immunogens, as antigens in immunoassays including enzyme-linked immunosorbent assays (ELISA), RIAs and other non-enzyme linked antibody binding assays or procedures known in the art for the detection of anti-Moraxella, transferrin receptor protein antibodies. In ELISA assays, the transferrin receptor protein, analogs and/or fragments corresponding to portions of TfR protein, are immobilized onto a selected surface, for example, a surface capable of binding proteins or peptides such as the wells of a polystyrene microtiter plate. After washing to remove incompletely adsorbed transferrin receptor, analogs and/or fragments, a non-specific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by non-specific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution such as PBS/Tween or a borate buffer.

Following formation of specific immunocomplexes between the test sample and the bound transferrin receptor protein, analogs and/or fragments and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then achieved by measuring the degree of color generation using, for example, a spectrophotometer.

3. Use of Sequences as Hybridization Probes

The nucleotide sequences of the present invention, comprising the sequence of the transferrin receptor gene, now allow for the identification and cloning of the transferrin receptor genes from any species of Moraxella.

The nucleotide sequences comprising the sequence of the transferrin receptor genes of the present invention are useful for their ability to selectively form duplex molecules with complementary stretches of other TfR genes. Depending on the application, a variety of hybridization conditions may be employed to achieve varying degrees of selectivity of the probe toward the other TfR genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90% homology.

In a clinical diagnostic embodiment, the nucleic acid sequences of the TfR genes of the present invention may be used in combination with an appropriate means, such as a label, for determining hybridization. A wide variety of appropriate indicator means are known in the art, including radioactive, enzymatic or other ligands, such as avidin/biotin and digoxigenin-labelling, which are capable of providing a detectable signal. In some diagnostic embodiments, an enzyme tag such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing TfR gene sequences.

The nucleic acid sequences of TfR genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the TfR genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of Moraxella. The selected probe may be at least 18 bp and may be in the range of about 30 to 90 bp.

4. Expression of the Transferrin Receptor Genes

Plasmid vectors containing replicon and control sequences which are derived from species compatible with the host cell may be used for the expression of the transferrin receptor genes in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the β-lactamase (penicillinase) and lactose promoter systems and other microbial promoters, such as the T7 promoter system as described in U.S. Pat. No. 4,952,496. Details concerning the nucleotide sequences of promoters are known, enabling a skilled worker to ligate them functionally with genes. The particular promoter used will generally be a matter of choice depending upon the desired results. Hosts that are appropriate for expression of the transferrin receptor genes, fragments, analogs or variants thereof, may include *E. coli*, Bacillus species, Haemophilus, fungi, yeast, Moraxella, Bordetella, or the baculovirus expression system may be used.

In accordance with this invention, it is preferred to make the transferrin receptor protein, fragment or analog thereof, by recombinant methods, particularly since the naturally occurring TfR protein as purified from a culture of a species of Moraxella may include trace amounts of toxic materials or other contaminants. This problem can be avoided by using recombinantly produced TfR protein in heterologous systems which can be isolated from the host in a manner to minimize contaminants in the purified material. Particularly desirable hosts for expression in this regard include Gram positive bacteria which do not have LPS and are, therefore, endotoxin free. Such hosts include species of Bacillus and may be particularly useful for the production of non-pyrogenic transferrin receptor, fragments or analogs thereof. Furthermore, recombinant methods of production permit the manufacture of Tbp1 or Tbp2 or respective analogs or fragments thereof, separate from one another which is distinct from the normal combined proteins present in Moraxella.

Sequence Alignment and Analysis

Sequence alignments were performed using the ALIGN (Trademark) or GENALIGN (Trademark) computer programs (Inteligenetics Suite 5.4, Oxford Molecular). ALIGN® uses the Needleman-Wunsch algorithm (ref. 32) and its later modifications to locate regions of similarity between two sequences using the default parameters of the program. Finding regions of maximum similarity between two sequences can be solved in a rigorous manner using the iterative matrix calculation of the Needleman and Wunsch 1997 algorithm. The analysis is restricted to regions with no internal deletions or insertions, joined by a minimum number of loop-outs or deletions. Sellers (ref. 33) developed a true metric measure of the "distance" between sequences and Waterman (ref. 34) extended this algorithm to include insertions and deletions of arbitrary length. Smith (ref. 35) improved the early algorithms to find the subsequences of maximum similarity. The algorithm has been used to analyze sequences as long as 5000 bases by dividing these sequences into segments of 200 to 400 bases, and then reassembling them into a final best match. This method of dividing the sequence and then reassembling it has proven quite robust. The algorithm permits the size of the segment to be specified which the program searches for similarities. The program then assembles the segments after checking overlaps of adjacent subsequences. The weighting of deletions and the relative size of overlaps may be controlled. The program displays the results to show the differences in closely related sequences.

GENALIGN® is a multiple alignment program. Up to 99 sequences using the Martinez/Regions (ref. 36) or Needleman-Wunsch (ref. 32) method may be analyzed for alignment. GENALIGN places the sequences in an order that puts the most closely aligned sequence pairs adjacent to each other. A consensus sequence is displayed under the multiple sequence alignments. The sequences used in developing the consensus sequence file for use in other programs. GENEALIGN allows the parameters of the search to be changed so that alternate alignments of the sequences can be formed.

Biological Deposits

Certain vectors that contain at least a portion coding for a transferrin receptor protein from strains of *Moraxella catarrhalis* strain 4223 and Q8 and a strain of *M. catarrhalis* RH408 that are described and referred to herein have been deposited with the American Type Culture Collection (ATCC) located at 12301 Parklawn Drive, Rockville, Md., USA, pursuant to the Budapest Treaty and prior to the filing of this application. Samples of the deposited vectors and bacterial strain will become available to the public and the restrictions imposed on access to the deposits will be removed upon grant of a patent based upon this United States patent application. In addition, the deposit will be replaced if viable samples cannot be dispensed by the Depository. The invention described and claimed herein is not to be limited in scope by the biological materials deposited, since the deposited embodiment is intended only as an illustration of the invention. Any equivalent or similar vectors or strains that encode similar or equivalent antigens as described in this application are within the scope of the invention.

Deposit Summary

| DEPOSIT | ATCC DESIGNATION | DATE DEPOSITED |
|---|---|---|
| Phage LEM3-24 | 97,381 | December 4, 1995 |
| Phage SLRD-A | 97,380 | December 4, 1995 |
| Plasmid pLEM29 | 97,461 | March 8, 1996 |
| Plasmid pSLRD35A | 97,833 | January 13, 1997 |

-continued

Deposit Summary

| DEPOSIT | ATCC DESIGNATION | DATE DEPOSITED |
|---|---|---|
| Plasmid pLEM37 | 97,834 | January 13, 1997 |
| Strain RH408 | 55,637 | December 9, 1994 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry and immunology used but not explicitly described in this disclosure and these Examples are amply reported in the scientific literature and are well within the ability of those skilled in the art.

Example 1

This Example illustrates the preparation and immunization of guinea pigs with Tbp1 and Tbp2 proteins from *M. catarrhalis.*

Tbp1 and Tbp2 proteins were obtained as follows:

Iron-starved crude total membrane preparations were diluted to 4 mg protein/ml in 50 mM Tris.HCl-1M NaCl, pH 8, in a total volume of 384 ml. Membranes were solubilized by the addition of 8 ml each of 0.5M EDTA and 30% sarkosyl and samples were incubated for 2 hours at room temperature, with gentle agitation. Solubilized membranes were centrifuged at 10K rpm for 20 min. 15 ml of apo-hTf-Sepharose 4B were added to the supernatant, and incubated for 2 hours at room temperature, with gentle shaking. The mixture was added into a column. The column was washed with 50 ml of 50 mM Tris.HCl-1 M NaCl-250 mM guanidine hydrochloride, to remove contaminating proteins. Tbp2 was eluted from the column by the addition of 100 ml of 1.5M guanidine hydrochloride. Tbp1 was eluted by the addition of 100 ml of 3M guanidine hydrochloride. The first 20 ml fractions were dialyzed against 3 changes of 50 mM Tris.HCl, pH 8.0. Samples were stored at −20° C., or dialyzed against ammonium bicarbonate and lyophilized.

Guinea pigs (Charles River) were immunized intramuscularly on day +1 with a 10 μg dose of Tbp1 or Tbp2 emulsified in complete Freund's adjuvant. Animals were boosted on days +14 and +29 with the same dose of protein emulsified in incomplete Freund's adjuvant. Blood samples were taken on day +42, and sera were used for analysis of bactericidal antibody activity. In addition, all antisera were assessed by immunoblot analysis for reactivity with *M. catarrhalis* 4223 proteins.

The bactericidal antibody activity of guinea pig anti-*M. catarrhalis* 4223 Tbp1 or Tbp2 antisera was determined as follows. A non-clumping *M. catarrhalis* strain RH408, derived from isolate 4223, was inoculated into 20 ml of BHI broth, and grown for 18 hr at 37° C., shaking at 170 rpm. One ml of this culture was used to inoculate 20 ml of BHI supplemented with 25 mM ethylenediamine-di-hydroxyphenylacetic acid (EDDA; Sigma). The culture was grown to an $OD_{578}$ of 0.5. The cells were diluted 1:200,000 in 140 mM NaCl, 93 mM $NaHCO_3$, 2 mM Na barbiturate, 4 mM barbituric acid, 0.5 mM $MgCl_2.6H_2O$, 0.4 mM $CaCl_2.2H_2O$, pH 7.6 (Veronal buffer), containing 0.1% bovine serum albumin (VBS) and placed on ice. Guinea pig anti-*M. catarrhalis* 4223 Tbp1 or Tpb2 antisera, along with prebleed control antisera, were heated to 56° C. for 30 min. to inactivate endogenous complement. Serial twofold dilutions of each antisera in VBS were added to the wells of a 96-well Nunclon microtitre plate (Nunc, Roskilde, Denmark). Dilutions started at 1:8, and were prepared to a final volume of 25 μL in each well. 25 μL of diluted bacterial cells were added to each of the wells. A guinea pig complement (Biowhittaker, Walkersville, Md.) was diluted 1:10 in VBS, and 25 μL portions were added to each well. The plates were incubated at 37° C. for 60 min, gently shaking at 70 rpm on a rotary platform. 50 μL of each reaction mixture were plated onto Mueller Hinton (Becton-Dickinson, Cockeysville, Md.) agar plates. The plates were incubated at 37° C. for 72 hr and the number of colonies per plate were counted. Bactericidal titres were assessed as the reciprocal of the highest dilution of antiserum capable of killing greater than 50% of bacteria compared with controls containing pre-immune sera. Results shown in Table 1 below illustrate the ability of the anti-Tbp1 and anti-Tbp2 guinea pig antisera to lyze *M. catarrhalis.*

Example 2

This Example illustrates the preparation of chromosomal DNA from *M. catarrhalis* strains 4223 and Q8.

*M. catarrhalis* isolate 4223 was inoculated into 100 ml of BHI broth, and incubated for 18 hr at 37° C. with shaking. The cells were harvested by centrifugation at 10,000×g for 20 min. The pellet was used for extraction of *M. catarrhalis* 4223 chromosomal DNA.

The cell pellet was resuspended in 20 ml of 10 mM Tris-HCl (pH 7.5)-1.0 mM EDTA (TE). Pronase and SDS were added to final concentrations of 500 μg/ml and 1.0%, respectively, and the suspension was incubated at 37° C. for 2 hr. After several sequential extractions with phenol, phenol:chloroform (1:1), and chloroform:isoamyl alcohol (24:1), the aqueous extract was dialysed, at 4° C., against 1.0 M NaCl for 4 hr, and against TE (pH 7.5) for a further 48 hr with three buffer changes. Two volumes of ethanol were added to the dialysate, and the DNA was spooled onto a glass rod. The DNA was allowed to air-dry, and was dissolved in 3.0 ml of water. Concentration was estimated, by UV spectrophotometry, to be about 290 μg/ml.

*M. catarrhalis* strain Q8 was grown in BHI broth as described in Example 1. Cells were pelleted from 50 ml of culture by centrifugation at 5000 rpm for 20 minutes, at 4° C. The cell pellet was resuspended in 10 ml of TE (10 mM Tris-HCl, 1 mM EDTA, pH 7.5) and proteinase K and SDS were added to final concentrations of 500 μg/ml and 1%, respectively. The sample was incubated at 37° C. for 4 hours until a clear lysate was obtained. The lysate was extracted twice with Tris-saturated phenol/chloroform (1:1), and twice with chloroform. The final aqueous phase was dialysed for 24 hours against 2×1000 ml of 1 M NaCl at 4° C., changing the buffer once, and for 24 hours against 2×1000 ml of TE at 4° C., changing the buffer once. The final dialysate was precipitated with two volume of 100% ethanol. The DNA was spooled, dried and resuspended in 5 to 10 ml of TE buffer.

Example 3

This Example illustrates the construction of *M. catarrhalis* chromosomal libraries in EMBL3.

A series of Sau3A restriction digests of chromosomal DNA, in final volumes of 10 μL each, were carried out in order to optimize the conditions necessary to generate maximal amounts of restriction fragments within a 15 to 23 kb size range. Using the optimized digestion conditions, a large-scale digestion was set up in a 100 μL volume, containing the following: 50 μL of chromosomal DNA (290 μg/ml), 33 μL water, 10 μL 10× Sau3A buffer (New England Biolabs), 1.0 μL BSA (10 mg/ml, New England Biolabs), and 6.3 μL Sau3A (0.04 U/μL). Following a 15 min. incubation at 37° C., the digestion was terminated by the addition of 10 μL of 100 mM Tris-HCl (pH 8.0)-10 mM EDTA-0.1% bromophenol blue-50% glycerol (loading buffer). Digested DNA was electrophoresed through a 0.5% agarose gel in 40 mM Tris acetate-2 mM $Na_2EDTA.2H_2O$ (pH8.5) (TAE buffer) at 50 V for 6 hr. The region containing restriction fragments within a 15 to 23 kb molecular size range was excised from the gel, and placed into dialysis tubing containing 3.0 ml of TAE buffer. DNA was electroeluted from the gel fragment by applying a field strength of 1.0 V/cm for 18 hr. Electroeluted DNA was extracted once each with phenol and phenol:chloroform (1:1), and precipitated with ethanol. The dried DNA was dissolved in 5.0 μL water.

Size-fractionated chromosomal DNA was ligated with BamHI-digested EMBL3 arms (Promega), using T4 DNA ligase in a final volume of 9 μL. The entire ligation mixture was packaged into lambda phage using a commercial packaging kit (Amersham), following manufacturer's instructions.

The packaged DNA library was amplified on solid media. 0.1 ml aliquots of *Escherichia coli* strain NM539 in 10 mM $MgSO_4$ ($OD_{260}$=0.5) were incubated at 37° C. for 15 min. with 15 to 25 μL of the packaged DNA library. Samples were mixed with 3 ml of 0.6% agarose containing 1.0% BBL trypticase peptone-0.5% NaCl (BBL top agarose), and mixtures were plated onto 1.5% agar plates containing 1.0% BBL trypticase peptone-0.5% NaCl, and incubated at 37° C. for 18 hr. 3 ml quantities of 50 mM Tris-HCl (pH 7.5)-8 mM magnesium sulfate heptahydrate-100 mM NaCl-0.01% (w/v) gelatin (SM buffer) were added to each plate, and plates were left at 4° C. for 7 hr. SM buffer containing phage was collected from the plates, pooled together, and stored in a screwcap tube at 4° C., with chloroform.

Chromosomal DNA from *M. catarrhalis* strain Q8 was digested with Sau3A I (0.1 unit/30 μg DNA) at 37° C. for 30 minutes and size-fractionated on a 0.6% low melting point agarose gel. DNA fragments of 15–23 kb were excised and the DNA was electroeluted for 25 minutes in dialysis tubing containing TAE (40 mM Tris acetate pH 8.5, 2 mM EDTA) at 150 V. The DNA was extracted once with phenol/chloroform (1:1), precipitated, and resuspended in water. The DNA was ligated overnight with EMBL3 BamH I arms (Promega) and the ligation mixture was packaged using the Lambda in vitro packaging kit (Stratagene) and plated onto *E. coli* LE392 cells. The library was titrated and stored at 4° C. in the presence of 0.3% chloroform.

Example 4

This Example illustrates screening of the *M. catarrhalis* libraries.

Ten μL aliquots of phage stock from the EMBL3/4223 sample prepared in Example 3 above were combined each with 100 μL of *E. coli* strain LE392 in 10 mM MgSO4 ($OD_{260}$=0.5) (plating cells), and incubated at 37° C. for 15 min. The samples were mixed with 3 ml each of BBL top agarose, and the mixtures were poured onto 1.5% agarose plates containing 1% bacto tryptone-0.5% bacto yeast extract-0.05% NaCl (LB agarose; Difco) and supplemented with 200 μM EDDA. The plates were incubated at 37° C. for 18 hr. Plaques were lifted onto nitrocellulose filters (Amersham Hybond-C Extra) using a standard protocol, and the filters were immersed into 5% bovine serum albumin (BSA; Boehringer) in 20 mM Tris-HCl (pH 7.5)-150 mM NaCl (TBS) for 30 min at room temperature, or 4° C. overnight. Filters were incubated for at least 1 hr at room temperature, or 18 hr at 4° C., in TBS containing a 1/1000 dilution of guinea pig anti-*M. catarrhalis* 4223 Tbp1 antiserum. Following four sequential 10 min. washes in TBS with 0.05% Tween 20 (TBS-Tween), filters were incubated for 30 min. at room temperature in TBS-Tween containing a 1/4000 dilution of recombinant Protein G labelled with horseradish peroxidase (rprotein G-HRP; Zymed). Filters were washed as above, and submerged into CN/DAB substrate solution (Pierce). Color development was arrested by immersing the filters into water. Positive plaques were cored from the plates, and each placed into 0.5 ml of SM buffer containing a few drops of chloroform. The screening procedure was repeated two more times, until 100% of the lifted plaques were positive using the guinea pig anti-*M. catarrhalis* 4223 Tbp1 antiserum.

The EMBL3/Q8 library was plated onto LE392 cells on YT plates using 0.7% top agar in YT as overlay. Plaques were lifted onto nitrocellulose filters and the filters were probed with oligonucleotide probes labelled with $^{32}P\alpha$-dCTP (Random Primed DNA labeling kit, Boehringer Mannheim). The pre-hybridization was performed in sodium chloride/sodium citrate (SSC) buffer (ref. 27) at 37° C. for 1 hour and the hybridization was performed at 42° C. overnight. The probes were based upon an internal sequence of 4223 tbpA:

IRDLTRYDPG (Seq ID No. 31)

4236-RD 5'ATTCGAGACTTAACACGCTATGACCCTGGC 3' (Seq ID No 32)

4237-RD 5'ATTCGTGATTTAACTCGCTATGACCCTGGT 3' (Seq ID No 33).

Putative plaques were re-plated and submitted to second and third rounds of screening using the same procedures. Phage clone SLRD-A was used to subclone the tfr genes for sequence analysis.

Example 5

This Example illustrates immunoblot analysis of the phage lysates using anti-*M. catarrhalis* 4223 Tbp1 and Tbp2 antisera.

Proteins expressed by the phage eluants selected in Example 4 above were precipitated as follows. 60 μL of each phage eluant were combined with 200 μL *E. coli* LE392 plating cells, and incubated at 37° C. for 15 min. The mixture was inoculated into 10 ml of 1.0% NZamine A-0.5% NaCl-0.1% casamino acids-0.5% yeast extract-0.2% magnesium sulfate heptahydrate (NZCYM broth), supplemented with 200 mM EDDA, and grown at 37° C. for 18 hr, with shaking. DNAse was added to 1.0 ml of the culture, to a final concentration of 50 μg/ml, and the sample was incubated at 37° C. for 30 min. Trichloroacetic acid was added to a final concentration of 12.5%, and the mixture was left on ice for 15 min. Proteins were pelleted by centrifugation at 13,000×g for 10 min, and the pellet was washed with 1.0 ml of acetone. The pellet was air-dried and resuspended in 50 μL 4% SDS-20 mM Tris-HCl (pH 8.0)-0.2 mM EDTA (lysis buffer).

Following SDS-PAGE electrophoresis through an 11.5% gel, the proteins were transferred to Immobilon-P filters (Millipore) at a constant voltage of 20 V for 18 hr, in 25 mM Tris-HCl,220 mM glycine-20% methanol (transfer buffer). Membranes were blocked in 5% BSA in TBS for 30 min. at room temperature. Blots were exposed either to guinea pig anti-*M. catarrhalis* 4223 Tbp1, or to guinea pig anti-*M. catarrhalis* 4223 Tbp2 antiserum, diluted 1/500 in TBS-Tween, for 2 hr at room temperature. Following three sequential 10 min. washes in TBS-Tween, membranes were incubated in TBS-Tween containing a 1/4000 dilution of rProtein G-HRP for 30 min. at room temperature. Membranes were washed as described above, and immersed into CN/DAB substrate solution. Color development was arrested by immersing blots into water.

Three EMBL3 phage clones expressed both a 115 kDa protein which reacted with anti-Tbp1 antiserum, and an 80 kDa protein, which reacted with anti-Tbp2 antiserum on Western blots and were thus concluded to contain genes encoding the transferrin receptor proteins of *Moraxella catarrhalis*.

Example 6

This Example illustrates the subcloning of the *M. catarrhalis* 4223 Tbp1 protein gene, tbpA.

Plate lysate cultures of the recombinant phage described in Example 5 were prepared by combining phage eluant and *E. coli* LE392 plating cells, to produce confluent lysis on LB agar plates. Phage DNA was extracted from the plate lysates using a Wizard Lambda Preps DNA Purification System (Promega), according to manufacturer's instructions.

The EMBL3 clone LM3-24 was found to contain a 13.2 kb insert, flanked by two SalI sites. A probe to a tbpA gene was prepared and consisted of a 300 base pair amplified product generated by PCR using two degenerate oligonucleotide primers corresponding to an amino acid sequence of part of the Tbp1 protein (FIG. 1). The primer sequences were based upon the amino acid sequences NEVTGLG (SEQ ID NO: 17) and GAINEIE (SEQ ID NO: 18), which had been found to be conserved among the deduced amino acid sequences from several different *N. meningitidis* and *Haemophilus influenzae* tbpA genes. The amplified product was cloned into pCRII (Invitrogen, San Diego, Calif.) and sequenced. The deduced amino acid sequence shared homology with other putative amino acid sequences derived from *N. meningitidis* and *H. influenzae* tbpA genes (FIGS. 12A to 12G). The subclone was linearized with NotI (New England Biolabs), and labelled using a digoxigenin random-labelling kit (Boehringer Mannheim), according to manufacturer's instructions. The concentration of the probe was estimated to be 2 ng/μL.

DNA from the phage clone was digested with HindIII, AvrII, SalI/SphI, or SalI/AvrII, and electrophoresed through a 0.8% agarose gel. DNA was transferred to a nylon membrane (Genescreen Plus, Dupont) using an LKB VacuGene XL vacuum transfer apparatus (Pharmacia). Following transfer, the blot was air-dried, and pre-hybridized in 5× SSC-0.1% N-lauroylsarcosine-0.02% sodium dodecyl sulfate-1.0% blocking reagent (Boehringer Mannheim) in 10 mM maleic acid-15 mM NaCl (pH 7.5) (pre-hybridization solution). Labelled probe was added to the pre-hybridization solution to a final concentration of 6 ng/ml, and the blot was incubated in the probe solution at 42° C. for 18 hr. The blot was washed twice in 2× SSC-0.1% SDS, for 5 min. each at room temperature, then twice in 0.1× SSC-0.1% SDS for 15 min. each at 60° C. Following the washes, the membrane was equilibrated in 100 mM maleic acid-150 mM NaCl (pH 7.5) (buffer 1) for 1 min, then left in 1.0% blocking reagent (Boehringer Mannheim) in buffer 1 (buffer 2) for 60 min, at room temperature. The blot was exposed to anti-DIG-alkaline phosphatase (Boehringer Mannheim) diluted 1/5000 in buffer 2, for 30 min. at room temperature. Following two 15 min. washes in buffer 1, the blot was equilibrated in 100 mM Tris-HCl (pH 9.5), 100 mM NaCl, 50 mM $MgCl_2$ (buffer 3) for 2 min. The blot was wetted with Lumigen PPD substrate (Boehringer-Mannheim), diluted 1/100 in buffer 3, then wrapped in Saran wrap, and exposed to X-ray film for 30 min. The probe hybridized to a 3.8 kb HindIII-HindIII, a 2.0 kb AvrII-AvrII, and a 4.2 kb SalI-SphI fragment.

In order to subclone the 3.8 kb HindIII-HindIII fragment into pACYC177, phage DNA from the EMBL3 clone, and plasmid DNA from the vector pACYC177 (New England Biolabs), were digested with HindIII, and fractionated by electrophoresis on a 0.8% agarose gel. The 3.8 kb HindIII-HindIII phage DNA fragment, and the 3.9 kb HindIII-HindIII pACYC177 fragment, were excised from the gel and purified using a Geneclean kit (Bio 101 Inc., LaJolla, Calif.), according to manufacturer's directions. Purified insert and vector were ligated together using T4 DNA ligase (New England Biolabs), and transformed into *E. coli* HB101 (Gibco BRL). A Qiagen Plasmid Midi-Kit (Qiagen) was used to extract and purify sequencing-quality DNA from one of the ampicillin-resistant/kanamycin-sensitive transformants, which was found to carry a 3.8 kb HindIII-HindIII insert. The subclone was named pLEM3. As described in Example 7, below, subsequent sequencing revealed that pLEM3. contained the first about 2.0 kb of tbpA sequence (FIGS. 2 and 5A to 5J).

In order to subclone the remaining 1 kb of the tbpA gene, a 1.6 kb HindIII-HindIII fragment was subcloned into pACYC177 as described above, and transformed by electroporation into *E. coli* HB101 (Gibco BRL). A Midi-Plasmid DNA kit (Qiagen) was used to extract plasmid DNA from a putative kanamycin-sensitive transformant carrying a plasmid with a 1.6 kb HindIII-HindIII insert. The subclone was termed pLEM25. As described in Example 7 below, sequencing revealed that pLEM25 contained the remaining 1 kb of the tbpA gene (FIGS. 2 and 5A to 5J).

Example 7

This Example illustrates the subcloning of the *M. catarrhalis* 4223 tbpB gene.

As described above, in all Neisseriae and Haemophilus species examined prior to the present invention, tbpB genes have been found immediately upstream of the tbpA genes which share homology with the tbpA gene of *M. catarrhalis* 4223. However, the sequence upstream of *M. catarrhalis* 4223 did not correspond with other sequences encoding tbpB.

In order to localize the tbpB gene within the EMBL3 phage clone, a Southern blot was carried out using a degenerate probe from a highly conserved amino acid region within the Tbp2 protein. A degenerate oligonucleotide probe, was designed corresponding to the sequence encoding EGGFYGP (SEQ ID NO: 30), which is conserved within the Tbp2 protein in a variety of Neisseriae and Haemophilus species. The probe was labelled with digoxigenin using an oligonucleotide tailing kit (Boehringer Mannheim), following the manufacturer's instructions. HindIII-digested EMBL3 clone DNA was fractionated through a 0.8% agarose gel, and transferred to a Geneclean Plus nylon membrane as described in Example 6. Following hybridization as described above, the membrane was washed twice in 2× SSC-0.1% SDS, for 5 min. each at room temperature, then twice in 0.1× SSC-0.1% SDS for 15 min. each, at 50° C. Detection of the labelled probe was carried out as described above. The probe hybridized to a 5.5 kb NheI-SalI fragment.

The 5.5 kb NheI-SalI fragment was subcloned into pBR328 as follows. LEM3-24 DNA, and pBR328 DNA, were digested with NheI-SalI, and electrophoresed through 0.8% agarose. The 5.5 kb NheI-SalI fragment, and the 4.9 kb pBR328 NheI-SalI fragments were excised from the gel, and purified using a Geneclean kit as described in Example 6. The fragments were ligated together using T4 DNA ligase, and transformed into *E. coli* DH5. A Midi-Plasmid DNA kit (Qiagen) was used to extract DNA from an ampicillin resistant/tetracycline sensitive clone containing a 5.5 kb NheI-SalI insert. This subclone was termed pLEM23. Sequencing revealed that pLEM23 contained 2 kb of the tbpB gene from *M. catarrhalis* 4223 (FIG. 2).

Example 8

This Example illustrates the subcloning of *M. catarrhalis* Q8 tfr genes.

The *M. catarrhalis* Q8 tfr genes were subcloned as follows. Phage DNA was prepared from plates. Briefly, the top agarose layer from three confluent plates was scraped into 9 ml of SM buffer (0.1 M NaCl, 0.2% $MgSO_4$, 50 mM Tris-HCl, pH 7.6, 0.01% gelatin) and 100 $\mu$l of chloroform was added. The mixture was vortexed for 10 sec, then incubated at room temperature for 2h. The cell debris was removed by centrifugation at 8000 rpm for 15 min at 4° C. in an SS34 rotor (Sorvall model RC5C). The phage was pelleted by centrifugation at 35,000 rpm in a 70.1 Ti rotor at 10° C. for 2h (Beckman model L8-80) and was resuspended in 500 $\mu$l of SM buffer. The sample was incubated at 4° C. overnight, then RNAse and DNAse were added to final concentrations of 40 $\mu$g/ml and 10 $\mu$g/ml, respectively and the mixture incubated at 37° C. for 1 h. To the mixture were added 10 $\mu$l of 0.5 M EDTA and 5 $\mu$l of 10% SDS and the sample was incubated at 6° C. for 15 min. The mixture was extracted twice with phenol/chloroform (1:1) and twice with chloroform and the DNA was precipitated by the addition of 2.5 volumes of absolute ethanol.

Figure 4:
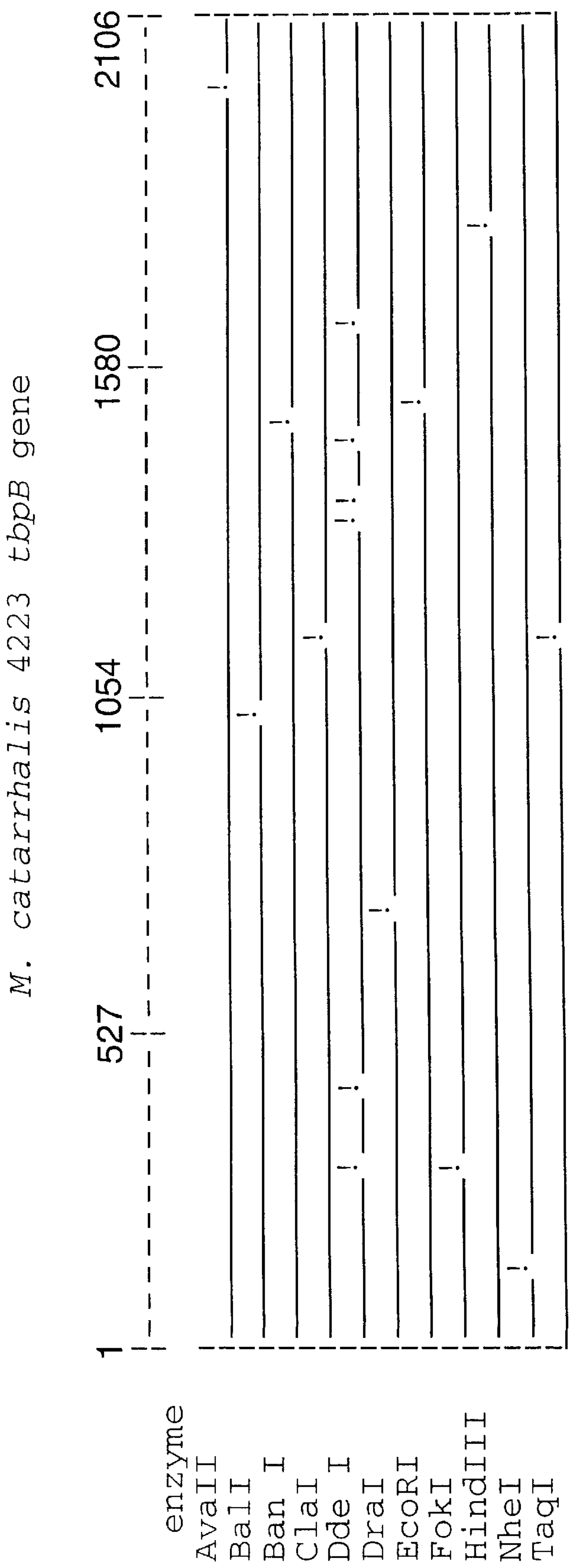
FIG. 4 shows a restriction map of the tbpB gene for *M. catarrhalis* 4223.

A partial restriction map was generated and fragments were subcloned using the external Sal I sites from EMBL3 and internal AvrII or EcoR I sites as indicated in FIG. 4. In order to facilitate the subcloning, plasmid pSKMA was constructed which introduces a novel multiple cloning site into pBluescript.SK (Stratagene). Oligonucleotides were used to introduce restriction sites for Mst II, Sfi I, and Avr II between the Sal I and Hind III sites of pBluescript.SK:

```
                         Sfi I
        Sal I       Cla I    Mst II    Avr II HindIII
          ↓           ↓        ↓    ↓     ↓      ↓
4639-RD 5' TCGACGGTAT CGATGGCC TTAG GGGC CTAGGA 3'   (SEQ ID NO: 34)

4640-RD 3'     GCCATA GCTACCGG AATC CCCG GATCCTTCGA  (SEQ ID NO: 35)
```

Figure 7:
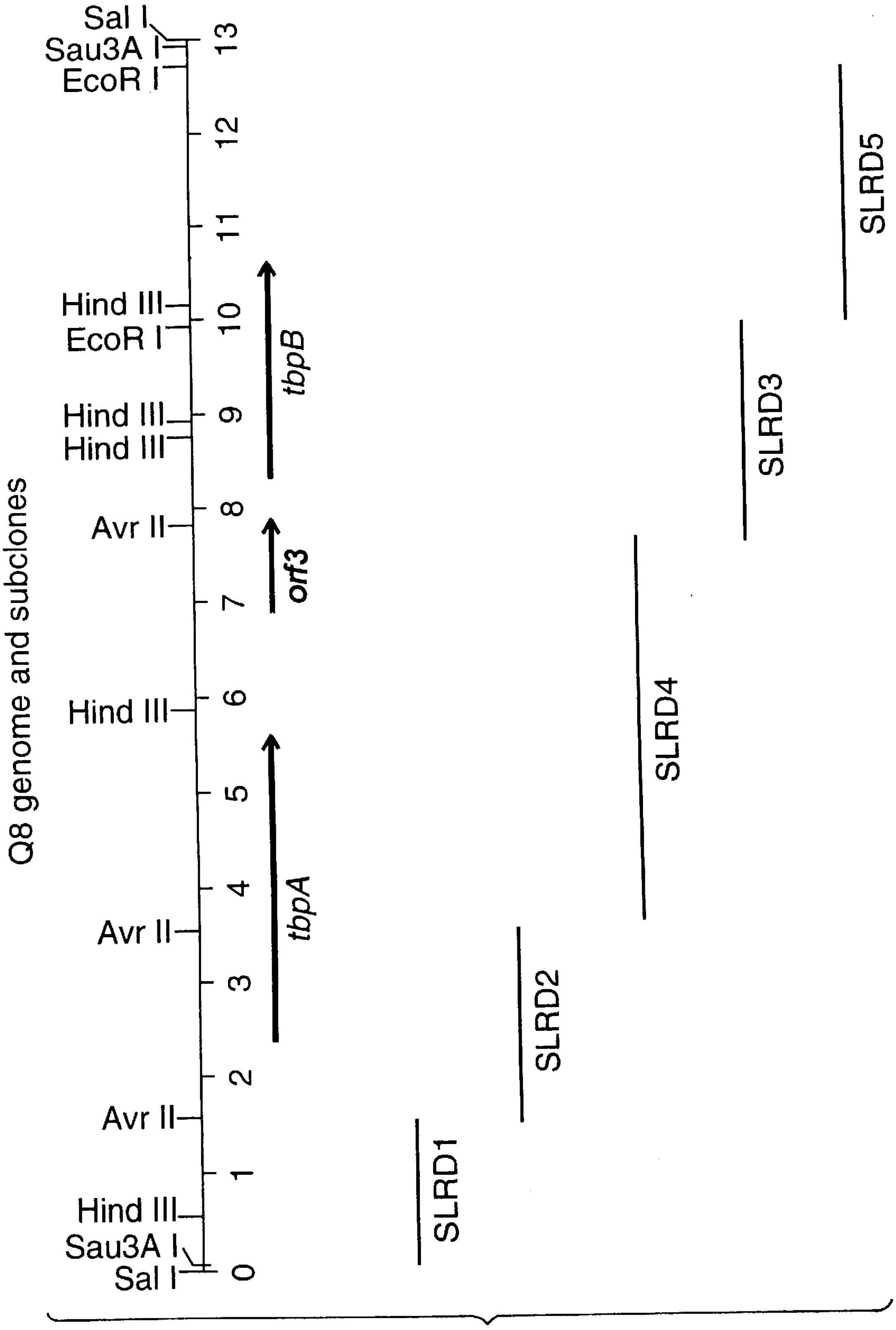
FIG. 7 shows a restriction map of clone SLRD-A containing the tbpA and tbpB genes and orf 3 gene from *M. catarrhalis* Q8.

Plasmid pSLRD1 contains a ~1.5 kb Sal I-Avr II fragment cloned into pSKMA; plasmids pSLRD2 and pSLRD4 contain ~2 kb and 4 kb AvrII-AvrII fragments cloned into pSKMA, respectively and contain the complete tbpA gene. Plasmid pSLRD3 contains a ~2.3 kb AvrII-EcoR I fragment cloned into pSKMA and plasmid SLRD5 is a 22.7 kb EcoRI-EcoRI fragment cloned into pSKMA. These two clones contain the complete tbpB gene (FIG. 7).

Example 9

This Example illustrates sequencing of the *M. catarrhalis* tbp genes.

Both strands of the tbp genes subcloned according to Examples 6 to 8 were sequenced using an Applied Biosystems DNA sequencer. The sequences of the *M. catarrhalis* 4223 and Q8 tbpA genes are shown in FIGS. 5A to 5J and 10A to 10Q respectively. A derived amino acid sequence was compared with other Tbp1 amino acid sequences, including those of *Neisseriae meningitidis, Neisseriae gonorrhoeae*, and *Haemophilus influenzae* (FIGS. 12A to 12G). The sequence of the *M. catarrhalis* 4223 and Q8 tbpB genes are shown in FIGS. 6A to 6G and 11A to 11O respectively. In order to obtain sequence from the putative beginning of the tbpB gene of *M. catarrhalis* 4223, sequence data were obtained directly from the clone LEM3-24 DNA. This sequence was verified by screening clone DS-1754-1. The sequence of the translated tbpB genes from *M. catarrhalis* 4223 and Q8 shared homology with deduced Tbp2 amino acid sequences of *Neisseria meningitidis, Neisseria gonorrhoeae*, and *Haemophilus influenzae* (FIG. 13A to 13F).

Example 10

Figure 14A:
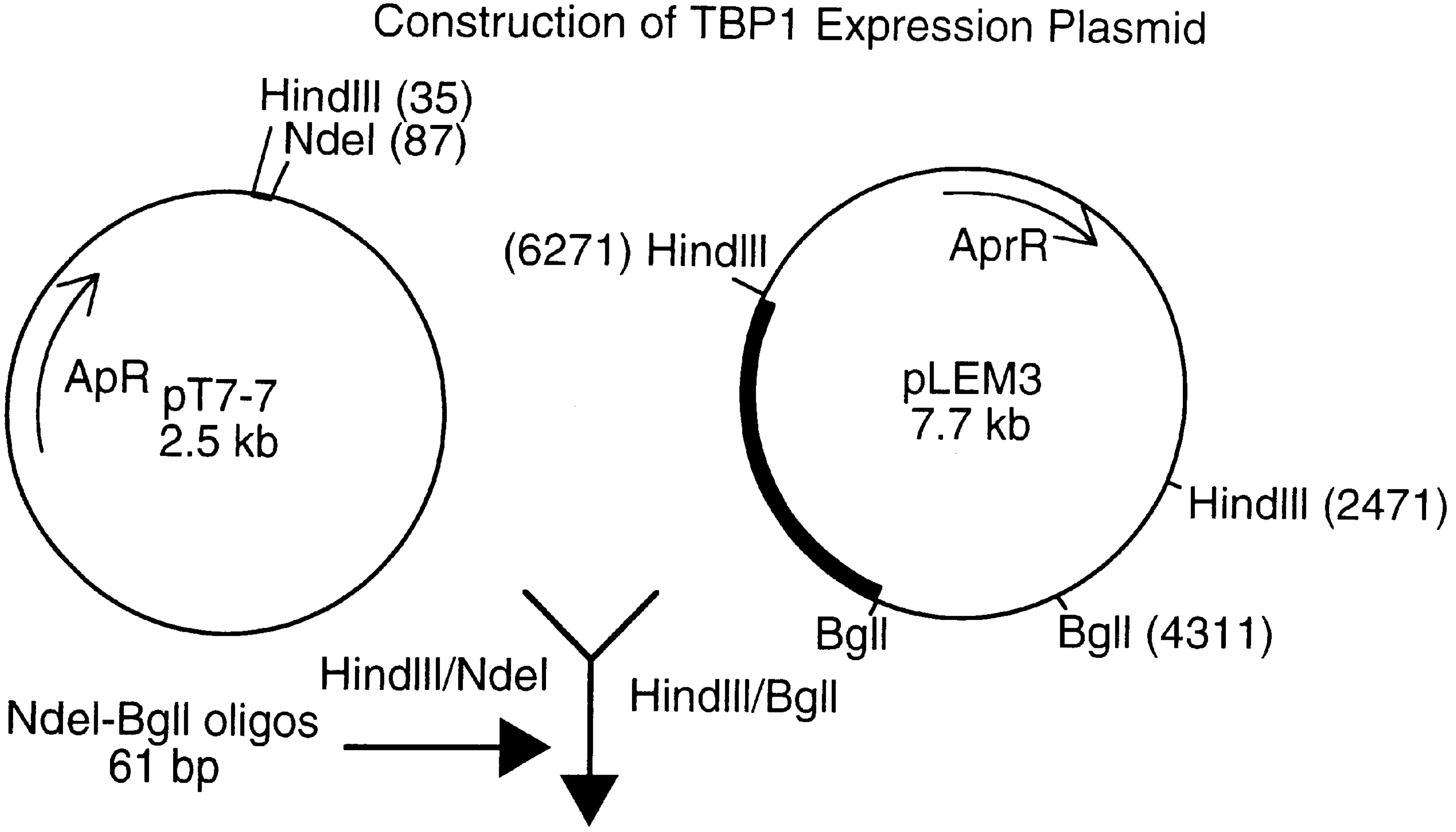
FIGS. 14A and 14B show the construction of plasmid pLEM29 for expression of recombinant Tbp1 protein from *E. coli;*
Figure 14B:
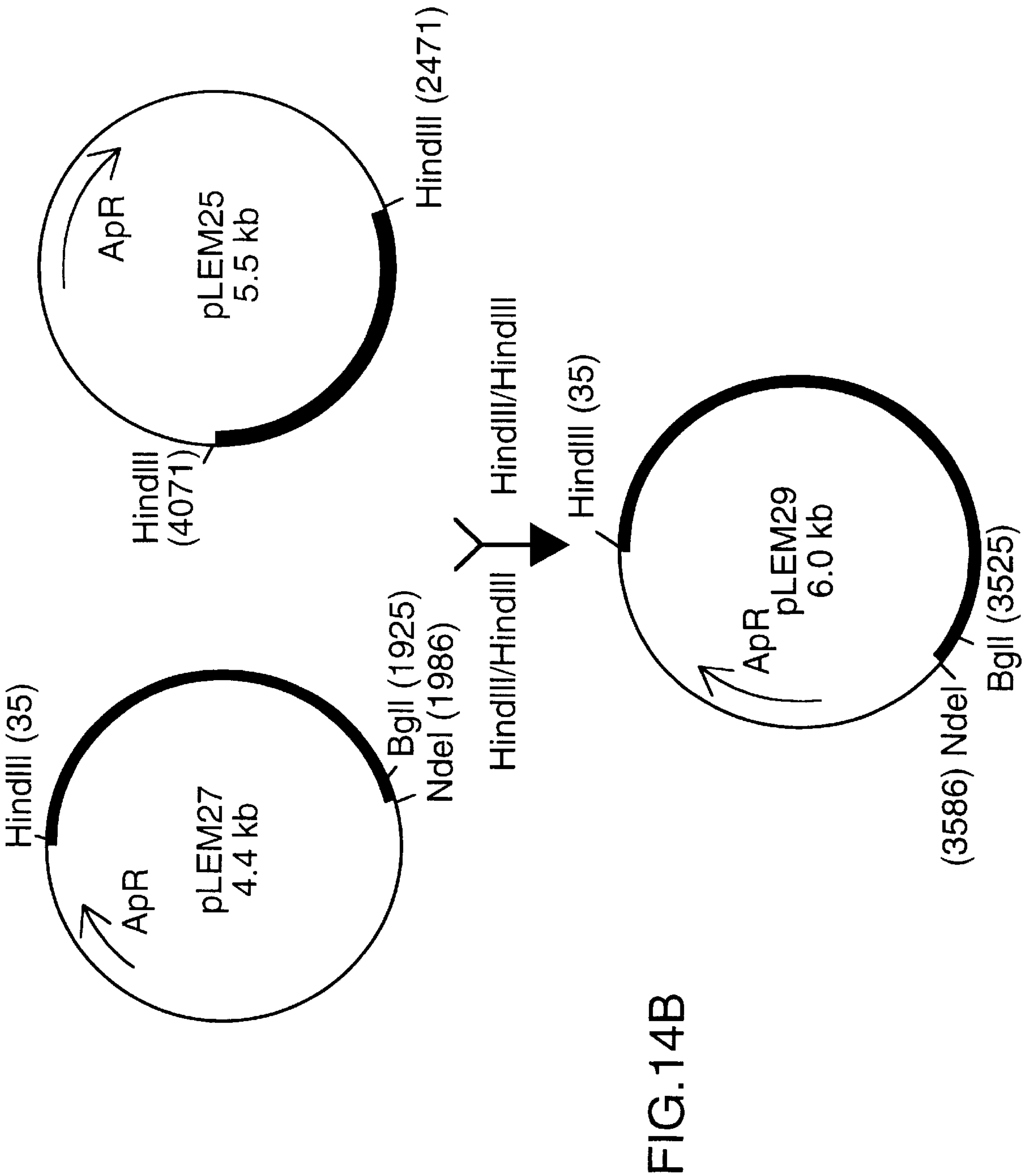

This Example illustrates the generation of an expression vector to produce recombinant Tbp1 protein. The construction scheme is shown in FIGS. 14A to 14B.

Plasmid DNA from subclone pLEM3, prepared as described in Example 6, was digested with HindIII and BglI to generate a 1.84 kb BglI-HindIII fragment, containing approximately two-thirds of the tbpA gene. BamHI was added to the digest to eliminate a comigrating 1.89 kb BglI-HindIII vector fragment. In addition, plasmid DNA from the vector pT7-7 was digested with NdeI and HindIII. To create the beginning of the tbpA gene, an oligonucleotide was synthesized based upon the first 61 bases of the tbpA gene to the BglI site; an NdeI site was incorporated into the 5' end. Purified insert, vector and oligonucleotide were ligated together using T4 ligase (New England Biolabs), and transformed into *E. coli* DH5α. DNA was purified from one of the 4.4 kb ampicillin-resistant transformants containing correct restriction sites (pLEM27).

Purified pLEM27 DNA was digested with HindIII, ligated to the 1.6 kb HindIII-HindIII insert fragment of pLEM25 prepared as described in Example 6, and transformed into *E. coli* DH5α. DNA was purified from an ampicillin-resistant transformant containing the correct restriction sites (pLEM29), and was transformed by electroporation into BL21 (DE3) (Novagen; Madison, Wis.) to produce *E. coli* pLEM29B-1.

Figure 15:
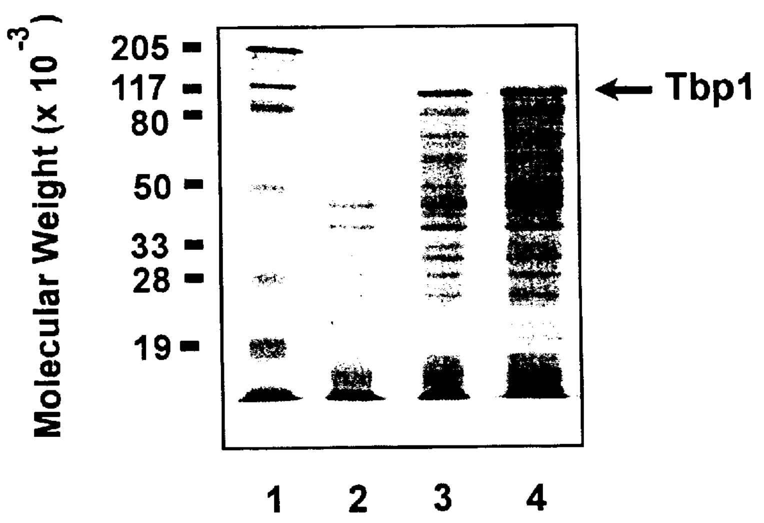
FIG. 15 shows an SDS-PAGE analysis of the expression of Tbp1 protein by *E. coli* cells transformed with plasmid pLEM29.

A single isolated transformed colony was used to inoculate 100 ml of YT broth containing 100 μg/ml ampicillin, and the culture was grown at 37° C. overnight, shaking at 200 rpm. 200 μl of the overnight culture were inoculated into 10 ml of YT broth containing 100 μg/ml ampicillin, and the culture was grown at 37° C. to an $OD_{578}$ of 0.35. The culture was induced by the addition of 30 μl of 100 mM IPTG, and the culture was grown at 37° C. for an additional 3 hours. One ml of culture was removed at the time of induction (t=0), and at t=1 hr and t=3 hrs. One ml samples were pelleted by centrifugation, and resuspended in 4% SDS-20 mM Tris.Cl, pH 8–200 μM EDTA (lysis buffer). Samples were fractionated on an 11.5% SDS-PAGE gel, and transferred onto Immobilon filters (Amersham). Blots were developed using anti-Tbp1 (*M. catarrhalis* 4223) antiserum, diluted 1:1000, as the primary antibody, and rproteinG conjugated with horseradish peroxidase (Zymed) as the secondary antibody. A chemiluminescent substrate (Lumiglo; Kirkegaard and Perry Laboratories, Gaithersburg, Md.) was used for detection. Induced recombinant proteins were visible on the Coomassie-stained gels (FIG. 15). The anti-Tbp1 (4223) antiserum recognized the recombinant proteins on Western blots.

Example 11

This Example illustrates the extraction and purification of recombinant Tbp1 of *M. catarrhalis* 4223.

Figure 16:
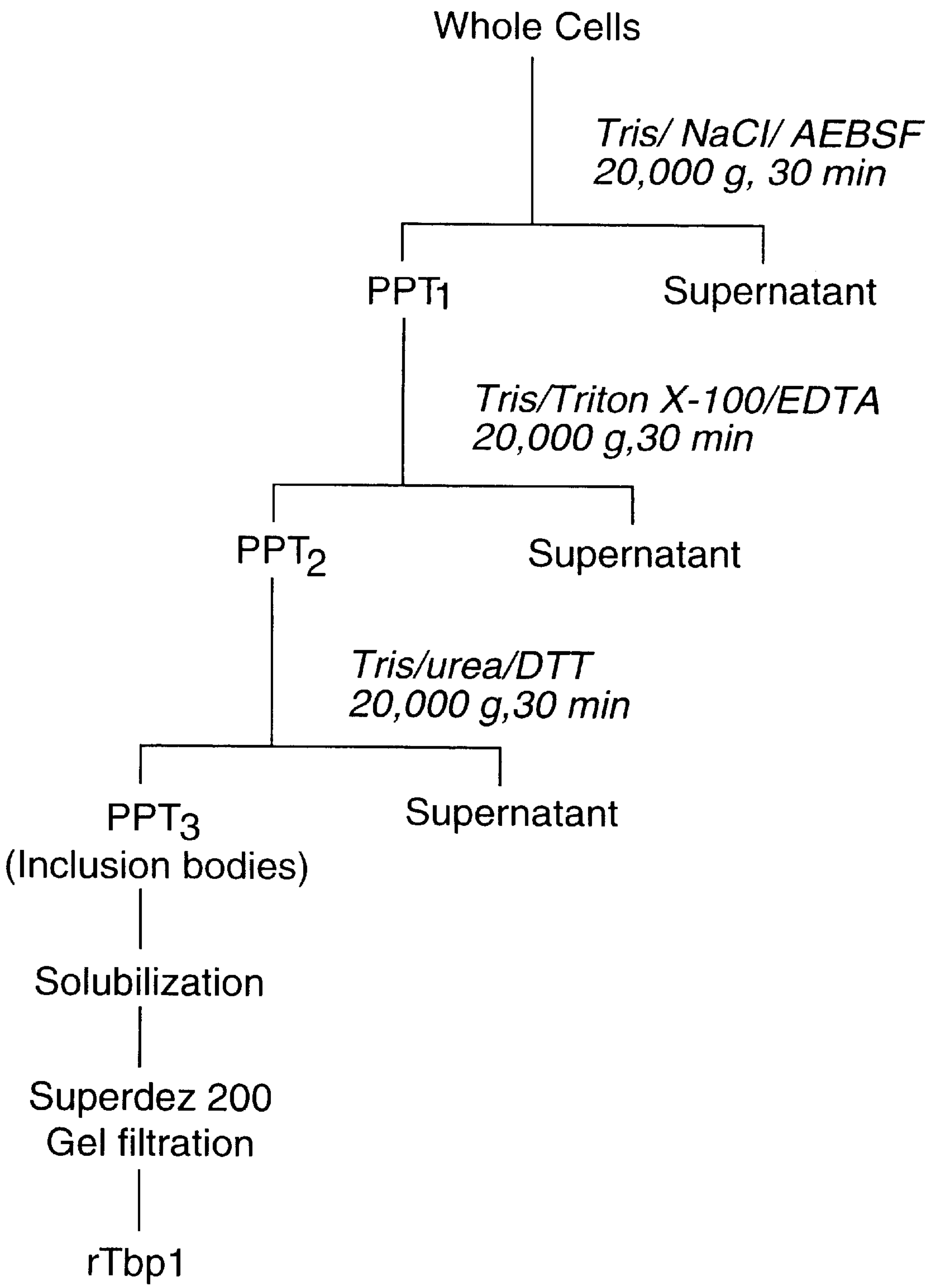
FIG. 16 shows a flow chart for purification of recombinant Tbp1 protein.

Recombinant Tbp1 protein, which is contained in inclusion bodies, was purified from *E. coli* cells expressing the tbpA gene (Example 10), by a procedure as shown in FIG. 16. *E. coli* cells from a 500 ml culture, prepared as described in Example 10, were resuspended in 50 ml of 50 mM Tris-HCl, pH 8.0 containing 0.1 M NaCl and 5 mM AEBSF (protease inhibitor), and disrupted by sonication (3×10 min. 70% duty circle). The extract was centrifuged at 20,000×g for 30 min. and the resultant supernatant which contained>85% of the soluble proteins from *E. coli* was discarded.

The remaining pellet (FIG. 16, $PPT_1$) was further extracted in 50 ml of 50 mM Tris, pH 8.0 containing 0.5% Triton X-100 and 10 mM EDTA. After centrifugation at 20,000×g for 30 min., the supernatant containing residual soluble proteins and the majority of the membrane proteins was discarded.

The remaining pellet (FIG. 16, $PPT_2$) was further extracted in 50 ml of 50 mM Tris, pH 8.0 containing 2M urea and 5 mM dithiothroitol (DTT). After centrifugation at 20,000×g for 30 min., the resultant pellet (FIG. 16, $PPT_3$) obtained after the above extraction contained the purified inclusion bodies.

Figure 17:
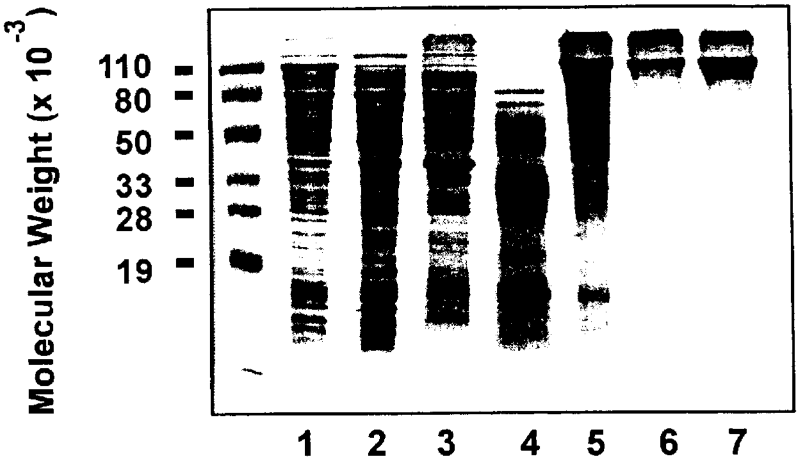
FIG. 17 shows an SDS-PAGE analysis of purified recombinant Tbp1 protein.

The Tbp1 protein was solubilized from PPT3 in 50 mM Tris, pH 8.0, containing 6 M guanidine hydrochloride and 5 mM DTT. After centrifugation, the resultant supernatant was further purified on a Superdex 200 gel filtration column equilibrated in 50 mM Tris, pH 8.0, containing 2M guanidine hydrochloride and 5 mM DTT. The fractions were analyzed by SDS-PAGE and those containing purified Tbp1 were pooled. Triton X-100 was added to the pooled Tbp1 fraction to a final concentration of 0.1%. The fraction was then dialyzed overnight at 4° C. against 50 mM Tris, pH 8.0 and then centrifuged at 20,000×g for 30 min. The protein remained soluble under these conditions-and the purified Tbp1 was stored at −20° C. The purification procedure shown in FIG. 16 produced Tbp1 protein that was at least 70% pure as determined by SDS-PAGE analysis (FIG. 17).

Example 12

This Example illustrates the construction of an expression plasmid for rTbp2 of *M. catarrhalis* 4223 without a leader sequence.

Figure 18A:
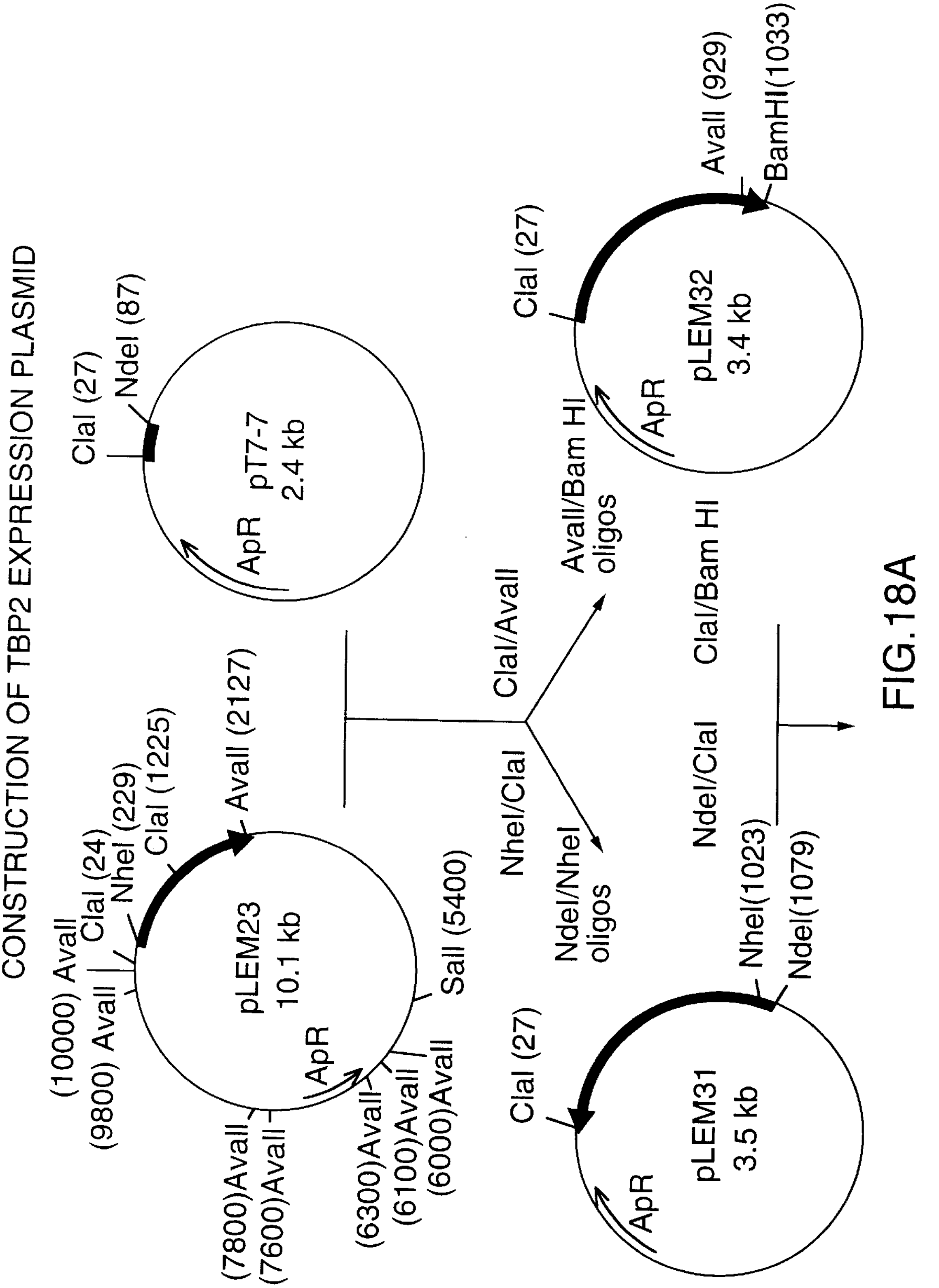
FIGS. 18A and 18B show the construction of plasmid pLEM33 and pLEM37 for expression of TbpA gene from *M. catarrhalis* 4223 in *E. coli* without and with a leader sequence respectively.
Figure 18B:
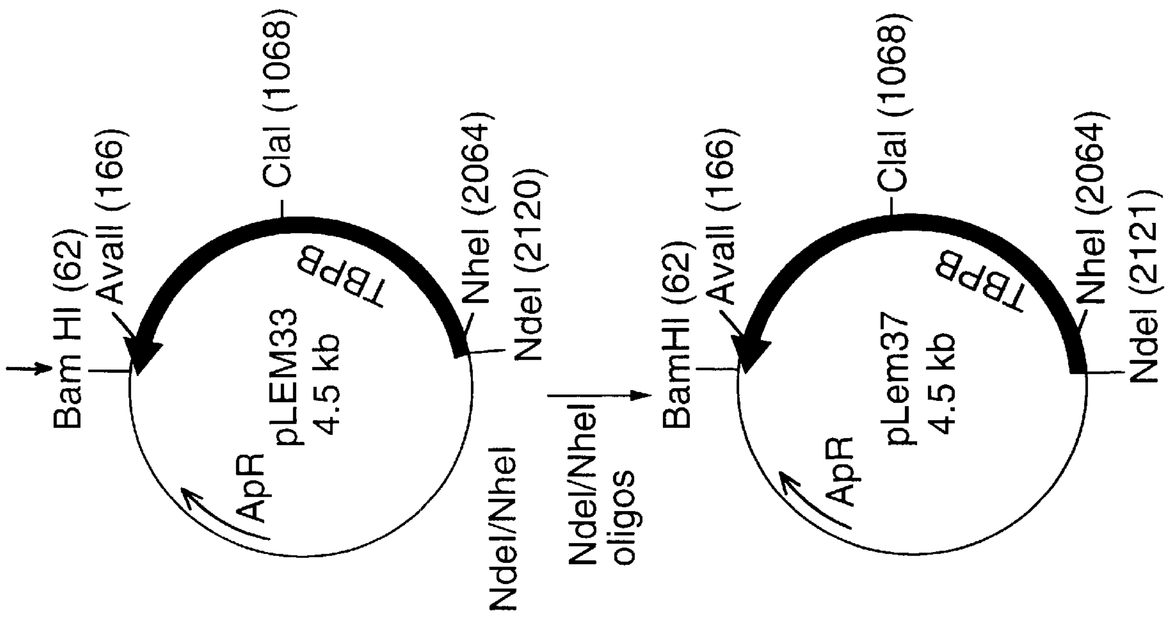

The construction scheme for the plasmid expressing rTbp2 is shown in FIG. 18A and 18B. Oligonucleotides were used to construct the first approximately 58 bp of the *M. catarrhalis* 4223 tbpB gene encoding the mature protein. An NdeI site was incorporated into the 5' end of the oligonucleotides:

5'TATGTGTGGTGGCAGTGGTGGT-TCAAATCCACCTGCTCCTACGCCCATT CCAAATG (SEQ ID NO: 36) 3'

3'ACACACCACCGTCACCACCAAGTTTAG-GTGGACGAGGATGCGGGTAAGG TTTACGATC (SEQ ID NO: 37) 5'

An NheI-ClaI fragment, containing approximately 1 kb of the tbpB gene from pLEM23, prepared as described in Example 7, was ligated to the above oligonucleotides and inserted into pT7-7 cut with NdeI-ClaI, generating pLEM31, which thus contains the 5'-half of tbpB. Oligonucleotides also were used to construct the last approximately 104 bp of the tbpB gene, from the AvaII site to the end of the gene. A BamHI site was incorporated into the 3' end of the oligonucleotides:

5'GTCCAAATGCAAACGAGATGGGCGGGT-CATTTACACACAACGCCGATG ACAGCAAAGC-CTCTGTGGTCTTTGGCACAAAAAGACAA-CAAGAAGTTAAGTAGTA G (SEQ ID NO: 38) 3'

3'GTTTACGTTTGCTCTACCCGCCCAG-TAAATGTGTGTTGCGGCTACTGTC GTTTCG-GAGACACCAGAAACCGTGTTTTTCTGT-TGTTCTTCAATTCATCATCCTAG (SEQ ID NO: 39) 5'

A ClaI-AvaII fragment from pLEM23, containing approximately 0.9 kb of the 3'-end of the tbpB gene, was ligated to the AvaII-BamHI oligonucleotides, and inserted into pT7-7 cut with ClaI-BamHI, generating pLEM32. The 1.0 kb NdeI-ClaI insert from pLEM31 and the 1.0 kb ClaI-BamHI insert from pLEM32 were then inserted into pT7-7 cut with NdeI-BamHI, generating pLEM33 which has a full-length tbpB gene under the direction of the T7 promoter.

Figure 19:
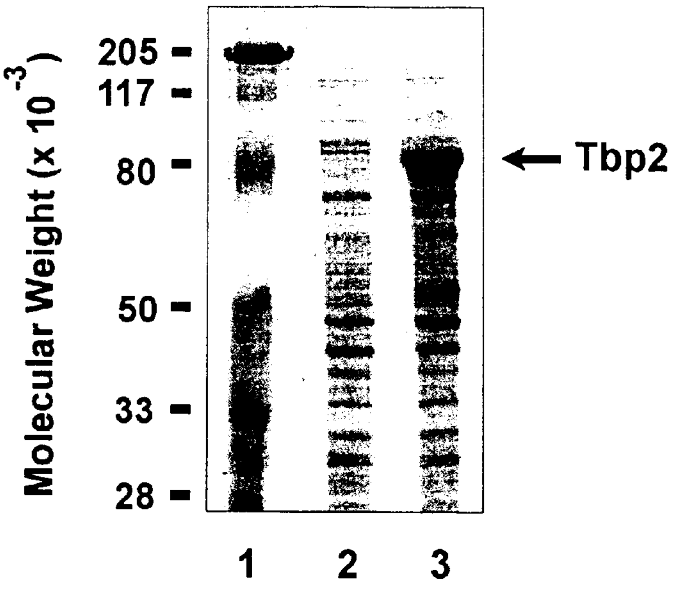
FIG. 19 shows an SDS-PAGE analysis of the expression of rTbp2 protein by *E. coli* cells transformed with plasmid pLEM37.

DNA was purified from pLEM33 and transformed by electroporation into electrocompetent BL21(DE3) cells (Novagen; Madison, Wis.), to generate strain pLEM33B-1. Strain pLEM33B-1 was grown, and induced using IPTG, as described above in Example 10. Expressed proteins were resolved by SDS-PAGE and transferred to membranes suitable for immunoblotting. Blots were developed using anti-4223 Tbp2 antiserum, diluted 1:4000, as the primary antibody, and rprotein G conjugated with horseradish peroxidase (Zymed) as the secondary antibody. A chemiluminescent substrate (Lumiglo; Kirkegaard and Perry Laboratories, Gaithersburg, Md.) was used for detection. Induced recombinant proteins were visible on the Coomassie blue-stained gels (FIG. 19). The anti-4223 Tbp2 antiserum recognized the recombinant proteins on Western blots.

Example 13

This Example illustrates the generation of an expression plasmid for rTbp2 of *M. catarrhalis* 4223 with a leader sequence.

The construction scheme is shown in FIGS. 18A to 18B. Oligonucleotides containing the natural leader sequence of the *M. catarrhalis* 4223 tbpB gene were used to construct the first approximately 115 bp of the tbpB gene to the NheI site. An NdeI site was incorporated into the 5' end of the oligonucleotides:

5'TATGAAACACATTCCTTTAACCACACT-GTGTGTGGCAATCTCTGCCGTC TTATTAAC-CGCTTGTGGTGGCAGTGGTGGT-TCAAATCCACCTGCTCCTACGCCCAT TCCAAATG (SEQ ID NO: 40) 3'

3'ACTTTGTGTAAGGAAATTGGTGTGACA-CACACCGTTAGAGACGGCAGAA TAATTGGC-GAACACCACCGTCACCACCAAGTTTAG-GTGGACGAGGATGCGGGTAAG GTTTACGATC (SEQ ID NO: 41) 5'

The NdeI-NheI oligonucleotides were ligated to pLEM33 cut with NdeI-NheI, generating pLEM37, which thus contains a full-length 4223 tbpB gene encoding the Tbp2 protein with its leader sequence, driven by the T7 promoter.

DNA from pLEM37 was purified and transformed by electroporation into electrocompetent BL21(DE3) cells (Novagen; Madison, Wis.), to generate strain pLEM37B-2. pLEM37B-2 was grown, and induced using IPTG, as described above in Example 10. Expressed proteins were resolved by SDS-PAGE and transferred to membranes suitable for immunoblotting. Blots were developed using anti-4223 Tbp2 antiserum, diluted 1:4000, as the primary antibody, and rprotein G conjugated with horseradish peroxidase (Zymed) as the secondary antibody. A chemiluminescent substrate (Lumiglo; Kirkegaard and Perry Laboratories, Gaithersburg, Md.) was used for detection. Induced recombinant proteins were visible on Coomassie-blue stained gels (FIG. 21). The anti-4223 Tbp2 antiserum recognized the recombinant proteins on Western blots.

Example 14

This Example illustrates the construction of an expression plasmid for rTbp2 of *M. catarrhalis* Q8 without a leader sequence.

Figure 20A:
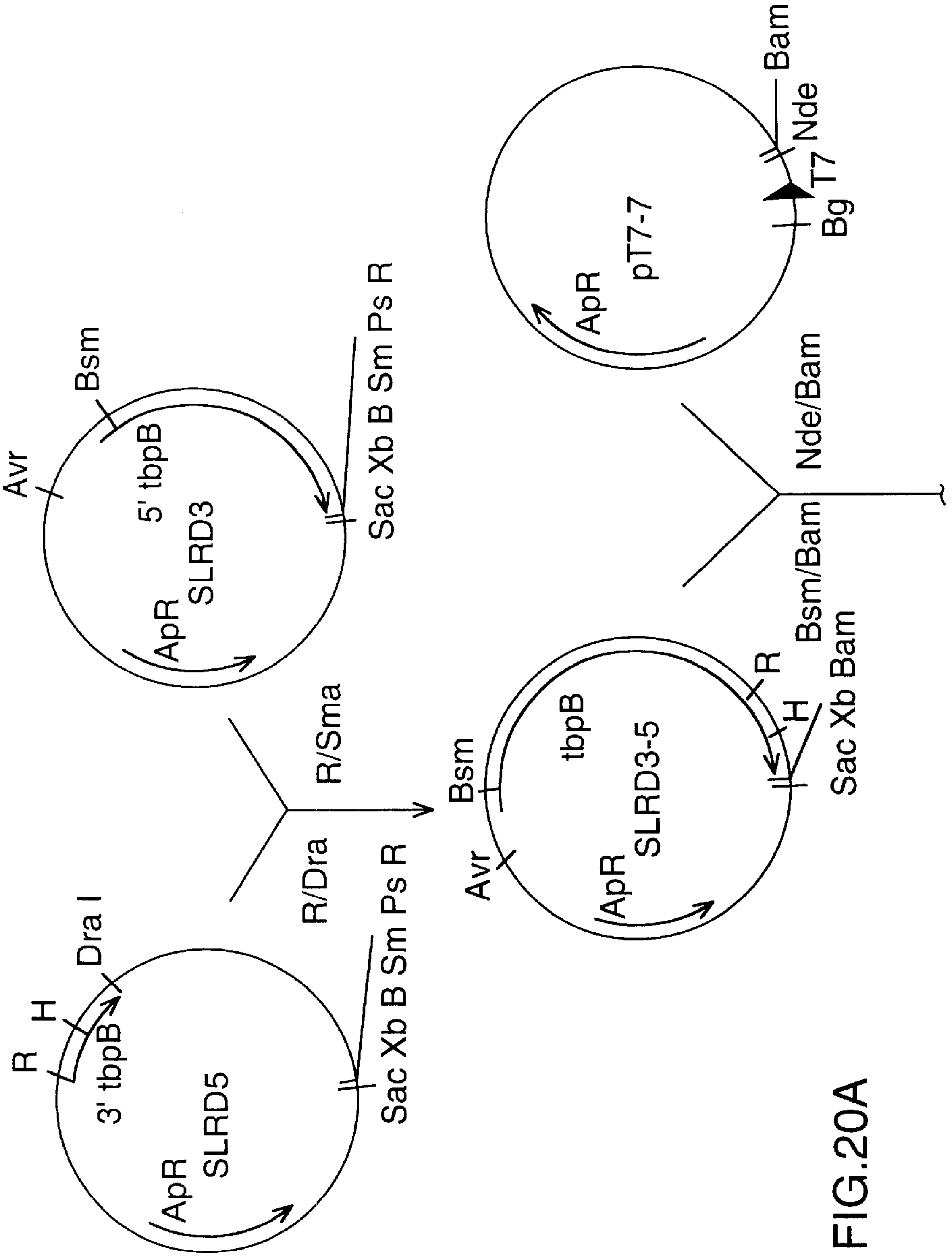
FIGS. 20A and 20B show the construction of plasmid sLRD35B for expression of the tbpB gene from *M. catarrhalis* Q8 in *E. coli* without a leader sequence, and the construction of plasmid SLRD35A for expression of the tbpB gene from *M. catarrhalis* Q8 in *E. coli* with a leader sequence. Restriction site B=BamHI; Bg=Bgl II; H=Hind III; R=EcoRI.
Figure 20B:
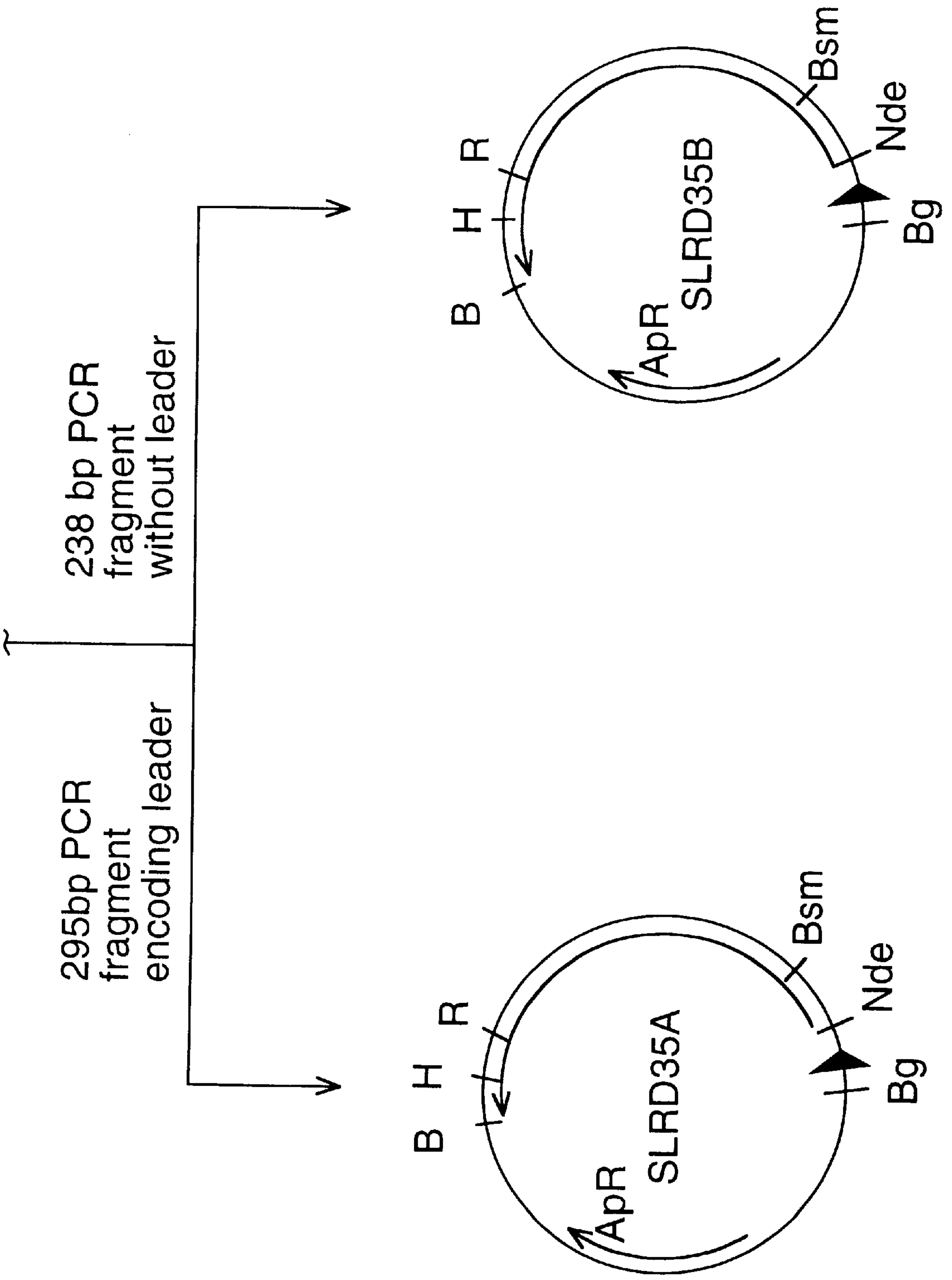

The construction scheme for rTbp2 is shown in FIGS. 20 and 20B. The 5'-end of the tbpB gene of *M. catarrhalis* Q8 was PCR amplified from the $Cys^1$ codon of the mature protein through the Bsm I restriction site. An Nde I restriction site was introduced at the 5' end, for later cloning into pT7-7, and the final PCR fragment was 238 bp in length. The PCR primers are indicated below:

```
             NdeI   C   G   G   S   S   G   G   F   N
5' GAATTCCATATG TGT GGT GGG AGC TCT GGT GGT TTC AAT C   (SEQ ID No: 42)
      3'   5247.RD
```

5'CCCATGGCAGGTTCTTGAATGCCTGAAACT 3'5236.RD (SEQ ID NO: 43)

The Q8 tbpB gene was subcloned in two fragments contained on plasmids SLRD3 and SLRD5, prepared as described in Example 8. Plasmid SLRD3-5 was constructed to contain the full-length tbpB gene by digesting SLRD5 with EcoR I and Dra I, which releases the 3'-end of tbpB, and inserting this ~619 bp fragment into SLRD3 which had been digested with EcoR I and Sma I. The 1.85 kb Bsm I-BamH I fragment from SLRD 3-5 was ligated with the 238 bp PCR fragment and inserted into pT7-7 that had been digested with Nde I and BamH I, generating plasmid SLRD35B. This plasmid thus contains the full-length tbpB gene without its leader sequence, under the direction of the T7 promoter. DNA from SLRD35B was purified and transformed by electroporation into electrocompetent BL21 (DE3) cells to generate strain SLRD35BD which was grown and induced using IPTG, as described above in Example 10. Expressed proteins were resolved by SDS-PAGE and the induced Tbp2 protein was clearly visible by Coomassie blue staining (FIG. 19).

Example 15

This Example illustrates the generation of an expression plasmid for rTbp2 of *M. catarrhalis* Q8 with a leader sequence.

The construction scheme for the rTbp2 is shown in FIGS. 20A and 20B. The 5'-end of the Q8 tbpB gene was PCR amplified from the ATG start codon to the Bsm I restiction site. An Nde I site was engineered at the 5'-end, to facilitate cloning into the pT7-7 expression vector, and the final PCR fragment was 295 bp. The PCR primers are indicated below:

```
         Nde I   K   H   I   P   L   T
5' GAATTCCATATG AAA CAC ATT CCT TTA ACC 3'      5235.RD  (SEQ ID NO: 44)
```

5'CCCATGGCAGGTTCTTGAATGCCTGAAACT 3'5236.RD (SEQ ID NO: 43)

SLRD3-5 (Example 14) was digested with Bsm I and BamH I, generating a 1.85 kb fragment, which was ligated with the 295 bp PCR fragment and ligated into pT7-7 that had been digested with Nde I and BamH I. The resulting plasmid SLRD35A thus contains the full-length Q8 tbpB gene with its endogenous leader sequence under the control of the T7 promoter. DNA from SLRD35A was purified and transformed by electroporation into electrocompetent BL21 (DE3) cells to generate strain SLRD35AD which was grown and induced using IPTG, as described above in Example 10. Expressed proteins were resolved by SDS-PAGE and the induced Tbp2 protein was clearly visible by Coomassie blue staining (FIG. 19).

Example 16

Figure 22:
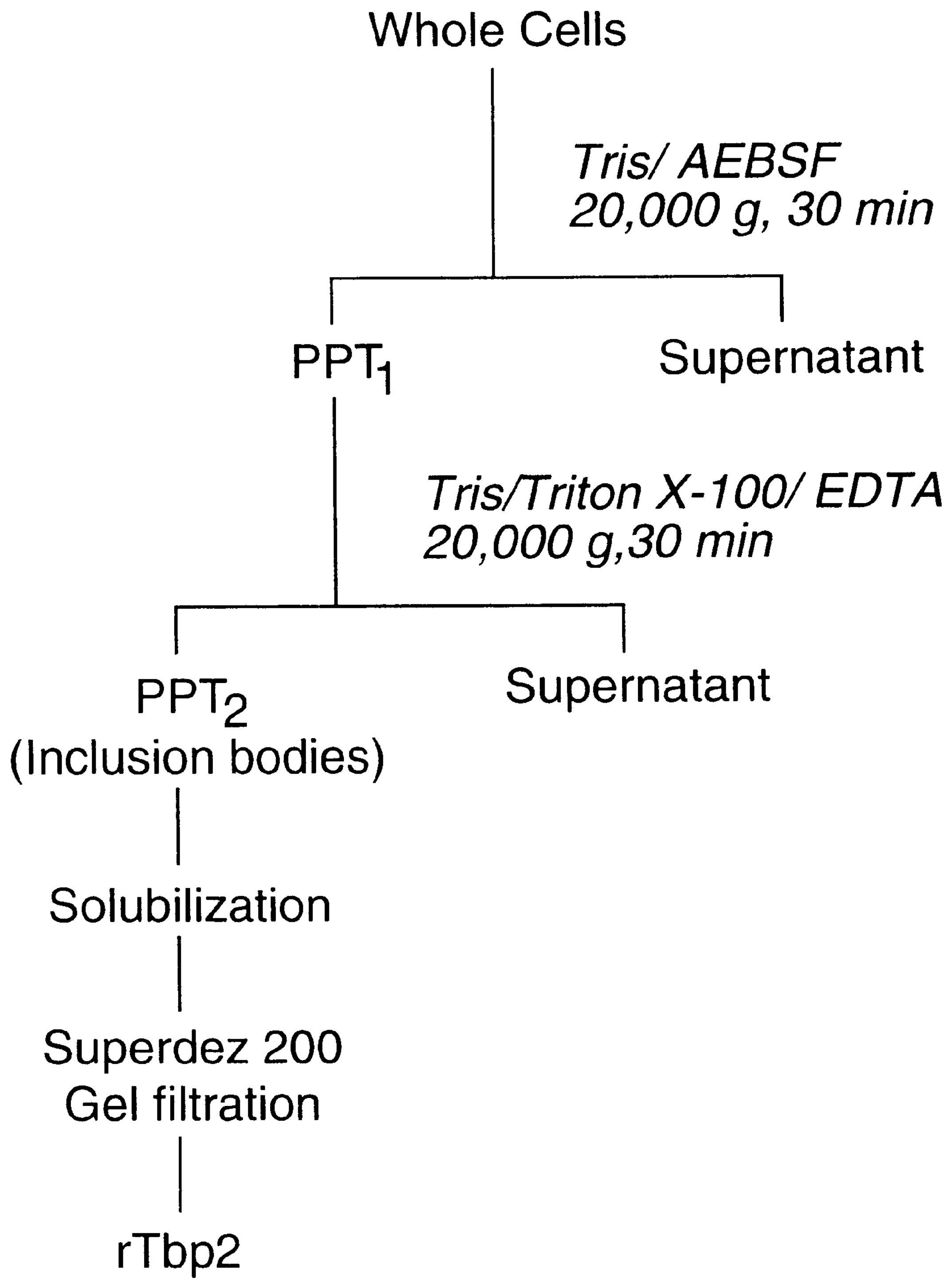
FIG. 22 shows a flow chart for purification of recombinant Tbp2 protein from *E. coli;*
Figure 23:
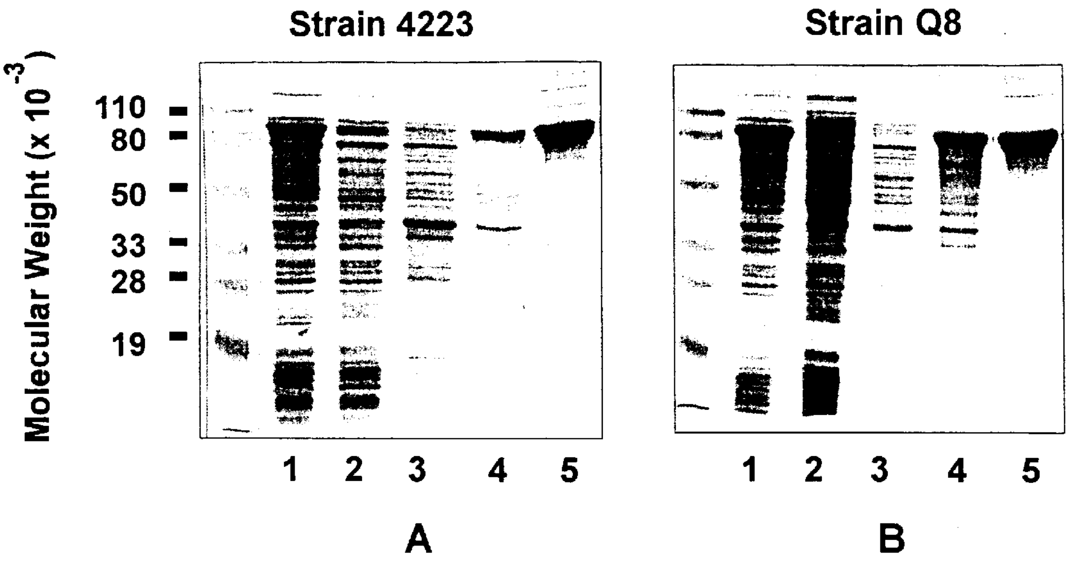
FIG. 23, which includes Panels A and B, shows an SDS-PAGE analysis of the purification of recombinant Tbp2 protein from *M. catarrhalis* strains 4223 (Panel A) and Q8 (Panel B) from expression in *E. coli;*

This Example illustrates the extraction and purification of rTbp2 of *M. catarrhalis* 4223 and Q8 from *E. coli.* pLEM37B (4223) and SLRD35AD (Q8) transformants were grown to produce Tbp2 in inclusion bodies and then the Tbp2 was purified according to the scheme in FIG. 22. *E. coli* cells from a 500 mL culture, were resuspended in 50 mL of 50 mM Tris-HCl, pH 8.0 containing 5 mM AEBSF (protease inhibitor), and disrupted by sonication (3×10 min, 70% duty circle). The extract was centrifuged at 20,000×g for 30 min and the resultant supernatant which contained>95% of the soluble proteins from *E. coli* was discarded.

The remaining pellet ($PPT_1$) was further extracted in 50 mL of 50 mM Tris, pH 8.0 containing 0.5% Triton X-100 and 10 mM EDTA. The mixture was stirred at 4° C. for at least 2 hours and then centrifuged at 20,000×g for 30 min and the supernatant containing residual soluble proteins and the majority of the membrane proteins was discarded.

The resultant pellet ($PPT_2$) obtained after the above extraction contained the inclusion bodies. The Tbp2 protein was solubilized in 50 mM Tris, pH 8.0, containing 6 M guanidine and 5 mM DTT. After centrifugation, the resultant supernatant was further purified on a Superdex 200 gel filtration column equilibrated in 50 mM Tris, pH 8.0, containing 2 M guanidine and 5 mM DTT. The fractions were analyzed by SDS-PAGE and those containing purified Tbp2 were pooled. Triton X-100 was added to the pooled Tbp2 fraction to a final concentration of 0.1%. The fraction was then dialyzed overnight at 4° C. against PBS, and then centrifuged at 20,000×g for 30 min. The protein remained soluble under these conditions and the purified Tbp2 was stored at −20° C. FIG. 22 shows the SDS PAGE analysis of fractions of the purification process for rTbp2 from strain 4223 (Panel A) and strain Q8 (Panel B). The rTbp2 was at least 70% pure.

Groups of five BALB/c mice were injected three times subcutaneously (s.c.) on days 1, 29 and 43 with purified rTbp2 (0.3 mg to 10 mg) from *M. catarrhalis* strains 4223 and Q8 in the presence or absence of $AlPO_4$ (1.5 mg per dose). Blood samples were taken on days 14, 28, 42 and 56 for analysing the anti-rTbp2 antibody titers by EIAs.

Groups of two rabbits and two guinea pigs (Charles River, Quebec) were immunized intramuscularly (i.m.) on day 1 with a 5 mg dose of purified rTbp2 protein emulsified in complete Freund's adjuvant (CFA). Animals were boosted on days 14 and 29 with the same dose of protein emulsified in incomplete Freund's adjuvant (IFA). Blood samples were taken on day 42 for analysing anti-rTbp2 antibody titers and bactericidal activity. Table 2 below shows the bactericidal activity of antibodies raised to the recombinant tranferrin binding proteins rTbp1 (4223), rTbp2 (4223) and rTbp2 (Q8), prepared as described in these Examples, against *M. catarrhalis* strains 4223 and Q8.

Example 17

This Example illustrates the binding of Tbp2 to human transferrin in vitro.

Figure 24:
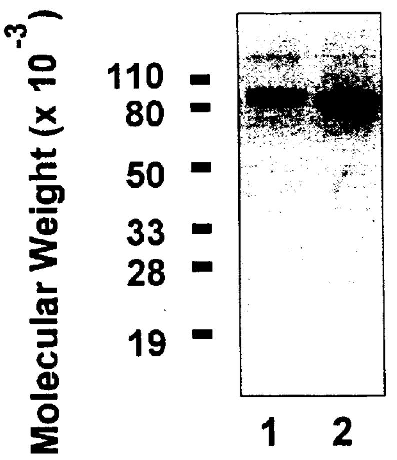
FIG. 24 shows the binding of Tbp2 to human transferrin.

Transferrin-binding activity of Tbp2 was assessed according to the procedures of Schryvers and Lee (ref. 28) with modifications. Briefly, purified rTbp2 was subjected to discontinuous electrophoresis through 12.5% SDS-PAGE gels. The proteins were electrophoretically transferred to PVDF membrane and incubated with horseradish peroxidase-conjugated human transferrin (HRP-human transferrin, 1:50 dilution) (Jackson ImmunoResearch Labs Inc., Mississauga, Ontario) at 4° C. for overnight. LumiGLO substrate (Kirkegaard & Perry Laboratories, Inc., Gaithersburg, Md.) was used for chemiluminescent detection of HRP activity according to the manufacturer's instructions. Both 4223 rTbp2 and Q8 rTbp2 bind to human transferrin under these conditions, as shown in FIG. 24.

Example 18

This Example illustrates antigenic conservation of Tbp2 amongst *M. catarrhalis* strains.

Whole cell lysates of *M. catarrhalis* strains and *E. coli* strains expressing recombinant Tbp2 proteins were separated by SDS-PAGE and electrophoretically transferred to PVDF membrane. Guinea pig anti-4223 rTbp2 or anti-Q8 rTbp2 antisera were used as first antibody and alkaline phosphatase conjugated goat anti-guinea pig antibody was used as second antibody to detect Tbp2. *M. catarrhalis* strains 3, 56, 135, 585, 4223, 5191, 8185 and ATCC 25240 were tested and all showed specific reactivity with anti-4223 rTbp2 or anti-Q8 rTbp2 antibody (FIG. 25).

Table 3 illustrates the ability of anti-rTbp2 antibodies from one *M. catarrhalis* strain to recognize native or recombinant protein from a homologous or heterologous *M. catarrhalis* strain.

Example 19

This Example illustrates the cloning of the tbpB gene from an *M. catarrhalis* strain M35 genomic library.

An EMBL3 phage library was prepared in the same manner as described in Example 3 for strains 4223 and Q8 from chromosomal DNA prepared from strain *M. catarrhalis* in the same manner as described in Example 2 for strains 4223 and Q8. The M35 phage library was screened with a digoxigenin-labelled (Boehringer Mannheim, Laval, Quebec) 4223 tbpA gene probe (see Example 4). Phage clone M35-2.3 was found to contain a 13 kb insert of the M35 tfr genes. The tbpB gene was localized to a 7.5 kb NheI-Sal I fragment by restriction enzyme and Southern blot analyses and was subcloned into pBR328 for sequence analysis, generating plasmid pLEM40.

A partial restriction map of the M35 tbpB gene is shown in FIG. 26. The nucleotide and deduced amino acid sequences of the M35 tbpB gene are shown in FIGS. 27A to 27K. The M35 tbpB gene encodes a 706 amino acid protein of molecular weight 76.5 kDa. When the M35 tbpB sequence was aligned with the 4223 tbpB protein, it was found to be 86% identical and 90% similar.

Example 20

This Example illustrates the PCR amplification of the tbpB genes from *M. catarrhalis* strains R1, 3 and LES1.

Oligonucleotide primers were based upon the following sequences, which are found in the intergenic regions surrounding 4223 tbpB:

5'GATGGGATAAGCACGCCCTACTT 3' (SEQ ID NO: 58) sense primer (4940)

5'CCCATCAGCCAAACAAACATTGTGT 3' (SEQ ID NO: 59) antisense primer (4967)

PCR amplification was performed in buffer containing 100 mM Tris-HCI (pH 8.9), 25 mM KCI, 5 mM $(NH_4)_2SO_4$ and 2 mM $MgSO_4$. Each 100 μl reaction mixture contained 10 ng of chromosomal DNA, 1 μg each primer, 2.5 U Pwo DNA polymerase (Boehringer Mannheim) and 0.2 mM dNTPs (perkin Elmer, Foster City, Calif.). The cycling conditions were 25 cycles of 95° C. for 30 sec, 45° C. for 1.0 min and 72° C. for 2.0 min, followed by a 10 min elongation at 72° C. Specific 2.4 kb fragments were amplified and DNA was purified for direct sequencing by agarose gel extraction, using a Geneclean kit (Bio 101 Inc., Vista, Calif.). Plasmid DNA for sequencing was prepared using a Qiagen Plasmid Midi kit (Qiagen, Chatsworth, Calif.). DNA samples were sequenced using an ABI model 373A DNA sequencer using dye terminator chemistry. Oligonucleotide primers of 17 to 25 bases in length were used to sequence both strands of the genes.

Partial restriction maps of the *M. catarrhalis* strain R1, 3 and LES1 tbpB genes are shown in FIGS. 28, 29 and 30 respectively. The nucleotide and deduced amino acid sequences of the strain R1, 3 and LES1 tbpB genes are shown in FIGS. 31A to 31G, 32A to 32K and 33A to M', respectively. The strain 3 tbpB gene encodes a 712 amino acid protein of molecular weight 76.9 kDa which is more closely related to the strain Q8 Tbp2 protein than to the 4223 Tbp2 protein. The Q8 and strain 3 Tbp2 proteins are 71% identical and 79% similar, whereas the 4223 and strain 3 Tbp2 proteins are 51% identical and 64% similar. The strain LES1 tbpB gene encodes a 713 amino acid protein of molecular weight 76.8 kDa which is 63% identical to both the 4223 and Q8 Tbp2 proteins.

From the sequence analysis, there appear to be at least two gene families which can be identified for *M. catarrhalis* tbpB, one comprising strains 4223, R1 and M35 and the other comprising strains Q8 and 3, with strain LES1 being equally related to both families. This finding is similar to that of the *N. meningitidis* tbpB genes which can be divided into two sub-groups (ref. 29). There is limited sequence homology between the *M. catarrhalis* Tbp2 proteins and those from other organisms such as *Actinobacillus pleuropneumoniae, H. influenzae, N. gonorrhoeae, N. meningitidis* and *P. haemolytical* (ref. 30). The homology is scattered in small peptide motifs throughout the sequence and is illustrated by underlining in FIGS. 34A to 34D. The conserved LEGGFYG (SEQ ID NO: 60) epitope was present, as found in Tbp2 from other *M. catarrhalis* strains as well as the *H. influenzae* and *N. meningitidis* Tbp2 proteins.

Example 21

This Example illustrates the bactericidal antibody activity of guinea pig anti-4223 rTbp2 and anti-Q8 rTbp2 antibodies.

The bactericidal antibody assay was performed as described by ref. 31. Briefly, the *M. catarrhalis* strains were grown to an $OD_{578}$ of 0.5 in BHI medium containing 25 mM EDDA. The bacteria were diluted so that the pre-bleed control plates contained 100 to 300 cfu. Guinea pig anti-rTbp2 antisera and pre-bleed controls, were heated to 56° C. for 30 min to inactivate endogenous complement and were diluted 1:64 with veronal buffer containing 0.1% BSA (VBS). Guinea pig complement was diluted 1:10 in VBS. Twenty-five μl each of diluted antiserum, bacteria and complement were added to duplicate wells of a 96 well microtiter plate. The plates were incubated at 37° C. for 60 min, gently shaking at 70 rpm on a rotary platform. Fifty μl of each reaction mixture were plated onto Mueller Hinton agar plates which were incubated at 37° C. for 24 h, then room temperature for 24 h, before the bacteria were counted. Antisera were determined to be bactericidial if ≧50% of bacteria were killed compared with negative controls. Each assay was repeated at least twice in duplicate and the results are shown in Table 3.

The anti-rTbp2 bactericidal antibody activity corelates with the putative gene families identified by sequencing, as described in Example 20. Anti-4223 rTbp2 antibody kills those strains within its own family, i.e. 4223, R1 and M35, while anti-Q8 rTbpB antibody kills those strains within its family, i.e. Q8, 3 and LES1. The anti-4223 rTbp2 antibody also killed strains VH-9, H-04 and ATCC 25240 indicating that the latter strains may be part of the 4223 family. Strain H-04 was also killed by anti-Q8 rTbpB antibody.

Example 22

This Example illustrates the sequence analysis of the open reading frame (ORF) within the intergenic. region between *M. catarrhalis* tbpA and tbpB.

The intergenic region was sequenced for strains 4223 and Q8 and a single open reading frame was identified. This orf, identified as orf3, was located about 1 kb downstream of tbpA and about 273 bp upstream of tbpB in each genome (FIG. 2—strain 4223; FIG. 7—strain Q8). The nucleotide and deduced amino acid sequences of the entire 4223 tbpA-orf3-tbpB gene loci are shown in FIGS. 35A –35M'. The encoded 4223 and Q8 ORF3 proteins are 98% identical, 512 amino acid proteins, of molecular weight 58.1 kDa and 57.9 kDa, respectively. The alignment of the ORF3 protein sequences is shown in FIG. 36.

SUMMARY OF THE DISCLOSURE

In summary of this disclosure, the present invention provides purified and isolated DNA molecules containing transferrin receptor genes of *Moraxella catarrhalis*, the sequences of these transferrin receptor genes, and the derived amino acid sequences thereof. The genes and DNA sequences are useful for diagnosis, immunization, and the generation of diagnostic and immunological reagents. Immunogenic compositions, including vaccines, based upon expressed recombinant Tbp1 and/or Tbp2, portions thereof, or analogs thereof, can be prepared for prevention of diseases caused by Moraxella. Modifications are possible within the scope of this invention.

TABLE I

BACTERICIDAL ANTIBODY TITRES FOR *M. CATARRHALIS* ANTIGENS

| ANTIGEN[1] | SOURCE OF ANTISERA[2] | BACTERICIDAL TITRE[3] RH408[4] Pre-Immune | BACTERICIDAL TITRE[3] RH408[4] Post-Immune | BACTERICIDAL TITRE Q8[5] Pre-Immune | BACTERICIDAL TITRE Q8[5] Post-Immune |
|---|---|---|---|---|---|
| TBP1 | GP | <3.0 | 4.2–6.9 | <3.0 | 4.4–6.2 |
| TBP2 | GP | <3.0 | 12.0–13.6 | <3.0 | <3.0–4.0 |

[1]antigens isolated from *M. catarrhalis* 4223
[2]GP = guinea pig
[3]bactericidal titres: expressed in $\log_2$ as the dilution of antiserum capable of killing 50% of cells
[4]*M. catarrhalis* RH408 is a non-clumping derivative of *M. catarrhalis* 4223
[5]*M. catarrhalis* Q8 is a clinical isolate which displays a non-clumping phenotype

TABLE 2

| Antigen | Bactericidal titre - RH408 pre-immune | Bactericidal titre - RH408 post-immune | Bactericidal titre - Q8 pre-immune | Bactericidal titre - Q8 post-immune |
|---|---|---|---|---|
| rTbp1 (4223) | <3.0 | <3.0 | <3.0 | <3.0 |
| rTbp2 (4223) | <3.0 | 10–15 | <3.0 | <3.0 |
| rTbp2 (Q8) | NT | NT | <3.0 | 5.5–7.5 |

Antibody titres are expressed in $\log_2$ as the dilution of antiserum capable of killing 50% of cells
NT = not tested

TABLE 3

ELISA titres for anti-rTbp2 antibodies recognizing native or rTbp2 from strain 4223 or rTbp2 from strain Q8

| Coated antigen | Anti-rTbp2 (4223) Antibody Titres Rabbit antisera | Anti-rTbp2 (4223) Antibody Titres Guinea pig antisera | Anti-rTbp2 (Q8) Antibody Titres Rabbit antisera | Anti-rTbp2 (Q8) Antibody Titres Guinea pig antisera |
|---|---|---|---|---|
| Native Tbp2 | 409,600 | 1,638,400 | 25,600 | 51,200 |
| (4223) | 204,800 | 1,638,400 | 25,600 | 102,400 |
| rTbp2 (4223) | 409,600 | 1,638,400 | 102,400 | 204,800 |
| | 409,600 | 1,638,400 | 102,400 | 204,800 |
| rTbp2 (Q8) | 409,600 | 1,638,400 | 1,638,400 | 1,638,400 |
| | 102,400 | 1,638,400 | 409,600 | 1,638,400 |

TABLE 4

Bactericidal antibody activity of guinea pig anti-rTbpB antisera

| *M. catarrhalis* strain | Bactericidal Antibody Activity* Anti-A223 rTbp2 | Bactericidal Antibody Activity* Anti-Q8 rTbp2 |
|---|---|---|
| 4223 | ++ | – |
| M35 | ++ | – |
| R1 | ++ | – |
| LES1 | – | + |
| Q8 | – | ++ |
| 3 | – | ± |
| VH-9 | ++ | – |
| H-04 | ++ | ++ |
| ATCC 25240 | ** | – |

*killing by antiserum diluted 1:64 compared to negative controls: – indicates 0 to 25% killing; ± indicates 26 to 49%; + indicates 50 to 75%; ++ indicates 76 to 100% killing.

REFERENCES

1. Brorson, J-E., A. Axelsson, and S. E. Holm. 1976. Studies on *Branhamella catarrhalis* (*Neisseria catarrhalis* ) with special reference to maxillary sinusitis. Scan. J. Infect. Dis. 8:151–155.
2. Catlin, B. W., 1990. *Branhamella catarrhalis*: an organism gaining respect as a pathogen. Clin. Microbiol. Rev. 3: 293–320.
3. Hager, H., A. Verghese, S. Alvarez, and S. L. Berk. 1987. *Branhamella catarrhalis* respiratory infections. Rev. Infect. Dis. 9:1140–1149.
4. McLeod, D. T., F. Ahmad, M. J. Croughan, and M. A. Calder. 1986. Bronchopulmonary infection due to *M. catarrhalis*. Clinical features and therapeutic response. Drugs 31(Suppl.3):109–112.
5. Nicotra, B., M. Rivera, J. I. Luman, and R. J. Wallace. 1986. *Branhamella catarrhalis* as a lower respiratory tract pathogen in patients with chronic lung disease. Arch.Intern.Med. 146:890–893.
6. Ninane, G., J. Joly, and M. Kraytman. 1978. Bronchopulmonary infection due to *Branhamella catarrhalis* 11 cases assessed by transtracheal puncture. Br.Med.Jr. 1:276–278.
7. Srinivasan, G., M. J. Raff, W. C. Templeton, S. J. Givens, R. C. Graves, and J. C. Mel. 1981. *Branhamella catarrhalis* pneumonia. Report of two cases and review of the literature. Am.Rev. Respir. Dis. 123:553–555.
8. West, M., S. L. Berk, and J. K. Smith. 1982. *Branhamella catarrhalis* pneumonia. South.Med. J. 75:1021–1023.
9. Christensen, J. J., and B. Bruun. 1985. Bacteremia caused by a beta-lactamase producing strain of *Branhamella catarrhalis*. Acta.Pathol. Microbiol. Immunol. Scand. Sect.B 93:273–275.

10. Craig, D. B., and P. A. Wehrle. 1983. *Branhamella catarrhalis* septic arthritis. J. Rheumatol. 10:985–986.
11. Guthrie, R., K. Bakenhaster, R.Nelson, and R. Woskobnick. 1988. *Branhamella catarrhalis* sepsis: a case report and review of the literature. J.Infect.Dis. 158:907–908.
12. Hiroshi, S., E. J. Anaissie, N.Khardori, and G. P. Bodey. 1988. *Branhamella catarrhalis* septicemia in patients with leukemia. Cancer 61:2315–2317.
13. O'Neill, J. H., and P. W. Mathieson. 1987. Meningitis due to *Branhamella catarrhalis*. Aust. N. Z. J. Med. 17:241–242.
14. Murphy, T. F. 1989. The surface of *Branhamella catarrhalis*: a systematic approach to the surface antigens of an emerging pathogen. Pediatr. Infect. Dis. J. 8:S75-S77.
15. Van Hare, G. F., P. A. Shurin, C. D. Marchant, N. A. Cartelli, C. E. Johnson, D. Fulton, S. Carlin, and C. H. Kim. Acute otitis media caused by *Branhamella catarrhalis*: biology and therapy. Rev. Infect. Dis. 9:16–27.
16. Jorgensen, J. H., Doern, G. V., Maher, L. A., Howell, A. W., and Redding, J. S., 1990 Antimicrobial resistance among respiratory isolates of *Haemophilus influenza, Moraxella catarrhalis*, and *Streptococcus pneumoniae* in the United States. Antibicrob. Agents Chemother. 34: 2075–2080.
17. Schryvers, A. B. and Morris, L. J. 1988 Identification and Characterization of the transferrin receptor from *Neisseria meningitidis*. Mol. Microbiol. 2:281–288.
18. Lee, B. C., Schryvers, A. B. Specificity of the lactoferrin and transferrin receptors in *Neisseria gonorrhoeae*. Mol. Microbiol. 1988; 2-827–9.
19. Schryvers, A. B. Characterization of the human transferrin and lactoferrin receptors in *Haemophilus influenzae*. Mol. Microbiol. 1988; 2: 467–72.
20. Schryvers, A. B. and Lee, B. C. (1988) Comparative analysis of the transferrin and lactoferrin binding proteins in the family Neisseriaceae. Can. J. Microbiol. 35, 409–415.
21. Yu, R. and Schryvers, A. B., 1993. The interaction between human transferrin and transferrin binding protein 2 from *Moraxella* (Branhamella) *catarrhalis* differs from that of other human pathogens. Microbiol. Pathogenesis, 15:433–445.
22. O'Hagan, 1992. Clin. Pharmokinet. 22:1.
23. Ulmer et al., 1993. Curr. Opinion Invest. Drugs 2: 983–989.
24. Lockhoff, O., 1991. glycolipds as immunomoclutators: Synthesis and properits. Chem. Int. Ed. Engl. 30: 1611–1620.
25. Nixon-George, 1990. J. Immunol. 14: 4798–4802.
26. Wallace, R. J. Jr., Nash, D. R., and Steingrube, V. A. 1990. Antibiotic susceptibilites and drug resistance in *Moraxella* (Branhaemella) *catarrhalis*. Am. J. Med. 88 (5A): 465-50S.
27. F. M. Ausubel et al., Short protocols in Molecular Biology, Greene Publishing Associates and John Wiley and Sons.
28. Schryvers, A. B., Lee, B. C. 1989. Comparative analysis of the transferrin and lactoferrin binding proteins in the family Neisseriaceae. Can. J. Microbiol. 35: 409–415.
29. Legrain, M., V. Mazarin, S. W. Irwin, B. Bouchon, M-J. Quentin-Millet, E. Jacobs, and A. B. Schryvers. 1993, Cloning and characterization of *Neisseria meningitidis* genes encoding the transferrin-binding proteins Tbp1 and Tbp2. Gene 130: 73–80.
30. Ogunnariwo, J. W., Woo, T. K. W., Lo, R. Y. C., Gonzalez, G. C., and Schryvers, A. B. Characterization of the *Pasteurella haemolytica* transferrin receptor genes and the recombinant receptor proteins. Microb. Pathog. 23:273–284 (1997).
31. Yang, Y. P., Myers, L. E., McGuinness, U., Chong, P., Kwok, Y., Klein, M. H. and Harkness R. E. The major outer membrane protein, C. D, extracted from *Moraxella* (Branhamella) *catarrhalis* is a potential vaccine antigen that induces bactericidal antibodies. FEMS Immun. Med. Microbiol. 17:187–199 (1997).
32. Needleman, S. B., and Wunsch, C. D. 1970, J. Mol Biol. 48:443–453.
33. Sellers, P. H. 1974 On the theory and computation of evolutionary distances. J. Appl. Math(Siam) 26:787–793.
34. Waterman, M. S., Smith, T. F., and Beyer, W. A. 1976. Advan. Math. 20:367–387.
35. Smith, T. F., and Waterman, M. S. 1981 Identification of common molecular subsequences. J. Mol. Biol. 147:195–197.
36. Jimenez-Montano, M. and Zamora-Cortina, L. 1981 Evolutionary model for the generation of amino acid sequences and its application to the study of mammal alpha-hemoglobin chains. Proc. VII Int. Biophysics Congress, Mexico City.
37. Sobel, E. and Martinez, H. M. 1985 A Multiple Sequence Alignment Program. Nucleic Acid Res. 14:363–374.

---

What we claim is:

1. A purified and isolated nucleic acid molecule consisting of a DNA sequence selected from the group consisting of:

(a) a DNA sequence as set out in FIG. 5, 6, 10, 11, 27, 31, 32 or 33 (SEQ ID NOS: 1, 2, 3, 4, 5, 6, 7, 8, 45, 47, 48, 50 or 52) or the complementary DNA sequence thereto; and (b) a DNA sequence encoding an amino acid sequence as set out in FIG. 5, 6, 10, 11, 27, 31, 32 or 33 (SEQ ID NOS: 9, 10, 11, 12, 13, 14, 15, 16, 46, 49, 51 or 53) or the complementary DNA sequence thereto.

2. A purified and isolated nucleic acid molecule consisting of a DNA sequence selected from the group consisting of:

(a) a DNA sequence as set forth in FIGS. 27, 31, 32 or 33 (SEQ ID Nos: 45, 47, 48, 50 or 52) or the complementary DNA sequence thereto; and (b) a DNA sequence encoding an amino acid sequence as set forth in FIGS. 27, 31, 32 or 33 (SEQ ID Nos: 46, 49, 51 or 53) or the complementary sequence thereto.

Figure 3:
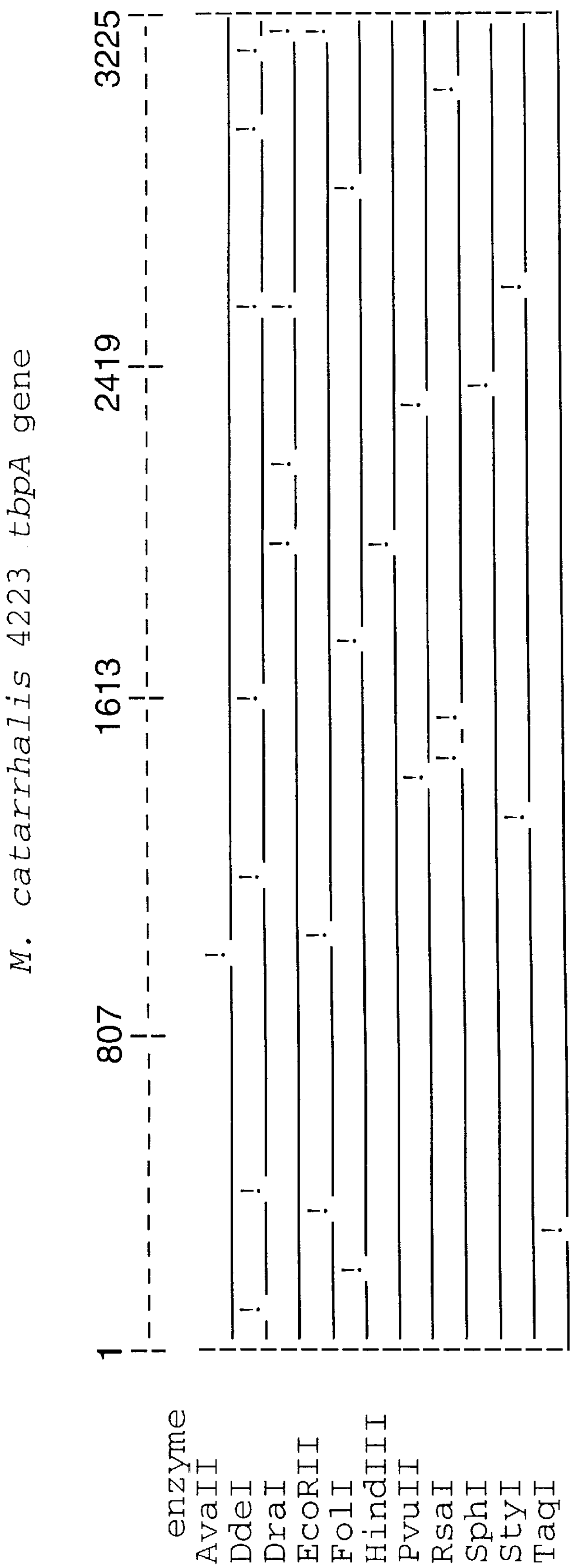
FIG. 3 shows a restriction map of the tbpA gene for *M. catarrhalis* 4223.
Figure 8:
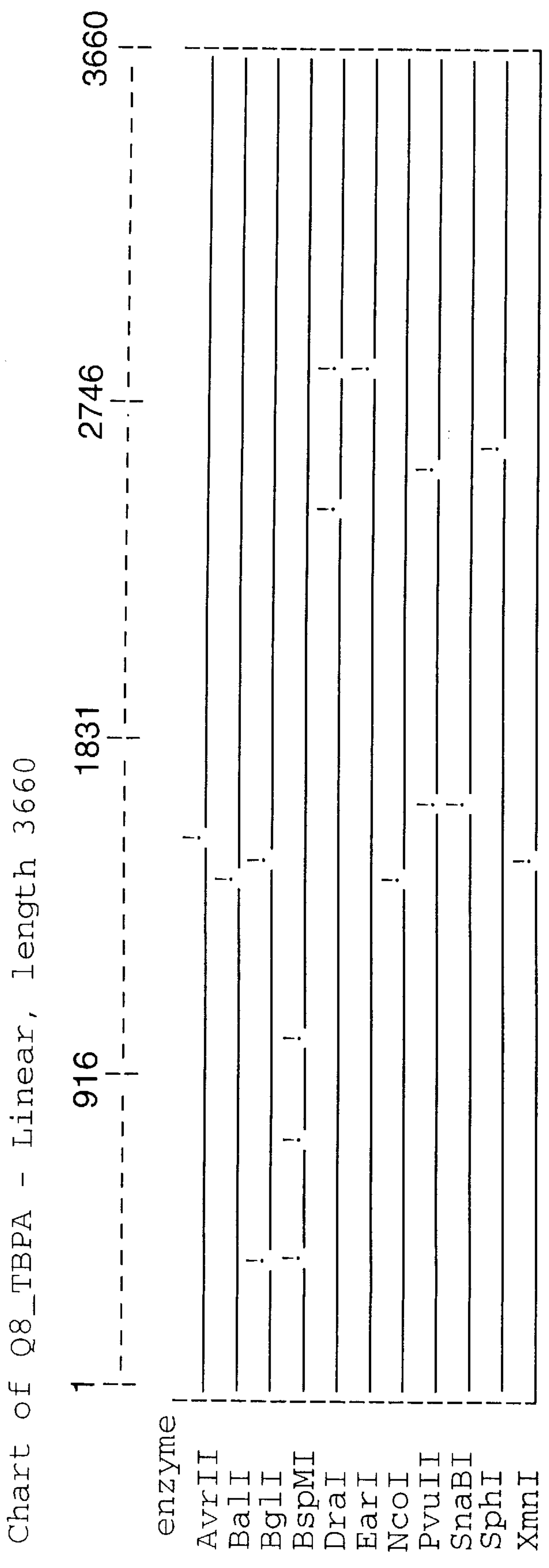
FIG. 8 shows a restriction map of the tbpA gene from *M. catarrhalis* Q8.
Figure 9:
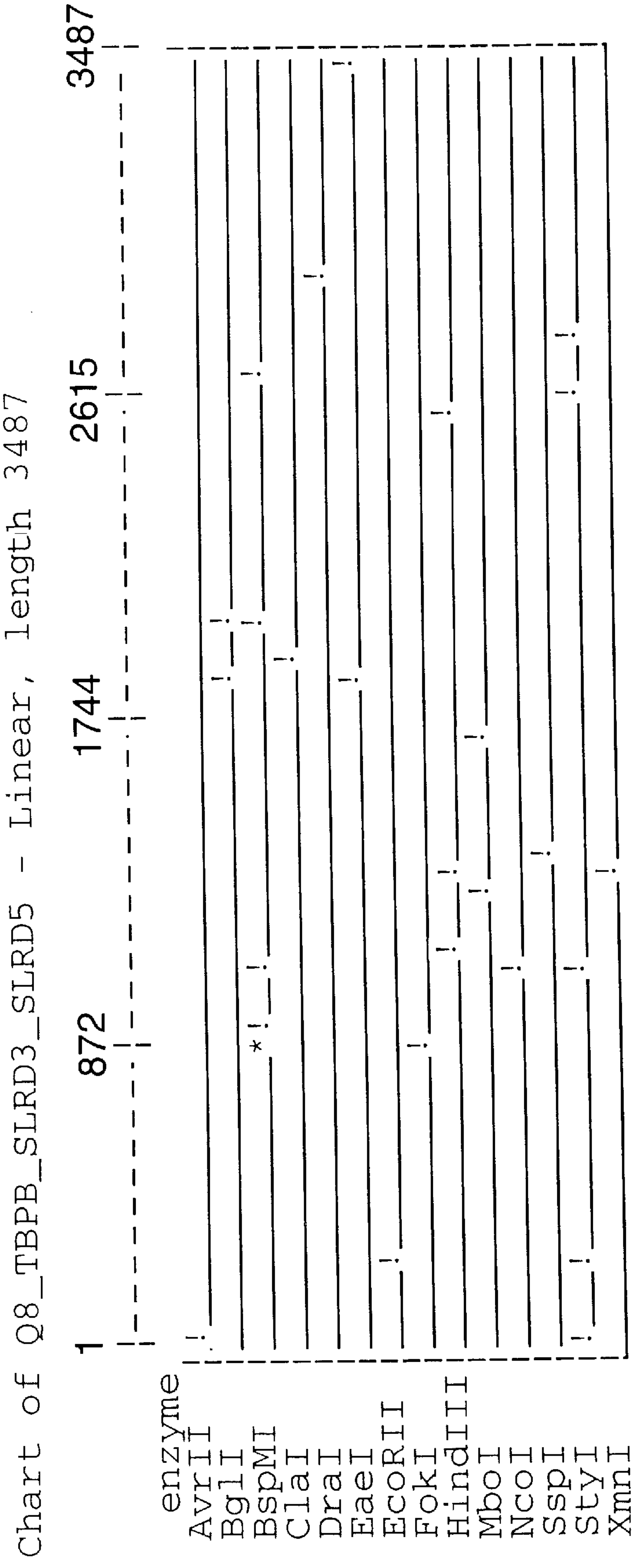
FIG. 9 shows a restriction map of the tbpB gene from *M. catarrhalis* Q8.

3. A purified and isolated nucleic acid molecule consisting of a DNA sequence possessing a restriction map selected from the group consisting of:

nucleotides 1 to 3225 of *M. catarrhalis* strain 4223 tbpA gene as set forth in FIG. 3, nucleotides 1 to 2106 of *M. catarrhalis* strain 4223 tbpB gene as set forth in FIG. 4, nucleotides 1 to 3660 of *M. catarthalis* strain Q8 tbpA gene as set forth in FIG. 8, nucleotides 1 to 3487 of *M. catarrhalis* strain Q8 tbpB gene as set forth in FIG. 9, nucleotides 1 to 2121 of *M. catarrhalis* strain M35 tbpB gene as set forth in FIG. 26, nucleotides 1 to 2145 of *M. catarrhalis* strain R1 tbpB gene as set forth in FIG. 28, nucleotides 1 to 2129 of *M. catarrhalis* strain 3 tbpB gene as set forth in FIG. 29, and nucleotides 1 to 2142 of *M. catarrhalis* strain LES1 tbpB gene as set forth in FIG. 30.

4. A purified and isolated nucleic acid molecule encoding a functional transferrin receptor protein of a strain of *Moraxella catarrhalis* consisting of a DNA sequence which has at least about 90% sequence identity to any one of the DNA sequences selected from the group consisting of:

(a) a DNA sequence as set forth in FIG. 5, 6, 10, 11, 27, 31, 32 or 33 (SEQ ID NOS: 1, 2, 3, 4, 5, 6, 7, 8, 48, 50, 51, 53 or 55); or (b) a DNA sequence encoding an amino acid sequence as set forth in FIG. 5, 6, 10, 11, 27, 31, 32 or 33 (SEQ ID NOS: 9, 10, 11, 12, 13, 14, 15, 16, 49, 52, 54 or 56).

5. A vector adapted for transformation of a host comprising the nucleic acid molecule of claim 1 or 2.

6. A vector adapted for transformation of a host comprising the nucleic acid molecule of claim 1 and further comprising expression means operatively coupled to the nucleic acid molecule for expression by the host of a transferrin receptor protein of a strain of Moraxella encoded by one of said DNA sequences.

7. The vector of claim 6 which is of a plasmid selected from the group consisting of pLEM-37 having ATCC Deposit No. 97,834, SLRD35-A having ATCC Deposit No. 97,833 and SLRD35-B shown in FIG. 20B.

8. A transformed host containing an expression vector as claimed in claim 6.

9. A method of forming a substantially pure recombinant transferrin receptor protein of a strain of Moraxella, which comprises:

growing the transformed host of claim 8 to express a transferrin receptor protein as inclusion bodies, purifying the inclusion bodies free from cellular material and soluble proteins, solubilizing transferrin receptor protein from the purified inclusion bodies, and purifying the transferrin receptor protein free from other solubilized materials.

10. The method of claim 9 wherein said transferrin receptor protein comprises Tbp1 alone, Tbp2 alone or a mixture of Tbp1 and Tbp2.

11. The method of claim 10 wherein said transferrin receptor protein is at least about 70% pure.

12. The method of claim 11 wherein said transferrin receptor protein is at least about 90% pure.

13. A diagnostic kit for determining the presence, in a sample, of nucleic acid encoding a transferrin receptor protein of a strain of Moraxella, comprising:

(a) the nucleic acid molecule of claim 1;

(b) means for contacting the nucleic acid molecule with the sample to produce duplexes comprising the nucleic acid molecule and any said nucleic acid present in the sample and hybridizable with the nucleic acid molecule; and (c) means for determining production of the duplexes.

* * * * *

SEQUENCE LISTING (1) GENERAL INFORMATION:

(iii) NUMBER OF SEQUENCES: 60

(2) INFORMATION FOR SEQ ID NO:1:

(i) SEQUENCE CHARACTERISTICS:
(A) LENGTH: 3438 base pairs
(B) TYPE: nucleic acid
(C) STRANDEDNESS: single
(D) TOPOLOGY: linear (xi) SEQUENCE DESCRIPTION: SEQ ID NO:1:

```
TATTTTGACA AGCTATACAC TAAAATCAAA AATTAATCAC TTTGGTTGGG TGGTTTTAGC     60

AAGCAAATGG TTATTTTGGT AAACAATTAA GTTCTTAAAA ACGATACACG CTCATAAACA    120

GATGGTTTTT GGCATCTGCA ATTTGATGCC TGCCTTGTGA TTGGTTGGGG TGTATCGGTG    180
```

-continued

```
TATCAAAGTG CAAAAGCCAA CAGGTGGTCA TTGATGAATC AATCAAAACA AAACAACAAA    240
TCCAAAAAAT CCAAACAAGT ATTAAAACTT AGTGCCTTGT CTTTGGGTCT GCTTAACATC    300
ACGCAGGTGG CACTGGCAAA CACAACGGCC GATAAGGCGG AGGCAACAGA TAAGACAAAC    360
CTTGTTGTTG TCTTGGATGA AACTGTTGTA ACAGCGAAGA AAAACGCCCG TAAAGCCAAC    420
GAAGTTACAG GCTTGGTAAA GGTGGTCAAA ACTGCCGAGA CCATCAATAA AGAACAAGTG    480
CTAAACATTC GAGACTTAAC ACGCTATGAC CCTGGCATTG CTGTGGTTGA GCAAGGTCGT    540
GGGGCAAGCT CAGGCTATTC TATTCGTGGT ATGGATAAAA ATCGTGTGGC GGTATTGGTT    600
GATGGCATCA ATCAAGCCCA GCACTATGCC CTACAAGGCC CTGTGGCAGG CAAAAATTAT    660
GCCGCAGGTG GGGCAATCAA CGAAATAGAA TACGAAAATG TCCGCTCCGT TGAGATTAGT    720
AAAGGTGCAA ATTCAAGTGA ATACGGCTCT GGGGCATTAT CTGGCTCTGT GGCATTTGTT    780
ACCAAAACCG CCGATGACAT CATCAAAGAT GGTAAAGATT GGGGCGTGCA GACCAAAACC    840
GCCTATGCCA GTAAAAATAA CGCATGGGTT AATTCTGTGG CAGCAGCAGG CAAGGCAGGT    900
TCTTTTAGCG GTCTTATCAT CTACACCGAC CGCCGTGGTC AAGAATACAA GGCACATGAT    960
GATGCCTATC AGGGTAGCCA AAGTTTTGAT AGAGCGGTGG CAACCACTGA CCCAAATAAC   1020
CGAACATTTT TAATAGCAAA TGAATGTGCC AATGGTAATT ATGAGGCGTG TGCTGCTGGC   1080
GGTCAAACCA AACTTCAAGC CAAGCCAACC AATGTGCGTG ATAAGGTCAA TGTCAAAGAT   1140
TATACAGGTC CTAACCGCCT TATCCCAAAC CCACTCACCC AAGACAGCAA ATCCTTACTG   1200
CTTCGCCCAG GTTATCAGCT AAACGATAAG CACTATGTCG GTGGTGTGTA TGAAATCACC   1260
AAACAAAACT ACGCCATGCA AGATAAAACC GTGCCTGCTT ATCTGACGGT TCATGACATT   1320
GAAAAATCAA GGCTCAGCAA CCATGCCCAA GCCAATGGCT ATTATCAAGG CAATAATCTT   1380
GGTGAACGCA TTCGTGATAC CATTGGGCCA GATTCAGGTT ATGGCATCAA CTATGCTCAT   1440
GGCGTATTTT ATGATGAAAA ACACCAAAAA GACCGCCTAG GGCTTGAATA TGTTTATGAC   1500
AGCAAAGGTG AAAATAAATG GTTTGATGAT GTGCGTGTGT CTTATGATAA GCAAGACATT   1560
ACGCTACGCA GCCAGCTGAC CAACACGCAC TGTTCAACCT ATCCGCACAT TGACAAAAAT   1620
TGTACGCCTG ATGTCAATAA ACCTTTTTCG GTAAAAGAGG TGGATAACAA TGCCTACAAA   1680
GAACAGCACA ATTTAATCAA AGCCGTCTTT AACAAAAAAA TGGCGTTGGG CAGTACGCAT   1740
CATCACATCA ACCTGCAAGT TGGCTATGAT AAATTCAATT CAAGCCTGAG CCGTGAAGAT   1800
TATCGTTTGG CAACCCATCA GTCTTATGAA AAACTTGATT ACACCCCACC AAGTAACCCT   1860
TTGCCAGATA AGTTTAAGCC CATTTTAGGT TCAAACAACA AACCCATTTG CCTTGATGCT   1920
TATGGTTATG GTCATGACCA TCCACAGGCT TGTAACGCCA AAAACAGCAC TTATCAAAAT   1980
TTTGCCATCA AAAAAGGCAT AGAGCAATAC AACCAAAAAA CCAATACCGA TAAGATTGAT   2040
TATCAAGCCA TCATTGACCA ATATGATAAA CAAAACCCCA ACAGCACCCT AAAACCCTTT   2100
GAGAAAATCA AACAAAGTTT GGGGCAAGAA AAATACAACA AGATAGACGA ACTTGGCTTT   2160
AAAGCTTATA AAGATTTACG CAACGAATGG GCGGGTTGGA CTAATGACAA CAGCCAACAA   2220
AATGCCAATA AAGGCACGGA TAATATCTAT CAGCCAAATC AAGCAACTGT GGTCAAAGAT   2280
GACAAATGTA AATATAGCGA GACCAACAGC TATGCTGATT GCTCAACCAC TGCGCACATC   2340
AGTGGTGATA ATTATTTCAT CGCTTTAAAA GACAACATGA CCATCAATAA ATATGTTGAT   2400
TTGGGGCTGG GTGCTCGCTA TGACAGAATC AAACACAAAT CTGATGTGCC TTTGGTAGAC   2460
AACAGTGCCA GCAACCAGCT GTCTTGGAAT TTTGGCGTGG TCGTCAAGCC CACCAATTGG   2520
```

-continued

```
CTGGACATCG CTTATAGAAG CTCGCAAGGC TTTCGCATGC CAAGTTTTTC TGAAATGTAT   2580

GGCGAACGCT TTGGCGTAAC CATCGGTAAA GGCACGCAAC ATGGCTGTAA GGGTCTTTAT   2640

TACATTTGTC AGCAGACTGT CCATCAAACC AAGCTAAAAC CTGAAAAATC CTTTAACCAA   2700

GAAATCGGAG CGACTTTACA TAACCACTTA GGCAGTCTTG AGGTTAGTTA TTTTAAAAAT   2760

CGCTATACCG ATTTGATTGT TGGTAAAAGT GAAGAGATTA GAACCCTAAC CCAAGGTGAT   2820

AATGCAGGCA AACAGCGTGG TAAAGGTGAT TTGGGCTTTC ATAATGGACA AGATGCTGAT   2880

TTGACAGGCA TTAACATTCT TGGCAGACTT GACCTAAACG CTGTCAATAG TCGCCTTCCC   2940

TATGGATTAT ACTCAACACT GGCTTATAAC AAAGTTGATG TTAAAGGAAA AACCTTAAAC   3000

CCAACTTTGG CAGGAACAAA CATACTGTTT GATGCCATCC AGCCATCTCG TTATGTGGTG   3060

GGGCTTGGCT ATGATGCCCC AAGCCAAAAA TGGGGAGCAA ACGCCATATT TACCCATTCT   3120

GATGCCAAAA ATCCAAGCGA GCTTTTGGCA GATAAGAACT TAGGTAATGG CAACATTCAA   3180

ACAAAACAAG CCACCAAAGC AAAATCCACG CCGTGGCAAA CACTTGATTT GTCAGGTTAT   3240

GTAAACATAA AAGATAATTT TACCTTGCGT GCTGGCGTGT ACAATGTATT TAATACCTAT   3300

TACACCACTT GGGAGGCTTT ACGCCAAACA GCAGAAGGGG CGGTCAATCA GCATACAGGA   3360

CTGAGCCAAG ATAAGCATTA TGGTCGCTAT GCCGCTCCTG GACGCAATTA CCAATTGGCA   3420

CTTGAAATGA AGTTTTAA                                                 3438
```

(2) INFORMATION FOR SEQ ID NO:2:

(i) SEQUENCE CHARACTERISTICS:
(A) LENGTH: 3222 base pairs
(B) TYPE: nucleic acid
(C) STRANDEDNESS: single
(D) TOPOLOGY: linear (xi) SEQUENCE DESCRIPTION: SEQ ID NO:2:

```
ATGAATCAAT CAAAACAAAA CAACAAATCC AAAAAATCCA AACAAGTATT AAAACTTAGT     60

GCCTTGTCTT TGGGTCTGCT TAACATCACG CAGGTGGCAC TGGCAAACAC AACGGCCGAT    120

AAGGCGGAGG CAACAGATAA GACAAACCTT GTTGTTGTCT TGGATGAAAC TGTTGTAACA    180

GCGAAGAAAA ACGCCCGTAA AGCCAACGAA GTTACAGGGC TTGGTAAGGT GGTCAAAACT    240

GCCGAGACCA TCAATAAAGA ACAAGTGCTA AACATTCGAG ACTTAACACG CTATGACCCT    300

GGCATTGCTG TGGTTGAGCA AGGTCGTGGG GCAAGCTCAG GCTATTCTAT TCGTGGTATG    360

GATAAAAATC GTGTGGCGGT ATTGGTTGAT GGCATCAATC AAGCCCAGCA CTATGCCCTA    420

CAAGGCCCTG TGGCAGGCAA AAATTATGCC GCAGGTGGGG CAATCAACGA AATAGAATAC    480

GAAAATGTCC GCTCCGTTGA GATTAGTAAA GGTGCAAATT CAAGTGAATA CGGCTCTGGG    540

GCATTATCTG GCTCTGTGGC ATTTGTTACC AAAACCGCCG ATGACATCAT CAAAGATGGT    600

AAAGATTGGG GCGTGCAGAC CAAAACCGCC TATGCCAGTA AAAATAACGC ATGGGTTAAT    660

TCTGTGGCAG CAGCAGGCAA GGCAGGTTCT TTTAGCGGTC TTATCATCTA CACCGACCGC    720

CGTGGTCAAG AATACAAGGC ACATGATGAT GCCTATCAGG GTAGCCAAAG TTTTGATAGA    780

GCGGTGGCAA CCACTGACCC AAATAACCGA ACATTTTTAA TAGCAAATGA ATGTGCCAAT    840

GGTAATTATG AGGCGTGTGC TGCTGGCGGT CAAACCAAAC TTCAAGCCAA GCCAACCAAT    900

GTGCGTGATA AGGTCAATGT CAAAGATTAT ACAGGTCCTA ACCGCCTTAT CCCAAACCCA    960

CTCACCCAAG ACAGCAAATC CTTACTGCTT CGCCCAGGTT ATCAGCTAAA CGATAAGCAC   1020

TATGTCGGTG GTGTGTATGA AATCACCAAA CAAAACTACG CCATGCAAGA TAAAACCGTG   1080
```

-continued

```
CCTGCTTATC TGACGGTTCA TGACATTGAA AAATCAAGGC TCAGCAACCA TGCCCAAGCC   1140

AATGGCTATT ATCAAGGCAA TAATCTTGGT GAACGCATTC GTGATACCAT TGGGCCAGAT   1200

TCAGGTTATG GCATCAACTA TGCTCATGGC GTATTTTATG ATGAAAAACA CCAAAAAGAC   1260

CGCCTAGGGC TTGAATATGT TTATGACAGC AAAGGTGAAA ATAAATGGTT TGATGATGTG   1320

CGTGTGTCTT ATGATAAGCA AGACATTACG CTACGCAGCC AGCTGACCAA CACGCACTGT   1380

TCAACCTATC CGCACATTGA CAAAAATTGT ACGCCTGATG TCAATAAACC TTTTTCGGTA   1440

AAAGAGGTGG ATAACAATGC CTACAAAGAA CAGCACAATT TAATCAAAGC CGTCTTTAAC   1500

AAAAAAATGG CGTTGGGCAG TACGCATCAT CACATCAACC TGCAAGTTGG CTATGATAAA   1560

TTCAATTCAA GCCTGAGCCG TGAAGATTAT CGTTTGGCAA CCCATCAGTC TTATGAAAAA   1620

CTTGATTACA CCCCACCAAG TAACCCTTTG CCAGATAAGT TTAAGCCCAT TTTAGGTTCA   1680

AACAACAAAC CCATTTGCCT TGATGCTTAT GGTTATGGTC ATGACCATCC ACAGGCTTGT   1740

AACGCCAAAA ACAGCACTTA TCAAAATTTT GCCATCAAAA AAGGCATAGA GCAATACAAC   1800

CAAAAAACCA ATACCGATAA GATTGATTAT CAAGCCATCA TTGACCAATA TGATAAACAA   1860

AACCCCAACA GCACCCTAAA ACCCTTTGAG AAAATCAAAC AAAGTTTGGG GCAAGAAAAA   1920

TACAACAAGA TAGACGAACT TGGCTTTAAA GCTTATAAAG ATTTACGCAA CGAATGGGCG   1980

GGTTGGACTA ATGACAACAG CCAACAAAAT GCCAATAAAG GCACGGATAA TATCTATCAG   2040

CCAAATCAAG CAACTGTGGT CAAAGATGAC AAATGTAAAT ATAGCGAGAC CAACAGCTAT   2100

GCTGATTGCT CAACCACTGC GCACATCAGT GGTGATAATT ATTTCATCGC TTTAAAAGAC   2160

AACATGACCA TCAATAAATA TGTTGATTTG GGGCTGGGTG CTCGCTATGA CAGAATCAAA   2220

CACAAATCTG ATGTGCCTTT GGTAGACAAC AGTGCCAGCA ACCAGCTGTC TTGGAATTTT   2280

GGCGTGGTCG TCAAGCCCAC CAATTGGCTG GACATCGCTT ATAGAAGCTC GCAAGGCTTT   2340

CGCATGCCAA GTTTTTCTGA AATGTATGGC GAACGCTTTG GCGTAACCAT CGGTAAAGGC   2400

ACGCAACATG GCTGTAAGGG TCTTTATTAC ATTTGTCAGC AGACTGTCCA TCAAACCAAG   2460

CTAAAACCTG AAAAATCCTT TAACCAAGAA ATCGGAGCGA CTTTACATAA CCACTTAGGC   2520

AGTCTTGAGG TTAGTTATTT TAAAAATCGC TATACCGATT TGATTGTTGG TAAAAGTGAA   2580

GAGATTAGAA CCCTAACCCA AGGTGATAAT GCAGGCAAAC AGCGTGGTAA AGGTGATTTG   2640

GGCTTTCATA ATGGACAAGA TGCTGATTTG ACAGGCATTA ACATTCTTGG CAGACTTGAC   2700

CTAAACGCTG TCAATAGTCG CCTTCCCTAT GGATTATACT CAACACTGGC TTATAACAAA   2760

GTTGATGTTA AAGGAAAAAC CTTAAACCCA ACTTTGGCAG GAACAAACAT ACTGTTTGAT   2820

GCCATCCAGC CATCTCGTTA TGTGGTGGGG CTTGGCTATG ATGCCCCAAG CCAAAAATGG   2880

GGAGCAAACG CCATATTTAC CCATTCTGAT GCCAAAAATC CAAGCGAGCT TTTGGCAGAT   2940

AAGAACTTAG GTAATGGCAA CATTCAAACA AAACAAGCCA CCAAAGCAAA ATCCACGCCG   3000

TGGCAAACAC TTGATTTGTC AGGTTATGTA AACATAAAAG ATAATTTTAC CTTGCGTGCT   3060

GGCGTGTACA ATGTATTTAA TACCTATTAC ACCACTTGGG AGGCTTTACG CCAAACAGCA   3120

GAAGGGGCGG TCAATCAGCA TACAGGACTG AGCCAAGATA AGCATTATGG TCGCTATGCC   3180

GCTCCTGGAC GCAATTACCA ATTGGCACTT GAAATGAAGT TT                      3222
```

(2) INFORMATION FOR SEQ ID NO:3:

(i) SEQUENCE CHARACTERISTICS:
(A) LENGTH: 2247 base pairs
(B) TYPE: nucleic acid
(C) STRANDEDNESS: single -continued (D) TOPOLOGY: linear (xi) SEQUENCE DESCRIPTION: SEQ ID NO:3:

```
GTAAATTTGC CGTATTTTGT CTATCATAAA TGCATTTATC AAATGCTCAA ATAAATACGC     60
AAATGCACAT TGTCAGCATG CCAAAATAGG CATCAACAGA CTTTTTTAGA TAATACCATC    120
AACCCATCAG AGGATTATTT TATGAAACAC ATTCCTTTAA CCACACTGTG TGTGGCAATC    180
TCTGCCGTCT TATTAACCGC TTGTGGTGGC AGTGGTGGTT CAAATCCACC TGCTCCTACG    240
CCCATTCCAA ATGCTAGCGG TTCAGGTAAT ACTGGCAACA CTGGTAATGC TGGCGGTACT    300
GATAATACAG CCAATGCAGG TAATACAGGC GGTACAAACT CTGGTACAGG CAGTGCCAAC    360
ACACCAGAGC CAAAATATCA AGATGTACCA ACTGAGAAAA ATGAAAAAGA TAAAGTTTCA    420
TCCATTCAAG AACCTGCCAT GGGTTATGGC ATGGCTTTGA GTAAAATTAA TCTACACAAC    480
CGACAAGACA CGCCATTAGA TGAAAAAAAT ATCATTACCT TAGACGGTAA AAAACAAGTT    540
GCAGAAGGTA AAAAATCGCC ATTGCCATTT TCGTTAGATG TAGAAAATAA ATTGCTTGAT    600
GGCTATATAG CAAAAATGAA TGTAGCGGAT AAAAATGCCA TTGGTGACAG AATTAAGAAA    660
GGTAATAAAG AAATCTCCGA TGAAGAACTT GCCAAACAAA TCAAAGAAGC TGTGCGTAAA    720
AGCCATGAGT TTCAGCAAGT ATTATCATCA CTGGAAAACA AAATTTTTCA TTCAAATGAC    780
GGAACAACCA AAGCAACCAC ACGAGATTTA AAATATGTTG ATTATGGTTA CTACTTGGCG    840
AATGATGGCA ATTATCTAAC CGTCAAAACA GACAAACTTT GGAATTTAGG CCCTGTGGGT    900
GGTGTGTTTT ATAATGGCAC AACGACCGCC AAAGAGTTGC CCACACAAGA TGCGGTCAAA    960
TATAAAGGAC ATTGGGACTT TATGACCGAT GTTGCCAACA GAAGAAACCG ATTTAGCGAA   1020
GTGAAAGAAA ACTCTCAAGC AGGCTGGTAT TATGGAGCAT CTTCAAAAGA TGAATACAAC   1080
CGCTTATTAA CTAAAGAAGA CTCTGCCCCT GATGGTCATA GCGGTGAATA TGGCCATAGC   1140
AGTGAGTTTA CTGTTAATTT TAAGGAAAAA AAATTAACAG GTAAGCTGTT TAGTAACCTA   1200
CAAGACCGCC ATAAGGGCAA TGTTACAAAA ACCGAACGCT ATGACATCGA TGCCAATATC   1260
CACGGCAACC GCTTCCGTGG CAGTGCCACC GCAAGCAATA AAAATGACAC AAGCAAACAC   1320
CCCTTTACCA GTGATGCCAA CAATAGGCTA GAAGGTGGTT TTTATGGGCC AAAAGGCGAG   1380
GAGCTGGCAG GTAAATTCTT AACCAATGAC AACAAACTCT TTGGCGTCTT TGGTGCTAAA   1440
CGAGAGAGTA AAGCTGAGGA AAAAACCGAA GCCATCTTAG ATGCCTATGC ACTTGGGACA   1500
TTTAATACAA GTAACGCAAC CACATTCACC CCATTTACCG AAAAACAACT GGATAACTTT   1560
GGCAATGCCA AAAAATTGGT CTTAGGTTCT ACCGTCATTG ATTTGGTGCC TACTGATGCC   1620
ACCAAAAATG AATTCACCAA AGACAAGCCA GAGTCTGCCA CAAACGAAGC GGGCGAGACT   1680
TTGATGGTGA ATGATGAAGT TAGCGTCAAA ACCTATGGCA AAAACTTTGA ATACCTAAAA   1740
TTTGGTGAGC TTAGTATCGG TGGTAGCCAT AGCGTCTTTT TACAAGGCGA ACGCACCGCT   1800
ACCACAGGCG AGAAAGCCGT ACCAACCACA GGCACAGCCA AATATTTGGG GAACTGGGTA   1860
GGATACATCA CAGGAAAGGA CACAGGAACG GGCACAGGAA AAGCTTTTAC CGATGCCCAA   1920
GATGTTGCTG ATTTTGACAT TGATTTTGGA AATAAATCAG TCAGCGGTAA ACTTATCACC   1980
AAAGGCCGCC AAGACCCTGT ATTTAGCATC ACAGGTCAAA TCGCAGGCAA TGGCTGGACA   2040
GGCACAGCCA GCACCACCAA AGCGGACGCA GGAGGCTACA AGATAGATTC TAGCAGTACA   2100
GGCAAATCCA TCGTCATCAA AGATGCCAAT GTTACAGGGG GCTTTTATGG TCCAAATGCA   2160
AACGAGATGG GCGGGTCATT TACACACAAC GCCGATGACA GCAAAGCCTC TGTGGTCTTT   2220
GGCACAAAAA GACAACAAGA AGTTAAG                                       2247
```

-continued (2) INFORMATION FOR SEQ ID NO:4:

(i) SEQUENCE CHARACTERISTICS:
(A) LENGTH: 2106 base pairs
(B) TYPE: nucleic acid
(C) STRANDEDNESS: single
(D) TOPOLOGY: linear (xi) SEQUENCE DESCRIPTION: SEQ ID NO:4:

ATGAAACACA TTCCTTTAAC CACACTGTGT GTGGCAATCT CTGCCGTCTT ATTAACCGCT 60

TGTGGTGGCA GTGGTGGTTC AAATCCACCT GCTCCTACGC CCATTCCAAA TGCTAGCGGT 120

TCAGGTAATA CTGGCAACAC TGGTAATGCT GGCGGTACTG ATAATACAGC CAATGCAGGT 180

AATACAGGCG GTACAAACTC TGGTACAGGC AGTGCCAACA CACCAGAGCC AAAATATCAA 240

GATGTACCAA CTGAGAAAAA TGAAAAAGAT AAAGTTTCAT CCATTCAAGA ACCTGCCATG 300

GGTTATGGCA TGGCTTTGAG TAAAATTAAT CTACACAACC GACAAGACAC GCCATTAGAT 360

GAAAAAAATA TCATTACCTT AGACGGTAAA AAACAAGTTG CAGAAGGTAA AAAATCGCCA 420

TTGCCATTTT CGTTAGATGT AGAAAATAAA TTGCTTGATG GCTATATAGC AAAAATGAAT 480

GTAGCGGATA AAAATGCCAT TGGTGACAGA ATTAAGAAAG GTAATAAAGA AATCTCCGAT 540

GAAGAACTTG CCAAACAAAT CAAAGAAGCT GTGCGTAAAA GCCATGAGTT TCAGCAAGTA 600

TTATCATCAC TGGAAAACAA AATTTTTCAT TCAAATGACG GAACAACCAA AGCAACCACA 660

CGAGATTTAA AATATGTTGA TTATGGTTAC TACTTGGCGA ATGATGGCAA TTATCTAACC 720

GTCAAAACAG ACAAACTTTG GAATTTAGGC CCTGTGGGTG GTGTGTTTTA TAATGGCACA 780

ACGACCGCCA AAGAGTTGCC CACACAAGAT GCGGTCAAAT ATAAAGGACA TTGGGACTTT 840

ATGACCGATG TTGCCAACAG AAGAAACCGA TTTAGCGAAG TGAAAGAAAA CTCTCAAGCA 900

GGCTGGTATT ATGGAGCATC TTCAAAAGAT GAATACAACC GCTTATTAAC TAAAGAAGAC 960

TCTGCCCCTG ATGGTCATAG CGGTGAATAT GGCCATAGCA GTGAGTTTAC TGTTAATTTT 1020

AAGGAAAAAA AATTAACAGG TAAGCTGTTT AGTAACCTAC AAGACCGCCA TAAGGGCAAT 1080

GTTACAAAAA CCGAACGCTA TGACATCGAT GCCAATATCC ACGGCAACCG CTTCCGTGGC 1140

AGTGCCACCG CAAGCAATAA AAATGACACA AGCAAACACC CCTTTACCAG TGATGCCAAC 1200

AATAGGCTAG AAGGTGGTTT TTATGGGCCA AAAGGCGAGG AGCTGGCAGG TAAATTCTTA 1260

ACCAATGACA ACAAACTCTT TGGCGTCTTT GGTGCTAAAC GAGAGAGTAA AGCTGAGGAA 1320

AAAACCGAAG CCATCTTAGA TGCCTATGCA CTTGGGACAT TTAATACAAG TAACGCAACC 1380

ACATTCACCC CATTTACCGA AAAACAACTG GATAACTTTG GCAATGCCAA AAAATTGGTC 1440

TTAGGTTCTA CCGTCATTGA TTTGGTGCCT ACTGATGCCA CCAAAAATGA ATTCACCAAA 1500

GACAAGCCAG AGTCTGCCAC AAACGAAGCG GGCGAGACTT TGATGGTGAA TGATGAAGTT 1560

AGCGTCAAAA CCTATGGCAA AAACTTTGAA TACCTAAAAT TTGGTGAGCT TAGTATCGGT 1620

GGTAGCCATA GCGTCTTTTT ACAAGGCGAA CGCACCGCTA CCACAGGCGA GAAAGCCGTA 1680

CCAACCACAG GCACAGCCAA ATATTTGGGG AACTGGGTAG GATACATCAC AGGAAAGGAC 1740

ACAGGAACGG GCACAGGAAA AAGCTTTACC GATGCCCAAG ATGTTGCTGA TTTTGACATT 1800

GATTTTGGAA ATAAATCAGT CAGCGGTAAA CTTATCACCA AAGGCCGCCA AGACCCTGTA 1860

TTTAGCATCA CAGGTCAAAT CGCAGGCAAT GGCTGGACAG GCACAGCCAG CACCACCAAA 1920

GCGGACGCAG GAGGCTACAA GATAGATTCT AGCAGTACAG GCAAATCCAT CGTCATCAAA 1980

GATGCCAATG TTACAGGGGG CTTTTATGGT CCAAATGCAA ACGAGATGGG CGGGTCATTT 2040

-continued

```
ACACACAACG CCGATGACAG CAAAGCCTCT GTGGTCTTTG GCACAAAAAG ACAACAAGAA   2100

GTTAAG                                                              2106
```

(2) INFORMATION FOR SEQ ID NO:5:

(i) SEQUENCE CHARACTERISTICS:
(A) LENGTH: 3660 base pairs
(B) TYPE: nucleic acid
(C) STRANDEDNESS: single
(D) TOPOLOGY: linear (xi) SEQUENCE DESCRIPTION: SEQ ID NO:5:

```
AATTGATACA AAATGGTTTG TATTATCACT TGTATTTGTA TTATAATTTT ACTTATTTTT     60

ACAAACTATA CACTAAAATC AAAAATTAAT CACTTTGGTT GGGTGGTTTT AGCAAGCAAA    120

TGGTTATTTT GGTAAACAAT TAAGTTCTTA AAAACGATAC ACGCTCATAA ACAGATGGTT    180

TTTGGCATCT TCAATTTGAT GCCTGCCTTG TGATTGGTTG GGGGTGTATT GATGTATCCA    240

AGTACAAAAG CCAACAGGTG GTCATTGATG AATCAATCCA AAAAATCCAA AAAATCCAAA    300

CAAGTATTAA AACTTAGTGC CTTGTCTTTG GGTCTGCTTA ACATCACGCA GGTGGCACTG    360

GCAAACACAA CGGCCGATAA GGCGGAGGCA ACAGATAAGA CAAACCTTGT TGTTGTCTTG    420

GATGAAACTG TTGTAACAGC GAAGAAAAAC GCCCGTAAAG CCAACGAAGT TACAGGGCTT    480

GGTAAGGTGG TCAAAACTGC CGAGACCATC AATAAAGAAC AAGTGCTAAA CATTCGAGAC    540

TTAACACGCT ATGACCCTGG CATTGCTGTG GTTGAGCAAG GTCGTGGGGC AAGCTCAGGC    600

TATTCTATTC GTGGTATGGA TAAAAATCGT GTGGCGGTAT TGGTTGATGG CATCAATCAA    660

GCCCAGCACT ATGCCCTACA AGGCCCTGTG GCAGGCAAAA ATTATGCCGC AGGTGGGGCA    720

ATCAACGAAA TAGAATACGA AAATGTCCGC TCCGTTGAGA TTAGTAAAGG TGCAAATTCA    780

AGTGAATACG GCTCTGGGGC ATTATCTGGC TCTGTGGCAT TTGTTACCAA AACCGCCGAT    840

GACATCATCA AAGATGGTAA AGATTGGGGC GTGCAGACCA AAACCGCCTA TGCCAGTAAA    900

AATAACGCAT GGGTTAATTC TGTGGCAGCA GCAGGCAAGG CAGGTTCTTT TAGCGGTCTT    960

ATCATCTACA CCGACCGCCG TGGTCAAGAA TACAAGGCAC ATGATGATGC CTATCAGGGT   1020

AGCCAAAGTT TTGATAGAGC GGTGGCAACC ACTGACCCAA ATAACCCAAA ATTTTTAATA   1080

GCAAATGAAT GTGCCAATGG TAATTATGAG GCGTGTGCTG CTGGCGGTCA AACCAAACTC   1140

CAAGCTAAGC CAACCAATGT GCGTGATAAG GTCAATGTCA AAGATTATAC AGGTCCTAAC   1200

CGCCTTATCC CAAACCCACT CACCCAAGAC AGCAAATCCT TACTGCTTCG CCCAGGTTAT   1260

CAGCTAAACG ATAAGCACTA TGTCGGTGGT GTGTATGAAA TCACCAAACA AAACTACGCC   1320

ATGCAAGATA AAACCGTGCC TGCTTATCTG ACGGTTCATG ACATTGAAAA ATCAAGGCTC   1380

AGCAACCATG GCCAAGCCAA TGGCTATTAT CAAGGCAATA ACCTTGGTGA ACGCATTCGT   1440

GATGCCATTG GGGCAAATTC AGGTTATGGC ATCAACTATG CTCATGGCGT ATTTTATGAC   1500

GAAAAACACC AAAAAGACCG CCTAGGGCTT GAATATGTTT ATGACAGCAA AGGTGAAAAT   1560

AAATGGTTTG ATGATGTGCG TGTGTCTTAT GACAAGCAAG ACATTACGCT ACGTAGCCAG   1620

CTGACCAACA CGCACTGTTC AACCTATCCG CACATTGACA AAAATTGTAC GCCTGATGTC   1680

AATAAACCTT TTTCGGTAAA AGAGGTGGAT AACAATGCCT ACAAAGAACA GCACAATTTA   1740

ATCAAAGCCG TCTTTAACAA AAAAATGGCA TTGGGCAATA CGCATCATCA CATCAATCTG   1800

CAAGTTGGCT ATGATAAATT CAATTCAAGC CTTAGCCGTG AAGATTATCG TTTGGCAACC   1860

CATCAATCTT ATCAAAAACT TGATTACACC CCACCAAGTA ACCCTTTGCC AGATAAGTTT   1920
```

-continued

```
AAGCCCATTT TAGGTTCAAA CAACAGACCC ATTTGCCTTG ATGCTTATGG TTATGGTCAT   1980

GACCATCCAC AGGCTTGTAA CGCCAAAAAC AGCACTTATC AAAACTTTGC CATCAAAAAA   2040

GGCATAGAGC AATACAACCA AACCAATACC GATAAGATTG ATTATCAAGC CGTCATTGAC   2100

CAATATGATA AACAAAACCC CAACAGCACC CTAAAACCCT TTGAGAAAAT CAAACAAAGT   2160

TTGGGGCAAG AAAAATACGA CGAGATAGAC AGACTGGGCT TTAATGCTTA TAAAGATTTA   2220

CGCAACGAAT GGGCGGGTTG GACTAATGAC AACAGCCAAC AAAACGCCAA TAAAGGCACG   2280

GATAATATCT ATCAGCCAAA TCAAGCAACT GTGGTCAAAG ATGACAAATG TAAATATAGC   2340

GAGACCAACA GCTATGCTGA TTGCTCAACC ACTCGCCACA TCAGCGGTGA TAATTATTTC   2400

ATCGCTTTAA AAGACAACAT GACCATCAAT AAATATGTTG ATTTGGGGCT GGGTGCTCGC   2460

TATGACAGAA TCAAACACAA ATCTGATGTG CCTTTGGTAG ACAACAGTGC CAGCAACCAG   2520

CTGTCTTGGA ATTTTGGCGT GGTCGTCAAG CCCACCAATT GGCTGGACAT CGCTTATAGA   2580

AGCTCGCAAG GCTTTCGCAT GCCAAGTTTT TCTGAAATGT ATGGCGAACG CTTTGGCGTA   2640

ACCATCGGTA AAGGCACGCA ACATGGCTGT AAGGGTCTTT ATTACATTTG TCAGCAGACT   2700

GTCCATCAAA CCAAGCTAAA ACCTGAAAAA TCCTTTAACC AAGAAATCGG AGCGACTTTA   2760

CATAACCACT TAGGCAGTCT TGAGGTTAGT TATTTTAAAA ATCGCTATAC CGATTTGATT   2820

GTTGGTAAAA GTGAAGAGAT TAGAACCCTA ACCCAAGGTG ATAATGCAGG CAAACAGCGT   2880

GGTAAAGGTG ATTTGGGCTT TCATAATGGG CAAGATGCTG ATTTGACAGG CATTAACATT   2940

CTTGGCAGAC TTGACCTAAA CGCTGTCAAT AGTCGCCTTC CCTATGGATT ATACTCAACA   3000

CTGGCTTATA ACAAAGTTGA TGTTAAAGGA AAAACCTTAA ACCCAACTTT GGCAGGAACA   3060

AACATACTGT TTGATGCCAT TCAGCCATCT CGTTATGTGG TGGGGCTTGG CTATGATGCC   3120

CCAAGCCAAA AATGGGGAGC AAACGCCATA TTTACCCATT CTGATGCCAA AAATCCAAGC   3180

GAGCTTTTGG CAGATAAGAA CTTAGGTAAT GGCAACAATC AAACAAAACA AGCCACCAAA   3240

GCAAAATCCA CGCCGTGGCA AACACTTGAT TTGTCAGGTT ATGTAAACAT AAAAGATAAT   3300

TTTACCTTGC GTGCTGGCGT GTACAATGTA TTTAATACCT ATTACACCAC TTGGGAGGCT   3360

TTACGCCAAA CAGCAGAAGG GGCGGTCAAT CAGCATACAG GACTGAGCCA AGATAAGCAT   3420

TATGGTCGCT ATGCCGCTCC TGGACGCAAT TACCAATTGG CACTTGAAAT GAAGTTTTAA   3480

CCAGTGGCTT TGATGTGATC ATGCCAAATC CCAATCAACC AATGAATAAA GCCCCCATCT   3540

ACCATGAGGG CTTTATTTTA TCATCGCTGA GTATGCTCTT AGCGGTCATC ACTCAGATTA   3600

GTCATTAATT TATTAGCGAT TAATTTATTA GTAATCACGC TGCTCTTTGA TGATTTTAAG   3660
```

(2) INFORMATION FOR SEQ ID NO:6:

(i) SEQUENCE CHARACTERISTICS:
(A) LENGTH: 3210 base pairs
(B) TYPE: nucleic acid
(C) STRANDEDNESS: single
(D) TOPOLOGY: linear (xi) SEQUENCE DESCRIPTION: SEQ ID NO:6:

```
ATGAATCAAT CCAAAAAATC CAAAAAATCC AAACAAGTAT TAAAACTTAG TGCCTTGTCT     60

TTGGGTCTGC TTAACATCAC GCAGGTGGCA CTGGCAAACA CAACGGCCGA TAAGGCGGAG    120

GCAACAGATA AGACAAACCT TGTTGTTGTC TTGGATGAAA CTGTTGTAAC AGCGAAGAAA    180

AACGCCCGTA AAGCCAACGA AGTTACAGGG CTTGGTAAGG TGGTCAAAAC TGCCGAGACC    240

ATCAATAAAG AACAAGTGCT AAACATTCGA GACTTAACAC GCTATGACCC TGGCATTGCT    300
```

-continued

```
GTGGTTGAGC AAGGTCGTGG GGCAAGCTCA GGCTATTCTA TTCGTGGTAT GGATAAAAAT    360
CGTGTGGCGG TATTGGTTGA TGGCATCAAT CAAGCCCAGC ACTATGCCCT ACAAGGCCCT    420
GTGGCAGGCA AAAATTATGC CGCAGGTGGG GCAATCAACG AAATAGAATA CGAAAATGTC    480
CGCTCCGTTG AGATTAGTAA AGGTGCAAAT TCAAGTGAAT ACGGCTCTGG GGCATTATCT    540
GGCTCTGTGG CATTTGTTAC CAAAACCGCC GATGACATCA TCAAAGATGG TAAAGATTGG    600
GGCGTGCAGA CCAAAACCGC CTATGCCAGT AAAAATAACG CATGGGTTAA TTCTGTGGCA    660
GCAGCAGGCA AGGCAGGTTC TTTTAGCGGT CTTATCATCT ACACCGACCG CCGTGGTCAA    720
GAATACAAGG CACATGATGA TGCCTATCAG GGTAGCCAAA GTTTTGATAG AGCGGTGGCA    780
ACCACTGACC CAAATAACCC AAAATTTTTA ATAGCAAATG AATGTGCCAA TGGTAATTAT    840
GAGGCGTGTG CTGCTGGCGG TCAAACCAAA CTCCAAGCTA AGCCAACCAA TGTGCGTGAT    900
AAGGTCAATG TCAAAGATTA TACAGGTCCT AACCGCCTTA TCCCAAACCC ACTCACCCAA    960
GACAGCAAAT CCTTACTGCT TCGCCCAGGT TATCAGCTAA ACGATAAGCA CTATGTCGGT   1020
GGTGTGTATG AAATCACCAA ACAAAACTAC GCCATGCAAG ATAAAACCGT GCCTGCTTAT   1080
CTGACGGTTC ATGACATTGA AAAATCAAGG CTCAGCAACC ATGGCCAAGC CAATGGCTAT   1140
TATCAAGGCA ATAACCTTGG TGAACGCATT CGTGATGCCA TTGGGGCAAA TTCAGGTTAT   1200
GGCATCAACT ATGCTCATGG CGTATTTTAT GACGAAAAAC ACCAAAAAGA CCGCCTAGGG   1260
CTTGAATATG TTTATGACAG CAAAGGTGAA AATAAATGGT TTGATGATGT GCGTGTGTCT   1320
TATGACAAGC AAGACATTAC GCTACGTAGC CAGCTGACCA ACACGCACTG TTCAACCTAT   1380
CCGCACATTG ACAAAAATTG TACGCCTGAT GTCAATAAAC CTTTTTCGGT AAAAGAGGTG   1440
GATAACAATG CCTACAAAGA ACAGCACAAT TTAATCAAAG CCGTCTTTAA CAAAAAAATG   1500
GCATTGGGCA ATACGCATCA TCACATCAAT CTGCAAGTTG GCTATGATAA ATTCAATTCA   1560
AGCCTTAGCC GTGAAGATTA TCGTTTGGCA ACCCATCAAT CTTATCAAAA ACTTGATTAC   1620
ACCCCACCAA GTAACCCTTT GCCAGATAAG TTTAAGCCCA TTTTAGGTTC AAACAACAGA   1680
CCCATTTGCC TTGATGCTTA TGGTTATGGT CATGACCATC CACAGGCTTG TAACGCCAAA   1740
AACAGCACTT ATCAAAACTT TGCCATCAAA AAAGGCATAG AGCAATACAA CCAAACCAAT   1800
ACCGATAAGA TTGATTATCA AGCCGTCATT GACCAATATG ATAAACAAAA CCCCAACAGC   1860
ACCCTAAAAC CCTTTGAGAA AATCAAACAA AGTTTGGGGC AAGAAAAATA CGACGAGATA   1920
GACAGACTGG GCTTTAATGC TTATAAAGAT TTACGCAACG AATGGGCGGG TTGGACTAAT   1980
GACAACAGCC AACAAAACGC CAATAAAGGC ACGGATAATA TCTATCAGCC AAATCAAGCA   2040
ACTGTGGTCA AAGATGACAA ATGTAAATAT AGCGAGACCA ACAGCTATGC TGATTGCTCA   2100
ACCACTCGCC ACATCAGCGG TGATAATTAT TTCATCGCTT TAAAAGACAA CATGACCATC   2160
AATAAATATG TTGATTTGGG GCTGGGTGCT CGCTATGACA GAATCAAACA CAAATCTGAT   2220
GTGCCTTTGG TAGACAACAG TGCCAGCAAC CAGCTGTCTT GGAATTTTGG CGTGGTCGTC   2280
AAGCCCACCA ATTGGCTGGA CATCGCTTAT AGAAGCTCGC AAGGCTTTCG CATGCCAAGT   2340
TTTTCTGAAA TGTATGGCGA ACGCTTTGGC GTAACCATCG GTAAAGGCAC GCAACATGGC   2400
TGTAAGGGTC TTTATTACAT TTGTCAGCAG ACTGTCCATC AAACCAAGCT AAAACCTGAA   2460
AAATCCTTTA ACCAAGAAAT CGGAGCGACT TTACATAACC ACTTAGGCAG TCTTGAGGTT   2520
AGTTATTTTA AAAATCGCTA TACCGATTTG ATTGTTGGTA AAAGTGAAGA GATTAGAACC   2580
CTAACCCAAG GTGATAATGC AGGCAAACAG CGTGGTAAAG GTGATTTGGG CTTTCATAAT   2640
```

-continued

```
GGGCAAGATG CTGATTTGAC AGGCATTAAC ATTCTTGGCA GACTTGACCT AAACGCTGTC   2700

AATAGTCGCC TTCCCTATGG ATTATACTCA ACACTGGCTT ATAACAAAGT TGATGTTAAA   2760

GGAAAAACCT TAAACCCAAC TTTGGCAGGA ACAAACATAC TGTTTGATGC CATTCAGCCA   2820

TCTCGTTATG TGGTGGGGCT TGGCTATGAT GCCCCAAGCC AAAAATGGGG AGCAAACGCC   2880

ATATTTACCC ATTCTGATGC CAAAAATCCA AGCGAGCTTT TGGCAGATAA GAACTTAGGT   2940

AATGGCAACA ATCAAACAAA ACAAGCCACC AAAGCAAAAT CCACGCCGTG GCAAACACTT   3000

GATTTGTCAG GTTATGTAAA CATAAAAGAT AATTTTACCT TGCGTGCTGG CGTGTACAAT   3060

GTATTTAATA CCTATTACAC CACTTGGGAG GCTTTACGCC AAACAGCAGA AGGGGCGGTC   3120

AATCAGCATA CAGGACTGAG CCAAGATAAG CATTATGGTC GCTATGCCGC TCCTGGACGC   3180

AATTACCAAT TGGCACTTGA AATGAAGTTT                                    3210
```

(2) INFORMATION FOR SEQ ID NO:7:

(i) SEQUENCE CHARACTERISTICS:
(A) LENGTH: 3435 base pairs
(B) TYPE: nucleic acid
(C) STRANDEDNESS: single
(D) TOPOLOGY: linear (xi) SEQUENCE DESCRIPTION: SEQ ID NO:7:

```
CCTAGGGCTG ACAGTAACAA CACTTTATAC AGCACATCAT TGATTTATTA CCCAAATGCC     60

ACACGCTATT ATCTTTTGGG GGCAGACTTT TATGATGAAA AAGTGCCACA AGACCCATCT    120

GACAGCTATG AGCGTCGTGG CATACGCACA GCTTGGGGGC AAGAATGGGC GGGCGGTCTT    180

TCAAGCCGTG CCCAAATCAG CATCAACAAA CGCCATTACC AAGGAGCAAA CCTAACCAGC    240

GGTGGACAAA TTCGCCAGGA TAAACAGATG CAAGCGTCTT TATCGCTTTG GCACAGAGAC    300

ATTCACAAAT GGGGCATCAC GCCACGGCTG ACCATCAGCA CAAACATCAA TAAAAGCAAT    360

GACATCAAGG CAAATTATCA CAAAAATCAA ATGTTTGTTG AGTTTAGTCG CATTTTTTGA    420

TGGGATAAGC ATGCCCTACT TTTGTTTTTT GTAAAAAAAT GTACCATCAT AGACAATATC    480

AAGAAAAAAT CAAGAAAAAA GATTACAAAT TTAATGATAA TTGTTATTGT TTATGTTATT    540

ATTTATCAAT GTAAATTTGC CGTATTTTGT CCATCATAAA CGCATTTATC AAATGCTCAA    600

ATAAATACGC CAAATGCACA TTGTCAACAT GCCAAAATAG GCATTAACAG ACTTTTTTAG    660

ATAATACCAT CAACCCATCA GAGGATTATT TTATGAAACA CATTCCTTTA ACCACACTGT    720

GTGTGGCAAT CTCTGCCGTC TTATTAACCG CTTGTGGTGG TAGCAGTGGT GGTTTCAATC    780

CACCTGCCTC TACGCCCATC CCAAATGCAG GTAATTCAGG TAATGCTGGC AATGCTGGCA    840

ATGCTGGCGG TACTGGCGGT GCAAACTCTG GTGCAGGTAA TGCTGGCGGT ACTGGCGGTG    900

CAAACTCTGG TGCAGGCAGT GCCAGCACAC CAGAACCAAA ATATAAAGAT GTGCCAACCG    960

ATGAAAATAA AAAAGCTGAA GTTTCAGGCA TTCAAGAACC TGCCATGGGT TATGGCGTGG   1020

AATTAAAGCT TCGTAACTGG ATACCACAAG AACAGGAAGA ACATGCCAAA ATCAATACAA   1080

ATGATGTTGT AAAACTTGAA GGTGACTTGA AGCATAATCC ATTTGACAAC TCTATTTGGC   1140

AAAACATCAA AAATAGCAAA GAAGTACAAA CTGTTTACAA CCAAGAGAAG CAAAACATTG   1200

AAGATCAAAT CAAAAGAGAA AATAAACAAC GCCCTGACAA AAAACTTGAT GACGTGGCAC   1260

TACAAGCTTA TATTGAAAAA GTTCTTGATG ACCGTCTAAC AGAACTTGCT AAACCCATTT   1320

ATGAAAAAAA TATTAATTAT TCACATGATA AGCAGAATAA AGCACGCACT CGTGATTTGA   1380

AGTATGTGCG TTCTGGTTAT ATTTATCGCT CAGGTTATTC TAATATCATT CCAAAGAAAA   1440
```

-continued

```
TAGCTAAAAC TGGTTTTGAT GGTGCTTTAT TTTATCAAGG TACACAAACT GCTAAACAAT   1500

TGCCTGTATC TCAAGTTAAG TATAAAGGCA CTTGGGATTT TATGACCGAT GCCAAAAAAG   1560

GACAATCATT TAGCAGTTTT GGTACATCGC AACGTCTTGC TGGTGATCGT TATAGTGCAA   1620

TGTCTTACCA TGAATACCCA TCTTTATTAA CTGATGAGAA AAACAAACCA GATAATTATA   1680

ACGGTGAATA TGGTCATAGC AGTGAGTTTA CGGTAGATTT TAGTAAAAAG AGCCTAAAAG   1740

GTGAGCTGTC TAGTAACATA CAAGACGGCC ATAAGGGCAG TGTTAATAAA ACCAAACGCT   1800

ATGACATCGA TGCCAATATC TACGGCAACC GCTTCCGTGG CAGTGCCACC GCAAGCGATA   1860

CAACAGAAGC AAGCAAAAGC AAACACCCCT TTACCAGCGA TGCCAAAAAT AGCCTAGAAG   1920

GCGGTTTTTA TGGACCAAAC GCCGAGGAGC TGGCAGGTAA ATTCCTAACC AATGACAACA   1980

AACTCTTTGG CGTCTTTGGT GCTAAACGAG AGAGTGAAGC TAAGGAAAAA ACCGAAGCCA   2040

TCTTAGATGC CTATGCACTT GGGACATTTA ATAAACCTGG TACGACCAAT CCCGCCTTTA   2100

CCGCTAACAG CAAAAAAGAA CTGGATAACT TTGGCAATGC CAAAAAGTTG GTCTTGGGTT   2160

CTACCGTCAT TGATTTGGTG CCTACCGGTG CCACCAAAGA TGTCAATGAA TTCAAAGAAA   2220

AGCCAAAGTC TGCCACAAAC AAAGCGGGCG AGACTTTGAT GGTGAATGAT GAAGTTATCG   2280

TCAAAACCTA TGGCTATGGC AGAAACTTTG AATACCTAAA ATTTGGTGAG CTTAGTATCG   2340

GTGGTAGCCA TAGCGTCTTT TTACAAGGCG AACGCACCGC TGAGAAAGCC GTACCAACCG   2400

AAGGCACAGC CAAATATCTG GGGAACTGGG TAGGATACAT CACAGGAAAG GACACAGGAA   2460

CGAGCACAGG AAAAAGCTTT AATGAGGCCC AAGATATTGC TGATTTTGAC ATTGACTTTG   2520

AGAGAAAATC AGTTAAAGGC AAACTGACCA CCCAAGGCCG CCAAGACCCT GTATTTAACA   2580

TCACAGGTCA AATCGCAGGT AATGGCTGGA CAGGCACAGC CAGCACCGCC AAAGCGAACG   2640

TAGGGGGCTA CAAGATAGAT TCTAGCAGTA CAGGCAAATC CATCGTCATC GAAAATGCCA   2700

AGGTTACAGG TGGCTTTTAT GGTCCAAATG CAAACGAGAT GGGCGGGTCA TTTACACACG   2760

ATACCGATGA CAGTAAAGCC TCTGTGGTCT TTGGCACAAA AAGACAAGAA GAAGTTAAGT   2820

AGTAATTTAA ACACAATGCT TGGTTCGGCT GATGGGATTG ACGCTTAATC AAACATGAAT   2880

GATTAAGATG ATAAACCCAA GCCATGCCAA TGATTGATAG CAACGATGGC AGATGATGAG   2940

TTTTCATTAT CTGCCATTAT TATTGCTTAA TTATTGCTTG TCATTTGGTG GTGTTATCAC   3000

ATTAATCATT AAAATTAACA TAATAAATGA TTAAATGATA TTTAATGAAA GTCAGGGTTA   3060

TTTTGGTCAT GGTTTTTCAT GATTATTTAA CTTATAATGC GTTATGGTTA GCAAAAAGCT   3120

AAGTCTGTCA ATGAAGCTAT GGTGAGTGAT TGTGCAAAAG ATGGTCAAAA AAATCGGTAT   3180

GGTGCTGTCA GGCGTGGTGA TGGTTCTGTT AATGATAATA ACAACGCCAA GCCATGCTAC   3240

TGCCAAGTTG TTGCCGACCT CTCAAGAAAA TCCAACCAAA ACTATGGTAG ATAGCTTTGG   3300

TCGTGAAACG CCACGAGGGG CAGTTCAGGG GCTATTGCGT GCAATTGCAG CAGAAGACTA   3360

TGAGCTGGCT GCCAACTATT TGGACGGCCG TTATTTGGCA AAAACCCAAA CGCCCAATCG   3420

TGAGATTGTT GAGCA                                                    3435
```

(2) INFORMATION FOR SEQ ID NO:8:

(i) SEQUENCE CHARACTERISTICS:
(A) LENGTH: 2127 base pairs
(B) TYPE: nucleic acid
(C) STRANDEDNESS: single
(D) TOPOLOGY: linear (xi) SEQUENCE DESCRIPTION: SEQ ID NO:8:

-continued

```
ATGAAACACA TTCCTTTAAC CACACTGTGT GTGGCAATCT CTGCCGTCTT ATTAACCGCT     60
TGTGGTGGTA GCAGTGGTGG TTTCAATCCA CCTGCCTCTA CGCCCATCCC AAATGCAGGT    120
AATTCAGGTA ATGCTGGCAA TGCTGGCAAT GCTGGCGGTA CTGGCGGTGC AAACTCTGGT    180
GCAGGTAATG CTGGCGGTAC TGGCGGTGCA AACTCTGGTG CAGGCAGTGC CAGCACACCA    240
GAACCAAAAT ATAAAGATGT GCCAACCGAT GAAAATAAAA AAGCTGAAGT TTCAGGCATT    300
CAAGAACCTG CCATGGGTTA TGGCGTGGAA TTAAAGCTTC GTAACTGGAT ACCACAAGAA    360
CAGGAAGAAC ATGCCAAAAT CAATACAAAT GATGTTGTAA AACTTGAAGG TGACTTGAAG    420
CATAATCCAT TTGACAACTC TATTTGGCAA AACATCAAAA ATAGCAAAGA AGTACAAACT    480
GTTTACAACC AAGAGAAGCA AAACATTGAA GATCAAATCA AAAGAGAAAA TAAACAACGC    540
CCTGACAAAA AACTTGATGA CGTGGCACTA CAAGCTTATA TTGAAAAAGT TCTTGATGAC    600
CGTCTAACAG AACTTGCTAA ACCCATTTAT GAAAAAAATA TTAATTATTC ACATGATAAG    660
CAGAATAAAG CACGCACTCG TGATTTGAAG TATGTGCGTT CTGGTTATAT TTATCGCTCA    720
GGTTATTCTA ATATCATTCC AAAGAAAATA GCTAAAACTG GTTTTGATGG TGCTTTATTT    780
TATCAAGGTA CACAAACTGC TAAACAATTG CCTGTATCTC AAGTTAAGTA TAAAGGCACT    840
TGGGATTTTA TGACCGATGC CAAAAAAGGA CAATCATTTA GCAGTTTTGG TACATCGCAA    900
CGTCTTGCTG GTGATCGTTA TAGTGCAATG TCTTACCATG AATACCCATC TTTATTAACT    960
GATGAGAAAA ACAAACCAGA TAATTATAAC GGTGAATATG GTCATAGCAG TGAGTTTACG   1020
GTAGATTTTA GTAAAAAGAG CCTAAAAGGT GAGCTGTCTA GTAACATACA AGACGGCCAT   1080
AAGGGCAGTG TTAATAAAAC CAAACGCTAT GACATCGATG CCAATATCTA CGGCAACCGC   1140
TTCCGTGGCA GTGCCACCGC AAGCGATACA ACAGAAGCAA GCAAAAGCAA ACACCCCTTT   1200
ACCAGCGATG CCAAAAATAG CCTAGAAGGC GGTTTTTATG GACCAAACGC CGAGGAGCTG   1260
GCAGGTAAAT TCCTAACCAA TGACAACAAA CTCTTTGGCG TCTTTGGTGC TAAACGAGAG   1320
AGTGAAGCTA AGGAAAAAAC CGAAGCCATC TTAGATGCCT ATGCACTTGG GACATTTAAT   1380
AAACCTGGTA CGACCAATCC CGCCTTTACC GCTAACAGCA AAAAAGAACT GGATAACTTT   1440
GGCAATGCCA AAAAGTTGGT CTTGGGTTCT ACCGTCATTG ATTTGGTGCC TACCGGTGCC   1500
ACCAAAGATG TCAATGAATT CAAAGAAAAG CCAAAGTCTG CCACAAACAA AGCGGGCGAG   1560
ACTTTGATGG TGAATGATGA AGTTATCGTC AAAACCTATG GCTATGGCAG AAACTTTGAA   1620
TACCTAAAAT TTGGTGAGCT TAGTATCGGT GGTAGCCATA GCGTCTTTTT ACAAGGCGAA   1680
CGCACCGCTG AGAAAGCCGT ACCAACCGAA GGCACAGCCA AATATCTGGG GAACTGGGTA   1740
GGATACATCA CAGGAAAGGA CACAGGAACG AGCACAGGAA AAGCTTTAA TGAGGCCCAA   1800
GATATTGCTG ATTTTGACAT TGACTTTGAG AGAAAATCAG TTAAAGGCAA ACTGACCACC   1860
CAAGGCCGCC AAGACCCTGT ATTTAACATC ACAGGTCAAA TCGCAGGTAA TGGCTGGACA   1920
GGCACAGCCA GCACCGCCAA AGCGAACGTA GGGGGCTACA AGATAGATTC TAGCAGTACA   1980
GGCAAATCCA TCGTCATCGA AAATGCCAAG GTTACAGGTG GCTTTTATGG TCCAAATGCA   2040
AACGAGATGG GCGGGTCATT TACACACGAT ACCGATGACA GTAAAGCCTC TGTGGTCTTT   2100
GGCACAAAAA GACAAGAAGA AGTTAAG                                       2127
```

(2) INFORMATION FOR SEQ ID NO:9:

(i) SEQUENCE CHARACTERISTICS:
(A) LENGTH: 1074 amino acids
(B) TYPE: amino acid
(C) STRANDEDNESS: single -continued (D) TOPOLOGY: linear (xi) SEQUENCE DESCRIPTION: SEQ ID NO:9:

```
Met Asn Gln Ser Lys Gln Asn Asn Lys Ser Lys Lys Ser Lys Gln Val
1               5                   10                  15

Leu Lys Leu Ser Ala Leu Ser Leu Gly Leu Leu Asn Ile Thr Gln Val
            20                  25                  30

Ala Leu Ala Asn Thr Thr Ala Asp Lys Ala Glu Ala Thr Asp Lys Thr
        35                  40                  45

Asn Leu Val Val Val Leu Asp Glu Thr Val Val Thr Ala Lys Lys Asn
    50                  55                  60

Ala Arg Lys Ala Asn Glu Val Thr Gly Leu Gly Lys Val Val Lys Thr
65                  70                  75                  80

Ala Glu Thr Ile Asn Lys Glu Gln Val Leu Asn Ile Arg Asp Leu Thr
                85                  90                  95

Arg Tyr Asp Pro Gly Ile Ala Val Val Glu Gln Gly Arg Gly Ala Ser
            100                 105                 110

Ser Gly Tyr Ser Ile Arg Gly Met Asp Lys Asn Arg Val Ala Val Leu
        115                 120                 125

Val Asp Gly Ile Asn Gln Ala Gln His Tyr Ala Leu Gln Gly Pro Val
    130                 135                 140

Ala Gly Lys Asn Tyr Ala Ala Gly Gly Ala Ile Asn Glu Ile Glu Tyr
145                 150                 155                 160

Glu Asn Val Arg Ser Val Glu Ile Ser Lys Gly Ala Asn Ser Ser Glu
                165                 170                 175

Tyr Gly Ser Gly Ala Leu Ser Gly Ser Val Ala Phe Val Thr Lys Thr
            180                 185                 190

Ala Asp Asp Ile Ile Lys Asp Gly Lys Asp Trp Gly Val Gln Thr Lys
        195                 200                 205

Thr Ala Tyr Ala Ser Lys Asn Asn Ala Trp Val Asn Ser Val Ala Ala
    210                 215                 220

Ala Gly Lys Ala Gly Ser Phe Ser Gly Leu Ile Ile Tyr Thr Asp Arg
225                 230                 235                 240

Arg Gly Gln Glu Tyr Lys Ala His Asp Asp Ala Tyr Gln Gly Ser Gln
                245                 250                 255

Ser Phe Asp Arg Ala Val Ala Thr Thr Asp Pro Asn Asn Arg Thr Phe
            260                 265                 270

Leu Ile Ala Asn Glu Cys Ala Asn Gly Asn Tyr Glu Ala Cys Ala Ala
        275                 280                 285

Gly Gly Gln Thr Lys Leu Gln Ala Lys Pro Thr Asn Val Arg Asp Lys
    290                 295                 300

Val Asn Val Lys Asp Tyr Thr Gly Pro Asn Arg Leu Ile Pro Asn Pro
305                 310                 315                 320

Leu Thr Gln Asp Ser Lys Ser Leu Leu Leu Arg Pro Gly Tyr Gln Leu
                325                 330                 335

Asn Asp Lys His Tyr Val Gly Gly Val Tyr Glu Ile Thr Lys Gln Asn
            340                 345                 350

Tyr Ala Met Gln Asp Lys Thr Val Pro Ala Tyr Leu Thr Val His Asp
        355                 360                 365

Ile Glu Lys Ser Arg Leu Ser Asn His Ala Gln Ala Asn Gly Tyr Tyr
    370                 375                 380

Gln Gly Asn Asn Leu Gly Glu Arg Ile Arg Asp Thr Ile Gly Pro Asp
385                 390                 395                 400
```

-continued

```
Ser Gly Tyr Gly Ile Asn Tyr Ala His Gly Val Phe Tyr Asp Glu Lys
                405                 410                 415

His Gln Lys Asp Arg Leu Gly Leu Glu Tyr Val Tyr Asp Ser Lys Gly
            420                 425                 430

Glu Asn Lys Trp Phe Asp Asp Val Arg Val Ser Tyr Asp Lys Gln Asp
        435                 440                 445

Ile Thr Leu Arg Ser Gln Leu Thr Asn Thr His Cys Ser Thr Tyr Pro
    450                 455                 460

His Ile Asp Lys Asn Cys Thr Pro Asp Val Asn Lys Pro Phe Ser Val
465                 470                 475                 480

Lys Glu Val Asp Asn Asn Ala Tyr Lys Glu Gln His Asn Leu Ile Lys
                485                 490                 495

Ala Val Phe Asn Lys Lys Met Ala Leu Gly Ser Thr His His His Ile
            500                 505                 510

Asn Leu Gln Val Gly Tyr Asp Lys Phe Asn Ser Ser Leu Ser Arg Glu
        515                 520                 525

Asp Tyr Arg Leu Ala Thr His Gln Ser Tyr Glu Lys Leu Asp Tyr Thr
    530                 535                 540

Pro Pro Ser Asn Pro Leu Pro Asp Lys Phe Lys Pro Ile Leu Gly Ser
545                 550                 555                 560

Asn Asn Lys Pro Ile Cys Leu Asp Ala Tyr Gly Tyr Gly His Asp His
                565                 570                 575

Pro Gln Ala Cys Asn Ala Lys Asn Ser Thr Tyr Gln Asn Phe Ala Ile
            580                 585                 590

Lys Lys Gly Ile Glu Gln Tyr Asn Gln Lys Thr Asn Thr Asp Lys Ile
        595                 600                 605

Asp Tyr Gln Ala Ile Ile Asp Gln Tyr Asp Lys Gln Asn Pro Asn Ser
    610                 615                 620

Thr Leu Lys Pro Phe Glu Lys Ile Lys Gln Ser Leu Gly Gln Glu Lys
625                 630                 635                 640

Tyr Asn Lys Ile Asp Glu Leu Gly Phe Lys Ala Tyr Lys Asp Leu Arg
                645                 650                 655

Asn Glu Trp Ala Gly Trp Thr Asn Asp Asn Ser Gln Gln Asn Ala Asn
            660                 665                 670

Lys Gly Thr Asp Asn Ile Tyr Gln Pro Asn Gln Ala Thr Val Val Lys
        675                 680                 685

Asp Asp Lys Cys Lys Tyr Ser Glu Thr Asn Ser Tyr Ala Asp Cys Ser
    690                 695                 700

Thr Thr Ala His Ile Ser Gly Asp Asn Tyr Phe Ile Ala Leu Lys Asp
705                 710                 715                 720

Asn Met Thr Ile Asn Lys Tyr Val Asp Leu Gly Leu Gly Ala Arg Tyr
                725                 730                 735

Asp Arg Ile Lys His Lys Ser Asp Val Pro Leu Val Asp Asn Ser Ala
            740                 745                 750

Ser Asn Gln Leu Ser Trp Asn Phe Gly Val Val Val Lys Pro Thr Asn
        755                 760                 765

Trp Leu Asp Ile Ala Tyr Arg Ser Ser Gln Gly Phe Arg Met Pro Ser
    770                 775                 780

Phe Ser Glu Met Tyr Gly Glu Arg Phe Gly Val Thr Ile Gly Lys Gly
785                 790                 795                 800

Thr Gln His Gly Cys Lys Gly Leu Tyr Tyr Ile Cys Gln Gln Thr Val
                805                 810                 815

His Gln Thr Lys Leu Lys Pro Glu Lys Ser Phe Asn Gln Glu Ile Gly
```

-continued

```
            820                 825                 830

Ala Thr Leu His Asn His Leu Gly Ser Leu Glu Val Ser Tyr Phe Lys
        835                 840                 845

Asn Arg Tyr Thr Asp Leu Ile Val Gly Lys Ser Glu Glu Ile Arg Thr
    850                 855                 860

Leu Thr Gln Gly Asp Asn Ala Gly Lys Gln Arg Gly Lys Gly Asp Leu
865                 870                 875                 880

Gly Phe His Asn Gly Gln Asp Ala Asp Leu Thr Gly Ile Asn Ile Leu
                885                 890                 895

Gly Arg Leu Asp Leu Asn Ala Val Asn Ser Arg Leu Pro Tyr Gly Leu
            900                 905                 910

Tyr Ser Thr Leu Ala Tyr Asn Lys Val Asp Val Lys Gly Lys Thr Leu
        915                 920                 925

Asn Pro Thr Leu Ala Gly Thr Asn Ile Leu Phe Asp Ala Ile Gln Pro
    930                 935                 940

Ser Arg Tyr Val Val Gly Leu Gly Tyr Asp Ala Pro Ser Gln Lys Trp
945                 950                 955                 960

Gly Ala Asn Ala Ile Phe Thr His Ser Asp Ala Lys Asn Pro Ser Glu
                965                 970                 975

Leu Leu Ala Asp Lys Asn Leu Gly Asn Gly Asn Ile Gln Thr Lys Gln
            980                 985                 990

Ala Thr Lys Ala Lys Ser Thr Pro Trp Gln Thr Leu Asp Leu Ser Gly
        995                 1000                1005

Tyr Val Asn Ile Lys Asp Asn Phe Thr Leu Arg Ala Gly Val Tyr Asn
    1010                1015                1020

Val Phe Asn Thr Tyr Tyr Thr Thr Trp Glu Ala Leu Arg Gln Thr Ala
1025                1030                1035                1040

Glu Gly Ala Val Asn Gln His Thr Gly Leu Ser Gln Asp Lys His Tyr
                1045                1050                1055

Gly Arg Tyr Ala Ala Pro Gly Arg Asn Tyr Gln Leu Ala Leu Glu Met
            1060                1065                1070

Lys Phe
```

(2) INFORMATION FOR SEQ ID NO:10:

(i) SEQUENCE CHARACTERISTICS:
(A) LENGTH: 1053 amino acids
(B) TYPE: amino acid
(C) STRANDEDNESS: single
(D) TOPOLOGY: linear (xi) SEQUENCE DESCRIPTION: SEQ ID NO:10:

```
Leu Ser Leu Gly Leu Leu Asn Ile Thr Gln Val Ala Leu Ala Asn Thr
1               5                   10                  15

Thr Ala Asp Lys Ala Glu Ala Thr Asp Lys Thr Asn Leu Val Val Val
            20                  25                  30

Leu Asp Glu Thr Val Val Thr Ala Lys Lys Asn Ala Arg Lys Ala Asn
        35                  40                  45

Glu Val Thr Gly Leu Gly Lys Val Val Lys Thr Ala Glu Thr Ile Asn
    50                  55                  60

Lys Glu Gln Val Leu Asn Ile Arg Asp Leu Thr Arg Tyr Asp Pro Gly
65                  70                  75                  80

Ile Ala Val Val Glu Gln Gly Arg Gly Ala Ser Ser Gly Tyr Ser Ile
                85                  90                  95

Arg Gly Met Asp Lys Asn Arg Val Ala Val Leu Val Asp Gly Ile Asn
```

-continued

```
            100                 105                 110

Gln Ala Gln His Tyr Ala Leu Gln Gly Pro Val Ala Gly Lys Asn Tyr
        115                 120                 125

Ala Ala Gly Gly Ala Ile Asn Glu Ile Glu Tyr Glu Asn Val Arg Ser
    130                 135                 140

Val Glu Ile Ser Lys Gly Ala Asn Ser Ser Glu Tyr Gly Ser Gly Ala
145                 150                 155                 160

Leu Ser Gly Ser Val Ala Phe Val Thr Lys Thr Ala Asp Asp Ile Ile
                165                 170                 175

Lys Asp Gly Lys Asp Trp Gly Val Gln Thr Lys Thr Ala Tyr Ala Ser
            180                 185                 190

Lys Asn Asn Ala Trp Val Asn Ser Val Ala Ala Ala Gly Lys Ala Gly
        195                 200                 205

Ser Phe Ser Gly Leu Ile Ile Tyr Thr Asp Arg Arg Gly Gln Glu Tyr
    210                 215                 220

Lys Ala His Asp Asp Ala Tyr Gln Gly Ser Gln Ser Phe Asp Arg Ala
225                 230                 235                 240

Val Ala Thr Thr Asp Pro Asn Asn Arg Thr Phe Leu Ile Ala Asn Glu
                245                 250                 255

Cys Ala Asn Gly Asn Tyr Glu Ala Cys Ala Ala Gly Gly Gln Thr Lys
            260                 265                 270

Leu Gln Ala Lys Pro Thr Asn Val Arg Asp Lys Val Asn Val Lys Asp
        275                 280                 285

Tyr Thr Gly Pro Asn Arg Leu Ile Pro Asn Pro Leu Thr Gln Asp Ser
    290                 295                 300

Lys Ser Leu Leu Leu Arg Pro Gly Tyr Gln Leu Asn Asp Lys His Tyr
305                 310                 315                 320

Val Gly Gly Val Tyr Glu Ile Thr Lys Gln Asn Tyr Ala Met Gln Asp
                325                 330                 335

Lys Thr Val Pro Ala Tyr Leu Thr Val His Asp Ile Glu Lys Ser Arg
            340                 345                 350

Leu Ser Asn His Ala Gln Ala Asn Gly Tyr Tyr Gln Gly Asn Asn Leu
        355                 360                 365

Gly Glu Arg Ile Arg Asp Thr Ile Gly Pro Asp Ser Gly Tyr Gly Ile
    370                 375                 380

Asn Tyr Ala His Gly Val Phe Tyr Asp Glu Lys His Gln Lys Asp Arg
385                 390                 395                 400

Leu Gly Leu Glu Tyr Val Tyr Asp Ser Lys Gly Glu Asn Lys Trp Phe
                405                 410                 415

Asp Asp Val Arg Val Ser Tyr Asp Lys Gln Asp Ile Thr Leu Arg Ser
            420                 425                 430

Gln Leu Thr Asn Thr His Cys Ser Thr Tyr Pro His Ile Asp Lys Asn
        435                 440                 445

Cys Thr Pro Asp Val Asn Lys Pro Phe Ser Val Lys Glu Val Asp Asn
    450                 455                 460

Asn Ala Tyr Lys Glu Gln His Asn Leu Ile Lys Ala Val Phe Asn Lys
465                 470                 475                 480

Lys Met Ala Leu Gly Ser Thr His His His Ile Asn Leu Gln Val Gly
                485                 490                 495

Tyr Asp Lys Phe Asn Ser Ser Leu Ser Arg Glu Asp Tyr Arg Leu Ala
            500                 505                 510

Thr His Gln Ser Tyr Glu Lys Leu Asp Tyr Thr Pro Pro Ser Asn Pro
        515                 520                 525
```

-continued

```
Leu Pro Asp Lys Phe Lys Pro Ile Leu Gly Ser Asn Asn Lys Pro Ile
    530                 535                 540

Cys Leu Asp Ala Tyr Gly Tyr Gly His Asp His Pro Gln Ala Cys Asn
545                 550                 555                 560

Ala Lys Asn Ser Thr Tyr Gln Asn Phe Ala Ile Lys Lys Gly Ile Glu
                565                 570                 575

Gln Tyr Asn Gln Lys Thr Asn Thr Asp Lys Ile Asp Tyr Gln Ala Ile
            580                 585                 590

Ile Asp Gln Tyr Asp Lys Gln Asn Pro Asn Ser Thr Leu Lys Pro Phe
        595                 600                 605

Glu Lys Ile Lys Gln Ser Leu Gly Gln Glu Lys Tyr Asn Lys Ile Asp
    610                 615                 620

Glu Leu Gly Phe Lys Ala Tyr Lys Asp Leu Arg Asn Glu Trp Ala Gly
625                 630                 635                 640

Trp Thr Asn Asp Asn Ser Gln Gln Asn Ala Asn Lys Gly Thr Asp Asn
                645                 650                 655

Ile Tyr Gln Pro Asn Gln Ala Thr Val Val Lys Asp Asp Lys Cys Lys
            660                 665                 670

Tyr Ser Glu Thr Asn Ser Tyr Ala Asp Cys Ser Thr Thr Ala His Ile
        675                 680                 685

Ser Gly Asp Asn Tyr Phe Ile Ala Leu Lys Asp Asn Met Thr Ile Asn
    690                 695                 700

Lys Tyr Val Asp Leu Gly Leu Gly Ala Arg Tyr Asp Arg Ile Lys His
705                 710                 715                 720

Lys Ser Asp Val Pro Leu Val Asp Asn Ser Ala Ser Asn Gln Leu Ser
                725                 730                 735

Trp Asn Phe Gly Val Val Val Lys Pro Thr Asn Trp Leu Asp Ile Ala
            740                 745                 750

Tyr Arg Ser Ser Gln Gly Phe Arg Met Pro Ser Phe Ser Glu Met Tyr
        755                 760                 765

Gly Glu Arg Phe Gly Val Thr Ile Gly Lys Gly Thr Gln His Gly Cys
    770                 775                 780

Lys Gly Leu Tyr Tyr Ile Cys Gln Gln Thr Val His Gln Thr Lys Leu
785                 790                 795                 800

Lys Pro Glu Lys Ser Phe Asn Gln Glu Ile Gly Ala Thr Leu His Asn
                805                 810                 815

His Leu Gly Ser Leu Glu Val Ser Tyr Phe Lys Asn Arg Tyr Thr Asp
            820                 825                 830

Leu Ile Val Gly Lys Ser Glu Glu Ile Arg Thr Leu Thr Gln Gly Asp
        835                 840                 845

Asn Ala Gly Lys Gln Arg Gly Lys Gly Asp Leu Gly Phe His Asn Gly
    850                 855                 860

Gln Asp Ala Asp Leu Thr Gly Ile Asn Ile Leu Gly Arg Leu Asp Leu
865                 870                 875                 880

Asn Ala Val Asn Ser Arg Leu Pro Tyr Gly Leu Tyr Ser Thr Leu Ala
                885                 890                 895

Tyr Asn Lys Val Asp Val Lys Gly Lys Thr Leu Asn Pro Thr Leu Ala
            900                 905                 910

Gly Thr Asn Ile Leu Phe Asp Ala Ile Gln Pro Ser Arg Tyr Val Val
        915                 920                 925

Gly Leu Gly Tyr Asp Ala Pro Ser Gln Lys Trp Gly Ala Asn Ala Ile
    930                 935                 940
```

-continued

```
Phe Thr His Ser Asp Ala Lys Asn Pro Ser Glu Leu Leu Ala Asp Lys
945                 950                 955                 960

Asn Leu Gly Asn Gly Asn Ile Gln Thr Lys Gln Ala Thr Lys Ala Lys
                965                 970                 975

Ser Thr Pro Trp Gln Thr Leu Asp Leu Ser Gly Tyr Val Asn Ile Lys
            980                 985                 990

Asp Asn Phe Thr Leu Arg Ala Gly Val Tyr Asn Val Phe Asn Thr Tyr
        995                 1000                1005

Tyr Thr Thr Trp Glu Ala Leu Arg Gln Thr Ala Glu Gly Ala Val Asn
    1010                1015                1020

Gln His Thr Gly Leu Ser Gln Asp Lys His Tyr Gly Arg Tyr Ala Ala
1025                1030                1035                1040

Pro Gly Arg Asn Tyr Gln Leu Ala Leu Glu Met Lys Phe
                1045                1050
```

(2) INFORMATION FOR SEQ ID NO:11:

(i) SEQUENCE CHARACTERISTICS:
(A) LENGTH: 702 amino acids
(B) TYPE: amino acid
(C) STRANDEDNESS: single
(D) TOPOLOGY: linear (xi) SEQUENCE DESCRIPTION: SEQ ID NO:11:

```
Met Lys His Ile Pro Leu Thr Thr Leu Cys Val Ala Ile Ser Ala Val
1               5                   10                  15

Leu Leu Thr Ala Cys Gly Gly Ser Gly Gly Ser Asn Pro Pro Ala Pro
            20                  25                  30

Thr Pro Ile Pro Asn Ala Ser Gly Ser Gly Asn Thr Gly Asn Thr Gly
        35                  40                  45

Asn Ala Gly Gly Thr Asp Asn Thr Ala Asn Ala Gly Asn Thr Gly Gly
    50                  55                  60

Thr Asn Ser Gly Thr Gly Ser Ala Asn Thr Pro Glu Pro Lys Tyr Gln
65                  70                  75                  80

Asp Val Pro Thr Glu Lys Asn Glu Lys Asp Lys Val Ser Ser Ile Gln
                85                  90                  95

Glu Pro Ala Met Gly Tyr Gly Met Ala Leu Ser Lys Ile Asn Leu His
            100                 105                 110

Asn Arg Gln Asp Thr Pro Leu Asp Glu Lys Asn Ile Ile Thr Leu Asp
        115                 120                 125

Gly Lys Lys Gln Val Ala Glu Gly Lys Lys Ser Pro Leu Pro Phe Ser
    130                 135                 140

Leu Asp Val Glu Asn Lys Leu Leu Asp Gly Tyr Ile Ala Lys Met Asn
145                 150                 155                 160

Val Ala Asp Lys Asn Ala Ile Gly Asp Arg Ile Lys Lys Gly Asn Lys
                165                 170                 175

Glu Ile Ser Asp Glu Glu Leu Ala Lys Gln Ile Lys Glu Ala Val Arg
            180                 185                 190

Lys Ser His Glu Phe Gln Gln Val Leu Ser Ser Leu Glu Asn Lys Ile
        195                 200                 205

Phe His Ser Asn Asp Gly Thr Thr Lys Ala Thr Thr Arg Asp Leu Lys
    210                 215                 220

Tyr Val Asp Tyr Gly Tyr Tyr Leu Ala Asn Asp Gly Asn Tyr Leu Thr
225                 230                 235                 240

Val Lys Thr Asp Lys Leu Trp Asn Leu Gly Pro Val Gly Gly Val Phe
                245                 250                 255
```

-continued

```
Tyr Asn Gly Thr Thr Thr Ala Lys Glu Leu Pro Thr Gln Asp Ala Val
            260                 265                 270

Lys Tyr Lys Gly His Trp Asp Phe Met Thr Asp Val Ala Asn Arg Arg
        275                 280                 285

Asn Arg Phe Ser Glu Val Lys Glu Asn Ser Gln Ala Gly Trp Tyr Tyr
    290                 295                 300

Gly Ala Ser Ser Lys Asp Glu Tyr Asn Arg Leu Leu Thr Lys Glu Asp
305                 310                 315                 320

Ser Ala Pro Asp Gly His Ser Gly Glu Tyr Gly His Ser Ser Glu Phe
                325                 330                 335

Thr Val Asn Phe Lys Glu Lys Lys Leu Thr Gly Lys Leu Phe Ser Asn
            340                 345                 350

Leu Gln Asp Arg His Lys Gly Asn Val Thr Lys Thr Glu Arg Tyr Asp
        355                 360                 365

Ile Asp Ala Asn Ile His Gly Asn Arg Phe Arg Gly Ser Ala Thr Ala
    370                 375                 380

Ser Asn Lys Asn Asp Thr Ser Lys His Pro Phe Thr Ser Asp Ala Asn
385                 390                 395                 400

Asn Arg Leu Glu Gly Gly Phe Tyr Gly Pro Lys Gly Glu Glu Leu Ala
                405                 410                 415

Gly Lys Phe Leu Thr Asn Asp Asn Lys Leu Phe Gly Val Phe Gly Ala
            420                 425                 430

Lys Arg Glu Ser Lys Ala Glu Glu Lys Thr Glu Ala Ile Leu Asp Ala
        435                 440                 445

Tyr Ala Leu Gly Thr Phe Asn Thr Ser Asn Ala Thr Thr Phe Thr Pro
    450                 455                 460

Phe Thr Glu Lys Gln Leu Asp Asn Phe Gly Asn Ala Lys Lys Leu Val
465                 470                 475                 480

Leu Gly Ser Thr Val Ile Asp Leu Val Pro Thr Asp Ala Thr Lys Asn
                485                 490                 495

Glu Phe Thr Lys Asp Lys Pro Glu Ser Ala Thr Asn Glu Ala Gly Glu
            500                 505                 510

Thr Leu Met Val Asn Asp Glu Val Ser Val Lys Thr Tyr Gly Lys Asn
        515                 520                 525

Phe Glu Tyr Leu Lys Phe Gly Glu Leu Ser Ile Gly Gly Ser His Ser
    530                 535                 540

Val Phe Leu Gln Gly Glu Arg Thr Ala Thr Thr Gly Glu Lys Ala Val
545                 550                 555                 560

Pro Thr Thr Gly Thr Ala Lys Tyr Leu Gly Asn Trp Val Gly Tyr Ile
                565                 570                 575

Thr Gly Lys Asp Thr Gly Thr Gly Thr Gly Lys Ser Phe Thr Asp Ala
            580                 585                 590

Gln Asp Val Ala Asp Phe Asp Ile Asp Phe Gly Asn Lys Ser Val Ser
        595                 600                 605

Gly Lys Leu Ile Thr Lys Gly Arg Gln Asp Pro Val Phe Ser Ile Thr
    610                 615                 620

Gly Gln Ile Ala Gly Asn Gly Trp Thr Gly Thr Ala Ser Thr Thr Lys
625                 630                 635                 640

Ala Asp Ala Gly Gly Tyr Lys Ile Asp Ser Ser Ser Thr Gly Lys Ser
                645                 650                 655

Ile Val Ile Lys Asp Ala Asn Val Thr Gly Gly Phe Tyr Gly Pro Asn
            660                 665                 670
```

-continued

```
Ala Asn Glu Met Gly Gly Ser Phe Thr His Asn Ala Asp Asp Ser Lys
        675                 680                 685

Ala Ser Val Val Phe Gly Thr Lys Arg Gln Gln Glu Val Lys
    690                 695                 700
```

(2) INFORMATION FOR SEQ ID NO:12:

(i) SEQUENCE CHARACTERISTICS:
(A) LENGTH: 682 amino acids
(B) TYPE: amino acid
(C) STRANDEDNESS: single
(D) TOPOLOGY: linear (xi) SEQUENCE DESCRIPTION: SEQ ID NO:12:

```
Cys Gly Gly Ser Gly Gly Ser Asn Pro Pro Ala Pro Thr Pro Ile Pro
1               5                   10                  15

Asn Ala Ser Gly Ser Gly Asn Thr Gly Asn Thr Gly Asn Ala Gly Gly
            20                  25                  30

Thr Asp Asn Thr Ala Asn Ala Gly Asn Thr Gly Gly Thr Asn Ser Gly
        35                  40                  45

Thr Gly Ser Ala Asn Thr Pro Glu Pro Lys Tyr Gln Asp Val Pro Thr
    50                  55                  60

Glu Lys Asn Glu Lys Asp Lys Val Ser Ser Ile Gln Glu Pro Ala Met
65                  70                  75                  80

Gly Tyr Gly Met Ala Leu Ser Lys Ile Asn Leu His Asn Arg Gln Asp
                85                  90                  95

Thr Pro Leu Asp Glu Lys Asn Ile Ile Thr Leu Asp Gly Lys Lys Gln
            100                 105                 110

Val Ala Glu Gly Lys Lys Ser Pro Leu Pro Phe Ser Leu Asp Val Glu
        115                 120                 125

Asn Lys Leu Leu Asp Gly Tyr Ile Ala Lys Met Asn Val Ala Asp Lys
    130                 135                 140

Asn Ala Ile Gly Asp Arg Ile Lys Lys Gly Asn Lys Glu Ile Ser Asp
145                 150                 155                 160

Glu Glu Leu Ala Lys Gln Ile Lys Glu Ala Val Arg Lys Ser His Glu
                165                 170                 175

Phe Gln Gln Val Leu Ser Ser Leu Glu Asn Lys Ile Phe His Ser Asn
            180                 185                 190

Asp Gly Thr Thr Lys Ala Thr Thr Arg Asp Leu Lys Tyr Val Asp Tyr
        195                 200                 205

Gly Tyr Tyr Leu Ala Asn Asp Gly Asn Tyr Leu Thr Val Lys Thr Asp
    210                 215                 220

Lys Leu Trp Asn Leu Gly Pro Val Gly Gly Val Phe Tyr Asn Gly Thr
225                 230                 235                 240

Thr Thr Ala Lys Glu Leu Pro Thr Gln Asp Ala Val Lys Tyr Lys Gly
                245                 250                 255

His Trp Asp Phe Met Thr Asp Val Ala Asn Arg Arg Asn Arg Phe Ser
            260                 265                 270

Glu Val Lys Glu Asn Ser Gln Ala Gly Trp Tyr Tyr Gly Ala Ser Ser
        275                 280                 285

Lys Asp Glu Tyr Asn Arg Leu Leu Thr Lys Glu Asp Ser Ala Pro Asp
    290                 295                 300

Gly His Ser Gly Glu Tyr Gly His Ser Ser Glu Phe Thr Val Asn Phe
305                 310                 315                 320

Lys Glu Lys Lys Leu Thr Gly Lys Leu Phe Ser Asn Leu Gln Asp Arg
                325                 330                 335
```

-continued

```
His Lys Gly Asn Val Thr Lys Thr Glu Arg Tyr Asp Ile Asp Ala Asn
            340                 345                 350

Ile His Gly Asn Arg Phe Arg Gly Ser Ala Thr Ala Ser Asn Lys Asn
        355                 360                 365

Asp Thr Ser Lys His Pro Phe Thr Ser Asp Ala Asn Asn Arg Leu Glu
    370                 375                 380

Gly Gly Phe Tyr Gly Pro Lys Gly Glu Glu Leu Ala Gly Lys Phe Leu
385                 390                 395                 400

Thr Asn Asp Asn Lys Leu Phe Gly Val Phe Gly Ala Lys Arg Glu Ser
                405                 410                 415

Lys Ala Glu Glu Lys Thr Glu Ala Ile Leu Asp Ala Tyr Ala Leu Gly
            420                 425                 430

Thr Phe Asn Thr Ser Asn Ala Thr Thr Phe Thr Pro Phe Thr Glu Lys
        435                 440                 445

Gln Leu Asp Asn Phe Gly Asn Ala Lys Lys Leu Val Leu Gly Ser Thr
    450                 455                 460

Val Ile Asp Leu Val Pro Thr Asp Ala Thr Lys Asn Glu Phe Thr Lys
465                 470                 475                 480

Asp Lys Pro Glu Ser Ala Thr Asn Glu Ala Gly Glu Thr Leu Met Val
                485                 490                 495

Asn Asp Glu Val Ser Val Lys Thr Tyr Gly Lys Asn Phe Glu Tyr Leu
            500                 505                 510

Lys Phe Gly Glu Leu Ser Ile Gly Gly Ser His Ser Val Phe Leu Gln
        515                 520                 525

Gly Glu Arg Thr Ala Thr Thr Gly Glu Lys Ala Val Pro Thr Thr Gly
    530                 535                 540

Thr Ala Lys Tyr Leu Gly Asn Trp Val Gly Tyr Ile Thr Gly Lys Asp
545                 550                 555                 560

Thr Gly Thr Gly Thr Gly Lys Ser Phe Thr Asp Ala Gln Asp Val Ala
                565                 570                 575

Asp Phe Asp Ile Asp Phe Gly Asn Lys Ser Val Ser Gly Lys Leu Ile
            580                 585                 590

Thr Lys Gly Arg Gln Asp Pro Val Phe Ser Ile Thr Gly Gln Ile Ala
        595                 600                 605

Gly Asn Gly Trp Thr Gly Thr Ala Ser Thr Thr Lys Ala Asp Ala Gly
    610                 615                 620

Gly Tyr Lys Ile Asp Ser Ser Ser Thr Gly Lys Ser Ile Val Ile Lys
625                 630                 635                 640

Asp Ala Asn Val Thr Gly Gly Phe Tyr Gly Pro Asn Ala Asn Glu Met
                645                 650                 655

Gly Gly Ser Phe Thr His Asn Ala Asp Asp Ser Lys Ala Ser Val Val
            660                 665                 670

Phe Gly Thr Lys Arg Gln Gln Glu Val Lys
        675                 680
```

(2) INFORMATION FOR SEQ ID NO:13:

(i) SEQUENCE CHARACTERISTICS:
(A) LENGTH: 1070 amino acids
(B) TYPE: amino acid
(C) STRANDEDNESS: single
(D) TOPOLOGY: linear (xi) SEQUENCE DESCRIPTION: SEQ ID NO:13:

```
Met Asn Gln Ser Lys Lys Ser Lys Lys Ser Lys Gln Val Leu Lys Leu
```

-continued

```
1               5                   10                  15

Ser Ala Leu Ser Leu Gly Leu Leu Asn Ile Thr Gln Val Ala Leu Ala
            20                  25                  30

Asn Thr Thr Ala Asp Lys Ala Glu Ala Thr Asp Lys Thr Asn Leu Val
        35                  40                  45

Val Val Leu Asp Glu Thr Val Val Thr Ala Lys Lys Asn Ala Arg Lys
    50                  55                  60

Ala Asn Glu Val Thr Gly Leu Gly Lys Val Val Lys Thr Ala Glu Thr
65                  70                  75                  80

Ile Asn Lys Glu Gln Val Leu Asn Ile Arg Asp Leu Thr Arg Tyr Asp
                85                  90                  95

Pro Gly Ile Ala Val Val Glu Gln Gly Arg Gly Ala Ser Ser Gly Tyr
            100                 105                 110

Ser Ile Arg Gly Met Asp Lys Asn Arg Val Ala Val Leu Val Asp Gly
        115                 120                 125

Ile Asn Gln Ala Gln His Tyr Ala Leu Gln Gly Pro Val Ala Gly Lys
    130                 135                 140

Asn Tyr Ala Ala Gly Gly Ala Ile Asn Glu Ile Glu Tyr Glu Asn Val
145                 150                 155                 160

Arg Ser Val Glu Ile Ser Lys Gly Ala Asn Ser Ser Glu Tyr Gly Ser
                165                 170                 175

Gly Ala Leu Ser Gly Ser Val Ala Phe Val Thr Lys Thr Ala Asp Asp
            180                 185                 190

Ile Ile Lys Asp Gly Lys Asp Trp Gly Val Gln Thr Lys Thr Ala Tyr
        195                 200                 205

Ala Ser Lys Asn Asn Ala Trp Val Asn Ser Val Ala Ala Ala Gly Lys
    210                 215                 220

Ala Gly Ser Phe Ser Gly Leu Ile Ile Tyr Thr Asp Arg Arg Gly Gln
225                 230                 235                 240

Glu Tyr Lys Ala His Asp Asp Ala Tyr Gln Gly Ser Gln Ser Phe Asp
                245                 250                 255

Arg Ala Val Ala Thr Thr Asp Pro Asn Asn Pro Lys Phe Leu Ile Ala
            260                 265                 270

Asn Glu Cys Ala Asn Gly Asn Tyr Glu Ala Cys Ala Ala Gly Gly Gln
        275                 280                 285

Thr Lys Leu Gln Ala Lys Pro Thr Asn Val Arg Asp Lys Val Asn Val
    290                 295                 300

Lys Asp Tyr Thr Gly Pro Asn Arg Leu Ile Pro Asn Pro Leu Thr Gln
305                 310                 315                 320

Asp Ser Lys Ser Leu Leu Leu Arg Pro Gly Tyr Gln Leu Asn Asp Lys
                325                 330                 335

His Tyr Val Gly Gly Val Tyr Glu Ile Thr Lys Gln Asn Tyr Ala Met
            340                 345                 350

Gln Asp Lys Thr Val Pro Ala Tyr Leu Thr Val His Asp Ile Glu Lys
        355                 360                 365

Ser Arg Leu Ser Asn His Gly Gln Ala Asn Gly Tyr Tyr Gln Gly Asn
    370                 375                 380

Asn Leu Gly Glu Arg Ile Arg Asp Ala Ile Gly Ala Asn Ser Gly Tyr
385                 390                 395                 400

Gly Ile Asn Tyr Ala His Gly Val Phe Tyr Asp Glu Lys His Gln Lys
                405                 410                 415

Asp Arg Leu Gly Leu Glu Tyr Val Tyr Asp Ser Lys Gly Glu Asn Lys
            420                 425                 430
```

-continued

```
Trp Phe Asp Asp Val Arg Val Ser Tyr Asp Lys Gln Asp Ile Thr Leu
        435                 440                 445

Arg Ser Gln Leu Thr Asn Thr His Cys Ser Thr Tyr Pro His Ile Asp
    450                 455                 460

Lys Asn Cys Thr Pro Asp Val Asn Lys Pro Phe Ser Val Lys Glu Val
465                 470                 475                 480

Asp Asn Asn Ala Tyr Lys Glu Gln His Asn Leu Ile Lys Ala Val Phe
                485                 490                 495

Asn Lys Lys Met Ala Leu Gly Asn Thr His His His Ile Asn Leu Gln
            500                 505                 510

Val Gly Tyr Asp Lys Phe Asn Ser Ser Leu Ser Arg Glu Asp Tyr Arg
        515                 520                 525

Leu Ala Thr His Gln Ser Tyr Gln Lys Leu Asp Tyr Thr Pro Pro Ser
    530                 535                 540

Asn Pro Leu Pro Asp Lys Phe Lys Pro Ile Leu Gly Ser Asn Asn Arg
545                 550                 555                 560

Pro Ile Cys Leu Asp Ala Tyr Gly Tyr Gly His Asp His Pro Gln Ala
                565                 570                 575

Cys Asn Ala Lys Asn Ser Thr Tyr Gln Asn Phe Ala Ile Lys Lys Gly
            580                 585                 590

Ile Glu Gln Tyr Asn Gln Thr Asn Thr Asp Lys Ile Asp Tyr Gln Ala
        595                 600                 605

Val Ile Asp Gln Tyr Asp Lys Gln Asn Pro Asn Ser Thr Leu Lys Pro
    610                 615                 620

Phe Glu Lys Ile Lys Gln Ser Leu Gly Gln Glu Lys Tyr Asp Glu Ile
625                 630                 635                 640

Asp Arg Leu Gly Phe Asn Ala Tyr Lys Asp Leu Arg Asn Glu Trp Ala
                645                 650                 655

Gly Trp Thr Asn Asp Asn Ser Gln Gln Asn Ala Asn Lys Gly Thr Asp
            660                 665                 670

Asn Ile Tyr Gln Pro Asn Gln Ala Thr Val Val Lys Asp Asp Lys Cys
        675                 680                 685

Lys Tyr Ser Glu Thr Asn Ser Tyr Ala Asp Cys Ser Thr Thr Arg His
    690                 695                 700

Ile Ser Gly Asp Asn Tyr Phe Ile Ala Leu Lys Asp Asn Met Thr Ile
705                 710                 715                 720

Asn Lys Tyr Val Asp Leu Gly Leu Gly Ala Arg Tyr Asp Arg Ile Lys
                725                 730                 735

His Lys Ser Asp Val Pro Leu Val Asp Asn Ser Ala Ser Asn Gln Leu
            740                 745                 750

Ser Trp Asn Phe Gly Val Val Val Lys Pro Thr Asn Trp Leu Asp Ile
        755                 760                 765

Ala Tyr Arg Ser Ser Gln Gly Phe Arg Met Pro Ser Phe Ser Glu Met
    770                 775                 780

Tyr Gly Glu Arg Phe Gly Val Thr Ile Gly Lys Gly Thr Gln His Gly
785                 790                 795                 800

Cys Lys Gly Leu Tyr Tyr Ile Cys Gln Gln Thr Val His Gln Thr Lys
                805                 810                 815

Leu Lys Pro Glu Lys Ser Phe Asn Gln Glu Ile Gly Ala Thr Leu His
            820                 825                 830

Asn His Leu Gly Ser Leu Glu Val Ser Tyr Phe Lys Asn Arg Tyr Thr
        835                 840                 845
```

-continued

Asp Leu Ile Val Gly Lys Ser Glu Glu Ile Arg Thr Leu Thr Gln Gly
    850                 855                 860

Asp Asn Ala Gly Lys Gln Arg Gly Lys Gly Asp Leu Gly Phe His Asn
865                 870                 875                 880

Gly Gln Asp Ala Asp Leu Thr Gly Ile Asn Ile Leu Gly Arg Leu Asp
                885                 890                 895

Leu Asn Ala Val Asn Ser Arg Leu Pro Tyr Gly Leu Tyr Ser Thr Leu
            900                 905                 910

Ala Tyr Asn Lys Val Asp Val Lys Gly Lys Thr Leu Asn Pro Thr Leu
        915                 920                 925

Ala Gly Thr Asn Ile Leu Phe Asp Ala Ile Gln Pro Ser Arg Tyr Val
    930                 935                 940

Val Gly Leu Gly Tyr Asp Ala Pro Ser Gln Lys Trp Gly Ala Asn Ala
945                 950                 955                 960

Ile Phe Thr His Ser Asp Ala Lys Asn Pro Ser Glu Leu Leu Ala Asp
                965                 970                 975

Lys Asn Leu Gly Asn Gly Asn Asn Gln Thr Lys Gln Ala Thr Lys Ala
            980                 985                 990

Lys Ser Thr Pro Trp Gln Thr Leu Asp Leu Ser Gly Tyr Val Asn Ile
        995                 1000                1005

Lys Asp Asn Phe Thr Leu Arg Ala Gly Val Tyr Asn Val Phe Asn Thr
    1010                1015                1020

Tyr Tyr Thr Thr Trp Glu Ala Leu Arg Gln Thr Ala Glu Gly Ala Val
1025                1030                1035                1040

Asn Gln His Thr Gly Leu Ser Gln Asp Lys His Tyr Gly Arg Tyr Ala
                1045                1050                1055

Ala Pro Gly Arg Asn Tyr Gln Leu Ala Leu Glu Met Lys Phe
            1060                1065                1070

(2) INFORMATION FOR SEQ ID NO:14:

(i) SEQUENCE CHARACTERISTICS:
(A) LENGTH: 1052 amino acids
(B) TYPE: amino acid
(C) STRANDEDNESS: single
(D) TOPOLOGY: linear (xi) SEQUENCE DESCRIPTION: SEQ ID NO:14:

Leu Ser Leu Gly Leu Leu Asn Ile Thr Gln Val Ala Leu Ala Asn Thr
1               5                   10                  15

Thr Ala Asp Lys Ala Glu Ala Thr Asp Lys Thr Asn Leu Val Val Val
            20                  25                  30

Leu Asp Glu Thr Val Val Thr Ala Lys Lys Asn Ala Arg Lys Ala Asn
        35                  40                  45

Glu Val Thr Gly Leu Gly Lys Val Val Lys Thr Ala Glu Thr Ile Asn
    50                  55                  60

Lys Glu Gln Val Leu Asn Ile Arg Asp Leu Thr Arg Tyr Asp Pro Gly
65                  70                  75                  80

Ile Ala Val Val Glu Gln Gly Arg Gly Ala Ser Ser Gly Tyr Ser Ile
                85                  90                  95

Arg Gly Met Asp Lys Asn Arg Val Ala Val Leu Val Asp Gly Ile Asn
            100                 105                 110

Gln Ala Gln His Tyr Ala Leu Gln Gly Pro Val Ala Gly Lys Asn Tyr
        115                 120                 125

Ala Ala Gly Gly Ala Ile Asn Glu Ile Glu Tyr Glu Asn Val Arg Ser
    130                 135                 140

-continued

```
Val Glu Ile Ser Lys Gly Ala Asn Ser Ser Glu Tyr Gly Ser Gly Ala
145                 150                 155                 160

Leu Ser Gly Ser Val Ala Phe Val Thr Lys Thr Ala Asp Asp Ile Ile
                165                 170                 175

Lys Asp Gly Lys Asp Trp Gly Val Gln Thr Lys Thr Ala Tyr Ala Ser
            180                 185                 190

Lys Asn Asn Ala Trp Val Asn Ser Val Ala Ala Ala Gly Lys Ala Gly
        195                 200                 205

Ser Phe Ser Gly Leu Ile Ile Tyr Thr Asp Arg Arg Gly Gln Glu Tyr
    210                 215                 220

Lys Ala His Asp Asp Ala Tyr Gln Gly Ser Gln Ser Phe Asp Arg Ala
225                 230                 235                 240

Val Ala Thr Thr Asp Pro Asn Asn Pro Lys Phe Leu Ile Ala Asn Glu
                245                 250                 255

Cys Ala Asn Gly Asn Tyr Glu Ala Cys Ala Ala Gly Gly Gln Thr Lys
            260                 265                 270

Leu Gln Ala Lys Pro Thr Asn Val Arg Asp Lys Val Asn Val Lys Asp
        275                 280                 285

Tyr Thr Gly Pro Asn Arg Leu Ile Pro Asn Pro Leu Thr Gln Asp Ser
    290                 295                 300

Lys Ser Leu Leu Leu Arg Pro Gly Tyr Gln Leu Asn Asp Lys His Tyr
305                 310                 315                 320

Val Gly Gly Val Tyr Glu Ile Thr Lys Gln Asn Tyr Ala Met Gln Asp
                325                 330                 335

Lys Thr Val Pro Ala Tyr Leu Thr Val His Asp Ile Glu Lys Ser Arg
            340                 345                 350

Leu Ser Asn His Gly Gln Ala Asn Gly Tyr Tyr Gln Gly Asn Asn Leu
        355                 360                 365

Gly Glu Arg Ile Arg Asp Ala Ile Gly Ala Asn Ser Gly Tyr Gly Ile
    370                 375                 380

Asn Tyr Ala His Gly Val Phe Tyr Asp Glu Lys His Gln Lys Asp Arg
385                 390                 395                 400

Leu Gly Leu Glu Tyr Val Tyr Asp Ser Lys Gly Glu Asn Lys Trp Phe
                405                 410                 415

Asp Asp Val Arg Val Ser Tyr Asp Lys Gln Asp Ile Thr Leu Arg Ser
            420                 425                 430

Gln Leu Thr Asn Thr His Cys Ser Thr Tyr Pro His Ile Asp Lys Asn
        435                 440                 445

Cys Thr Pro Asp Val Asn Lys Pro Phe Ser Val Lys Glu Val Asp Asn
    450                 455                 460

Asn Ala Tyr Lys Glu Gln His Asn Leu Ile Lys Ala Val Phe Asn Lys
465                 470                 475                 480

Lys Met Ala Leu Gly Asn Thr His His His Ile Asn Leu Gln Val Gly
                485                 490                 495

Tyr Asp Lys Phe Asn Ser Ser Leu Ser Arg Glu Asp Tyr Arg Leu Ala
            500                 505                 510

Thr His Gln Ser Tyr Gln Lys Leu Asp Tyr Thr Pro Pro Ser Asn Pro
        515                 520                 525

Leu Pro Asp Lys Phe Lys Pro Ile Leu Gly Ser Asn Asn Arg Pro Ile
    530                 535                 540

Cys Leu Asp Ala Tyr Gly Tyr Gly His Asp His Pro Gln Ala Cys Asn
545                 550                 555                 560
```

-continued

```
Ala Lys Asn Ser Thr Tyr Gln Asn Phe Ala Ile Lys Lys Gly Ile Glu
                565                 570                 575

Gln Tyr Asn Gln Thr Asn Thr Asp Lys Ile Asp Tyr Gln Ala Val Ile
            580                 585                 590

Asp Gln Tyr Asp Lys Gln Asn Pro Asn Ser Thr Leu Lys Pro Phe Glu
        595                 600                 605

Lys Ile Lys Gln Ser Leu Gly Gln Glu Lys Tyr Asp Glu Ile Asp Arg
    610                 615                 620

Leu Gly Phe Asn Ala Tyr Lys Asp Leu Arg Asn Glu Trp Ala Gly Trp
625                 630                 635                 640

Thr Asn Asp Asn Ser Gln Gln Asn Ala Asn Lys Gly Thr Asp Asn Ile
                645                 650                 655

Tyr Gln Pro Asn Gln Ala Thr Val Val Lys Asp Asp Lys Cys Lys Tyr
            660                 665                 670

Ser Glu Thr Asn Ser Tyr Ala Asp Cys Ser Thr Thr Arg His Ile Ser
        675                 680                 685

Gly Asp Asn Tyr Phe Ile Ala Leu Lys Asp Asn Met Thr Ile Asn Lys
    690                 695                 700

Tyr Val Asp Leu Gly Leu Gly Ala Arg Tyr Asp Arg Ile Lys His Lys
705                 710                 715                 720

Ser Asp Val Pro Leu Val Asp Asn Ser Ala Ser Asn Gln Leu Ser Trp
                725                 730                 735

Asn Phe Gly Val Val Val Lys Pro Thr Asn Trp Leu Asp Ile Ala Tyr
            740                 745                 750

Arg Ser Ser Gln Gly Phe Arg Met Pro Ser Phe Ser Glu Met Tyr Gly
        755                 760                 765

Glu Arg Phe Gly Val Thr Ile Gly Lys Gly Thr Gln His Gly Cys Lys
    770                 775                 780

Gly Leu Tyr Tyr Ile Cys Gln Gln Thr Val His Gln Thr Lys Leu Lys
785                 790                 795                 800

Pro Glu Lys Ser Phe Asn Gln Glu Ile Gly Ala Thr Leu His Asn His
                805                 810                 815

Leu Gly Ser Leu Glu Val Ser Tyr Phe Lys Asn Arg Tyr Thr Asp Leu
            820                 825                 830

Ile Val Gly Lys Ser Glu Glu Ile Arg Thr Leu Thr Gln Gly Asp Asn
        835                 840                 845

Ala Gly Lys Gln Arg Gly Lys Gly Asp Leu Gly Phe His Asn Gly Gln
    850                 855                 860

Asp Ala Asp Leu Thr Gly Ile Asn Ile Leu Gly Arg Leu Asp Leu Asn
865                 870                 875                 880

Ala Val Asn Ser Arg Leu Pro Tyr Gly Leu Tyr Ser Thr Leu Ala Tyr
                885                 890                 895

Asn Lys Val Asp Val Lys Gly Lys Thr Leu Asn Pro Thr Leu Ala Gly
            900                 905                 910

Thr Asn Ile Leu Phe Asp Ala Ile Gln Pro Ser Arg Tyr Val Val Gly
        915                 920                 925

Leu Gly Tyr Asp Ala Pro Ser Gln Lys Trp Gly Ala Asn Ala Ile Phe
    930                 935                 940

Thr His Ser Asp Ala Lys Asn Pro Ser Glu Leu Leu Ala Asp Lys Asn
945                 950                 955                 960

Leu Gly Asn Gly Asn Asn Gln Thr Lys Gln Ala Thr Lys Ala Lys Ser
                965                 970                 975

Thr Pro Trp Gln Thr Leu Asp Leu Ser Gly Tyr Val Asn Ile Lys Asp
```

-continued

```
            980                 985                 990

Asn Phe Thr Leu Arg Ala Gly Val Tyr Asn Val Phe Asn Thr Tyr Tyr
        995                 1000                1005

Thr Thr Trp Glu Ala Leu Arg Gln Thr Ala Glu Gly Ala Val Asn Gln
    1010                1015                1020

His Thr Gly Leu Ser Gln Asp Lys His Tyr Gly Arg Tyr Ala Ala Pro
1025                1030                1035                1040

Gly Arg Asn Tyr Gln Leu Ala Leu Glu Met Lys Phe
                1045                1050


(2) INFORMATION FOR SEQ ID NO:15:

     (i) SEQUENCE CHARACTERISTICS:
          (A) LENGTH: 709 amino acids
          (B) TYPE: amino acid
          (C) STRANDEDNESS: single
          (D) TOPOLOGY: linear

    (xi) SEQUENCE DESCRIPTION: SEQ ID NO:15:

Met Lys His Ile Pro Leu Thr Thr Leu Cys Val Ala Ile Ser Ala Val
1               5                   10                  15

Leu Leu Thr Ala Cys Gly Gly Ser Ser Gly Gly Phe Asn Pro Pro Ala
            20                  25                  30

Ser Thr Pro Ile Pro Asn Ala Gly Asn Ser Gly Asn Ala Gly Asn Ala
        35                  40                  45

Gly Asn Ala Gly Gly Thr Gly Gly Ala Asn Ser Gly Ala Gly Asn Ala
    50                  55                  60

Gly Gly Thr Gly Gly Ala Asn Ser Gly Ala Gly Ser Ala Ser Thr Pro
65                  70                  75                  80

Glu Pro Lys Tyr Lys Asp Val Pro Thr Asp Glu Asn Lys Lys Ala Glu
                85                  90                  95

Val Ser Gly Ile Gln Glu Pro Ala Met Gly Tyr Gly Val Glu Leu Lys
            100                 105                 110

Leu Arg Asn Trp Ile Pro Gln Glu Gln Glu Glu His Ala Lys Ile Asn
        115                 120                 125

Thr Asn Asp Val Val Lys Leu Glu Gly Asp Leu Lys His Asn Pro Phe
    130                 135                 140

Asp Asn Ser Ile Trp Gln Asn Ile Lys Asn Ser Lys Glu Val Gln Thr
145                 150                 155                 160

Val Tyr Asn Gln Glu Lys Gln Asn Ile Glu Asp Gln Ile Lys Arg Glu
                165                 170                 175

Asn Lys Gln Arg Pro Asp Lys Lys Leu Asp Asp Val Ala Leu Gln Ala
            180                 185                 190

Tyr Ile Glu Lys Val Leu Asp Asp Arg Leu Thr Glu Leu Ala Lys Pro
        195                 200                 205

Ile Tyr Glu Lys Asn Ile Asn Tyr Ser His Asp Lys Gln Asn Lys Ala
    210                 215                 220

Arg Thr Arg Asp Leu Lys Tyr Val Arg Ser Gly Tyr Ile Tyr Arg Ser
225                 230                 235                 240

Gly Tyr Ser Asn Ile Ile Pro Lys Lys Ile Ala Lys Thr Gly Phe Asp
                245                 250                 255

Gly Ala Leu Phe Tyr Gln Gly Thr Gln Thr Ala Lys Gln Leu Pro Val
            260                 265                 270

Ser Gln Val Lys Tyr Lys Gly Thr Trp Asp Phe Met Thr Asp Ala Lys
        275                 280                 285
```

-continued

```
Lys Gly Gln Ser Phe Ser Ser Phe Gly Thr Ser Gln Arg Leu Ala Gly
    290                 295                 300

Asp Arg Tyr Ser Ala Met Ser Tyr His Glu Tyr Pro Ser Leu Leu Thr
305                 310                 315                 320

Asp Glu Lys Asn Lys Pro Asp Asn Tyr Asn Gly Glu Tyr Gly His Ser
                325                 330                 335

Ser Glu Phe Thr Val Asp Phe Ser Lys Lys Ser Leu Lys Gly Glu Leu
            340                 345                 350

Ser Ser Asn Ile Gln Asp Gly His Lys Gly Ser Val Asn Lys Thr Lys
        355                 360                 365

Arg Tyr Asp Ile Asp Ala Asn Ile Tyr Gly Asn Arg Phe Arg Gly Ser
    370                 375                 380

Ala Thr Ala Ser Asp Thr Thr Glu Ala Ser Lys Ser Lys His Pro Phe
385                 390                 395                 400

Thr Ser Asp Ala Lys Asn Ser Leu Glu Gly Gly Phe Tyr Gly Pro Asn
                405                 410                 415

Ala Glu Glu Leu Ala Gly Lys Phe Leu Thr Asn Asp Asn Lys Leu Phe
            420                 425                 430

Gly Val Phe Gly Ala Lys Arg Glu Ser Glu Ala Lys Glu Lys Thr Glu
        435                 440                 445

Ala Ile Leu Asp Ala Tyr Ala Leu Gly Thr Phe Asn Lys Pro Gly Thr
    450                 455                 460

Thr Asn Pro Ala Phe Thr Ala Asn Ser Lys Lys Glu Leu Asp Asn Phe
465                 470                 475                 480

Gly Asn Ala Lys Lys Leu Val Leu Gly Ser Thr Val Ile Asp Leu Val
                485                 490                 495

Pro Thr Gly Ala Thr Lys Asp Val Asn Glu Phe Lys Glu Lys Pro Lys
            500                 505                 510

Ser Ala Thr Asn Lys Ala Gly Glu Thr Leu Met Val Asn Asp Glu Val
        515                 520                 525

Ile Val Lys Thr Tyr Gly Tyr Gly Arg Asn Phe Glu Tyr Leu Lys Phe
    530                 535                 540

Gly Glu Leu Ser Ile Gly Gly Ser His Ser Val Phe Leu Gln Gly Glu
545                 550                 555                 560

Arg Thr Ala Glu Lys Ala Val Pro Thr Glu Gly Thr Ala Lys Tyr Leu
                565                 570                 575

Gly Asn Trp Val Gly Tyr Ile Thr Gly Lys Asp Thr Gly Thr Ser Thr
            580                 585                 590

Gly Lys Ser Phe Asn Glu Ala Gln Asp Ile Ala Asp Phe Asp Ile Asp
        595                 600                 605

Phe Glu Arg Lys Ser Val Lys Gly Lys Leu Thr Thr Gln Gly Arg Gln
    610                 615                 620

Asp Pro Val Phe Asn Ile Thr Gly Gln Ile Ala Gly Asn Gly Trp Thr
625                 630                 635                 640

Gly Thr Ala Ser Thr Ala Lys Ala Asn Val Gly Gly Tyr Lys Ile Asp
                645                 650                 655

Ser Ser Ser Thr Gly Lys Ser Ile Val Ile Glu Asn Ala Lys Val Thr
            660                 665                 670

Gly Gly Phe Tyr Gly Pro Asn Ala Asn Glu Met Gly Gly Ser Phe Thr
        675                 680                 685

His Asp Thr Asp Asp Ser Lys Ala Ser Val Val Phe Gly Thr Lys Arg
    690                 695                 700

Gln Glu Glu Val Lys
```

-continued

705

(2) INFORMATION FOR SEQ ID NO:16:

(i) SEQUENCE CHARACTERISTICS:
(A) LENGTH: 689 amino acids
(B) TYPE: amino acid
(C) STRANDEDNESS: single
(D) TOPOLOGY: linear (xi) SEQUENCE DESCRIPTION: SEQ ID NO:16:

```
Cys Gly Gly Ser Ser Gly Gly Phe Asn Pro Pro Ala Ser Thr Pro Ile
1               5                   10                  15

Pro Asn Ala Gly Asn Ser Gly Asn Ala Gly Asn Ala Gly Asn Ala Gly
            20                  25                  30

Gly Thr Gly Gly Ala Asn Ser Gly Ala Gly Asn Ala Gly Gly Thr Gly
        35                  40                  45

Gly Ala Asn Ser Gly Ala Gly Ser Ala Ser Thr Pro Glu Pro Lys Tyr
    50                  55                  60

Lys Asp Val Pro Thr Asp Glu Asn Lys Lys Ala Glu Val Ser Gly Ile
65                  70                  75                  80

Gln Glu Pro Ala Met Gly Tyr Gly Val Glu Leu Lys Leu Arg Asn Trp
                85                  90                  95

Ile Pro Gln Glu Gln Glu Glu His Ala Lys Ile Asn Thr Asn Asp Val
            100                 105                 110

Val Lys Leu Glu Gly Asp Leu Lys His Asn Pro Phe Asp Asn Ser Ile
        115                 120                 125

Trp Gln Asn Ile Lys Asn Ser Lys Glu Val Gln Thr Val Tyr Asn Gln
    130                 135                 140

Glu Lys Gln Asn Ile Glu Asp Gln Ile Lys Arg Glu Asn Lys Gln Arg
145                 150                 155                 160

Pro Asp Lys Lys Leu Asp Asp Val Ala Leu Gln Ala Tyr Ile Glu Lys
                165                 170                 175

Val Leu Asp Asp Arg Leu Thr Glu Leu Ala Lys Pro Ile Tyr Glu Lys
            180                 185                 190

Asn Ile Asn Tyr Ser His Asp Lys Gln Asn Lys Ala Arg Thr Arg Asp
        195                 200                 205

Leu Lys Tyr Val Arg Ser Gly Tyr Ile Tyr Arg Ser Gly Tyr Ser Asn
    210                 215                 220

Ile Ile Pro Lys Lys Ile Ala Lys Thr Gly Phe Asp Gly Ala Leu Phe
225                 230                 235                 240

Tyr Gln Gly Thr Gln Thr Ala Lys Gln Leu Pro Val Ser Gln Val Lys
                245                 250                 255

Tyr Lys Gly Thr Trp Asp Phe Met Thr Asp Ala Lys Lys Gly Gln Ser
            260                 265                 270

Phe Ser Ser Phe Gly Thr Ser Gln Arg Leu Ala Gly Asp Arg Tyr Ser
        275                 280                 285

Ala Met Ser Tyr His Glu Tyr Pro Ser Leu Leu Thr Asp Glu Lys Asn
    290                 295                 300

Lys Pro Asp Asn Tyr Asn Gly Glu Tyr Gly His Ser Ser Glu Phe Thr
305                 310                 315                 320

Val Asp Phe Ser Lys Lys Ser Leu Lys Gly Glu Leu Ser Ser Asn Ile
                325                 330                 335

Gln Asp Gly His Lys Gly Ser Val Asn Lys Thr Lys Arg Tyr Asp Ile
            340                 345                 350
```

-continued

```
Asp Ala Asn Ile Tyr Gly Asn Arg Phe Arg Gly Ser Ala Thr Ala Ser
        355                 360                 365

Asp Thr Thr Glu Ala Ser Lys Ser Lys His Pro Phe Thr Ser Asp Ala
    370                 375                 380

Lys Asn Ser Leu Glu Gly Gly Phe Tyr Gly Pro Asn Ala Glu Glu Leu
385                 390                 395                 400

Ala Gly Lys Phe Leu Thr Asn Asp Asn Lys Leu Phe Gly Val Phe Gly
                405                 410                 415

Ala Lys Arg Glu Ser Glu Ala Lys Glu Lys Thr Glu Ala Ile Leu Asp
            420                 425                 430

Ala Tyr Ala Leu Gly Thr Phe Asn Lys Pro Gly Thr Thr Asn Pro Ala
        435                 440                 445

Phe Thr Ala Asn Ser Lys Lys Glu Leu Asp Asn Phe Gly Asn Ala Lys
    450                 455                 460

Lys Leu Val Leu Gly Ser Thr Val Ile Asp Leu Val Pro Thr Gly Ala
465                 470                 475                 480

Thr Lys Asp Val Asn Glu Phe Lys Glu Lys Pro Lys Ser Ala Thr Asn
                485                 490                 495

Lys Ala Gly Glu Thr Leu Met Val Asn Asp Glu Val Ile Val Lys Thr
            500                 505                 510

Tyr Gly Tyr Gly Arg Asn Phe Glu Tyr Leu Lys Phe Gly Glu Leu Ser
        515                 520                 525

Ile Gly Gly Ser His Ser Val Phe Leu Gln Gly Glu Arg Thr Ala Glu
    530                 535                 540

Lys Ala Val Pro Thr Glu Gly Thr Ala Lys Tyr Leu Gly Asn Trp Val
545                 550                 555                 560

Gly Tyr Ile Thr Gly Lys Asp Thr Gly Thr Ser Thr Gly Lys Ser Phe
                565                 570                 575

Asn Glu Ala Gln Asp Ile Ala Asp Phe Asp Ile Asp Phe Glu Arg Lys
            580                 585                 590

Ser Val Lys Gly Lys Leu Thr Thr Gln Gly Arg Gln Asp Pro Val Phe
        595                 600                 605

Asn Ile Thr Gly Gln Ile Ala Gly Asn Gly Trp Thr Gly Thr Ala Ser
    610                 615                 620

Thr Ala Lys Ala Asn Val Gly Gly Tyr Lys Ile Asp Ser Ser Ser Thr
625                 630                 635                 640

Gly Lys Ser Ile Val Ile Glu Asn Ala Lys Val Thr Gly Gly Phe Tyr
                645                 650                 655

Gly Pro Asn Ala Asn Glu Met Gly Gly Ser Phe Thr His Asp Thr Asp
            660                 665                 670

Asp Ser Lys Ala Ser Val Val Phe Gly Thr Lys Arg Gln Glu Glu Val
        675                 680                 685

Lys
```

(2) INFORMATION FOR SEQ ID NO:17:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:17:

```
Asn Glu Val Thr Gly Leu Gly
1               5
```

-continued (2) INFORMATION FOR SEQ ID NO:18:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:18:

```
Gly Ala Ile Asn Glu Ile Glu
1               5
```

(2) INFORMATION FOR SEQ ID NO:19:

(i) SEQUENCE CHARACTERISTICS:
(A) LENGTH: 60 base pairs
(B) TYPE: nucleic acid
(C) STRANDEDNESS: single
(D) TOPOLOGY: linear (xi) SEQUENCE DESCRIPTION: SEQ ID NO:19:

```
AATCAATCAA AACAAAACAA CAAATCCAAA AAATCCAAAC AAGTATTAAA ACTTAGTGCC     60
```

(2) INFORMATION FOR SEQ ID NO:20:

(i) SEQUENCE CHARACTERISTICS:
(A) LENGTH: 57 base pairs
(B) TYPE: nucleic acid
(C) STRANDEDNESS: single
(D) TOPOLOGY: linear (xi) SEQUENCE DESCRIPTION: SEQ ID NO:20:

```
AAACACATTC CTTTAACCAC ACTGTGTGTG GCAATCTCTG CCGTCTTATT AACCGCT        57
```

(2) INFORMATION FOR SEQ ID NO:21:

(i) SEQUENCE CHARACTERISTICS:
(A) LENGTH: 912 amino acids
(B) TYPE: amino acid
(C) STRANDEDNESS: single
(D) TOPOLOGY: linear (xi) SEQUENCE DESCRIPTION: SEQ ID NO:21:

```
Met Thr Lys Lys Pro Tyr Phe Arg Leu Ser Ile Ile Ser Cys Leu Leu
1               5                   10                  15

Ile Gly Cys Tyr Val Lys Ala Glu Thr Gln Ser Ile Lys Asp Thr Lys
            20                  25                  30

Glu Ala Ile Ser Ser Glu Val Asp Thr Gln Ser Thr Glu Asp Ser Glu
        35                  40                  45

Leu Glu Thr Ile Ser Val Thr Ala Glu Lys Ile Arg Asp Arg Lys Asp
    50                  55                  60

Asn Glu Val Thr Gly Leu Gly Lys Ile Ile Lys Thr Ser Glu Ser Ile
65                  70                  75                  80

Ser Arg Glu Gln Val Leu Asn Ile Arg Asp Leu Thr Arg Tyr Asp Pro
                85                  90                  95

Gly Ile Ser Val Val Glu Gln Gly Arg Gly Ala Ser Ser Gly Tyr Ser
            100                 105                 110

Ile Arg Gly Met Asp Arg Asn Arg Val Ala Leu Leu Val Asp Gly Leu
        115                 120                 125

Pro Gln Thr Gln Ser Tyr Val Val Gln Ser Pro Leu Val Ala Arg Ser
    130                 135                 140

Gly Tyr Ser Gly Thr Gly Ala Ile Asn Glu Ile Glu Tyr Glu Asn Val
```

-continued

```
145                 150                 155                 160

Lys Ala Val Glu Ile Ser Lys Gly Gly Ser Ser Ser Glu Tyr Gly Asn
                165                 170                 175

Gly Ala Leu Ala Gly Ser Val Thr Phe Gln Ser Lys Ser Ala Ala Asp
            180                 185                 190

Ile Leu Glu Gly Asp Lys Ser Trp Gly Ile Gln Thr Lys Asn Ala Tyr
        195                 200                 205

Ser Ser Lys Asn Lys Gly Phe Thr His Ser Leu Ala Val Ala Gly Lys
    210                 215                 220

Gln Gly Gly Phe Glu Gly Leu Ala Ile Tyr Thr Gln Arg Asn Ser Ile
225                 230                 235                 240

Glu Thr Gln Val His Lys Asp Ala Leu Lys Gly Val Gln Ser Tyr Asp
                245                 250                 255

Arg Leu Ile Ala Thr Thr Asp Lys Ser Ser Gly Tyr Phe Val Ile Gln
            260                 265                 270

Gly Glu Cys Pro Asn Gly Asp Asp Lys Cys Ala Ala Lys Pro Pro Ala
        275                 280                 285

Thr Leu Ser Thr Gln Ser Glu Thr Val Ser Val Ser Asp Tyr Thr Gly
    290                 295                 300

Ala Asn Arg Ile Lys Pro Asn Pro Met Lys Tyr Glu Ser Gln Ser Trp
305                 310                 315                 320

Phe Leu Arg Gly Gly Tyr His Phe Ser Glu Gln His Tyr Ile Gly Gly
                325                 330                 335

Ile Phe Glu Phe Thr Gln Gln Lys Phe Asp Ile Arg Asp Met Thr Phe
            340                 345                 350

Pro Ala Tyr Leu Ser Pro Thr Glu Arg Arg Asp Asp Ser Ser Arg Ser
        355                 360                 365

Phe Tyr Pro Met Gln Asp His Gly Ala Tyr Gln His Ile Glu Asp Gly
    370                 375                 380

Arg Gly Val Lys Tyr Ala Ser Gly Leu Tyr Phe Asp Glu His His Arg
385                 390                 395                 400

Lys Gln Arg Val Gly Ile Glu Tyr Ile Tyr Glu Asn Lys Asn Lys Ala
                405                 410                 415

Gly Ile Ile Asp Lys Ala Val Leu Ser Ala Asn Gln Gln Asn Ile Ile
            420                 425                 430

Leu Asp Ser Tyr Met Arg His Thr His Cys Ser Leu Tyr Pro Asn Pro
        435                 440                 445

Ser Lys Asn Cys Arg Pro Thr Leu Asp Lys Pro Tyr Ser Tyr Tyr Arg
    450                 455                 460

Ser Asp Arg Asn Val Tyr Lys Glu Lys His Asn Met Leu Gln Leu Asn
465                 470                 475                 480

Leu Glu Lys Lys Ile Gln Gln Asn Trp Leu Thr His Gln Ile Val Phe
                485                 490                 495

Asn Leu Gly Phe Asp Asp Phe Thr Ser Ala Leu Gln His Lys Asp Tyr
            500                 505                 510

Leu Thr Arg Arg Val Ile Ala Thr Ala Asp Ser Ile Pro Arg Lys Pro
        515                 520                 525

Gly Glu Thr Gly Lys Pro Arg Asn Gly Leu Gln Ser Gln Pro Tyr Leu
    530                 535                 540

Tyr Pro Lys Pro Glu Pro Tyr Phe Ala Gly Gln Asp His Cys Asn Tyr
545                 550                 555                 560

Gln Gly Ser Ser Ser Asn Tyr Arg Asp Cys Lys Val Arg Leu Ile Lys
                565                 570                 575
```

-continued

```
Gly Lys Asn Tyr Tyr Phe Ala Ala Arg Asn Asn Met Ala Leu Gly Lys
            580                 585                 590

Tyr Val Asp Leu Gly Leu Gly Ile Arg Tyr Asp Val Ser Arg Thr Lys
        595                 600                 605

Ala Asn Glu Ser Thr Ile Ser Val Gly Lys Phe Lys Asn Phe Ser Trp
    610                 615                 620

Asn Thr Gly Ile Val Ile Lys Pro Thr Glu Trp Leu Asp Leu Ser Tyr
625                 630                 635                 640

Arg Leu Ser Thr Gly Phe Arg Asn Pro Ser Phe Ser Glu Met Tyr Gly
                645                 650                 655

Trp Arg Tyr Gly Gly Lys Asn Asp Glu Val Tyr Val Gly Lys Phe Lys
            660                 665                 670

Pro Glu Thr Ser Arg Asn Gln Glu Phe Gly Leu Ala Leu Lys Gly Asp
        675                 680                 685

Phe Gly Asn Ile Glu Ile Ser His Phe Ser Asn Ala Tyr Arg Asn Leu
    690                 695                 700

Ile Ala Phe Ala Glu Glu Leu Ser Lys Asn Gly Thr Gly Lys Gly Asn
705                 710                 715                 720

Tyr Gly Tyr His Asn Ala Gln Asn Ala Lys Leu Val Gly Val Asn Ile
                725                 730                 735

Thr Ala Gln Leu Asp Phe Asn Gly Leu Trp Lys Arg Ile Pro Tyr Gly
            740                 745                 750

Trp Tyr Ala Thr Phe Ala Tyr Asn Gln Val Lys Val Lys Asp Gln Lys
        755                 760                 765

Ile Asn Ala Gly Leu Ala Ser Val Ser Ser Tyr Leu Phe Asp Ala Ile
    770                 775                 780

Gln Pro Ser Arg Tyr Ile Ile Gly Leu Gly Tyr Asp His Pro Ser Asn
785                 790                 795                 800

Thr Trp Gly Ile Asn Thr Met Phe Thr Gln Ser Lys Ala Lys Ser Gln
                805                 810                 815

Asn Glu Leu Leu Gly Lys Arg Ala Leu Gly Asn Asn Ser Arg Asp Val
            820                 825                 830

Lys Ser Thr Arg Lys Leu Thr Arg Ala Trp His Ile Leu Asp Val Ser
        835                 840                 845

Gly Tyr Tyr Met Ala Asn Lys Asn Ile Met Leu Arg Leu Gly Ile Tyr
    850                 855                 860

Asn Leu Phe Asn Tyr Arg Tyr Val Thr Trp Glu Ala Val Arg Gln Thr
865                 870                 875                 880

Ala Gln Gly Ala Val Asn Gln His Gln Asn Val Gly Ser Tyr Thr Arg
                885                 890                 895

Tyr Ala Ala Ser Gly Arg Asn Tyr Thr Leu Thr Leu Glu Met Lys Phe
            900                 905                 910
```

(2) INFORMATION FOR SEQ ID NO:22:

(i) SEQUENCE CHARACTERISTICS:
(A) LENGTH: 908 amino acids
(B) TYPE: amino acid
(C) STRANDEDNESS: single
(D) TOPOLOGY: linear (xi) SEQUENCE DESCRIPTION: SEQ ID NO:22:

```
Met Gln Gln Gln His Leu Phe Arg Leu Asn Ile Leu Cys Leu Ser Leu
1               5                   10                  15

Met Thr Ala Leu Pro Val Tyr Ala Glu Asn Val Gln Ala Glu Gln Ala
```

-continued

```
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Ser
    50                  55                  60

Ser Asp Thr Leu Ser Lys Glu Gln Val Leu Asn Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Val Ser Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Ser
145                 150                 155                 160

Glu Tyr Gly Asn Gly Ala Leu Ala Gly Ser Val Ala Phe Gln Thr Lys
                165                 170                 175

Thr Ala Ala Asp Ile Ile Gly Glu Gly Lys Gln Trp Gly Ile Gln Ser
            180                 185                 190

Lys Thr Ala Tyr Ser Gly Lys Asp His Ala Leu Thr Gln Ser Leu Ala
        195                 200                 205

Leu Ala Gly Arg Ser Gly Gly Ala Glu Ala Leu Leu Ile Tyr Thr Lys
    210                 215                 220

Arg Arg Gly Arg Glu Ile His Ala His Lys Asp Ala Gly Lys Gly Val
225                 230                 235                 240

Gln Ser Phe Asn Arg Leu Val Leu Asp Glu Asp Lys Lys Glu Gly Gly
                245                 250                 255

Ser Gln Tyr Arg Tyr Phe Ile Val Glu Glu Glu Cys His Asn Gly Tyr
            260                 265                 270

Ala Ala Cys Lys Asn Lys Leu Lys Glu Asp Ala Ser Val Lys Asp Glu
        275                 280                 285

Arg Lys Thr Val Ser Thr Gln Asp Tyr Thr Gly Ser Asn Arg Leu Leu
    290                 295                 300

Ala Asn Pro Leu Glu Tyr Gly Ser Gln Ser Trp Leu Phe Arg Pro Gly
305                 310                 315                 320

Trp His Leu Asp Asn Arg His Tyr Val Gly Ala Val Leu Glu Arg Thr
                325                 330                 335

Gln Gln Thr Phe Asp Thr Arg Asp Met Thr Val Pro Ala Tyr Phe Thr
            340                 345                 350

Ser Glu Asp Tyr Val Pro Gly Ser Leu Lys Gly Leu Gly Lys Tyr Ser
        355                 360                 365

Gly Asp Asn Lys Ala Glu Arg Leu Phe Val Gln Gly Glu Gly Ser Thr
    370                 375                 380

Leu Gln Gly Ile Gly Tyr Gly Thr Gly Val Phe Tyr Asp Glu Arg His
385                 390                 395                 400

Thr Lys Asn Arg Tyr Gly Val Glu Tyr Val Tyr His Asn Ala Asp Lys
                405                 410                 415

Asp Thr Trp Ala Asp Tyr Ala Arg Leu Ser Tyr Asp Arg Gln Gly Ile
            420                 425                 430

Asp Leu Asp Asn Arg Leu Gln Gln Thr His Cys Ser His Asp Gly Ser
        435                 440                 445
```

-continued

```
Asp Lys Asn Cys Arg Pro Asp Gly Asn Lys Pro Tyr Ser Phe Tyr Lys
    450                 455                 460

Ser Asp Arg Met Ile Tyr Glu Glu Ser Arg Asn Leu Phe Gln Ala Val
465                 470                 475                 480

Phe Lys Lys Ala Phe Asp Thr Ala Lys Ile Arg His Asn Leu Ser Ile
                485                 490                 495

Asn Leu Gly Tyr Asp Arg Phe Lys Ser Gln Leu Ser His Ser Asp Tyr
            500                 505                 510

Tyr Leu Gln Asn Ala Val Gln Ala Tyr Asp Leu Ile Thr Pro Pro Lys
        515                 520                 525

Pro Pro Phe Pro Asn Gly Ser Lys Asp Asn Pro Tyr Arg Val Ser Ile
    530                 535                 540

Gly Lys Thr Thr Val Asn Thr Ser Pro Ile Cys Arg Phe Gly Asn Asn
545                 550                 555                 560

Thr Tyr Thr Asp Cys Thr Pro Arg Asn Ile Gly Gly Asn Gly Tyr Tyr
                565                 570                 575

Ala Ala Val Gln Asp Asn Val Arg Leu Gly Arg Trp Ala Asp Val Gly
            580                 585                 590

Ala Gly Ile Arg Tyr Asp Tyr Arg Ser Thr His Ser Glu Asp Lys Ser
        595                 600                 605

Val Ser Thr Gly Thr His Arg Asn Leu Ser Trp Asn Ala Gly Val Val
    610                 615                 620

Leu Lys Pro Phe Thr Trp Met Asp Leu Thr Tyr Arg Ala Ser Thr Gly
625                 630                 635                 640

Phe Arg Leu Pro Ser Phe Ala Glu Met Tyr Gly Trp Arg Ala Gly Glu
                645                 650                 655

Ser Leu Lys Thr Leu Asp Leu Lys Pro Glu Lys Ser Phe Asn Arg Glu
            660                 665                 670

Ala Gly Ile Val Phe Lys Gly Asp Phe Gly Asn Leu Glu Ala Ser Tyr
        675                 680                 685

Phe Asn Asn Ala Tyr Arg Asp Leu Ile Ala Phe Gly Tyr Glu Thr Arg
    690                 695                 700

Thr Gln Asn Gly Gln Thr Ser Ala Ser Gly Asp Pro Gly Tyr Arg Asn
705                 710                 715                 720

Ala Gln Asn Ala Arg Ile Ala Gly Ile Asn Ile Leu Gly Lys Ile Asp
                725                 730                 735

Trp His Gly Val Trp Gly Gly Leu Pro Asp Gly Leu Tyr Ser Thr Leu
            740                 745                 750

Ala Tyr Asn Arg Ile Lys Val Lys Asp Ala Asp Ile Arg Ala Asp Arg
        755                 760                 765

Thr Phe Val Thr Ser Tyr Leu Phe Asp Ala Val Gln Pro Ser Arg Tyr
    770                 775                 780

Val Leu Gly Leu Gly Tyr Asp His Pro Asp Gly Ile Trp Gly Ile Asn
785                 790                 795                 800

Thr Met Phe Thr Tyr Ser Lys Ala Lys Ser Val Asp Glu Leu Leu Gly
                805                 810                 815

Ser Gln Ala Leu Leu Asn Gly Asn Ala Asn Ala Lys Lys Ala Ala Ser
            820                 825                 830

Arg Arg Thr Arg Pro Trp Tyr Val Thr Asp Val Ser Gly Tyr Tyr Asn
        835                 840                 845

Ile Lys Lys His Leu Thr Leu Arg Ala Gly Val Tyr Asn Leu Leu Asn
    850                 855                 860
```

-continued

```
Tyr Arg Tyr Val Thr Trp Glu Asn Val Arg Gln Thr Ala Gly Gly Ala
865                 870                 875                 880

Val Asn Gln His Lys Asn Val Gly Val Tyr Asn Arg Tyr Ala Ala Pro
                885                 890                 895

Gly Arg Asn Tyr Thr Phe Ser Leu Glu Met Lys Phe
            900                 905
```

(2) INFORMATION FOR SEQ ID NO:23:

(i) SEQUENCE CHARACTERISTICS:
(A) LENGTH: 911 amino acids
(B) TYPE: amino acid
(C) STRANDEDNESS: single
(D) TOPOLOGY: linear (xi) SEQUENCE DESCRIPTION: SEQ ID NO:23:

```
Met Gln Gln Gln His Leu Phe Arg Leu Asn Ile Leu Cys Leu Ser Leu
1               5                   10                  15

Met Thr Ala Leu Pro Ala Tyr Ala Glu Asn Val Gln Ala Gly Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Thr
    50                  55                  60

Ala Asp Thr Leu Ser Lys Glu Gln Val Leu Asp Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Leu Ala Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
            180                 185                 190

Lys Thr Ala Tyr Ser Gly Lys Asn Arg Gly Leu Thr Gln Ser Ile Ala
        195                 200                 205

Leu Ala Gly Arg Ile Gly Gly Ala Glu Ala Leu Leu Ile His Thr Gly
    210                 215                 220

Arg Arg Ala Gly Glu Ile Arg Ala His Glu Asp Ala Gly Arg Gly Val
225                 230                 235                 240

Gln Ser Phe Asn Arg Leu Val Pro Val Glu Asp Ser Ser Glu Tyr Ala
                245                 250                 255

Tyr Phe Ile Val Glu Asp Glu Cys Glu Gly Lys Asn Tyr Glu Thr Cys
            260                 265                 270

Lys Ser Lys Pro Lys Lys Asp Val Val Gly Lys Asp Glu Arg Gln Thr
        275                 280                 285

Val Ser Thr Arg Asp Tyr Thr Gly Pro Asn Arg Phe Leu Ala Asp Pro
    290                 295                 300

Leu Ser Tyr Glu Ser Arg Ser Trp Leu Phe Arg Pro Gly Phe Arg Phe
305                 310                 315                 320
```

-continued

```
Glu Asn Lys Arg His Tyr Ile Gly Gly Ile Leu Glu His Thr Gln Gln
                325                 330                 335

Thr Phe Asp Thr Arg Asp Met Thr Val Pro Ala Phe Leu Thr Lys Ala
            340                 345                 350

Val Phe Asp Ala Asn Ser Lys Gln Ala Gly Ser Leu Pro Gly Asn Gly
        355                 360                 365

Lys Tyr Ala Gly Asn His Lys Tyr Gly Gly Leu Phe Thr Asn Gly Glu
    370                 375                 380

Asn Gly Ala Leu Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Asp Tyr Ala Arg Leu Ser Tyr Asp Arg
            420                 425                 430

Gln Gly Ile Gly Leu Asp Asn His Phe Gln Gln Thr His Cys Ser Ala
        435                 440                 445

Asp Gly Ser Asp Lys Tyr Cys Arg Pro Ser Ala Asp Lys Pro Phe Ser
    450                 455                 460

Tyr Tyr Lys Ser Asp Arg Val Ile Tyr Gly Glu Ser His Arg Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Phe Asp Arg Phe Asp Ser Asn Leu Arg His
            500                 505                 510

Gln Asp Tyr Tyr Tyr Gln His Ala Asn Arg Ala Tyr Ser Ser Lys Thr
        515                 520                 525

Pro Pro Lys Thr Ala Asn Pro Asn Gly Asp Lys Ser Lys Pro Tyr Trp
    530                 535                 540

Val Ser Ile Gly Gly Gly Asn Val Val Thr Gly Gln Ile Cys Leu Phe
545                 550                 555                 560

Gly Asn Asn Thr Tyr Thr Asp Cys Thr Pro Arg Ser Ile Asn Gly Lys
                565                 570                 575

Ser Tyr Tyr Ala Ala Val Arg Asp Asn Val Arg Leu Gly Arg Trp Ala
            580                 585                 590

Asp Val Gly Ala Gly Leu Arg Tyr Asp Tyr Arg Ser Thr His Ser Asp
        595                 600                 605

Asp Gly Ser Val Ser Thr Gly Thr His Arg Thr Leu Ser Trp Asn Ala
    610                 615                 620

Gly Ile Val Leu Lys Pro Ala Asp Trp Leu Asp Leu Thr Tyr Arg Thr
625                 630                 635                 640

Ser Thr Gly Phe Arg Leu Pro Ser Phe Ala Glu Met Tyr Gly Trp Arg
                645                 650                 655

Ser Gly Val Gln Ser Lys Ala Val Lys Ile Asp Pro Glu Lys Ser Phe
            660                 665                 670

Asn Lys Glu Ala Gly Ile Val Phe Lys Gly Asp Phe Gly Asn Leu Glu
        675                 680                 685

Ala Ser Trp Phe Asn Asn Ala Tyr Arg Asp Leu Ile Val Arg Gly Tyr
    690                 695                 700

Glu Ala Gln Ile Lys Asn Gly Lys Glu Glu Ala Lys Gly Asp Pro Ala
705                 710                 715                 720

Tyr Leu Asn Ala Gln Ser Ala Arg Ile Thr Gly Ile Asn Ile Leu Gly
                725                 730                 735
```

-continued

```
Lys Ile Asp Trp Asn Gly Val Trp Asp Lys Leu Pro Glu Gly Trp Tyr
            740                 745                 750

Ser Thr Phe Ala Tyr Asn Arg Val His Val Arg Asp Ile Lys Lys Arg
        755                 760                 765

Ala Asp Arg Thr Asp Ile Gln Ser His Leu Phe Asp Ala Ile Gln Pro
    770                 775                 780

Ser Arg Tyr Val Val Gly Leu Gly Tyr Asp Gln Pro Glu Gly Lys Trp
785                 790                 795                 800

Gly Val Asn Gly Met Leu Thr Tyr Ser Lys Ala Lys Glu Ile Thr Glu
                805                 810                 815

Leu Leu Gly Ser Arg Ala Leu Leu Asn Gly Asn Ser Arg Asn Thr Lys
            820                 825                 830

Ala Thr Ala Arg Arg Thr Arg Pro Trp Tyr Ile Val Asp Val Ser Gly
        835                 840                 845

Tyr Tyr Thr Ile Lys Lys His Phe Thr Leu Arg Ala Gly Val Tyr Asn
    850                 855                 860

Leu Leu Asn Tyr Arg Tyr Val Thr Trp Glu Asn Val Arg Gln Thr Ala
865                 870                 875                 880

Gly Gly Ala Val Asn Gln His Lys Asn Val Gly Val Tyr Asn Arg Tyr
                885                 890                 895

Ala Ala Pro Gly Arg Asn Tyr Thr Phe Ser Leu Glu Met Lys Phe
            900                 905                 910
```

(2) INFORMATION FOR SEQ ID NO:24:

(i) SEQUENCE CHARACTERISTICS:
(A) LENGTH: 915 amino acids
(B) TYPE: amino acid
(C) STRANDEDNESS: single
(D) TOPOLOGY: linear (xi) SEQUENCE DESCRIPTION: SEQ ID NO:24:

```
Met Gln Gln Gln His Leu Phe Arg Leu Asn Ile Leu Cys Leu Ser Leu
1               5                   10                  15

Met Thr Ala Leu Pro Ala Tyr Ala Glu Asn Val Gln Ala Gly Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Thr
    50                  55                  60

Ala Asp Thr Leu Ser Lys Glu Gln Val Leu Asp Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Leu Ala Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Val
145                 150                 155                 160

Glu Gln Gly Ser Gly Ala Leu Ala Gly Ser Val Ala Phe Gln Thr Lys
                165                 170                 175

Thr Ala Asp Asp Val Ile Gly Glu Gly Arg Gln Trp Gly Ile Gln Ser
            180                 185                 190
```

-continued

```
Lys Thr Ala Tyr Ser Gly Lys Asn Arg Gly Leu Thr Gln Ser Leu Ala
        195                 200                 205

Leu Ala Gly Arg Ile Gly Gly Ala Glu Ala Leu Leu Ile Arg Thr Gly
    210                 215                 220

Arg His Ala Gly Glu Ile Arg Ala His Glu Ala Ala Gly Arg Gly Val
225                 230                 235                 240

Gln Ser Phe Asn Arg Leu Ala Pro Val Asp Asp Gly Ser Lys Tyr Ala
                245                 250                 255

Tyr Phe Ile Val Glu Glu Glu Cys Lys Asn Gly Gly His Glu Lys Cys
            260                 265                 270

Lys Ala Asn Pro Pro Lys Asp Val Val Gly Glu Asp Lys Arg Gln Thr
        275                 280                 285

Val Ser Thr Arg Asp Tyr Thr Gly Pro Asn Arg Phe Leu Ala Asp Pro
    290                 295                 300

Leu Ser Tyr Glu Ser Arg Ser Trp Leu Phe Arg Pro Gly Phe Arg Phe
305                 310                 315                 320

Glu Asn Lys Arg His Tyr Ile Gly Gly Ile Leu Glu Arg Thr Gln Gln
                325                 330                 335

Thr Phe Asp Thr Arg Asp Met Thr Val Pro Ala Phe Leu Thr Lys Ala
            340                 345                 350

Val Phe Asp Ala Asn Gln Lys Gln Ala Gly Ser Leu Arg Gly Asn Gly
        355                 360                 365

Lys Tyr Ala Gly Asn His Lys Tyr Gly Gly Leu Phe Thr Ser Gly Glu
    370                 375                 380

Asn Asn Ala Pro Val Gly Ala Glu Tyr Gly Thr Gly Val Phe Tyr Asp
385                 390                 395                 400

Glu Thr His Thr Lys Ser Arg Tyr Gly Leu Glu Tyr Val Tyr Thr Asn
                405                 410                 415

Ala Asp Lys Asp Thr Trp Ala Asp Tyr Ala Arg Leu Ser Tyr Asp Arg
            420                 425                 430

Gln Gly Ile Gly Leu Asp Asn His Phe Gln Gln Thr His Cys Ser Ala
        435                 440                 445

Asp Gly Ser Asp Lys Tyr Cys Arg Pro Ser Ala Asp Lys Pro Phe Ser
    450                 455                 460

Tyr Tyr Lys Ser Asp Arg Val Ile Tyr Gly Glu Ser His Lys Leu Leu
465                 470                 475                 480

Gln Ala Ala Phe Lys Lys Ser Phe Asp Thr Ala Lys Ile Arg His Asn
                485                 490                 495

Leu Ser Val Asn Leu Gly Tyr Asp Arg Phe Gly Ser Asn Leu Arg His
            500                 505                 510

Gln Asp Tyr Tyr Tyr Gln Ser Ala Asn Arg Ala Tyr Ser Ser Lys Thr
        515                 520                 525

Pro Pro Gln Asn Asn Gly Lys Lys Thr Ser Pro Asn Gly Arg Glu Lys
    530                 535                 540

Asn Pro Tyr Trp Val Ser Ile Gly Arg Gly Asn Val Val Thr Arg Gln
545                 550                 555                 560

Ile Cys Leu Phe Gly Asn Asn Thr Tyr Thr Asp Cys Thr Pro Arg Ser
                565                 570                 575

Ile Asn Gly Lys Ser Tyr Tyr Ala Ala Val Arg Asp Asn Val Arg Leu
            580                 585                 590

Gly Arg Trp Ala Asp Val Gly Ala Gly Leu Arg Tyr Asp Tyr Arg Ser
        595                 600                 605
```

-continued

```
Thr His Ser Asp Asp Gly Ser Val Ser Thr Gly Thr His Arg Thr Leu
    610                 615                 620

Ser Trp Asn Ala Gly Ile Val Leu Lys Pro Ala Asp Trp Leu Asp Leu
625                 630                 635                 640

Thr Tyr Arg Thr Ser Thr Gly Phe Arg Leu Pro Ser Phe Ala Glu Met
                645                 650                 655

Tyr Gly Trp Arg Ser Gly Asp Lys Ile Lys Ala Val Lys Ile Asp Pro
            660                 665                 670

Glu Lys Ser Phe Asn Lys Glu Ala Gly Ile Val Phe Lys Gly Asp Phe
        675                 680                 685

Gly Asn Leu Glu Ala Ser Trp Phe Asn Asn Ala Tyr Arg Asp Leu Ile
    690                 695                 700

Val Arg Gly Tyr Glu Ala Gln Ile Lys Asp Gly Lys Glu Gln Val Lys
705                 710                 715                 720

Gly Asn Pro Ala Tyr Leu Asn Ala Gln Ser Ala Arg Ile Thr Gly Ile
                725                 730                 735

Asn Ile Leu Gly Lys Ile Asp Trp Asn Gly Val Trp Asp Lys Leu Pro
            740                 745                 750

Glu Gly Trp Tyr Ser Thr Phe Ala Tyr Asn Arg Val Arg Val Arg Asp
        755                 760                 765

Ile Lys Lys Arg Ala Asp Arg Thr Asp Ile Gln Ser His Leu Phe Asp
    770                 775                 780

Ala Ile Gln Pro Ser Arg Tyr Val Val Gly Ser Gly Tyr Asp Gln Pro
785                 790                 795                 800

Glu Gly Lys Trp Gly Val Asn Gly Met Leu Thr Tyr Ser Lys Ala Lys
                805                 810                 815

Glu Ile Thr Glu Leu Leu Gly Ser Arg Ala Leu Leu Asn Gly Asn Ser
            820                 825                 830

Arg Asn Thr Lys Ala Thr Ser Arg Arg Thr Arg Pro Trp Tyr Ile Val
        835                 840                 845

Asp Val Ser Gly Tyr Tyr Thr Val Lys Lys His Phe Thr Leu Arg Ala
    850                 855                 860

Gly Val Tyr Asn Leu Leu Asn His Arg Tyr Val Thr Trp Glu Asn Val
865                 870                 875                 880

Arg Gln Thr Ala Ala Gly Ala Val Asn Gln His Lys Asn Val Gly Val
                885                 890                 895

Tyr Asn Arg Tyr Ala Ala Pro Gly Arg Asn Tyr Thr Phe Ser Leu Glu
            900                 905                 910

Met Lys Phe
        915
```

(2) INFORMATION FOR SEQ ID NO:25:

(i) SEQUENCE CHARACTERISTICS:
(A) LENGTH: 657 amino acids
(B) TYPE: amino acid
(C) STRANDEDNESS: single
(D) TOPOLOGY: linear (xi) SEQUENCE DESCRIPTION: SEQ ID NO:25:

```
Met Lys Ser Val Pro Leu Ile Ser Gly Gly Leu Ser Phe Leu Leu Ser
1               5                   10                  15

Ala Cys Ser Gly Gly Gly Ser Phe Asp Val Asp Asn Val Ser Asn Thr
            20                  25                  30

Pro Ser Ser Lys Pro Arg Tyr Gln Asp Asp Thr Ser Asn Gln Arg Lys
        35                  40                  45
```

-continued

```
Lys Ser Asn Leu Lys Lys Leu Phe Ile Ser Leu Gly Tyr Gly Met Lys
    50                  55                  60

Leu Val Ala Gln Asn Leu Arg Gly Asn Lys Glu Pro Ser Phe Leu Asn
65                  70                  75                  80

Glu Asp Asp Tyr Ile Ser Tyr Phe Ser Ser Leu Ser Thr Ile Glu Lys
                85                  90                  95

Asp Val Lys Asp Asn Lys Asn Gly Ala Asp Leu Ile Gly Ser Ile Asp
            100                 105                 110

Glu Pro Ser Thr Thr Asn Pro Pro Glu Lys His His Gly Gln Lys Tyr
        115                 120                 125

Val Tyr Ser Gly Leu Tyr Tyr Thr Pro Ser Trp Ser Leu Asn Asp Ser
    130                 135                 140

Lys Asn Lys Phe Tyr Leu Gly Tyr Tyr Gly Tyr Ala Phe Tyr Tyr Gly
145                 150                 155                 160

Asn Lys Thr Ala Thr Asn Leu Pro Val Asn Gly Val Val Lys Tyr Lys
                165                 170                 175

Gly Thr Trp Asp Phe Ile Thr Ala Thr Lys Asn Gly Lys Arg Tyr Pro
            180                 185                 190

Leu Leu Ser Asn Gly Gly Ser His Ala Tyr Tyr Arg Arg Ser Ala Ile
        195                 200                 205

Pro Glu Asp Ile Asp Leu Glu Asn Asp Ser Lys Asn Gly Asp Ile Gly
    210                 215                 220

Leu Ile Ser Glu Phe Ser Ala Asp Phe Gly Thr Lys Lys Leu Thr Gly
225                 230                 235                 240

Gln Leu Ser Tyr Thr Lys Arg Lys Thr Asn Asn Gln Pro Tyr Glu Lys
                245                 250                 255

Lys Lys Leu Tyr Asp Ile Asp Ala Asp Ile Tyr Ser Asn Arg Phe Arg
            260                 265                 270

Gly Thr Val Lys Pro Thr Glu Lys Asp Ser Glu Glu His Pro Phe Thr
        275                 280                 285

Ser Glu Gly Thr Leu Glu Gly Gly Phe Tyr Pro Asn Ala Glu Glu Leu
    290                 295                 300

Gly Gly Lys Phe Leu Ala Thr Asp Asn Arg Val Phe Gly Val Phe Ser
305                 310                 315                 320

Ala Lys Glu Thr Glu Glu Thr Lys Lys Glu Ala Leu Ser Lys Glu Thr
                325                 330                 335

Leu Ile Asp Gly Lys Leu Ile Thr Phe Ser Thr Lys Lys Thr Asp Ala
            340                 345                 350

Lys Thr Asn Ala Thr Thr Ser Thr Ala Ala Asn Thr Thr Thr Asp Thr
        355                 360                 365

Thr Ala Asn Thr Ile Thr Asp Glu Lys Asn Phe Lys Thr Glu Asp Ile
    370                 375                 380

Ser Ser Phe Gly Glu Ala Asp Tyr Leu Leu Ile Asp Lys Tyr Pro Ile
385                 390                 395                 400

Pro Leu Leu Pro Asp Lys Asn Thr Asn Asp Phe Ile Ser Ser Lys His
                405                 410                 415

His Thr Val Gly Asn Lys Arg Tyr Lys Val Glu Ala Cys Cys Ser Asn
            420                 425                 430

Leu Tyr Val Lys Phe Gly Met Tyr Tyr Glu Asp Pro Leu Lys Glu Lys
        435                 440                 445

Glu Thr Glu Thr Glu Thr Glu Thr Glu Lys Asp Lys Glu Lys Glu Lys
    450                 455                 460
```

-continued

```
Glu Lys Asp Lys Asp Lys Glu Lys Gln Thr Ala Ala Thr Thr Asn Thr
465                 470                 475                 480

Tyr Tyr Gln Phe Leu Leu Gly His Arg Thr Pro Lys Asp Asp Ile Pro
                485                 490                 495

Lys Thr Gly Ser Ala Lys Tyr His Gly Ser Trp Phe Gly Tyr Ile Thr
            500                 505                 510

Asp Gly Lys Thr Ser Tyr Ser Pro Ser Gly Asp Lys Lys Arg Asp Lys
        515                 520                 525

Asn Ala Val Ala Glu Phe Asn Val Asp Phe Ala Glu Lys Lys Leu Thr
    530                 535                 540

Gly Glu Leu Lys Arg His Asp Thr Gly Asn Pro Val Phe Ser Ile Glu
545                 550                 555                 560

Ala Asn Phe Asn Asn Ser Ser Asn Ala Phe Thr Gly Thr Ala Thr Ala
                565                 570                 575

Thr Asn Phe Val Ile Asp Gly Lys Asn Ser Gln Asn Lys Asn Thr Pro
            580                 585                 590

Ile Asn Ile Thr Thr Lys Val Asn Gly Ala Phe Tyr Gly Pro Lys Ala
        595                 600                 605

Ser Glu Leu Gly Gly Tyr Phe Thr Tyr Asn Gly Asn Ser Thr Ala Thr
    610                 615                 620

Asn Ser Glu Ser Ser Ser Thr Val Ser Ser Ser Ser Asn Ser Lys Asn
625                 630                 635                 640

Ala Arg Ala Ala Val Val Phe Gly Ala Arg Gln Gln Val Glu Thr Thr
                645                 650                 655

Lys
```

(2) INFORMATION FOR SEQ ID NO:26:

(i) SEQUENCE CHARACTERISTICS:
(A) LENGTH: 601 amino acids
(B) TYPE: amino acid
(C) STRANDEDNESS: single
(D) TOPOLOGY: linear (xi) SEQUENCE DESCRIPTION: SEQ ID NO:26:

```
Met Asn Asn Pro Leu Val Asn Gln Ala Ala Met Val Leu Pro Val Phe
1               5                   10                  15

Leu Leu Ser Ala Cys Leu Gly Gly Gly Gly Ser Phe Asp Leu Asp Ser
            20                  25                  30

Val Glu Thr Val Gln Asp Met His Ser Lys Pro Lys Tyr Glu Asp Glu
        35                  40                  45

Lys Ser Gln Pro Glu Ser Gln Gln Asp Val Ser Glu Asn Ser Gly Ala
    50                  55                  60

Ala Tyr Gly Phe Ala Val Lys Leu Pro Arg Arg Asn Ala His Phe Asn
65                  70                  75                  80

Pro Lys Tyr Lys Glu Lys His Lys Pro Leu Gly Ser Met Asp Trp Lys
                85                  90                  95

Lys Leu Gln Arg Gly Glu Pro Asn Ser Phe Ser Glu Arg Asp Glu Leu
            100                 105                 110

Glu Lys Lys Arg Gly Ser Ser Glu Leu Ile Glu Ser Lys Trp Glu Asp
        115                 120                 125

Gly Gln Ser Arg Val Val Gly Tyr Thr Asn Phe Thr Tyr Val Arg Ser
    130                 135                 140

Gly Tyr Val Tyr Leu Asn Lys Asn Asn Ile Asp Ile Lys Asn Asn Ile
145                 150                 155                 160
```

-continued

```
Val Leu Phe Gly Pro Asp Gly Tyr Leu Tyr Tyr Lys Gly Lys Glu Pro
                165                 170                 175

Ser Lys Glu Leu Pro Ser Glu Lys Ile Thr Tyr Lys Gly Thr Trp Asp
            180                 185                 190

Tyr Val Thr Asp Ala Met Glu Lys Gln Arg Phe Glu Gly Leu Gly Ser
        195                 200                 205

Ala Ala Gly Gly Asp Lys Ser Gly Ala Leu Ser Ala Leu Glu Glu Gly
    210                 215                 220

Val Leu Arg Asn Gln Ala Glu Ala Ser Ser Gly His Thr Asp Phe Gly
225                 230                 235                 240

Met Thr Ser Glu Phe Glu Val Asp Phe Ser Asp Lys Thr Ile Lys Gly
                245                 250                 255

Thr Leu Tyr Arg Asn Asn Arg Ile Thr Gln Asn Asn Ser Glu Asn Lys
            260                 265                 270

Gln Ile Lys Thr Thr Arg Tyr Thr Ile Gln Ala Thr Leu His Gly Asn
        275                 280                 285

Arg Phe Lys Gly Lys Ala Leu Ala Ala Asp Lys Gly Ala Thr Asn Gly
    290                 295                 300

Ser His Pro Phe Ile Ser Asp Ser Asp Ser Leu Glu Gly Gly Phe Tyr
305                 310                 315                 320

Gly Pro Lys Gly Glu Glu Leu Ala Gly Lys Phe Leu Ser Asn Asp Asn
                325                 330                 335

Lys Val Ala Ala Val Phe Gly Ala Lys Gln Lys Asp Lys Lys Asp Gly
            340                 345                 350

Glu Asn Ala Ala Gly Pro Ala Thr Glu Thr Val Ile Asp Ala Tyr Arg
        355                 360                 365

Ile Thr Gly Glu Glu Phe Lys Lys Glu Gln Ile Asp Ser Phe Gly Asp
    370                 375                 380

Val Lys Lys Leu Leu Val Asp Gly Val Glu Leu Ser Leu Leu Pro Ser
385                 390                 395                 400

Glu Gly Asn Lys Ala Ala Phe Gln His Glu Ile Glu Gln Asn Gly Val
                405                 410                 415

Lys Ala Thr Val Cys Cys Ser Asn Leu Asp Tyr Met Ser Phe Gly Lys
            420                 425                 430

Leu Ser Lys Glu Asn Lys Asp Asp Met Phe Leu Gln Gly Val Arg Thr
        435                 440                 445

Pro Val Ser Asp Val Ala Ala Arg Thr Glu Ala Asn Ala Lys Tyr Arg
    450                 455                 460

Gly Thr Trp Tyr Gly Tyr Ile Ala Asn Gly Thr Ser Trp Ser Gly Glu
465                 470                 475                 480

Ala Ser Asn Gln Phe Thr Glu Gly Gly Asn Arg Ala Glu Phe Asp Val
                485                 490                 495

Asp Phe Ser Thr Lys Lys Ile Ser Gly Thr Leu Thr Ala Lys Asp Arg
            500                 505                 510

Thr Ser Pro Ala Phe Thr Ile Thr Ala Met Ile Lys Asp Asn Gly Phe
        515                 520                 525

Ser Gly Val Ala Lys Thr Gly Glu Asn Gly Phe Ala Leu Asp Pro Gln
    530                 535                 540

Asn Thr Gly Asn Ser His Tyr Thr His Ile Glu Ala Thr Val Ser Gly
545                 550                 555                 560

Gly Phe Tyr Gly Lys Asn Ala Ile Glu Met Gly Gly Ser Phe Ser Phe
                565                 570                 575

Pro Gly Asn Ala Pro Glu Gly Lys Gln Glu Lys Ala Ser Val Val Phe
```

-continued

```
            580                 585                 590

Gly Ala Lys Arg Gln Gln Leu Val Gln
        595                 600
```

(2) INFORMATION FOR SEQ ID NO:27:

(i) SEQUENCE CHARACTERISTICS:
(A) LENGTH: 711 amino acids
(B) TYPE: amino acid
(C) STRANDEDNESS: single
(D) TOPOLOGY: linear (xi) SEQUENCE DESCRIPTION: SEQ ID NO:27:

```
Met Asn Asn Pro Leu Val Asn Gln Ala Ala Met Val Leu Pro Val Phe
1               5                   10                  15

Leu Leu Ser Ala Cys Leu Gly Gly Gly Gly Ser Phe Asp Leu Asp Ser
            20                  25                  30

Val Asp Thr Glu Ala Pro Arg Pro Ala Pro Lys Tyr Gln Asp Val Ser
        35                  40                  45

Ser Glu Lys Pro Gln Ala Gln Gln Asp Gln Gly Gly Tyr Gly Phe Ala
    50                  55                  60

Met Arg Leu Lys Arg Arg Asn Trp Tyr Pro Gly Ala Glu Glu Ser Glu
65                  70                  75                  80

Val Lys Leu Asn Glu Ser Asp Trp Glu Ala Thr Gly Leu Pro Thr Lys
                85                  90                  95

Pro Lys Glu Leu Pro Lys Arg Gln Lys Ser Val Ile Glu Lys Val Glu
            100                 105                 110

Thr Asp Gly Asp Ser Asp Ile Tyr Ser Ser Pro Tyr Leu Thr Pro Ser
        115                 120                 125

Asn His Gln Asn Gly Ser Ala Gly Asn Gly Val Asn Gln Pro Lys Asn
    130                 135                 140

Gln Ala Thr Gly His Glu Asn Phe Gln Tyr Val Tyr Ser Gly Trp Phe
145                 150                 155                 160

Tyr His Ala Ala Ser Glu Lys Asp Phe Ser Asn Lys Lys Ile Trp Lys
                165                 170                 175

Ser Gly Asp Asp Gly Tyr Ile Phe Tyr His Gly Glu Lys Pro Ser Arg
            180                 185                 190

Gln Leu Pro Ala Ser Gly Lys Val Ile Tyr Lys Gly Val Trp His Phe
        195                 200                 205

Val Thr Asp Thr Lys Lys Gly Gln Asp Phe Arg Glu Ile Ile Gln Pro
    210                 215                 220

Ser Lys Lys Gln Gly Asp Arg Tyr Ser Gly Phe Ser Gly Asp Gly Ser
225                 230                 235                 240

Glu Glu Tyr Ser Asn Lys Asn Glu Ser Thr Leu Lys Asp Asp His Glu
                245                 250                 255

Gly Tyr Gly Phe Thr Ser Asn Leu Glu Val Asp Phe Gly Asn Lys Lys
            260                 265                 270

Leu Thr Gly Lys Leu Ile Arg Asn Asn Ala Ser Leu Asn Asn Asn Thr
        275                 280                 285

Asn Asn Asp Lys His Thr Thr Gln Tyr Tyr Ser Leu Asp Ala Gln Ile
    290                 295                 300

Thr Gly Gly Asn Pro Phe Asn Gly Thr Ala Thr Ala Thr Asp Lys Lys
305                 310                 315                 320

Glu Asn Glu Thr Lys Leu His Pro Phe Val Ser Asp Ser Ser Ser Leu
                325                 330                 335
```

-continued

```
Glu Gly Gly Phe Phe Gly Pro Gln Gly Glu Glu Leu Gly Phe Arg Phe
            340                 345                 350

Leu Thr Asp Asp Gln Lys Val Ala Val Val Gly Ser Ala Lys Thr Lys
        355                 360                 365

Asp Lys Leu Glu Asn Gly Ala Ala Ala Ser Gly Ser Gly Ala Ala Ala
    370                 375                 380

Ser Gly Gly Ala Ala Gly Thr Ser Ser Glu Asn Ser Lys Leu Thr Thr
385                 390                 395                 400

Val Leu Asp Ala Val Glu Leu Thr Leu Asn Asp Lys Lys Ile Lys Asn
                405                 410                 415

Leu Asp Asn Phe Ser Asn Ala Ala Gln Leu Val Val Asp Gly Ile Met
            420                 425                 430

Ile Pro Leu Leu Pro Lys Asp Ser Glu Ser Gly Asn Thr Gln Ala Asp
        435                 440                 445

Lys Gly Lys Asn Gly Gly Thr Glu Phe Thr Arg Lys Phe Glu His Thr
    450                 455                 460

Pro Glu Ser Asp Lys Lys Asp Ala Gln Ala Gly Thr Gln Thr Asn Gly
465                 470                 475                 480

Ala Gln Thr Ala Ser Asn Thr Ala Gly Asp Thr Asn Gly Lys Thr Lys
                485                 490                 495

Thr Tyr Glu Val Glu Val Cys Cys Ser Asn Leu Asn Tyr Leu Lys Tyr
            500                 505                 510

Gly Met Leu Thr Arg Lys Asn Ser Lys Ser Ala Met Gln Ala Gly Gly
        515                 520                 525

Asn Ser Ser Gln Ala Asp Ala Lys Thr Glu Gln Val Glu Gln Ser Met
    530                 535                 540

Phe Leu Gln Gly Glu Arg Thr Asp Glu Lys Glu Ile Pro Thr Asp Gln
545                 550                 555                 560

Asn Val Val Tyr Arg Gly Ser Trp Tyr Gly His Ile Ala Asn Gly Thr
                565                 570                 575

Ser Trp Ser Gly Asn Ala Ser Asp Lys Glu Gly Gly Asn Arg Ala Asp
            580                 585                 590

Phe Thr Ile Asn Phe Ala Asp Lys Lys Ile Thr Gly Lys Leu Thr Ala
        595                 600                 605

Glu Asn Arg Thr Ala Gln Thr Phe Thr Ile Glu Gly Met Ile Gln Gly
    610                 615                 620

Asn Gly Phe Glu Gly Thr Ala Lys Thr Ala Glu Ser Gly Phe Asp Leu
625                 630                 635                 640

Asp Gln Lys Asn Thr Thr Arg Thr Pro Lys Ala Tyr Ile Thr Asp Ala
                645                 650                 655

Lys Val Lys Gly Gly Phe Tyr Gly Pro Lys Ala Glu Glu Leu Gly Gly
            660                 665                 670

Trp Phe Ala Tyr Pro Gly Asp Lys Gln Thr Glu Lys Ala Thr Ala Thr
        675                 680                 685

Ser Ser Asp Gly Asn Ser Ala Ser Ser Ala Thr Val Val Phe Gly Ala
    690                 695                 700

Lys Arg Gln Gln Pro Val Gln
705                 710
```

(2) INFORMATION FOR SEQ ID NO:28:

(i) SEQUENCE CHARACTERISTICS:
(A) LENGTH: 708 amino acids
(B) TYPE: amino acid
(C) STRANDEDNESS: single -continued (D) TOPOLOGY: linear (xi) SEQUENCE DESCRIPTION: SEQ ID NO:28:

```
Met Asn Asn Pro Leu Val Asn Gln Ala Ala Met Val Leu Pro Val Phe
1               5                   10                  15

Leu Leu Ser Ala Cys Leu Gly Gly Gly Gly Ser Phe Asp Leu Asp Ser
            20                  25                  30

Val Asp Thr Glu Ala Pro Arg Pro Ala Pro Lys Tyr Gln Asp Val Ser
        35                  40                  45

Ser Glu Lys Pro Gln Ala Gln Lys Asp Gln Gly Gly Tyr Gly Phe Ala
    50                  55                  60

Met Arg Phe Lys Arg Arg Asn Trp His Pro Ser Ala Asn Pro Lys Glu
65                  70                  75                  80

Asp Glu Val Lys Leu Lys Asn Asp Asp Trp Glu Ala Thr Gly Leu Pro
                85                  90                  95

Thr Glu Pro Lys Lys Leu Pro Leu Lys Gln Gln Ser Val Ile Ser Glu
            100                 105                 110

Val Glu Thr Asn Gly Asn Ser Lys Met Tyr Thr Ser Pro Tyr Leu Ser
        115                 120                 125

Gln Asp Ala Asp Ser Ser His Ala Asn Gly Ala Asn Gln Pro Lys Asn
    130                 135                 140

Glu Val Thr Asp Tyr Lys Lys Phe Lys Tyr Val Tyr Ser Gly Trp Phe
145                 150                 155                 160

Tyr Lys His Ala Lys Ser Glu Val Lys Asn Glu Asn Gly Leu Val Ser
                165                 170                 175

Ala Lys Arg Gly Asp Asp Gly Tyr Ile Phe Tyr His Gly Asp Lys Pro
            180                 185                 190

Ser Arg Gln Leu Pro Ala Ser Glu Ala Val Thr Tyr Lys Gly Val Trp
        195                 200                 205

His Phe Val Thr Asp Thr Lys Gln Gly Gln Lys Phe Asn Asp Ile Leu
    210                 215                 220

Glu Thr Ser Lys Gly Gln Gly Asp Lys Tyr Ser Gly Phe Ser Gly Asp
225                 230                 235                 240

Glu Gly Glu Thr Thr Ser Asn Arg Thr Asp Ser Asn Leu Asn Asp Lys
                245                 250                 255

His Glu Gly Tyr Gly Phe Thr Ser Asn Phe Lys Val Asp Phe Asn Asn
            260                 265                 270

Lys Lys Leu Thr Gly Lys Leu Ile Arg Asn Asn Lys Val Ile Asn Thr
        275                 280                 285

Ala Ala Ser Asp Gly Tyr Thr Thr Glu Tyr Tyr Ser Leu Asp Ala Thr
    290                 295                 300

Leu Arg Gly Asn Arg Phe Ser Gly Lys Ala Ile Ala Thr Asp Lys Pro
305                 310                 315                 320

Asn Thr Gly Gly Thr Lys Leu His Pro Phe Val Phe Asp Ser Ser Ser
                325                 330                 335

Leu Ser Gly Gly Phe Phe Gly Pro Gln Gly Glu Glu Leu Gly Phe Arg
            340                 345                 350

Phe Leu Ser Asp Asp Gly Lys Val Ala Val Val Gly Ser Ala Lys Thr
        355                 360                 365

Lys Asp Ser Thr Ala Asn Gly Asn Ala Pro Ala Ala Ser Ser Gly Pro
    370                 375                 380

Gly Ala Ala Thr Met Pro Ser Glu Thr Arg Leu Thr Thr Val Leu Asp
385                 390                 395                 400
```

-continued

```
Ala Val Glu Leu Thr Pro Asp Gly Lys Glu Ile Lys Asn Leu Asp Asn
                405                 410                 415

Phe Ser Asn Ala Thr Arg Leu Val Val Asp Gly Ile Met Ile Pro Leu
            420                 425                 430

Leu Pro Thr Glu Ser Gly Asn Gly Gln Ala Asp Lys Gly Lys Asn Gly
        435                 440                 445

Gly Thr Asp Phe Thr Tyr Glu Thr Thr Tyr Thr Pro Glu Ser Asp Lys
    450                 455                 460

Lys Asp Thr Lys Ala Gln Thr Gly Ala Gly Gly Met Gln Thr Ala Ser
465                 470                 475                 480

Gly Thr Ala Thr Val Asn Gly Gly Gln Val Gly Thr Lys Thr Tyr Lys
                485                 490                 495

Val Gln Val Cys Cys Ser Asn Leu Asn Tyr Leu Lys Tyr Gly Leu Leu
            500                 505                 510

Thr Arg Glu Asn Asn Asn Ser Val Met Gln Ala Val Lys Asn Ser Ser
        515                 520                 525

Gln Ala Asp Ala Lys Thr Lys Gln Ile Glu Gln Ser Met Phe Leu Gln
    530                 535                 540

Gly Glu Arg Thr Asp Glu Asn Lys Ile Pro Gln Glu Gln Gly Ile Val
545                 550                 555                 560

Tyr Arg Gly Phe Trp Tyr Gly Arg Ile Ala Asn Gly Thr Ser Trp Ser
                565                 570                 575

Gly Lys Ala Ser Asn Ala Thr Asp Gly Asn Arg Ala Lys Phe Thr Val
            580                 585                 590

Asn Gly Asp Arg Lys Glu Ile Thr Gly Thr Leu Thr Ala Glu Asn Arg
        595                 600                 605

Ser Glu Ala Thr Phe Thr Ile Asp Ala Met Ile Glu Gly Asn Gly Phe
    610                 615                 620

Lys Gly Thr Ala Lys Thr Gly Asn Asp Gly Phe Ala Pro Asp Gln Asn
625                 630                 635                 640

Asn Ser Thr Val Thr His Lys Val His Ile Ala Asn Ala Glu Val Gln
                645                 650                 655

Gly Gly Phe Tyr Gly Pro Asn Ala Glu Glu Leu Gly Gly Trp Phe Ala
            660                 665                 670

Tyr Pro Gly Asn Glu Gln Thr Lys Asn Ala Thr Val Glu Ser Gly Asn
        675                 680                 685

Gly Asn Ser Ala Ser Ser Ala Thr Val Val Phe Gly Ala Lys Arg Gln
    690                 695                 700

Lys Leu Val Lys
705
```

(2) INFORMATION FOR SEQ ID NO:29:

(i) SEQUENCE CHARACTERISTICS:
(A) LENGTH: 280 base pairs
(B) TYPE: nucleic acid
(C) STRANDEDNESS: single
(D) TOPOLOGY: linear (xi) SEQUENCE DESCRIPTION: SEQ ID NO:29:

```
AGCCAACGAA GTTACAGGGC TTGGTAAGGT GGTCAAAACT GCCGAGACCA TCAATAAAGA     60

ACAAGTGCTA AACATTCGAG ACTTAACACG CTATGACCCT GGCATTGCTG TGGTTGAGCA    120

AGGTCGTGGG GCAAGCTCAG GCTATTCTAT TCGTGGTATG GATAAAAATC GTGTGGCGGT    180

ATTGGTTGAT GGCATCAATC AAGCCCAGCA CTATGCCCTA CAAGGCCCTG TGGCAGGCAA    240
```

-continued

AAATTATGCC GCAGGTGGGG CAATCAACGA AATAGAATAC 280

(2) INFORMATION FOR SEQ ID NO:30:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:30:

Glu Gly Gly Phe Tyr Gly Pro
1 5

(2) INFORMATION FOR SEQ ID NO:31:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO:31:

Ile Arg Asp Leu Thr Arg Tyr Asp Pro Gly
1 5 10

(2) INFORMATION FOR SEQ ID NO:32:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:32:

ATTCGAGACT TAACACGCTA TGACCCTGGC 30

(2) INFORMATION FOR SEQ ID NO:33:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:33:

ATTCGTGATT TAACTCGCTA TGACCCTGGT 30

(2) INFORMATION FOR SEQ ID NO:34:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:34:

TCGACGGTAT CGATGGCCTT AGGGGCCTAG GA 32

(2) INFORMATION FOR SEQ ID NO:35:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:35:

-continued

GCCATAGCTA CCGGAATCCC CGGATCCTTC GA 32

(2) INFORMATION FOR SEQ ID NO:36:

(i) SEQUENCE CHARACTERISTICS:
(A) LENGTH: 56 base pairs
(B) TYPE: nucleic acid
(C) STRANDEDNESS: single
(D) TOPOLOGY: linear (xi) SEQUENCE DESCRIPTION: SEQ ID NO:36:

TATGTGTGGT GGCAGTGGTG GTTCAAATCC ACCTGCTCCT ACGCCCATTC CAAATG 56

(2) INFORMATION FOR SEQ ID NO:37:

(i) SEQUENCE CHARACTERISTICS:
(A) LENGTH: 58 base pairs
(B) TYPE: nucleic acid
(C) STRANDEDNESS: single
(D) TOPOLOGY: linear (xi) SEQUENCE DESCRIPTION: SEQ ID NO:37:

ACACACCACC GTCACCACCA AGTTTAGGTG GACGAGGATG CGGGTAAGGT TTACGATC 58

(2) INFORMATION FOR SEQ ID NO:38:

(i) SEQUENCE CHARACTERISTICS:
(A) LENGTH: 104 base pairs
(B) TYPE: nucleic acid
(C) STRANDEDNESS: single
(D) TOPOLOGY: linear (xi) SEQUENCE DESCRIPTION: SEQ ID NO:38:

GTCCAAATGC AAACGAGATG GGCGGGTCAT TTACACACAA CGCCGATGAC AGCAAAGCCT 60

CTGTGGTCTT TGGCACAAAA AGACAACAAG AAGTTAAGTA GTAG 104

(2) INFORMATION FOR SEQ ID NO:39:

(i) SEQUENCE CHARACTERISTICS:
(A) LENGTH: 105 base pairs
(B) TYPE: nucleic acid
(C) STRANDEDNESS: single
(D) TOPOLOGY: linear (xi) SEQUENCE DESCRIPTION: SEQ ID NO:39:

GTTTACGTTT GCTCTACCCG CCCAGTAAAT GTGTGTTGCG GCTACTGTCG TTTCGGAGAC 60

ACCAGAAACC GTGTTTTTCT GTTGTTCTTC AATTCATCAT CCTAG 105

(2) INFORMATION FOR SEQ ID NO:40:

(i) SEQUENCE CHARACTERISTICS:
(A) LENGTH: 113 base pairs
(B) TYPE: nucleic acid
(C) STRANDEDNESS: single
(D) TOPOLOGY: linear (xi) SEQUENCE DESCRIPTION: SEQ ID NO:40:

TATGAAACAC ATTCCTTTAA CCACACTGTG TGTGGCAATC TCTGCCGTCT TATTAACCGC 60

TTGTGGTGGC AGTGGTGGTT CAAATCCACC TGCTCCTACG CCCATTCCAA ATG 113

(2) INFORMATION FOR SEQ ID NO:41:

(i) SEQUENCE CHARACTERISTICS:
(A) LENGTH: 115 base pairs

-continued (B) TYPE: nucleic acid
(C) STRANDEDNESS: single
(D) TOPOLOGY: linear (xi) SEQUENCE DESCRIPTION: SEQ ID NO:41:

ACTTTGTGTA AGGAAATTGG TGTGACACAC ACCGTTAGAG ACGGCAGAAT AATTGGCGAA 60

CACCACCGTC ACCACCAAGT TTAGGTGGAC GAGGATGCGG GTAAGGTTTA CGATC 115

(2) INFORMATION FOR SEQ ID NO:42:

(i) SEQUENCE CHARACTERISTICS:
(A) LENGTH: 40 base pairs
(B) TYPE: nucleic acid
(C) STRANDEDNESS: single
(D) TOPOLOGY: linear (xi) SEQUENCE DESCRIPTION: SEQ ID NO:42:

GAATTCCATA TGTGTGGTGG GAGCTCTGGT GGTTTCAATC 40

(2) INFORMATION FOR SEQ ID NO:43:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:43:

CCCATGGCAG GTTCTTGAAT GCCTGAAACT 30

(2) INFORMATION FOR SEQ ID NO:44:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:44:

GAATTCCATA TGAAACACAT TCCTTTAACC 30

(2) INFORMATION FOR SEQ ID NO:45:

(i) SEQUENCE CHARACTERISTICS:
(A) LENGTH: 2121 base pairs
(B) TYPE: nucleic acid
(C) STRANDEDNESS: single
(D) TOPOLOGY: linear (xi) SEQUENCE DESCRIPTION: SEQ ID NO:45:

ATGAAACACA TTCCTTTAAC CACACTGTGT GTGGCAATCT CTGCCGTCTT ATTAACCGCT 60

TGTGGTGGCA GTGGTGGTTC AAATCCACCT GCTCCTACGC CCATTCCAAA TGCTAGCGGT 120

TCAGGTAATA CTGGCAACAC TGGTAATGCT GGCGGTACTG ATAATACAGC CAATGCAGGT 180

AATACAGGCG GTACAAACTC TGGTACAGGC AGTGCCAACA CACCAGAACC AAAATATAAA 240

GATGTGCCAA CCGATGAAAA TAAAAAAGAT GAAGTGTCAG GCATTCAAGA ACCTGCCATG 300

GGTTATGGCA TGGCTTTGAG TAAAATGAAT CTACACAAAC AACAAGACAC GCCATTAGAT 360

GAAAAAGATA TCATTACCTT AGACGGTAAA AAACAAGTTG CAAAAGGTGA AAAATCGCCA 420

TTGCCATTTT CGTTGGATGT AGAAAATAAA TTGCTTGATG GCTATATAGC AAAAATGAAT 480

GAAGCGGATA AAAATGCCAT TGGTGACAGA ATTAAGAAAG ATAATAAAGA CAAGTCATTA 540

TCTAAAGCAG AGCTTGCCAA ACAAATCAAA GAAGATGTGC GTAAAAGCCA TGAGTTTCAG 600

-continued

```
CAAGTATTAT CATCACTGAA AAACAAAATT TTTCATTCAA ATGATGGAAC AACCAAAGCA    660

ACCACACGAG ATTTACAATA TGTTGATTAT GGTTACTACT TGGTGAATGA TGGCAATTAT    720

CTAACCGTCA AAACAGACGA ACTTTGGAAT TTAGGCCCTG TGGGCGGTGT GTTTTATAAT    780

GGCACAACGA CCGCCAAAGA GCTACCCACA CAAGATGCGG TCAAATATAA AGGACATTGG    840

GACTTTATGA CCGATGTTGC CAAACAAAGA AACCGATTTA GCGAAGTGAA AGAAAACCTT    900

CAAGCAGGTC GGTATTATGG AGCATCTTCA AAAGATGAAT ACAACCGCTT ATTAACTGAT    960

GAGAAAAACA AACCAGAGCG TTATAACGGT GAATATGGTC ATAGCAGTGA GTTTACTGTT   1020

AATTTTAAGG ACAAAAAATT AACAGGTGAG CTGTTTAGTA ACCTACAAGA CAGCCGTAAG   1080

GGCAATGTTA CGAAAACCAA ACGCTATGAC ATCGATGCCA ATATCTACGG CAACCGCTTC   1140

CGTGGCAGTG CCACCGCAAG CGATAAAGCA GAAGCAAGCA AAACCAAACA CCCCTTTACC   1200

AGCGATGCCA AAAATAGCCT AGAAGGCGGT TTTTATGGAC CAAACGCCGA GGAGCTGGCA   1260

GGTAAATTCC TAACCAATGA CAACAAACTC TTTGGCGTCT TTGGTGCTAA ACGAGAGAGT   1320

AAAGCTGGGG AAAAAAACCGA AGCCATCTTA GATGCCTATG CACTTGGGAC ATTTAACAAA  1380

AATAACGCAA CCACATTCAC CCCATTTACC AAAAAACAAC TGGATAACTT TGGCAATGCC   1440

AAAAAGTTGG TCTTGGGTTC TACCGTCATT GATTTGGTGC CTACCGGTGT CACCAAAGAT   1500

GTCAATGAAT TCACCAAAAA CAAGCCAGAT TCTGCCACAA ACAAAGCGGG CGAGACTTTG   1560

ATGGTGAATG ATAAAGTTAG CGTCAAAACC TATGGCTATG GCAGAAACTT TGAATACCTA   1620

AAATTTGGTG AGCTCAGTGT CGGCACAAGC AACAGCGTCT TTTTACAAGG CGAACGCACC   1680

GCTACCACAG GCGAGAAAGC CGTACCAACC AAAGGCACAG CCAAATATTT GGGGAACTGG   1740

GTAGGATACA TCACAGGAAA GGACTCATCA AAAAGCTTTA ATGAGGCCCA AGATGTTGCT   1800

GATTTTGACA TTGACTTTGA GAAAAAATCA GTTAAAGGCA AACTGACCAC CAAAGACCGC   1860

CAAGACCCTG TATTTAACAT CACAGGTGAC ATCGCAGGCA ATGGCTGGAC AGGCAAAGCC   1920

AGCACCACCA AAGCGGACGC AGGGGGCTAC AAGATAGATT CTAGCAGTAC AGGCAAATCC   1980

ATCGTCATCA AAGATGCCGA GGTTACAGGG GGCTTTTATG GTCCAAATGC AAACGAGATG   2040

GGCGGGTCAT TTACACACAA CACCGATGAC AGTAAAGCCT CTGTGGTCTT TGGCACAAAA   2100

AGACAAGAAG AAGTTAAGTA G                                             2121
```

(2) INFORMATION FOR SEQ ID NO:46:

(i) SEQUENCE CHARACTERISTICS:
(A) LENGTH: 706 amino acids
(B) TYPE: amino acid
(D) TOPOLOGY: linear (xi) SEQUENCE DESCRIPTION: SEQ ID NO:46:

```
Met Lys His Ile Pro Leu Thr Thr Leu Cys Val Ala Ile Ser Ala Val
  1               5                  10                  15

Leu Leu Thr Ala Cys Gly Gly Ser Gly Gly Ser Asn Pro Pro Ala Pro
             20                  25                  30

Thr Pro Ile Pro Asn Ala Ser Gly Ser Gly Asn Thr Gly Asn Thr Gly
         35                  40                  45

Asn Ala Gly Gly Thr Asp Asn Thr Ala Asn Ala Gly Asn Thr Gly Gly
     50                  55                  60

Thr Asn Ser Gly Thr Gly Ser Ala Asn Thr Pro Glu Pro Lys Tyr Lys
 65                  70                  75                  80

Asp Val Pro Thr Asp Glu Asn Lys Lys Asp Glu Val Ser Gly Ile Gln
```

-continued

```
                85                  90                  95

Glu Pro Ala Met Gly Tyr Gly Met Ala Leu Ser Lys Met Asn Leu His
            100                 105                 110

Lys Gln Gln Asp Thr Pro Leu Asp Glu Lys Asp Ile Ile Thr Leu Asp
        115                 120                 125

Gly Lys Lys Gln Val Ala Lys Gly Glu Lys Ser Pro Leu Pro Phe Ser
    130                 135                 140

Leu Asp Val Glu Asn Lys Leu Leu Asp Gly Tyr Ile Ala Lys Met Asn
145                 150                 155                 160

Glu Ala Asp Lys Asn Ala Ile Gly Asp Arg Ile Lys Lys Asp Asn Lys
                165                 170                 175

Asp Lys Ser Leu Ser Lys Ala Glu Leu Ala Lys Gln Ile Lys Glu Asp
            180                 185                 190

Val Arg Lys Ser His Glu Phe Gln Gln Val Leu Ser Ser Leu Lys Asn
        195                 200                 205

Lys Ile Phe His Ser Asn Asp Gly Thr Thr Lys Ala Thr Thr Arg Asp
    210                 215                 220

Leu Gln Tyr Val Asp Tyr Gly Tyr Tyr Leu Val Asn Asp Gly Asn Tyr
225                 230                 235                 240

Leu Thr Val Lys Thr Asp Glu Leu Trp Asn Leu Gly Pro Val Gly Gly
                245                 250                 255

Val Phe Tyr Asn Gly Thr Thr Thr Ala Lys Glu Leu Pro Thr Gln Asp
            260                 265                 270

Ala Val Lys Tyr Lys Gly His Trp Asp Phe Met Thr Asp Val Ala Lys
        275                 280                 285

Gln Arg Asn Arg Phe Ser Glu Val Lys Glu Asn Leu Gln Ala Gly Arg
    290                 295                 300

Tyr Tyr Gly Ala Ser Ser Lys Asp Glu Tyr Asn Arg Leu Leu Thr Asp
305                 310                 315                 320

Glu Lys Asn Lys Pro Glu Arg Tyr Asn Gly Glu Tyr Gly His Ser Ser
                325                 330                 335

Glu Phe Thr Val Asn Phe Lys Asp Lys Lys Leu Thr Gly Glu Leu Phe
            340                 345                 350

Ser Asn Leu Gln Asp Ser Arg Lys Gly Asn Val Thr Lys Thr Lys Arg
        355                 360                 365

Tyr Asp Ile Asp Ala Asn Ile Tyr Gly Asn Arg Phe Arg Gly Ser Ala
    370                 375                 380

Thr Ala Ser Asp Lys Ala Glu Ala Ser Lys Thr Lys His Pro Phe Thr
385                 390                 395                 400

Ser Asp Ala Lys Asn Ser Leu Glu Gly Gly Phe Tyr Gly Pro Asn Ala
                405                 410                 415

Glu Glu Leu Ala Gly Lys Phe Leu Thr Asn Asp Asn Lys Leu Phe Gly
            420                 425                 430

Val Phe Gly Ala Lys Arg Glu Ser Lys Ala Gly Glu Lys Thr Glu Ala
        435                 440                 445

Ile Leu Asp Ala Tyr Ala Leu Gly Thr Phe Asn Lys Asn Asn Ala Thr
    450                 455                 460

Thr Phe Thr Pro Phe Thr Lys Lys Gln Leu Asp Asn Phe Gly Asn Ala
465                 470                 475                 480

Lys Lys Leu Val Leu Gly Ser Thr Val Ile Asp Leu Val Pro Thr Gly
                485                 490                 495

Val Thr Lys Asp Val Asn Glu Phe Thr Lys Asn Lys Pro Asp Ser Ala
            500                 505                 510
```

-continued

```
Thr Asn Lys Ala Gly Glu Thr Leu Met Val Asn Asp Lys Val Ser Val
        515                 520                 525

Lys Thr Tyr Gly Tyr Gly Arg Asn Phe Glu Tyr Leu Lys Phe Gly Glu
    530                 535                 540

Leu Ser Val Gly Thr Ser Asn Ser Val Phe Leu Gln Gly Glu Arg Thr
545                 550                 555                 560

Ala Thr Thr Gly Glu Lys Ala Val Pro Thr Lys Gly Thr Ala Lys Tyr
                565                 570                 575

Leu Gly Asn Trp Val Gly Tyr Ile Thr Gly Lys Asp Ser Ser Lys Ser
            580                 585                 590

Phe Asn Glu Ala Gln Asp Val Ala Asp Phe Asp Ile Asp Phe Glu Lys
        595                 600                 605

Lys Ser Val Lys Gly Lys Leu Thr Thr Lys Asp Arg Gln Asp Pro Val
    610                 615                 620

Phe Asn Ile Thr Gly Asp Ile Ala Gly Asn Gly Trp Thr Gly Lys Ala
625                 630                 635                 640

Ser Thr Thr Lys Ala Asp Ala Gly Gly Tyr Lys Ile Asp Ser Ser Ser
                645                 650                 655

Thr Gly Lys Ser Ile Val Ile Lys Asp Ala Glu Val Thr Gly Gly Phe
            660                 665                 670

Tyr Gly Pro Asn Ala Asn Glu Met Gly Gly Ser Phe Thr His Asn Thr
        675                 680                 685

Asp Asp Ser Lys Ala Ser Val Val Phe Gly Thr Lys Arg Gln Glu Glu
    690                 695                 700

Val Lys
705
```

(2) INFORMATION FOR SEQ ID NO:47:

(i) SEQUENCE CHARACTERISTICS:
(A) LENGTH: 2287 base pairs
(B) TYPE: nucleic acid
(C) STRANDEDNESS: single
(D) TOPOLOGY: linear (xi) SEQUENCE DESCRIPTION: SEQ ID NO:47:

```
AAATTTGCCG TATTTTGTCT ATCATAAATG CATTTATCAT CAATGCCCAA ACAAATACGC     60

CAAATGCACA TTGTCAGCAT GCCAAAATAG GCATTAACAG ACTTTTTTAG ATAATACCAT    120

CAACCCATCA GAGGATTATT TTATGAAACA CATTCCTTTA ACCACACTGT GTGTGGCAAT    180

CTCTGCCGTC TTATTAACCG CTTGTGGTGG CAGTGGTGGT TCAAATCCAC CTGCTCCTAC    240

GCCCATTCCA AATGCTAGCG GTTCAGGTAA TACTGGCAAC ACTGGTAATG CTGGCGGTAC    300

TGATAATACA GCCAATGCAG GTAATACAGG CGGTACAAGC TCTGGTACAG GCAGTGCCAG    360

CACGTCAGAA CCAAAATATC AAGATGTGCC AACAACGCCC AATAACAAAG AACAAGTTTC    420

ATCCATTCAA GAACCTGCCA TGGGTTATGG CATGGCTTTG AGTAAAATTA ATCTATACGA    480

CCAACAAGAC ACGCCATTAG ATGCAAAAAA TATCATTACC TTAGACGGTA AAAAACAAGT    540

TGCTGACAAT CAAAAATCAC CATTGCCATT TTCGTTAGAT GTAGAAAATA AATTGCTTGA    600

TGGCTATATA GCAAAAATGA ATGAAGCGGA TAAAAATGCC ATTGGTGAAA GAATTAAGAG    660

AGAAAATGAA CAAAATAAAA AAATATCCGA TGAAGAACTT GCCAAAAAAA TCAAAGAAAA    720

TGTGCGTAAA AGCCCTGAGT TTCAGCAAGT ATTATCATCG ATAAAAGCGA AACTTTCCA     780

TTCAAATGAC AAAACAACCA AAGCAACCAC ACGAGATTTA AAATATGTTG ATTATGGTTA    840
```

-continued

```
CTACTTGGTG AATGATGCCA ATTATCTAAC CGTCAAAACA GACAAACCAA AACTTTGGAA    900

TTCAGGTCCT GTGGGCGGTG TGTTTTATAA TGGCTCAACG ACCGCCAAAG AGCTGCCCAC    960

ACAAGATGCG GTCAAATATA AAGGACATTG GGACTTTATG ACCGATGTTG CCAAAAAAAG   1020

AAACCGATTT AGCGAAGTAA AAGAAACCTA TCAAGCAGGC TGGTGGTATG GGGCATCTTC   1080

AAAAGATGAA TACAACCGCT TATTAACCAA AGCAGATGCC GCACCTGATA ATTATAGCGG   1140

TGAATATGGT CATAGCAGTG AATTTACTGT TAATTTTAAG GAAAAAAAAT TAACAGGTGA   1200

GCTGTTTAGT AACCTACAAG ACAGCCATAA ACAAAAAGTA ACCAAAAACAA AACGCTATGA   1260

TATTAAGGCT GATATCCACG GCAACCGCTT CCGTGGCAGT GCCACCGCAA CGGATAAGGC   1320

AGAAGACAGC AAAAGCAAAC ACCCCTTTAC CAGCCATGCC AAAGATAAGC TAGAAGGTGG   1380

TTTTTATGGA CCAAAAGGCG AGGAGCTGGC AGGTAAATTC TTAACCGATG ATAACAAACT   1440

CTTTGGTGTC TTTGGTGCCA AACAAGAGGG TAATGTAGAA AAAACCGAAG CCATCTTAGA   1500

TGCTTATGCA CTTGGGACAT TTAATAAACC TGGTACGACC AATCCCGCCT TTACCGCTAA   1560

CAGCAAAAAA GAACTGGATA ACTTTGGCAA TGCCAAAAAG TTGGTCTTGG GTTCTACCGT   1620

CATTGATTTG GTGCCTACTG ATGCCACCAA AGATGTCAAT GAATTCAAAG AAAAGCCAAA   1680

GTCTGCCACA AACAAAGCGG GCGAAACTTT GATGGTGAAT GATGAAGTTA GCGTCAAAAC   1740

CTATGGCAAA AACTTTGAAT ACCTAAAATT TGGTGAGCTT AGTGTCGGTG GTAGCCATAG   1800

CGTCTTTTTA CAAGGCGAAC GCACCGCTAC CACAGGCGAG AAAGCCGTAC CAACCACAGG   1860

CAAAGCCAAA TATTTGGGGA ACTGGGTAGG ATATATCACA GGAGCGGACT CATCAAAAGG   1920

CTCTACCGAT GGCAAAGGCT TTACCGATGC CAAAGATATT GCTGATTTTG ACATTGACTT   1980

TGAGAAAAAA TCAGTTAATG GCAAACTGAC CACCAAAGAC CGCCAAGACC CTGTCTTTAA   2040

CATCACAGGT GAAATCGCAG GCAATGGCTG GACAGGTAAA GCCAGCACCG CCGAAGCGAA   2100

CGCAGGGGGC TATAAGATAG ATTCTAGCAG TACAGGCAAA TCCATCGTCA TCAAAGATGC   2160

CGTGGTTACA GGTGGCTTTT ATGGTCCAAA TGCAACCGAG ATGGGTGGGT CATTTACACA   2220

CAACAGCGGT AATGATGGTA AAGTCTCTGT GGTCTTTGGC ACAAAAAAAC AAGAAGTTAA   2280

GAAGTGA                                                             2287
```

(2) INFORMATION FOR SEQ ID NO:48:

(i) SEQUENCE CHARACTERISTICS:
(A) LENGTH: 2145 base pairs
(B) TYPE: nucleic acid
(C) STRANDEDNESS: single
(D) TOPOLOGY: linear (xi) SEQUENCE DESCRIPTION: SEQ ID NO:48:

```
ATGAAACACA TTCCTTTAAC CACACTGTGT GTGGCAATCT CTGCCGTCTT ATTAACCGCT     60

TGTGGTGGCA GTGGTGGTTC AAATCCACCT GCTCCTACGC CCATTCCAAA TGCTAGCGGT    120

TCAGGTAATA CTGGCAACAC TGGTAATGCT GGCGGTACTG ATAATACAGC CAATGCAGGT    180

AATACAGGCG GTACAAGCTC TGGTACAGGC AGTGCCAGCA CGTCAGAACC AAAATATCAA    240

GATGTGCCAA CAACGCCCAA TAACAAAGAA CAAGTTTCAT CCATTCAAGA ACCTGCCATG    300

GGTTATGGCA TGGCTTTGAG TAAAATTAAT CTATACGACC AACAAGACAC GCCATTAGAT    360

GCAAAAAATA TCATTACCTT AGACGGTAAA AAACAAGTTG CTGACAATCA AAAATCACCA    420

TTGCCATTTT CGTTAGATGT AGAAAATAAA TTGCTTGATG GCTATATAGC AAAAATGAAT    480

GAAGCGGATA AAAATGCCAT TGGTGAAAGA ATTAAGAGAG AAAATGAACA AAATAAAAAA    540
```

-continued

```
ATATCCGATG AAGAACTTGC CAAAAAAATC AAAGAAAATG TGCGTAAAAG CCCTGAGTTT    600
CAGCAAGTAT TATCATCGAT AAAAGCGAAA ACTTTCCATT CAAATGACAA AACAACCAAA    660
GCAACCACAC GAGATTTAAA ATATGTTGAT TATGGTTACT ACTTGGTGAA TGATGCCAAT    720
TATCTAACCG TCAAAACAGA CAAACCAAAA CTTTGGAATT CAGGTCCTGT GGGCGGTGTG    780
TTTTATAATG GCTCAACGAC CGCCAAAGAG CTGCCCACAC AAGATGCGGT CAAATATAAA    840
GGACATTGGG ACTTTATGAC CGATGTTGCC AAAAAAAGAA ACCGATTTAG CGAAGTAAAA    900
GAAACCTATC AAGCAGGCTG GTGGTATGGG GCATCTTCAA AAGATGAATA CAACCGCTTA    960
TTAACCAAAG CAGATGCCGC ACCTGATAAT TATAGCGGTG AATATGGTCA TAGCAGTGAA   1020
TTTACTGTTA ATTTTAAGGA AAAAAAATTA ACAGGTGAGC TGTTTAGTAA CCTACAAGAC   1080
AGCCATAAAC AAAAAGTAAC CAAAACAAAA CGCTATGATA TTAAGGCTGA TATCCACGGC   1140
AACCGCTTCC GTGGCAGTGC CACCGCAACG GATAAGGCAG AAGACAGCAA AAGCAAACAC   1200
CCCTTTACCA GCCATGCCAA AGATAAGCTA GAAGGTGGTT TTTATGGACC AAAAGGCGAG   1260
GAGCTGGCAG GTAAATTCTT AACCGATGAT AACAAACTCT TTGGTGTCTT TGGTGCCAAA   1320
CAAGAGGGTA ATGTAGAAAA AACCGAAGCC ATCTTAGATG CTTATGCACT TGGGACATTT   1380
AATAAACCTG GTACGACCAA TCCCGCCTTT ACCGCTAACA GCAAAAAAGA ACTGGATAAC   1440
TTTGGCAATG CCAAAAAGTT GGTCTTGGGT TCTACCGTCA TTGATTTGGT GCCTACTGAT   1500
GCCACCAAAG ATGTCAATGA ATTCAAAGAA AAGCCAAAGT CTGCCACAAA CAAAGCGGGC   1560
GAAACTTTGA TGGTGAATGA TGAAGTTAGC GTCAAAACCT ATGGCAAAAA CTTTGAATAC   1620
CTAAAATTTG GTGAGCTTAG TGTCGGTGGT AGCCATAGCG TCTTTTTACA AGGCGAACGC   1680
ACCGCTACCA CAGGCGAGAA AGCCGTACCA ACCACAGGCA AAGCCAAATA TTTGGGGAAC   1740
TGGGTAGGAT ATATCACAGG AGCGGACTCA TCAAAAGGCT CTACCGATGG CAAAGGCTTT   1800
ACCGATGCCA AAGATATTGC TGATTTTGAC ATTGACTTTG AGAAAAAATC AGTTAATGGC   1860
AAACTGACCA CCAAAGACCG CCAAGACCCT GTCTTTAACA TCACAGGTGA AATCGCAGGC   1920
AATGGCTGGA CAGGTAAAGC CAGCACCGCC GAAGCGAACG CAGGGGGCTA TAAGATAGAT   1980
TCTAGCAGTA CAGGCAAATC CATCGTCATC AAAGATGCCG TGGTTACAGG TGGCTTTTAT   2040
GGTCCAAATG CAACCGAGAT GGGTGGGTCA TTTACACACA ACAGCGGTAA TGATGGTAAA   2100
GTCTCTGTGG TCTTTGGCAC AAAAAAACAA GAAGTTAAGA AGTGA                   2145
```

(2) INFORMATION FOR SEQ ID NO:49:

(i) SEQUENCE CHARACTERISTICS:
(A) LENGTH: 713 amino acids
(B) TYPE: amino acid
(D) TOPOLOGY: linear (xi) SEQUENCE DESCRIPTION: SEQ ID NO:49:

```
Met Lys His Ile Pro Leu Thr Thr Leu Cys Val Ala Ile Ser Ala Val
  1               5                  10                  15

Leu Leu Thr Ala Cys Gly Gly Ser Gly Gly Ser Asn Pro Pro Ala Pro
             20                  25                  30

Thr Pro Ile Pro Asn Ala Ser Gly Ser Gly Asn Thr Gly Asn Thr Gly
         35                  40                  45

Asn Ala Gly Gly Thr Asp Asn Thr Ala Asn Ala Gly Asn Thr Gly Gly
     50                  55                  60

Thr Ser Ser Gly Thr Gly Ser Ala Ser Thr Ser Glu Pro Lys Tyr Gln
 65                  70                  75                  80
```

-continued

```
Asp Val Pro Thr Thr Pro Asn Asn Lys Glu Gln Val Ser Ser Ile Gln
                85                  90                  95

Glu Pro Ala Met Gly Tyr Gly Met Ala Leu Ser Lys Ile Asn Leu Tyr
            100                 105                 110

Asp Gln Gln Asp Thr Pro Leu Asp Ala Lys Asn Ile Ile Thr Leu Asp
        115                 120                 125

Gly Lys Lys Gln Val Ala Asp Asn Gln Lys Ser Pro Leu Pro Phe Ser
    130                 135                 140

Leu Asp Val Glu Asn Lys Leu Leu Asp Gly Tyr Ile Ala Lys Met Asn
145                 150                 155                 160

Glu Ala Asp Lys Asn Ala Ile Gly Glu Arg Ile Lys Arg Glu Asn Glu
                165                 170                 175

Gln Asn Lys Lys Ile Ser Asp Glu Glu Leu Ala Lys Lys Ile Lys Glu
            180                 185                 190

Asn Val Arg Lys Ser Pro Glu Phe Gln Gln Val Leu Ser Ser Ile Lys
        195                 200                 205

Ala Lys Thr Phe His Ser Asn Asp Lys Thr Thr Lys Ala Thr Thr Arg
    210                 215                 220

Asp Leu Lys Tyr Val Asp Tyr Gly Tyr Tyr Leu Val Asn Asp Ala Asn
225                 230                 235                 240

Tyr Leu Thr Val Lys Thr Asp Lys Pro Lys Leu Trp Asn Ser Gly Pro
                245                 250                 255

Val Gly Gly Val Phe Tyr Asn Gly Ser Thr Thr Ala Lys Glu Leu Pro
            260                 265                 270

Thr Gln Asp Ala Val Lys Tyr Lys Gly His Trp Asp Phe Met Thr Asp
        275                 280                 285

Val Ala Lys Lys Arg Asn Arg Phe Ser Glu Val Lys Glu Thr Tyr Gln
    290                 295                 300

Ala Gly Trp Trp Tyr Gly Ala Ser Ser Lys Asp Glu Tyr Asn Arg Leu
305                 310                 315                 320

Leu Thr Lys Ala Asp Ala Ala Pro Asp Asn Tyr Ser Gly Glu Tyr Gly
                325                 330                 335

His Ser Ser Glu Phe Thr Val Asn Phe Lys Glu Lys Lys Leu Thr Gly
            340                 345                 350

Glu Leu Phe Ser Asn Leu Gln Asp Ser His Lys Gln Lys Val Thr Lys
        355                 360                 365

Thr Lys Arg Tyr Asp Ile Lys Ala Asp Ile His Gly Asn Arg Phe Arg
    370                 375                 380

Gly Ser Ala Thr Ala Thr Asp Lys Ala Glu Asp Ser Lys Ser Lys His
385                 390                 395                 400

Pro Phe Thr Ser His Ala Lys Asp Lys Leu Glu Gly Gly Phe Tyr Gly
                405                 410                 415

Pro Lys Gly Glu Glu Leu Ala Gly Lys Phe Leu Thr Asp Asp Asn Lys
            420                 425                 430

Leu Phe Gly Val Phe Gly Ala Lys Gln Glu Gly Asn Val Glu Lys Thr
        435                 440                 445

Glu Ala Ile Leu Asp Ala Tyr Ala Leu Gly Thr Phe Asn Lys Pro Gly
    450                 455                 460

Thr Thr Asn Pro Ala Phe Thr Ala Asn Ser Lys Lys Glu Leu Asp Asn
465                 470                 475                 480

Phe Gly Asn Ala Lys Lys Leu Val Leu Gly Ser Thr Val Ile Asp Leu
                485                 490                 495

Val Pro Thr Asp Ala Thr Lys Asp Val Asn Glu Phe Lys Glu Lys Pro
```

```
                500                  505                 510
Lys Ser Ala Thr Asn Lys Ala Gly Glu Thr Leu Met Val Asn Asp Glu
                515                 520                 525

Val Ser Val Lys Thr Tyr Gly Lys Asn Phe Glu Tyr Leu Lys Phe Gly
                530                 535                 540

Glu Leu Ser Val Gly Gly Ser His Ser Val Phe Leu Gln Gly Glu Arg
545                 550                 555                 560

Thr Ala Thr Thr Gly Glu Lys Ala Val Pro Thr Thr Gly Lys Ala Lys
                565                 570                 575

Tyr Leu Gly Asn Trp Val Gly Tyr Ile Thr Gly Ala Asp Ser Ser Lys
                580                 585                 590

Gly Ser Thr Asp Gly Lys Gly Phe Thr Asp Ala Lys Asp Ile Ala Asp
                595                 600                 605

Phe Asp Ile Asp Phe Glu Lys Lys Ser Val Asn Gly Lys Leu Thr Thr
                610                 615                 620

Lys Asp Arg Gln Asp Pro Val Phe Asn Ile Thr Gly Glu Ile Ala Gly
625                 630                 635                 640

Asn Gly Trp Thr Gly Lys Ala Ser Thr Ala Glu Ala Asn Ala Gly Gly
                645                 650                 655

Tyr Lys Ile Asp Ser Ser Ser Thr Gly Lys Ser Ile Val Ile Lys Asp
                660                 665                 670

Ala Val Val Thr Gly Gly Phe Tyr Gly Pro Asn Ala Thr Glu Met Gly
                675                 680                 685

Gly Ser Phe Thr His Asn Ser Gly Asn Asp Gly Lys Val Ser Val Val
                690                 695                 700

Phe Gly Thr Lys Lys Gln Glu Val Lys
705                 710

(2) INFORMATION FOR SEQ ID NO:50:

    (i) SEQUENCE CHARACTERISTICS:
        (A) LENGTH: 2139 base pairs
        (B) TYPE: nucleic acid
        (C) STRANDEDNESS: single
        (D) TOPOLOGY: linear

    (xi) SEQUENCE DESCRIPTION: SEQ ID NO:50:

ATGAAACACA TTCCTTTAAC CACACTGTGT GTGGCAATCT CTGCCGTCTT ATTAACCGCT      60

TGTGGTGGCA GTGGTGGTTC AAATCCACCT GCTCCTACGC CCATTCCAAA TGCAGGCGGT     120

GCAGGTAATG CTGGTAGCGG TACTGGCGGT GCAGGTAGCA CTGATAATGC AGCCAATGCA     180

GGCAGTACAG GCGGTGCAAG CTCTGGTACA GGCAGTGCCA GCACACAAAA ACCAAAATAT     240

CAAGATGTGC AACCGATAA AAATAAAAAA GATGAAGTGT CAGGCATTCA AGAACCTGCC      300

ATGGGTTATG GCGTGGAATT AAAGCTTCGT AACTGGATAC CACAAGAACA GGAAGAACAT     360

GCCAAAATCA ATACAAATGA TGTTGTAAAA CTTGAAGGTG ACTTGAAGCA TAATCCATTT     420

GACAACTCTA TTTGGCAAAA CATCAAAAAT AGCAAAGAAG TACAAACTGT TTACAACCAA     480

GAGAAGCAAA ACATTGAAAA TCAAATCAAA AAAGAAAATA AAGAACTTGA TAAAACGGCA     540

CTAAAAGCTC TTATTGAAAA AGTTCTTGAT GACTATCTAA CAAGTCTTGC TAAACCCATT     600

TATGAAAAAA ATATTAATGA TTCACATGAT AAGCAGAATA AAGCACGCAC TCGTGATTTG     660

AAGTATGTGC GTTCTGGTTA TATTTATCGC TCAGGTTATT CTAATATCGA CATTCAAAAG     720

AAAATAGCTA AAACTGGTTT TGATGGTGCT TTATTTTATA AAGGTACACA AACTGCTAAA     780

CAATTGCCTG TATCTGAGGT TAAGTATAAA GGCACTTGGG ATTTTATGAC CGATGCCAAA     840
```

-continued

```
AAAGGACAAT CATTTAGCAG TTTTGAAAGA CGAGCTGGTG ATCGCTATAG TGCAATGTCT    900

TCCCATGAGT ACCCATCTTT ATTAACTGAT GATAAAAACA AACCAGATAA TTATAACGAT    960

GAATATGGTC ATAGCAGTGA GTTTACGGTA GATTTTAGTA AAAAGAGCCT AACAGGTGGG   1020

CTGTTTAGTA ACCTACAAGA CCACCATAAG GGCAAGGTTA CGAAAACCAA ACGCTATGAC   1080

ATCAATGCCC GTATCCACGG TAACCGCTTC CGTGGCAGTG CCACCGCAAT CAATAAAGAT   1140

AATGAAAGCA AAGCCAAACA CCCCTTTACC AGCGATGCCG ACAATAGGCT AGAAGGCGGT   1200

TTTTATGGAC CAAACGCCGA GGAGCTGGCA GGTAAATTCC TAACCGATGA CAACAAACTC   1260

TTTGGTGTCT TGGTGCTAA ACAAGAGAGT GAAGCTAAGG AAACCGAAGC CATCTTAGAT   1320

GCTTATGCAC TTGGGACATT TAATAAATCT GGTACGACCA ATCCTGCCTT TACCGCCAAT   1380

AGTAAAAAAG AACTGGATAA CTTTGGCAAT ATTAATAAAT TGGTCTTGGG TTCTACTGTG   1440

ATAGACCTTA CTCAAGGTAA TGATTTTGTA AAAACCATTG ATAAAGAAAA GCCAGCCACC   1500

ACTACCAATC AAGCAGGCGA GCCTTTGACG GTGAATGATA AGGTTCGGGT ACAAGTTTGT   1560

TGTAGCAATC TTGAGCATCT AAAATTTGGC TCACTGAGTA TCGGTGATAG TAATAGCGTC   1620

TTTTTACAAG GTGAACGCAC CGCTACCAAA GGTGATAAAG ATAAAGCCAT GCCAGTTGCA   1680

GGAAATGCTA AATACCGTGG TACATGGGCA GGCTATGTTG CAGGCTCTGG CAATACCAGC   1740

AAAGCCTATG AAGCCCAACA ATTTGCTGAC AATGCCAACC GTGCCGAGTT TGATGTAGAC   1800

TTTGCTAACA AAAGCCTAAC TGGTAAGCTT ATTCCAAATA CGAGCAGTGA TGGTAAATCT   1860

GCTTTTGATA TTACTGCTAC AATTGATGGC AATGGTTTTA GTGGTAAAGC CAATACACCA   1920

GATATTGAAA CAGGTGGGTT AAAGATTGAC AGTAAGAACA GTGAAAGCGG CCGAGTAATT   1980

GTGAAAGATG CTATAGTTAT AGGTGGCTTT TATGGTCCAC AAGCTAATGA ACTGGGTGGC   2040

TCATTTACCT ACAAGAGCAA TGATGCTGGA AATCAAGACA AAGACAGTAG TGCATCTGTG   2100

GTCTTTGGTG CAAGAAAACA ACAAGAAGTC AAACCATGA                          2139
```

(2) INFORMATION FOR SEQ ID NO:51:

(i) SEQUENCE CHARACTERISTICS:
(A) LENGTH: 712 amino acids
(B) TYPE: amino acid
(C) STRANDEDNESS: single
(D) TOPOLOGY: linear (xi) SEQUENCE DESCRIPTION: SEQ ID NO:51:

```
Met Lys His Ile Pro Leu Thr Thr Leu Cys Val Ala Ile Ser Ala Val
1               5                   10                  15

Leu Leu Thr Ala Cys Gly Gly Ser Gly Gly Ser Asn Pro Pro Ala Pro
            20                  25                  30

Thr Pro Ile Pro Asn Ala Gly Gly Ala Gly Asn Ala Gly Ser Gly Thr
        35                  40                  45

Gly Gly Ala Gly Ser Thr Asp Asn Ala Ala Asn Ala Gly Ser Thr Gly
    50                  55                  60

Gly Ala Ser Ser Gly Thr Gly Ser Ala Ser Thr Gln Lys Pro Lys Tyr
65                  70                  75                  80

Gln Asp Val Pro Thr Asp Lys Asn Lys Lys Asp Glu Val Ser Gly Ile
                85                  90                  95

Gln Glu Pro Ala Met Gly Tyr Gly Val Glu Leu Lys Leu Arg Asn Trp
            100                 105                 110

Ile Pro Gln Glu Gln Glu Glu His Ala Lys Ile Asn Thr Asn Asp Val
        115                 120                 125
```

-continued

```
Val Lys Leu Glu Gly Asp Leu Lys His Asn Pro Phe Asp Asn Ser Ile
    130                 135                 140

Trp Gln Asn Ile Lys Asn Ser Lys Glu Val Gln Thr Val Tyr Asn Gln
145                 150                 155                 160

Glu Lys Gln Asn Ile Glu Asn Gln Ile Lys Lys Glu Asn Lys Glu Leu
                165                 170                 175

Asp Lys Thr Ala Leu Lys Ala Leu Ile Glu Lys Val Leu Asp Asp Tyr
            180                 185                 190

Leu Thr Ser Leu Ala Lys Pro Ile Tyr Glu Lys Asn Ile Asn Asp Ser
        195                 200                 205

His Asp Lys Gln Asn Lys Ala Arg Thr Arg Asp Leu Lys Tyr Val Arg
    210                 215                 220

Ser Gly Tyr Ile Tyr Arg Ser Gly Tyr Ser Asn Ile Asp Ile Gln Lys
225                 230                 235                 240

Lys Ile Ala Lys Thr Gly Phe Asp Gly Ala Leu Phe Tyr Lys Gly Thr
                245                 250                 255

Gln Thr Ala Lys Gln Leu Pro Val Ser Glu Val Lys Tyr Lys Gly Thr
            260                 265                 270

Trp Asp Phe Met Thr Asp Ala Lys Lys Gly Gln Ser Phe Ser Ser Phe
        275                 280                 285

Glu Arg Arg Ala Gly Asp Arg Tyr Ser Ala Met Ser Ser His Glu Tyr
    290                 295                 300

Pro Ser Leu Leu Thr Asp Asp Lys Asn Lys Pro Asp Asn Tyr Asn Asp
305                 310                 315                 320

Glu Tyr Gly His Ser Ser Glu Phe Thr Val Asp Phe Ser Lys Lys Ser
                325                 330                 335

Leu Thr Gly Gly Leu Phe Ser Asn Leu Gln Asp His His Lys Gly Lys
            340                 345                 350

Val Thr Lys Thr Lys Arg Tyr Asp Ile Asn Ala Arg Ile His Gly Asn
        355                 360                 365

Arg Phe Arg Gly Ser Ala Thr Ala Ile Asn Lys Asp Asn Glu Ser Lys
    370                 375                 380

Ala Lys His Pro Phe Thr Ser Asp Ala Asp Asn Arg Leu Glu Gly Gly
385                 390                 395                 400

Phe Tyr Gly Pro Asn Ala Glu Glu Leu Ala Gly Lys Phe Leu Thr Asp
                405                 410                 415

Asp Asn Lys Leu Phe Gly Val Phe Gly Ala Lys Gln Glu Ser Glu Ala
            420                 425                 430

Lys Glu Thr Glu Ala Ile Leu Asp Ala Tyr Ala Leu Gly Thr Phe Asn
        435                 440                 445

Lys Ser Gly Thr Thr Asn Pro Ala Phe Thr Ala Asn Ser Lys Lys Glu
    450                 455                 460

Leu Asp Asn Phe Gly Asn Ile Asn Lys Leu Val Leu Gly Ser Thr Val
465                 470                 475                 480

Ile Asp Leu Thr Gln Gly Asn Asp Phe Val Lys Thr Ile Asp Lys Glu
                485                 490                 495

Lys Pro Ala Thr Thr Thr Asn Gln Ala Gly Glu Pro Leu Thr Val Asn
            500                 505                 510

Asp Lys Val Arg Val Gln Val Cys Cys Ser Asn Leu Glu His Leu Lys
        515                 520                 525

Phe Gly Ser Leu Ser Ile Gly Asp Ser Asn Ser Val Phe Leu Gln Gly
    530                 535                 540
```

-continued

```
Glu Arg Thr Ala Thr Lys Gly Asp Lys Asp Lys Ala Met Pro Val Ala
545                 550                 555                 560

Gly Asn Ala Lys Tyr Arg Gly Thr Trp Ala Gly Tyr Val Ala Gly Ser
                565                 570                 575

Gly Asn Thr Ser Lys Ala Tyr Glu Ala Gln Gln Phe Ala Asp Asn Ala
            580                 585                 590

Asn Arg Ala Glu Phe Asp Val Asp Phe Ala Asn Lys Ser Leu Thr Gly
        595                 600                 605

Lys Leu Ile Pro Asn Thr Ser Ser Asp Gly Lys Ser Ala Phe Asp Ile
    610                 615                 620

Thr Ala Thr Ile Asp Gly Asn Gly Phe Ser Gly Lys Ala Asn Thr Pro
625                 630                 635                 640

Asp Ile Glu Thr Gly Gly Leu Lys Ile Asp Ser Lys Asn Ser Glu Ser
                645                 650                 655

Gly Arg Val Ile Val Lys Asp Ala Ile Val Ile Gly Gly Phe Tyr Gly
            660                 665                 670

Pro Gln Ala Asn Glu Leu Gly Gly Ser Phe Thr Tyr Lys Ser Asn Asp
        675                 680                 685

Ala Gly Asn Gln Asp Lys Asp Ser Ser Ala Ser Val Val Phe Gly Ala
    690                 695                 700

Arg Lys Gln Gln Glu Val Lys Pro
705                 710
```

(2) INFORMATION FOR SEQ ID NO:52:

(i) SEQUENCE CHARACTERISTICS:
(A) LENGTH: 2142 base pairs
(B) TYPE: nucleic acid
(C) STRANDEDNESS: single
(D) TOPOLOGY: linear (xi) SEQUENCE DESCRIPTION: SEQ ID NO:52:

```
ATGAAACACA TTCCTTTAAC CACACTGTGT GTGGCAATCT CTGCCGTCTT ATTAACCGCT     60

TGTGGTGGCA GTGGTGGTTC AAATCCACCT GCTCCTACGC CCATCCCAAA TGCAGGCAGT    120

GCAGGTAATG CTGGCGGTAC AGGAAATACA GGCGGTACTG GCAGTACTGA TAATGTAGGC    180

AATGCTGGCG GTGCAAACTC TGGTACAGGC AATGCAGGTA ATTCAGGTAA TGCAAACTCT    240

GGTACAGGCA GTGCCAACAC ACCAGAACCA AAATATCAAG ATGTGCCAAC CGATAAAAAT    300

GAAAAAGAAC AAGTTTCATC CATTCAAGAA CCTGCCATGG GTTATGCAAT GGAATTAAAG    360

CTTCGTAATG CTCACCCTCT TAACCCAAAT AAAAATAAAG AGGCTGAAAA ACGCATTGCC    420

TTAGACCAAA AAGATTTGGT GGCAGTAGAG GGCGACCTAA CCAACATTCC TTTTGATAAA    480

AATCTTATTG AATACCTTAA AAAATCATCC GAGGTTGTAA GTAAATTTGA AGCACAAAAA    540

GGCGGTATTG AAAATAACAC AAGACTGACA CACAAAGATT TATCATCAGA GCAAAAAGAA    600

GCAAAAGTCA AAGAAGCGTT GGACAATGCT TTAACTCAAT TTGCCCAAGA AAAATACAAG    660

GAGCTAATTG AGAACGCCCA TGATAAAAAA TCTGACGCAC GCAACCGTGA TCTAGAATAT    720

GTCAAGTCTG GTTTTAACTA TCTTTCTGGA TATACCGCCA CCGACCACGA CAAAAAAACC    780

AATTATCGTG GCTATTATGG TGCGTTGTAT TATAAAGGCA GCGAAACCGC CAAAGAGCTA    840

CCACAAACAA GTGCAAAATA TAAAGGTTAT TGGGACTTTA TGACAGATGC CACACTTGAT    900

AACAAATACA CGGATTTGCC AGGTATCGCC AGACAAACCC AGTGGCGTAG TCTTGTTTCT    960

ACTGATGAGT ATGCAACGCT CTTGACAGAC AAAAATAACA AGCCCAGTGA TTACAATGGT   1020

GCATATGGTC ATAGCAGTGA ATTTGATGTT AATTTTGCTG ATAAAAAAAT TAAAGGCAAA   1080
```

-continued

```
CTTATCAGTA ATCAGTTATC AGGCACAGCT GTAACCGCCA AAGAGCGTTA TAAAATAGAA   1140

GCTGATATCC ACGGCAACCG CTTCCGTGGC AGTGCCACCG CAAGCGATAA AGCAGAAGAC   1200

AGCAAAACCC AACACCCCTT TACCAGCGAT GCTACAAACA AGCTAGAAGG TGGTTTTTAT   1260

GGACCAAAAG GCGAGGAGCT GGCAGGTAAA TTCTTAACCG ATGACAACAA ACTCTTTGGG   1320

GTCTTTGGTG CTAAACGAGA TAAAGTAGAA AAAACCGAAG CCATCTTAGA TGCCTATGCA   1380

CTTGGGACAT TTAATAATAC AAATAAAGCA ACCACATTCA CCCCATTTAC CAAAAAACAA   1440

CTGGATAACT TTGGCAATGC CAAAAAGTTG GTCTTGGGTT CTACCGTCAT TAATTTGGTG   1500

TCTACCGATG CCACCAAAAA TGAATTCACC AAAAAAATTCA CCAAAGACAA GCCAACTTCT   1560

GCCACAAACA AAGCGGGCGA GACTTTGATG GTGAATGATG AAGTTATCGT CAAAACCTAT   1620

GGCAAAAACT TTGAATACCT AAAATTTGGT GAGCTTAGTG TCGGTGATAG CCATAGCGTC   1680

TTTTTACAAG GCGAACGCAC CGCTACCACA GGCGAGAAAG CCGTACCAAC CACAGGCAAA   1740

GCCAAATATC TGGGGAACTG GGTAGGATAC ATCACAGGAG CGGGCACAGG AAAAAGCTTT   1800

AATGAGGCCC AAGATATTGC TGATTTTGAC ATTGACTTTG AGAGAAAATC AGTTAAAGGC   1860

AAACTGACCA CCCAAGGCCG CACAGATCCT GTCTTTAACA TCAAAGGTGA AATTGCAGGC   1920

AATGGCTGGA CAGGCAAAGC CAGCACCACC AAAGCGGACG CAGGAGGCTA CAAGATAGAT   1980

TCTAGCAGTA CAGGCAAATC CATCGTCATC GAAAATGCCG AAGTTACTGG GGGCTTTTAT   2040

GGTCCAAATG CAAACGAGAT GGGCGGGTCA TTTACACACG ATACCGATGA CAGTAAAGCC   2100

TCTGTGGTCT TTGGCACAAA AAGACAACAA GAAGTTAAGT AG                      2142
```

(2) INFORMATION FOR SEQ ID NO:53:

(i) SEQUENCE CHARACTERISTICS:
(A) LENGTH: 713 amino acids
(B) TYPE: amino acid
(C) STRANDEDNESS: single
(D) TOPOLOGY: linear (xi) SEQUENCE DESCRIPTION: SEQ ID NO:53:

```
Met Lys His Ile Pro Leu Thr Thr Leu Cys Val Ala Ile Ser Ala Val
1               5                   10                  15

Leu Leu Thr Ala Cys Gly Gly Ser Gly Gly Ser Asn Pro Pro Ala Pro
            20                  25                  30

Thr Pro Ile Pro Asn Ala Gly Ser Ala Gly Asn Ala Gly Gly Thr Gly
        35                  40                  45

Asn Thr Gly Gly Thr Gly Ser Thr Asp Asn Val Gly Asn Ala Gly Gly
    50                  55                  60

Ala Asn Ser Gly Thr Gly Asn Ala Gly Asn Ser Gly Asn Ala Asn Ser
65                  70                  75                  80

Gly Thr Gly Ser Ala Asn Thr Pro Glu Pro Lys Tyr Gln Asp Val Pro
                85                  90                  95

Thr Asp Lys Asn Glu Lys Glu Gln Val Ser Ser Ile Gln Glu Pro Ala
            100                 105                 110

Met Gly Tyr Ala Met Glu Leu Lys Leu Arg Asn Ala His Pro Leu Asn
        115                 120                 125

Pro Asn Lys Asn Lys Glu Ala Glu Lys Arg Ile Ala Leu Asp Gln Lys
    130                 135                 140

Asp Leu Val Ala Val Glu Gly Asp Leu Thr Asn Ile Pro Phe Asp Lys
145                 150                 155                 160

Asn Leu Ile Glu Tyr Leu Lys Lys Ser Ser Glu Val Val Ser Lys Phe
```

-continued

```
                165                 170                 175

Glu Ala Gln Lys Gly Gly Ile Glu Asn Asn Thr Arg Leu Thr His Lys
            180                 185                 190

Asp Leu Ser Ser Glu Gln Lys Glu Ala Lys Val Lys Glu Ala Leu Asp
        195                 200                 205

Asn Ala Leu Thr Gln Phe Ala Gln Glu Lys Tyr Lys Glu Leu Ile Glu
    210                 215                 220

Asn Ala His Asp Lys Lys Ser Asp Ala Arg Asn Arg Asp Leu Glu Tyr
225                 230                 235                 240

Val Lys Ser Gly Phe Asn Tyr Leu Ser Gly Tyr Thr Ala Thr Asp His
                245                 250                 255

Asp Lys Lys Thr Asn Tyr Arg Gly Tyr Tyr Gly Ala Leu Tyr Tyr Lys
            260                 265                 270

Gly Ser Glu Thr Ala Lys Glu Leu Pro Gln Thr Ser Ala Lys Tyr Lys
        275                 280                 285

Gly Tyr Trp Asp Phe Met Thr Asp Ala Thr Leu Asp Asn Lys Tyr Thr
    290                 295                 300

Asp Leu Pro Gly Ile Ala Arg Gln Thr Gln Trp Arg Ser Leu Val Ser
305                 310                 315                 320

Thr Asp Glu Tyr Ala Thr Leu Leu Thr Asp Lys Asn Asn Lys Pro Ser
                325                 330                 335

Asp Tyr Asn Gly Ala Tyr Gly His Ser Ser Glu Phe Asp Val Asn Phe
            340                 345                 350

Ala Asp Lys Lys Ile Lys Gly Lys Leu Ile Ser Asn Gln Leu Ser Gly
        355                 360                 365

Thr Ala Val Thr Ala Lys Glu Arg Tyr Lys Ile Glu Ala Asp Ile His
    370                 375                 380

Gly Asn Arg Phe Arg Gly Ser Ala Thr Ala Ser Asp Lys Ala Glu Asp
385                 390                 395                 400

Ser Lys Thr Gln His Pro Phe Thr Ser Asp Ala Thr Asn Lys Leu Glu
                405                 410                 415

Gly Gly Phe Tyr Gly Pro Lys Gly Glu Glu Leu Ala Gly Lys Phe Leu
            420                 425                 430

Thr Asp Asp Asn Lys Leu Phe Gly Val Phe Gly Ala Lys Arg Asp Lys
        435                 440                 445

Val Glu Lys Thr Glu Ala Ile Leu Asp Ala Tyr Ala Leu Gly Thr Phe
    450                 455                 460

Asn Asn Thr Asn Lys Ala Thr Thr Phe Thr Pro Phe Thr Lys Lys Gln
465                 470                 475                 480

Leu Asp Asn Phe Gly Asn Ala Lys Lys Leu Val Leu Gly Ser Thr Val
                485                 490                 495

Ile Asn Leu Val Ser Thr Asp Ala Thr Lys Asn Glu Phe Thr Lys Lys
            500                 505                 510

Phe Thr Lys Asp Lys Pro Thr Ser Ala Thr Asn Lys Ala Gly Glu Thr
        515                 520                 525

Leu Met Val Asn Asp Glu Val Ile Val Lys Thr Tyr Gly Lys Asn Phe
    530                 535                 540

Glu Tyr Leu Lys Phe Gly Glu Leu Ser Val Gly Asp Ser His Ser Val
545                 550                 555                 560

Phe Leu Gln Gly Glu Arg Thr Ala Thr Thr Gly Glu Lys Ala Val Pro
                565                 570                 575

Thr Thr Gly Lys Ala Lys Tyr Leu Gly Asn Trp Val Gly Tyr Ile Thr
            580                 585                 590
```

-continued

```
Gly Ala Gly Thr Gly Lys Ser Phe Asn Glu Ala Gln Asp Ile Ala Asp
        595                 600                 605

Phe Asp Ile Asp Phe Glu Arg Lys Ser Val Lys Gly Lys Leu Thr Thr
    610                 615                 620

Gln Gly Arg Thr Asp Pro Val Phe Asn Ile Lys Gly Glu Ile Ala Gly
625                 630                 635                 640

Asn Gly Trp Thr Gly Lys Ala Ser Thr Thr Lys Ala Asp Ala Gly Gly
                645                 650                 655

Tyr Lys Ile Asp Ser Ser Ser Thr Gly Lys Ser Ile Val Ile Glu Asn
            660                 665                 670

Ala Glu Val Thr Gly Gly Phe Tyr Gly Pro Asn Ala Asn Glu Met Gly
        675                 680                 685

Gly Ser Phe Thr His Asp Thr Asp Asp Ser Lys Ala Ser Val Val Phe
    690                 695                 700

Gly Thr Lys Arg Gln Gln Glu Val Lys
705                 710
```

(2) INFORMATION FOR SEQ ID NO:54:

(i) SEQUENCE CHARACTERISTICS:
(A) LENGTH: 8266 base pairs
(B) TYPE: nucleic acid
(C) STRANDEDNESS: single
(D) TOPOLOGY: linear (xi) SEQUENCE DESCRIPTION: SEQ ID NO:54:

```
GATGCCTGCC TTGTGATTGG TTGGGGTGTA TCGGTGTATC AAAGTGCAAA AGCCAACAGG     60

TGGTCATTGA TGAATCAATC AAAACAAAAC AACAAATCCA AAAAATCCAA ACAAGTATTA    120

AAACTTAGTG CCTTGTCTTT GGGTCTGCTT AACATCACGC AGGTGGCACT GGCAAACACA    180

ACGGCCGATA AGGCGGAGGC AACAGATAAG ACAAACCTTG TTGTTGTCTT GGATGAAACT    240

GTTGTAACAG CGAAGAAAAA CGCCCGTAAA GCCAACGAAG TTACAGGGCT TGGTAAGGTG    300

GTCAAAACTG CCGAGACCAT CAATAAAGAA CAAGTGCTAA ACATTCGAGA CTTAACACGC    360

TATGACCCTG GCATTGCTGT GGTTGAGCAA GGTCGTGGGG CAAGCTCAGG CTATTCTATT    420

CGTGGTATGG ATAAAAATCG TGTGGCGGTA TTGGTTGATG GCATCAATCA AGCCCAGCAC    480

TATGCCCTAC AAGGCCCTGT GGCAGGCAAA AATTATGCCG CAGGTGGGGC AATCAACGAA    540

ATAGAATACG AAAATGTCCG CTCCGTTGAG ATTAGTAAAG GTGCAAATTC AAGTGAATAC    600

GGCTCTGGGG CATTATCTGG CTCTGTGGCA TTTGTTACCA AAACCGCCGA TGACATCATC    660

AAAGATGGTA AAGATTGGGG CGTGCAGACC AAAACCGCCT ATGCCAGTAA AAATAACGCA    720

TGGGTTAATT CTGTGGCAGC AGCAGGCAAG GCAGGTTCTT TTAGCGGTCT TATCATCTAC    780

ACCGACCGCC GTGGTCAAGA ATACAAGGCA CATGATGATG CCTATCAGGG TAGCCAAAGT    840

TTTGATAGAG CGGTGGCAAC CACTGACCCA AATAACCGAA CATTTTTAAT AGCAAATGAA    900

TGTGCCAATG GTAATTATGA GGCGTGTGCT GCTGGCGGTC AAACCAAACT TCAAGCCAAG    960

CCAACCAATG TGCGTGATAA GGTCAATGTC AAAGATTATA CAGGTCCTAA CCGCCTTATC   1020

CCAAACCCAC TCACCCAAGA CAGCAAATCC TTACTGCTTC GCCCAGGTTA TCAGCTAAAC   1080

GATAAGCACT ATGTCGGTGG TGTGTATGAA ATCACCAAAC AAAACTACGC CATGCAAGAT   1140

AAAACCGTGC CTGCTTATCT GGCGGTTCAT GACATTGAAA AATCAAGGCT CAGCAACCAT   1200

GCCCAAGCCA ATGGCTATTA TCAAGGCAAT AATCTTGGTG AACGCATTCG TGATACCATT   1260

GGGCCAGATT CAGGTTATGG CATCAACTAT GCTCATGGCG TATTTTATGA TGAAAAACAC   1320
```

-continued

```
CAAAAAGACC GCCTAGGGCT TGAATATGTT TATGACAGCA AAGGTGAAAA TAAATGGTTT   1380
GATGATGTGC GTGTGTCTTA TGATAAGCAA GACATTACGC TACGCAGCCA GCTGACCAAC   1440
ACGCACTGTT CAACCTATCC GCACATTGAC AAAAATTGTA CGCCTGATGT CAATAAACCT   1500
TTTTCGGTAA AAGAGGTGGA TAACAATGCC TACAAAGAAC AGCACAATTT AATCAAAGCC   1560
GTCTTTAACA AAAAAATGGC GTTGGGCAGT ACGCATCATC ACATCAACCT GCAAGTTGGC   1620
TATGATAAAT TCAATTCAAG CCTGAGCCGT GTAGAATATC GTTTGGCAAC CCATCAGTCT   1680
TATCAAAAAC TTGATTACAC CCCACCAAGT AACCCTTTGC CAGATAAGTT TAAGCCCATT   1740
TTAGGTTCAA ACAACAAACC CATTTGCCTT GATGCTTATG GTTATGGTCA TGACCATCCA   1800
CAGGCTTGTA ACGCCAAAAA CAGCACTTAT CAAAATTTTG CCATCAAAAA AGGCATAGAG   1860
CAATACAACC AAAAAACCAA TACCGATAAG ATTGATTATC AAGCCATCAT TGACCAATAT   1920
GATAAACAAA ACCCCAACAG CACCCTAAAA CCCTTTGAGA AATCAAACA AAGTTTGGGG   1980
CAAGAAAAAT ACAACAAGAT AGACGAACTT GGCTTTAAAG CTTATAAAGA TTTACGCAAC   2040
GAATGGGCGG GTTGGACTAA TGACAACAGC CAACAAAATG CCAATAAAGG CACGGATAAT   2100
ATCTATCAGC CAAATCAAGC AACTGTGGTC AAAGATGACA AATGTAAATA TAGCGAGACC   2160
AACAGCTATG CTGATTGCTC AACCACTCGC CACATCAGTG GTGATAATTA TTTCATCGCT   2220
TTAAAAGACA ACATGACCAT CAATAAATAT GTTGATTTGG GGCTGGGTGC TCGCTATGAC   2280
AGAATCAAAC ACAAATCTGA TGTGCCTTTG GTAGACAACA GTGCCAGCAA CCAGCTGTCT   2340
TGGAATTTTG GCGTGGTCGT CAAGCCCACC AATTGGCTGG ACATCGCTTA TAGAAGCTCG   2400
CAAGGCTTTC GCATGCCAAG TTTTTCTGAA ATGTATGGCG AACGCTTTGG CGTAACCATC   2460
GGTAAAGGCA CGCAACATGG CTGTAAGGGT CTTTATTACA TTTGTCAGCA GACTGTCCAT   2520
CAAACCAAGC TAAAACCTGA AAAATCCTTT AACCAAGAAA TCGGAGCGAC TTTACATAAC   2580
CACTTAGGCA GTCTTGAGGT TAGTTATTTT AAAAATCGCT ATACCGATTT GATTGTTGGT   2640
AAAAGTGAAG AGATTAGAAC CCTAACCCAA GGTGATAATG CAGGCAAACA GCGTGGTAAA   2700
GGTGATTTGG GCTTTCATAA TGGACAAGAT GCTGATTTGA CAGGAATTAA CATTCTTGGC   2760
AGACTTGACC TAAACGCTGC CAATAGTCGC CTTCCCTATG GATTATACTC AACACTGGCT   2820
TATAACAAAG TTGATGTTAA AGGAAAAACC TTAAACCCAA CTTTGGCAGG AACAAACATA   2880
CTGTTTGATG CCATCCAGCC ATCTCGTTAT GTGGTGGGGC TTGGCTATGA TGCCCCAAGC   2940
CAAAAATGGG GAGCAAACGC CATATTTACC CATTCTGATG CCAAAAATCC AAGCGAGCTT   3000
TTGGCAGATA AGAACTTAGG TAATGGCAAC ATTCAAACAA AACAAGCCAC CAAAGCAAAA   3060
TCCACGCCGT GGCAAACACT TGATTTGTCA GGTTATGTAA ACATAAAAGA TAATTTTACC   3120
TTGCGTGCTG GCGTGTACAA TGTATTTAAT ACCTATTACA CCACTTGGGA GGCTTTACGC   3180
CAAACAGCAA AAGGGGCGGT CAATCAGCAT ACAGGACTGA GCCAAGATAA GCATTATGGT   3240
CGCTATGCCG CTCCTGGACG CAATTACCAA TTGGCACTTG AAATGAAGTT TTAACCAGTG   3300
GCTTTGATGT GATTTTGGCA TGCCAAATCC CAATCAACCA ATGAATAAAG CCCCCATTAC   3360
CATGAGGGCT TTATTTTATC ATCGCTGAGT ATGCTCTTAG CGGTCATCAC TCAGATTAGT   3420
CATTAATTTA TTAGCGATTA ATTTATTAGT AATCACGCTG CTCTTTGATG ATTTTAAGTG   3480
ATGGGTATTC AAGAACGATG TCATACTCAG CACCGTTTTT ATAGGCTTCT ACTTCAAAGA   3540
CAGGCTTGCC TAAAAAGTCA TCAACTTCTA TATCGCCGAC TTGATAGCCA CGAGCAGCAA   3600
GCATTTGAAT GGCTTTTTGA CGATTTTGGG CAAAGTTGCT GTCGCCATAA GCTTGTGCTT   3660
```

-continued

```
TAATACGGTC GTTAGCAACT GCGGTGGTAG AGATACCAAC GGCAGGCAAC AAAACAGCAG   3720

CACTTAGTAC GCCAGCCAAC AGTTTATTGG TTAAATTTTT CATAGTAGTT TCCTAATTAT   3780

TATCATTGTA ATTCATGTTT ATCGTTATAA ACAATCGTTA TAAATAACTG TGTCGTGATA   3840

ACCATTAATC ACAAGTGGGT TAAATGCCTT TTGCCCAATG GCAAATAGGC ACAATGCTCT   3900

GCTTGTTCTA TGATGGTCTA TTATGATCAT CATTTTATTG ACCTATTTTT TTAATCGTAA   3960

TGTTTGTTTG ATGTTAGTAT AAATTTTATC AATCAAACAA TCACAAATTA TATCAATCAT   4020

AGACGGTAAA CAGGCTTCAT ATTTTACGCA TATTTCCCCA GATGTCTGTA GTGTTTCATA   4080

GATGATTTGT AAAACAATTG TCGGTCATTA TTATCAATTG TAAACTGATG GCTAATTTGT   4140

AACCTTATGG CTAATGATAA TATGAATAAA GCGTTATACT GTATCAAAGA ATGAGTAAAA   4200

ACCATCAATG GTATCTTATT TATCATCAGG TTGTGTTAAT AAGATGCCAA TTAAGCGACT   4260

AATTTTGTAA ATTAATTAAT AATCATTCAT ATTTGTATTT TTAAATACCA TAAAAAATGG   4320

TAAAATATGC TCGCTTTTTT GATAGGAGCT GTCATGACAA TCACGCCTGT TTATACCACA   4380

TTCACCCCCA CCAAAACACC CATAAAATTT TTTATGGCTG GCTTGACTTT TCTAATCGCT   4440

CATATCAGCC ATGCCGATGA TGGTCGCACC GACAATCAAG AGCTAATCAA TCAAGAAATA   4500

GCCACCCTTG AACCCATCAT TAACCATGCT CAGCCTGAGT TATTGTCCCA TGATGCATTA   4560

ACACCAAAAA TAGAACCAAT ACTGGCACAA ACACCAAATC CTGCCGAAGA TACGCTCATC   4620

GCCGATGAGG CGTTACTGCT TGATAACCCT GATTTGCTCA ATCACGCCCT AAATTCTGCT   4680

GTCATGACCA ATCATATGGC AGGCGTTCAC GCATTATTGC CCATTTATCA AAAACTGCCC   4740

AAAGACCATC AAAATGGCAT TTTACTTGGG TATGCCAATG CCTTGGCTGC TTTGGATAAG   4800

GGCAACGCCA AAAAAGCCAT TGATGAGCTA CGTCGCATCA TCGCCATCAT GCCTGAATAT   4860

AATGTGGTGC GTTTTCATCT GGCAAGGGCA TTATTTATGG ACAAACAAAA TGAAGCCGCC   4920

CTTGACCAGT TTAATAAATT ACATGCTGAC AACTTGCCAG AGGAGGTGCG GCAGGTTGTT   4980

GGGCAGTACA GACAAGCGCT AAAACAACGA GATTCATGGA CATGGCAAGT AGGCATGAAT   5040

CTGGCCAAAG AAGACAACAT CAATCAAACC CCCAAAAACA CCACGCAAGG TCAATGGACT   5100

TTTGACAAAC CCATTGACGC CATCACCCTA AGCTACCAAT TGGGGGCGGA TAAAAAGTGG   5160

TCTTTGCCCA AAGGGGCATA TGTGGGAGCG AACGCCCAAA TCTATGGCAA ACATCATCAA   5220

AATCACAAAA AATACAACGA CCATTGGGGC AGACTGGGGG CAAATTTGGG CTTTGCTGAT   5280

GCCAAAAAAG ACCTTAGCAT TGAGACCTAT GGTGAAAAAA GATTTTATGG GCATGAGCGT   5340

TATACCGACA CCATTGGCAT ACGCATGTCG GTTGATTATA GAATCAACCC AAAATTTCAA   5400

AGCCTAAACG CCATAGACAT ATCACGCCTA ACCAACCATC GGACGCCTAG GGCTGACAGT   5460

AATAACACTT TATACAGTAC CTCATTGATT TATTACCCAA ATGCCACACG CTATTATCTT   5520

TTGGGGGCAG ACTTTTATGA TGAAAAAGTG CCACAAGACC CATCTGACAG TTATCAACGC   5580

CGTGGCATAC GCACAGCGTG GGGGCAAGAA TGGGCGGGTG GTCTTTCAAG CCGTGCCCAA   5640

ATCAGCATCA ACAAACGCCA TTACCAAGGG GCAAACCTAA CCAGCGGTGG ACAAATTCGC   5700

CATGATAAAC AGATGCAAGC GTCTTTATCG CTTTGGCACA GAGACATTCA CAAATGGGGC   5760

ATCACGCCAC GGCTGACCAT CAGCACAAAC ATCAATAAAA GCAATGACAT CAAGGCAAAT   5820

TATCACAAAA ATCAAATGTT TGTTGAGTTT AGTCGCATTT TTTGATGGGA TAAGCACGCC   5880

CTACTTTTGT TTTTGTAAAA AAATGTGCCA TCATAGACAA TATCAAGAAA AAATCAAGAA   5940

AAAAAGATTA CAAATTTAAT GATAATTGTT ATTGTTTATG TTATTATTTA TCAATGTAAA   6000

TTTGCCGTAT TTTGTCTATC ATAAATGCAT TTATCAAATG CTCAAATAAA TACGCCAAAT   6060
```

-continued

```
GCACATTGTC AGCATGCCAA AATAGGCATC AACAGACTTT TTTAGATAAT ACCATCAACC   6120
CATCAGAGGA TTATTTTATG AAACACATTC CTTTAACCAC ACTGTGTGTG GCAATCTCTG   6180
CCGTCTTATT AACCGCTTGT GGTGGCAGTG GTGGTTCAAA TCCACCTGCT CCTACGCCCA   6240
TTCCAAATGC TAGCGGTTCA GGTAATACTG GCAACACTGG TAATGCTGGC GGTACTGATA   6300
ATACAGCCAA TGCAGGTAAT ACAGGCGGTA CAAACTCTGG TACAGGCAGT GCCAACACAC   6360
CAGAGCCAAA ATATCAAGAT GTACCAACTG AGAAAAATGA AAAAGATAAA GTTTCATCCA   6420
TTCAAGAACC TGCCATGGGT TATGGCATGG CTTTGAGTAA AATTAATCTA CACAACCGAC   6480
AAGACACGCC ATTAGATGAA AAAAATATCA TTACCTTAGA CGGTAAAAAA CAAGTTGCAG   6540
AAGGTAAAAA ATCGCCATTG CCATTTTCGT TAGATGTAGA AAATAAATTG CTTGATGGCT   6600
ATATAGCAAA AATGAATGTA GCGGATAAAA ATGCCATTGG TGACAGAATT AAGAAAGGTA   6660
ATAAAGAAAT CTCCGATGAA GAACTTGCCA AACAAATCAA AGAAGCTGTG CGTAAAAGCC   6720
ATGAGTTTCA GCAAGTATTA TCATCACTGG AAAACAAAAT TTTTCATTCA AATGACGGAA   6780
CAACCAAAGC AACCACACGA GATTTAAAAT ATGTTGATTA TGGTTACTAC TTGGCGAATG   6840
ATGGCAATTA TCTAACCGTC AAAACAGACA AACTTTGGAA TTTAGGCCCT GTGGGTGGTG   6900
TGTTTTATAA TGGCACAACG ACCGCCAAAG AGTTGCCCAC ACAAGATGCG GTCAAATATA   6960
AAGGACATTG GGACTTTATG ACCGATGTTG CCAACAGAAG AAACCGATTT AGCGAAGTGA   7020
AAGAAAACTC TCAAGCAGGC TGGTATTATG GAGCATCTTC AAAAGATGAA TACAACCGCT   7080
TATTAACTAA AGAAGACTCT GCCCCTGATG GTCATAGCGG TGAATATGGC CATAGCAGTG   7140
AGTTTACTGT TAATTTTAAG GAAAAAAAAT TAACAGGTAA GCTGTTTAGT AACCTACAAG   7200
ACCGCCATAA GGGCAATGTT ACAAAAAACCG AACGCTATGA CATCGATGCC AATATCCACG   7260
GCAACCGCTT CCGTGGCAGT GCCACCGCAA GCAATAAAAA TGACACAAGC AAACACCCCT   7320
TTACCAGTGA TGCCAACAAT AGGCTAGAAG GTGGTTTTTA TGGGCCAAAA GGCGAGGAGC   7380
TGGCAGGTAA ATTCTTAACC AATGACAACA AACTCTTTGG CGTCTTTGGT GCTAAACGAG   7440
AGAGTAAAGC TGAGGAAAAA ACCGAAGCCA TCTTAGATGC CTATGCACTT GGGACATTTA   7500
ATACAAGTAA CGCAACCACA TTCACCCCAT TTACCGAAAA ACAACTGGAT AACTTTGGCA   7560
ATGCCAAAAA ATTGGTCTTA GGTTCTACCG TCATTGATTT GGTGCCTACT GATGCCACCA   7620
AAAATGAATT CACCAAAGAC AAGCCAGAGT CTGCCACAAA CGAAGCGGGC GAGACTTTGA   7680
TGGTGAATGA TGAAGTTAGC GTCAAAACCT ATGGCAAAAA CTTTGAATAC CTAAAATTTG   7740
GTGAGCTTAG TATCGGTGGT AGCCATAGCG TCTTTTTACA AGGCGAACGC ACCGCTACCA   7800
CAGGCGAGAA AGCCGTACCA ACCACAGGCA CAGCCAAATA TTTGGGGAAC TGGGTAGGAT   7860
ACATCACAGG AAAGGACACA GGAACGGGCA CAGGAAAAAG CTTTACCGAT GCCCAAGATG   7920
TTGCTGATTT TGACATTGAT TTTGGAAATA AATCAGTCAG CGGTAAACTT ATCACCAAAG   7980
GCCGCCAAGA CCCTGTATTT AGCATCACAG GTCAAATCGC AGGCAATGGC TGGACAGGGA   8040
CAGCCAGCAC CACCAAAGCG GACGCAGGAG GCTACAAGAT AGATTCTAGC AGTACAGGCA   8100
AATCCATCGC CATCAAAGAT GCCAATGTTA CAGGGGGCTT TTATGGTCCA AATGCAAACG   8160
AGATGGGCGG GTCATTTACA CACAACGCCG ATGACAGCAA AGCCTCTGTG GTCTTTGGCA   8220
CAAAAAGACA ACAAGAAGTT AAGTAGTAAT TTAAACACAA TGTTTG                 8266
```

(2) INFORMATION FOR SEQ ID NO:55:

(i) SEQUENCE CHARACTERISTICS:

-continued (A) LENGTH: 1539 base pairs
(B) TYPE: nucleic acid
(C) STRANDEDNESS: single
(D) TOPOLOGY: linear (xi) SEQUENCE DESCRIPTION: SEQ ID NO:55:

```
ATGCTCGCTT TTTTGATAGG AGCTGTCATG ACAATCACGC CTGTTTATAC CACATTCACC     60

CCCACCAAAA CACCCATAAA ATTTTTTATG GCTGGCTTGA CTTTTCTAAT CGCTCATATC    120

AGCCATGCCG ATGATGGTCG CACCGACAAT CAAGAGCTAA TCAATCAAGA AATAGCCACC    180

CTTGAACCCA TCATTAACCA TGCTCAGCCT GAGTTATTGT CCCATGATGC ATTAACACCA    240

AAAATAGAAC CAATACTGGC ACAAACACCA AATCCTGCCG AAGATACGCT CATCGCCGAT    300

GAGGCGTTAC TGCTTGATAA CCCTGATTTG CTCAATCACG CCCTAAATTC TGCTGTCATG    360

ACCAATCATA TGGCAGGCGT TCACGCATTA TTGCCCATTT ATCAAAAACT GCCCAAAGAC    420

CATCAAAATG GCATTTTACT TGGGTATGCC AATGCCTTGG CTGCTTTGGA TAAGGGCAAC    480

GCCAAAAAAG CCATTGATGA GCTACGTCGC ATCATCGCCA TCATGCCTGA ATATAATGTG    540

GTGCGTTTTC ATCTGGCAAG GGCATTATTT ATGGACAAAC AAAATGAAGC CGCCCTTGAC    600

CAGTTTAATA AATTACATGC TGACAACTTG CCAGAGGAGG TGCGGCAGGT TGTTGGGCAG    660

TACAGACAAG CGCTAAAACA ACGAGATTCA TGGACATGGC AAGTAGGCAT GAATCTGGCC    720

AAAGAAGACA ACATCAATCA AACCCCCAAA AACACCACGC AAGGTCAATG GACTTTTGAC    780

AAACCCATTG ACGCCATCAC CCTAAGCTAC CAATTGGGGG CGGATAAAAA GTGGTCTTTG    840

CCCAAAGGGG CATATGTGGG AGCGAACGCC CAAATCTATG GCAAACATCA TCAAAATCAC    900

AAAAAATACA ACGACCATTG GGGCAGACTG GGGGCAAATT TGGGCTTTGC TGATGCCAAA    960

AAAGACCTTA GCATTGAGAC CTATGGTGAA AAAAGATTTT ATGGGCATGA GCGTTATACC   1020

GACACCATTG GCATACGCAT GTCGGTTGAT TATAGAATCA ACCCAAAATT TCAAAGCCTA   1080

AACGCCATAG ACATATCACG CCTAACCAAC CATCGGACGC CTAGGGCTGA CAGTAATAAC   1140

ACTTTATACA GTACCTCATT GATTTATTAC CCAAATGCCA CACGCTATTA TCTTTTGGGG   1200

GCAGACTTTT ATGATGAAAA AGTGCCACAA GACCCATCTG ACAGTTATCA ACGCCGTGGC   1260

ATACGCACAG CGTGGGGGCA AGAATGGGCG GGTGGTCTTT CAAGCCGTGC CCAAATCAGC   1320

ATCAACAAAC GCCATTACCA AGGGGCAAAC CTAACCAGCG GTGGACAAAT TCGCCATGAT   1380

AAACAGATGC AAGCGTCTTT ATCGCTTTGG CACAGAGACA TTCACAAATG GGGCATCACG   1440

CCACGGCTGA CCATCAGCAC AAACATCAAT AAAAGCAATG ACATCAAGGC AAATTATCAC   1500

AAAAATCAAA TGTTTGTTGA GTTTAGTCGC ATTTTTTGA                          1539
```

(2) INFORMATION FOR SEQ ID NO:56:

(i) SEQUENCE CHARACTERISTICS:
(A) LENGTH: 512 amino acids
(B) TYPE: amino acid
(C) STRANDEDNESS: single
(D) TOPOLOGY: linear (xi) SEQUENCE DESCRIPTION: SEQ ID NO:56:

```
Met Leu Ala Phe Leu Ile Gly Ala Val Met Thr Ile Thr Pro Val Tyr
1               5                   10                  15

Thr Thr Phe Thr Pro Thr Lys Thr Pro Ile Lys Phe Phe Met Ala Gly
            20                  25                  30

Leu Thr Phe Leu Ile Ala His Ile Ser His Ala Asp Asp Gly Arg Thr
        35                  40                  45
```

-continued

```
Asp Asn Gln Glu Leu Ile Asn Gln Glu Ile Ala Thr Leu Glu Pro Ile
    50                  55                  60

Ile Asn His Ala Gln Pro Glu Leu Leu Ser His Asp Ala Leu Thr Pro
65                  70                  75                  80

Lys Ile Glu Pro Ile Leu Ala Gln Thr Pro Asn Pro Ala Glu Asp Thr
                85                  90                  95

Leu Ile Ala Asp Glu Ala Leu Leu Leu Asp Asn Pro Asp Leu Leu Asn
            100                 105                 110

His Ala Leu Asn Ser Ala Val Met Thr Asn His Met Ala Gly Val His
        115                 120                 125

Ala Leu Leu Pro Ile Tyr Gln Lys Leu Pro Lys Asp His Gln Asn Gly
    130                 135                 140

Ile Leu Leu Gly Tyr Ala Asn Ala Leu Ala Ala Leu Asp Lys Gly Asn
145                 150                 155                 160

Ala Lys Lys Ala Ile Asp Glu Leu Arg Arg Ile Ile Ala Ile Met Pro
                165                 170                 175

Glu Tyr Asn Val Val Arg Phe His Leu Ala Arg Ala Leu Phe Met Asp
            180                 185                 190

Lys Gln Asn Glu Ala Ala Leu Asp Gln Phe Asn Lys Leu His Ala Asp
        195                 200                 205

Asn Leu Pro Glu Glu Val Arg Gln Val Val Gly Gln Tyr Arg Gln Ala
    210                 215                 220

Leu Lys Gln Arg Asp Ser Trp Thr Trp Gln Val Gly Met Asn Leu Ala
225                 230                 235                 240

Lys Glu Asp Asn Ile Asn Gln Thr Pro Lys Asn Thr Thr Gln Gly Gln
                245                 250                 255

Trp Thr Phe Asp Lys Pro Ile Asp Ala Ile Thr Leu Ser Tyr Gln Leu
            260                 265                 270

Gly Ala Asp Lys Lys Trp Ser Leu Pro Lys Gly Ala Tyr Val Gly Ala
        275                 280                 285

Asn Ala Gln Ile Tyr Gly Lys His His Gln Asn His Lys Lys Tyr Asn
    290                 295                 300

Asp His Trp Gly Arg Leu Gly Ala Asn Leu Gly Phe Ala Asp Ala Lys
305                 310                 315                 320

Lys Asp Leu Ser Ile Glu Thr Tyr Gly Glu Lys Arg Phe Tyr Gly His
                325                 330                 335

Glu Arg Tyr Thr Asp Thr Ile Gly Ile Arg Met Ser Val Asp Tyr Arg
            340                 345                 350

Ile Asn Pro Lys Phe Gln Ser Leu Asn Ala Ile Asp Ile Ser Arg Leu
        355                 360                 365

Thr Asn His Arg Thr Pro Arg Ala Asp Ser Asn Asn Thr Leu Tyr Ser
    370                 375                 380

Thr Ser Leu Ile Tyr Tyr Pro Asn Ala Thr Arg Tyr Tyr Leu Leu Gly
385                 390                 395                 400

Ala Asp Phe Tyr Asp Glu Lys Val Pro Gln Asp Pro Ser Asp Ser Tyr
                405                 410                 415

Gln Arg Arg Gly Ile Arg Thr Ala Trp Gly Gln Glu Trp Ala Gly Gly
            420                 425                 430

Leu Ser Ser Arg Ala Gln Ile Ser Ile Asn Lys Arg His Tyr Gln Gly
        435                 440                 445

Ala Asn Leu Thr Ser Gly Gly Gln Ile Arg His Asp Lys Gln Met Gln
    450                 455                 460

Ala Ser Leu Ser Leu Trp His Arg Asp Ile His Lys Trp Gly Ile Thr
```

-continued

```
465                 470                 475                 480

Pro Arg Leu Thr Ile Ser Thr Asn Ile Asn Lys Ser Asn Asp Ile Lys
                485                 490                 495

Ala Asn Tyr His Lys Asn Gln Met Phe Val Glu Phe Ser Arg Ile Phe
            500                 505                 510
```

(2) INFORMATION FOR SEQ ID NO:57:

(i) SEQUENCE CHARACTERISTICS:
(A) LENGTH: 512 amino acids
(B) TYPE: amino acid
(C) STRANDEDNESS: single
(D) TOPOLOGY: linear (xi) SEQUENCE DESCRIPTION: SEQ ID NO:57:

```
Met Leu Ala Phe Leu Ile Gly Ala Val Met Thr Ile Thr Pro Val Tyr
1               5                   10                  15

Thr Thr Phe Thr Pro Thr Lys Thr Pro Ile Lys Phe Phe Met Ala Gly
            20                  25                  30

Leu Thr Phe Leu Ile Ala His Ile Ser His Ala Asp Asp Gly Arg Thr
        35                  40                  45

Asp Asn Gln Glu Pro Ile Asn Gln Glu Ile Ala Thr Leu Glu Pro Ile
    50                  55                  60

Ile Asn His Ala Gln Pro Glu Leu Leu Ser His Gly Ala Leu Thr Pro
65                  70                  75                  80

Lys Thr Glu Pro Ile Leu Ala Gln Thr Pro Asn Pro Ala Glu Asp Thr
                85                  90                  95

Leu Ile Ala Asp Glu Ala Leu Leu Leu Asp Asn Pro Asp Leu Leu Asn
            100                 105                 110

His Ala Leu Asn Ser Ala Val Met Thr Asn Asn Met Ala Gly Val His
        115                 120                 125

Ala Leu Leu Pro Ile Tyr Gln Lys Leu Pro Lys Asp His Gln Asn Gly
    130                 135                 140

Ile Leu Leu Gly Tyr Ala Asn Ala Leu Val Ala Leu Asp Lys Gly Asn
145                 150                 155                 160

Ala Lys Ala Ala Ile Gly Glu Leu Arg Arg Ile Ile Ala Ile Met Pro
                165                 170                 175

Glu Tyr Asn Val Val Arg Phe His Leu Ala Arg Ala Leu Phe Met Asp
            180                 185                 190

Lys Gln Asn Glu Ala Ala Leu Asp Gln Phe Asn Lys Leu His Ala Asp
        195                 200                 205

Asn Leu Pro Glu Glu Val Arg Arg Val Val Gly Gln Tyr Arg Gln Ala
    210                 215                 220

Leu Lys Gln Arg Asp Ser Trp Thr Trp Gln Val Gly Met Asn Leu Ala
225                 230                 235                 240

Lys Glu Asp Asn Ile Asn Gln Thr Pro Lys Asn Thr Thr Gln Gly Gln
                245                 250                 255

Trp Thr Phe Asp Lys Pro Ile Asp Ala Ile Thr Leu Ser Tyr Gln Leu
            260                 265                 270

Gly Ala Asp Lys Lys Trp Ser Leu Pro Lys Gly Ala Tyr Val Gly Ala
        275                 280                 285

Asn Ala Gln Ile Tyr Gly Lys His His Gln Asn His Lys Lys Tyr Asn
    290                 295                 300

Asp His Trp Gly Arg Leu Gly Ala Asn Leu Gly Phe Ala Asp Ala Lys
305                 310                 315                 320
```

-continued

```
Lys Asp Leu Ser Ile Glu Thr Tyr Gly Glu Lys Arg Phe Tyr Gly His
                325                 330                 335

Glu Arg Tyr Thr Asp Thr Ile Gly Ile Arg Met Ser Ala Asp Tyr Arg
            340                 345                 350

Ile Asn Pro Lys Phe Gln Ser Leu Asn Ala Ile Asp Ile Ser Arg Leu
        355                 360                 365

Thr Asn His Arg Thr Pro Arg Ala Asp Ser Asn Asn Thr Leu Tyr Ser
    370                 375                 380

Thr Ser Leu Ile Tyr Tyr Pro Asn Ala Thr Arg Tyr Tyr Leu Leu Gly
385                 390                 395                 400

Ala Asp Phe Tyr Asp Glu Lys Val Pro Gln Asp Pro Ser Asp Ser Tyr
                405                 410                 415

Glu Arg Arg Gly Ile Arg Thr Ala Trp Gly Gln Glu Trp Ala Gly Gly
            420                 425                 430

Leu Ser Ser Arg Ala Gln Ile Ser Ile Asn Lys Arg His Tyr Gln Gly
        435                 440                 445

Ala Asn Leu Thr Ser Gly Gly Gln Ile Arg Gln Asp Lys Gln Met Gln
    450                 455                 460

Ala Ser Leu Ser Leu Trp His Arg Asp Ile His Lys Trp Gly Ile Thr
465                 470                 475                 480

Pro Arg Leu Thr Ile Ser Thr Asn Ile Asn Lys Ser Asn Asp Ile Lys
                485                 490                 495

Ala Asn Tyr His Lys Asn Gln Met Phe Val Glu Phe Ser Arg Ile Phe
            500                 505                 510
```

(2) INFORMATION FOR SEQ ID NO:58:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:58:

GATGGGATAA GCACGCCCTA CTT 23

(2) INFORMATION FOR SEQ ID NO:59:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:59:

CCCATCAGCC AAACAAACAT TGTGT 25

(2) INFORMATION FOR SEQ ID NO:60:

(i) SEQUENCE CHARACTERISTICS:
(A) LENGTH: 7 amino acids
(B) TYPE: amino acid
(C) STRANDEDNESS: single
(D) TOPOLOGY: linear (xi) SEQUENCE DESCRIPTION: SEQ ID NO:60:

```
Leu Glu Gly Gly Phe Tyr Gly
1               5
```